US008642263B2

(12) United States Patent
Laird et al.

(10) Patent No.: US 8,642,263 B2
(45) Date of Patent: Feb. 4, 2014

(54) HIGH THROUGHPUT METHODS COMPRISING ANALYSIS OF REPETITIVE ELEMENT DNA METHYLATION

(75) Inventors: Peter W. Laird, South Pasadena, CA (US); Daniel J. Weisenberger, Playa Del Rey, CA (US); Mihaela Campan, Los Angeles, CA (US); Tifany I. Long, Chino, CA (US)

(73) Assignee: University of Southern California, Los Angeles, CA (US)

( * ) Notice: Subject to any disclaimer, the term of this patent is extended or adjusted under 35 U.S.C. 154(b) by 173 days.

(21) Appl. No.: 11/719,033

(22) PCT Filed: Nov. 10, 2005

(86) PCT No.: PCT/US2005/042885
§ 371 (c)(1),
(2), (4) Date: Nov. 6, 2007

(87) PCT Pub. No.: WO2006/060308
PCT Pub. Date: Jun. 8, 2006

(65) Prior Publication Data
US 2009/0123915 A1    May 14, 2009

Related U.S. Application Data

(60) Provisional application No. 60/626,672, filed on Nov. 10, 2004, provisional application No. 60/730,600, filed on Oct. 26, 2005.

(51) Int. Cl.
*C12Q 1/68* (2006.01)

(52) U.S. Cl.
USPC ........................ 435/6.12; 435/6.1; 435/6.11

(58) Field of Classification Search
None
See application file for complete search history.

(56) References Cited

FOREIGN PATENT DOCUMENTS

WO    WO 00/70090    11/2000

OTHER PUBLICATIONS

Chalitchagorn, et al., "Distinctive pattern of LINE-1 methylation level in normal tissues and the association with carcinogenesis," Oncogene 23:8841-8846, 2004.
Eads et al., "MythyLight: a high-throughput assay to measure DNA methylation," Nucleic Acids Reserch 28(8):e32i-e32viii, 2000.
Ehrlich et al., "Amount and distribution of 5-methylcytosine in human DNA from different types of tissues or cells," Nucleic Acids Research 10(8):2709-2721, (1982).
Ehrlich, "DNA methylation in cancer: too much, but also too little," Oncogene 21:5400-5413, 2002.
Ehrlich et al., "Satellite DNA hypomethylation in karyotyped Wilms tumors," Cancer Genetics and Cytogenetics 141:97-105, 2003.
Florl et al., "Coordinate hypermethylation at specific genes in prostate carcinoma precedes LINE-1 hypomethylation," British Journal of Cancer 91:985-994, 2004.
Gama-Sousa et al., "The 5-methylcytosine content of highly repeated sequences in human DNA," Nucleic Acids Research 11(10):3087-3095, May 25, 1983.
Hansen et al., "The DNMT3B DNA methyltransferase gene is mutated in the ICF immunodeficiency syndromer," Proceedings of the National Academy of Sciences 96(25):14412-14417, Dec. 7, 1999.
Jeong et al., "Estimating the total mouse DNA methylation according to the B1 repetitive elements," Biochemical and Biophysical Research Communications 335:1211-1216, 2005.
Kimura et al., "Decrease of DNA methyltransferase 1 expression relative to cell proliferation in transition cell carcinoma," International Journal of Cancer 104(5):568-578, 2003.
Kochanek et al., "DNA methylation in the Alu sequences of diploid and haploid primary human cells," The EMBO Journal 12(3):1141-1151, 1993.
Laird, "The Power and the Promise of DNA Methylation Markers," Nature Reviews 3:253-266, 2003.
Narayan et al., "Hypomethylation of pericentromeric DNA in breast adenocarcinomas," International Journal of Cancer 77(6):833-838, Sep. 11, 1998.
Qu et al., "Frequent hypomethylation in Wilms tumors of pericentromeric DNA in chromosomes 1 and 16," Cancer Genetics and Cytogenetics 109(1):34-39, Feb. 1999.
Qu et al., "Satellite DNA hypomethylation vs. overall genomic hypomethylation in ovarian epithelial tumors of different malignant potential," Mutation Research 423(1-2):91-101, Jan. 25, 1999.
Rubin et al., "Alu repeated DNAs are differently methylated in primate germ cells," Nucleic Acids Research 22(23):5121-5127, 1994.
Schmid, "Human Alu subfamilies and their methylation reveled by blot hybridzation," Nucleic Acids Research 19(20):5613-5617, (1991).
Weisenberger et al., "Analysis of repetitive element DNA methylation by methyLight," Nucleic Acids Research 33(21):6823-6836, 2005.
Weisenberger et al., "Role of the DNA Methyltransferase Variant DNMT3b3 in DNA Methylation," Molecular Cancer Research 2: 62-72, Jan. 2004.
Widschwendter et al., "DNA Hypomethylation and Ovarian Cancer Biology," Cancer Research 64:4472-4480, 2004.
Xu et al., "Chromosome Instability and Immunodeficiency Syndrome Caused by Mutations in a DNA Methyltransferase Gene," Nature 402:187-191, 1999.
Yang, "A simple method for estimating global DNA methylation using bisulfite PCR of repetitive DNA elements," Nucleic Acids Research 32(3):e38i-e38vi, (2004).

*Primary Examiner* — James Martinell
(74) *Attorney, Agent, or Firm* — Barry L. Davison; Davis Wright Tremaine LLP

(57) ABSTRACT

Preferred aspects provide novel high-throughput, sensitive methods (e.g., real-time PCR-based (MethyLight™) reactions) for detection and/or measurement of global genomic 5-methylcytosine content, based on measurement of DNA methylation of Alu, LINE-1 repetitive sequences, and the chromosome 1 centromeric satellite alpha and juxtacentromeric satellite 2 repeat sequences. Additional aspects provide sensitive methods for determining the amount of a DNA (e.g., in formalin-fixed, paraffin-embedded tissues). Combined (mean) use of Alu and Sat2 repeat methylation measurements provides for a surprisingly close correlation with global genomic 5-methylcytosine content measurements obtained by HPLC. Methylation of Alu repeats was determined to be closely associated with HPLC-based global methylation levels, as was methylation of satellite 2 and LINE-1 global genomic 5-methylcytosine content. The assays provide surrogate markers for global genomic 5-methylcytosine content analyzes, and have substantial utility for high-throughput and population-based studies (e.g., genetic and dietary influences on global DNA methylation, folate deficiency, MTHFR gene polymorphisms, etc).

11 Claims, 7 Drawing Sheets

Fig. 1.

HIGH THROUGHPUT METHODS COMPRISING ANALYSIS OF REPETITIVE ELEMENT DNA METHYLATION

CROSS REFERENCE TO RELATED APPLICATIONS

The present application claims the benefit of priority to U.S. Provisional Application Ser. Nos. 60/626,672, filed on 10 Nov. 2004 and entitled HIGH THROUGHPUT METHODS COMPRISING ANALYSIS OF REPETITIVE ELEMENT DNA METHYLATION; and 60/730,600, filed on 26 Oct. 2005 of same title, both of which are incorporated by reference herein in their entireties.

STATEMENT REGARDING FEDERALLY-SPONSORED RESEARCH

This work was supported by NIH grants CA 81506 and CA 96958. The United States has certain rights in this invention, pursuant to 35 U.S.C. §202(c)(6).

FIELD OF THE INVENTION

The present invention relates generally to DNA detection and to DNA methylation, and in particular aspects to improved methods for detection of DNA based on repetitive sequences, and in other aspects to prognostic and diagnostic methods relating to cancer (e.g., Wilms Tumors and Ovarian Carcinomas) and cancer therapy, based on repetitive element DNA methylation.

BACKGROUND

Distribution and Methylation of CpG dinucleotide sequences. DNA methylation in mammalian cells is required for embryonic development, X-chromosome inactivation and genomic imprinting, and involves the addition of a methyl group to the C-5 position of cytosine, predominantly in a 5'-CpG-3' (CpG dinucleotide) sequence context (reviewed in (Bird, A., *Genes Dev.*, 16:6-21, 2002). This is accomplished by the activities of one or more DNA methyltransferases (DNMTs) that use S-adenosylmethionine (AdoMet) as a cofactor. CpG dinucleotides are underrepresented in the human genome by a factor of 5, due to the spontaneous deamination of 5-methylcytosine residues, resulting in C-to-T transition mutations at CpG dinucleotides (Laird, P. W., *Natl. Rev. Cancer* 3:253-266, 2003). However, there are regions of the genome, termed 'CpG islands' that have retained their expected CpG content (Gardener-Garden & Fommer, J. Mol. Biol., 196:261-282, 1987; and Takai and Jones, *Proc. Natl. Acad. Sci. USA* 99:3740-3745, 2002). Most CpG Islands overlap the 5' end of gene regions including promoters and are typically unmethylated in normal somatic tissues (see, e.g., Takai and Jones, *Proc. Natl. Acad. Sci. USA* 99:3740-3745, 2002; Jones and Baylin, *Natl. Rev. Genet.* 3:415-428, 2002). However, only 40% of promoter regions are associated with CpG islands (Id). The unique and repeated sequences in the remainder of the genome are often highly methylated at their CpG sites in somatic tissues (Ehrlich, *Oncogene* 21:5400-5413, 2002).

Aberrant CpG methylation in cancer. CpG dinucleotides are often aberrantly methylated in human cancers to give regional hypermethylation at some CpG islands despite an overall reduction in 5-methylcytosine in the DNA (despite, global CpG hypomethylation) (Gama-Sosa et al., *Nucl. Acids. Res.* 11:6883-6894, 1983; Feinberg and Vogelstein, *Nature* 301:89-92, 1983; Feinberg et al., *Cancer Res.* 48:1159-1161, 1988). The frequent hypomethylation of repetitive elements in diverse human cancers may largely account for the global hypomethylation commonly seen in human cancers (Ehrlich, 2002, supra).

Types, distribution and methylation of Repetitive DNA sequence elements. Repetitive elements comprise approximately 45% of the human genome (see e.g., Lander et al., *Nature* 409, 860-921, 2001; Jordan et al., *Trends Genet.* 19:68-72, 2003) and consist of interspersed repeats derived from non-autonomous or autonomous transposable elements (reviewed in Weiner, *Curr. Opin. Cell Biol.* 14:343-350, 2002; Deininger et al., *Curr. Opin. Genet. Dev.* 13:651-658, 2003; and Prak & Kazazian, *Natl. Rev. Genet.* 1:134-144, 2000) and tandem repeats of simple sequences (satellite DNA) or complex sequences. The most plentiful short interspersed nucleotide element (SINE) in human DNA is the Alu repeat, a 282 bp non-LTR (non-Long Terminal Repeat) DNA sequence, which comprises 10% of the human genome and is present in about 1 million copies per haploid genome (Weiner, 2002, supra). Other abundant non-LTR sequences are long interspersed nucleotide elements (LINEs) of up to 6 kb that comprise nearly 20% of the human genome (reviewed in Ehrlich, 2002, supra; and in Deininger, 2003, supra).

Long interspersed nuclear elements (LINEs) are autonomous retrotransposons that are DNA sequences up to about 6 kb (e.g., of about 4-6 kb) in length that comprise nearly 20% of the human genome (reviewed in Ehrlich, Supra; Deininger, Supra). LINE-1 elements are present at over 500,000 copies in the human genome, however, only 3,000-4,000 are full length and 30-100 are active retrotransposons (Id).

LINE-1 elements are usually methylated in somatic tissues, and LINE-1 hypomethylation is a common characteristic of human cancers (Kimura et al., *Int. J. Cancer* 104:568-578, 2003; Florl et al., *Br. J. Cancer* 91:985-994, 2004; Chalitchagom et al., *Oncogene* 23:8841-8846, 2004; and Yang et al., *Nucleic Acids Res.*, 32:e38, 2004). Moreover, Alu sequences are also normally methylated in somatic tissues (Gama-Sosa et al., Nucleic Acids Res., 11:3087-3095, 1983; Schmid, C. W., Nucleic Acids Res., 19:5613-5617, 1991; Kochanek et al, EMBO J. 12:1141-1151, 1993) and are thought to become hypomethylated in human cancer cells (Yang, 2004, supra). However, not all Alus are hypomethylated in human cancers. Alu sequences located upstream of the CDKN2A promoter were found to be hypermethylated in cancer cell lines (Weisenberger et al., Mol. Cancer Res., 2:62-72, 2004), and an Alu sequence located in intron 6 of TP53 showed extensive methylation in normal and cancer cells (Id).

While LINEs and SINEs are interspersed throughout the genome, satellite DNA is largely confined to the centromeres or centromere-adjacent (juxtacentromeric) heterochromatin and to the large region of heterochromatin on the long arm of the Y chromosome. Satellite α (Satα) repeats are composed of 170-bp sequences and represent the main DNA component of every human centromere (Lee et al., *Human Genet.* 100:291-304, 1997). Satellite 2 (Sat2) DNA sequences are found predominantly in juxtacentromeric heterochromatin of certain human chromosomes, and are most abundant in the long juxtacentromeric heterochromatin region of chromosome (Chr) 1. Sat2 sequences are composed of variants of two tandem repeats of ATTCCATTCG (SEQ ID NO:27) followed by one or two copies of ATG (Jeanpierre, M., *Ann. Genet.* 37:163-171, 1994). Both Chr1 Satα and Chr1 Sat2 sequences as well as Satα repeats present throughout all the centromeres are highly methylated in normal postnatal tissues, hypomethylated in sperm, and often hypomethylated in various cancers (Narayan et al., *Intl. J. Cancer* 77:833-838, 1998; Qu et al., *Mutat. Res.* 423:91-101, 1999; Qu, et al., Cancer Genet. Cytoget. 109:34-39, 1999; and Ehrlich et al., *Cancer Genet. Cytogenet.* 141:97-105, 2003). Additionally, Sat2 sequences on Chr1 and Chr16 are also hypomethylated in the ICF (immunodeficiency, centromeric region instability and facial abnormalities) syndrome, which usually involves mutations in DNMT3B ((Xu et al., *Nature* 402:187-191, 1999; Hansen et al., *Proc. Natl. Acad. Sci. USA* 96:14412-14417, 1999).

Prior art methods for determining repetitive element methylation. Although repetitive element DNA is abundant in the human genome, previous methods to determine repetitive element methylation have been based on restriction enzyme digestion and Southern blot analyses, which require large amounts of high-molecular weight genomic DNA (Gama-Sosa, Supra; Qu et al., *Mutat. Res.* 423:91-101, 1999; Ehrlich et al., *Cancer Genet. Cytogenet.*, 141:97-105, 2003; Ehrlich et al., *Nucleic Acids Res.*, 10:2709-2727, 1982; and Widschwendter et al., *Cancer Res.* 64:4472-2280, 2004 (A)). Moreover, accurate global genomic 5-methylcytosine content is often determined by high performance liquid chromatography (BPLC) (Id), which, although highly quantitative and reproducible, also requires large amounts of high-quality genomic DNA and is not suitable for high-throughput analyses. Alu or LINE-1 methylation levels were recently obtained by COBRA (Combined Bisulfite Restriction Analysis) and pyrosequencing of bisulfite converted DNA (Yang et al., *Nucleic Acids Res.*, 32:e38, 2004). Although these quantitative methods represent improvements in determining repetitive element DNA methylation levels, they have not been correlated with global hypomethylation (only with demethylation in particular cell lines as a consequence of treatment with 5-aza-2'deoxycytidine (DAC)), and both require post-PCR manipulation, are labor-intensive, and therefore may not be suitable for high-throughput analyses.

There is a pronounced need in the art for assays having utility to measure global DNA methylation using relatively small amounts of genomic DNA, and that are suitable for high-throughput analyses.

There is a pronounced need in the art for the development control reactions (e.g., an Alu-based control reaction) that are both more sensitive for detecting minute quantities of DNA, and that are far less sensitive/subject to local cancer-associated genetic alterations (e.g., to detect input DNA levels from samples with chromosomal instability, compared to single-copy control genes that we have traditionally used.

There is a pronounced need in the art for the development of a novel strategy that allows the discrimination between evolutionary- and bisulfite-based deamination of a particular DNA sequence, and for application of this strategy in the design of a bisulfite-specific real-time PCR reaction towards, for example, the Alu consensus sequence having utility for detecting small amounts of DNA (e.g., DNA from formalin-fixed, paraffin-embedded tissues or free tumor DNA in plasma or serum).

There is a pronounced need in the art for the testing and validation (e.g., on a panel of normal and tumor DNA samples for which HPLC-based global DNA methylation measurements has been performed) of high-throughput assays (e.g., MethyLight™) for determining the methylation status of Alu, LINE-1, and chromosome 1 centromeric satα and juxtacentromeric sat2 repeats.

There is a pronounced need in the art for the development of surrogate markers for estimating global DNA methylation levels.

SUMMARY OF THE INVENTION

Despite a substantial need for methods to correlate genomic 5-methylcytosine content with, for example, clinical outcome, dietary history, lifestyle, etc., rapid, high-throughput, accurate and easily accessible techniques that are applicable to many samples, including paraffin-embedded tissue DNA, are not available in the prior art.

Novel and useful advancements in methylation assay technology (e.g., MethyLight™ technology) are disclosed herein. Among a variety of art-recognized methylation assays, MethyLight™ is a quantitative, TaqMan™-based real-time PCR system to analyze DNA methylation profiles (Eads et al., *Nucl. Acids Res.* 28:e32, 2000).

Particular aspects provide a novel design strategy for development of methylatio-independent MethyLight™ control reactions, based on Alu repeat sequences depleted of CpG dicucleotides by evolutionary deamination on one strand. Particular embodiments provide an Alu sequence-based control reaction that has substantial utility for detecting minute quantities of DNA, and for detection of DNA for normalization in MethyLight™ applications, and that is much less susceptible to normalization errors caused by cancer associated aneuploidy and copy number changes and is thus more stable to reliably detect input DNA levels from samples with chromosomal instability.

Particular aspects provide novel strategies that allow for the discrimination between evolutionary and bisulfite-based deamination of a particular DNA sequence, and this strategy has been applied, for example, in the design of a bisulfite-specific real-time PCR reaction towards the Alu consensus sequence. The inventive reactions are useful for detecting, for example, small amounts of DNA, such as DNA from formalin-fixed, paraffin-embedded tissues or free tumor DNA in plasma or serum, because the reaction covers Alus interspersed throughout the genome.

Additional aspects provide quantitative bisulfite-based MethyLight™ assays having substantial utility for determining levels of methylated and unmethylated repetitive element DNA sequences, including the interspersed Alu and LINE-1 sequences, and the tandem centromeric satellite alpha (Sat) and juxtacentrometic satellite 2 (Sat2) DNA sequences. Such reactions are demonstrated herein to have methylation specificity on, for example, panels of methylated and unmethylated control DNA samples, and were additionally validated on separate panels of DNA samples from normal, aberrant, or tumor samples (e.g., Wilms Tumors and Ovarian Carcinomas) for which accurate HPLC-based global DNA methylation measurements were available.

In particular aspects, methylation of either interspersed or tandem repeats provides surrogate markers for estimating global DNA methylation levels.

In particular embodiments, Alu methylation was most closely associated with global DNA methylation measurements, followed by satellite alpha and LINE-1 methylation.

In preferred embodiments, the combination (mean) of Alu and Sat2 repeat methylation measurements provides for a surprisingly close correlation with global genomic 5-methylcytosine content measurements obtained by HPLC.

Therefore, the inventive methods and reactions provide surrogate markers for global DNA methylation measurements (e.g., measurement of global hypomethylation, etc.). Furthermore, because MethyLight™ is an assay that does not require large quantities of DNA or post-PCR manipulation, these assays have substantial utility for high-throughput and population-based studies, for example, to study genetic and dietary influences on global DNA methylation in human disease (e.g., folate deficiency, MTHFR gene polymorphisms, etc). Particular aspects underscore the widespread hypomethylation of diverse repeat sequences that coexists with localized hypermethylation of CpG islands in human cancers.

Particular aspects provide a high-throughput method for quantitative measurement of global genomic 5-methylcytosine content, comprising: obtaining a test sample comprising genomic DNA; and determining, using a quantitative real-time, bisulfite-based PCR assay, the methylation status of at least one CpG dinucleotide sequence of at least one repetitive genomic sequence selected from the group consisting of Alu, LINE-1, and Chr1 centromeric Satα and juxtacentromeric Sat2 repeat sequences, wherein the at least one repetitive genomic sequence provides a surrogate marker for global genomic 5-methylcytosine content, and wherein a quantitative measurement of global 5-methylcytosine content is thereby provided. Preferably, the quantitative real-time, bisulfite-based PCR assay comprises use of a MethyLight™ assay. In particular embodiment, the at least one repetitive genomic sequence is selected from the group consisting of Alu, Sat2 and LINE-1. In certain aspects, the at least one repetitive genomic sequence is that of Alu. Preferably, the quantitative measurement of global 5-methylcytosine content is based on a mean methylation measurement of Alu and Sat2 repetitive elements.

Additional aspects provide a high-throughput method for quantitative measurement of global genomic 5-methylcytosine content, comprising: obtaining a test sample comprising genomic DNA; and determining, using a quantitative real-time, bisulfite-based PCR assay, the methylation status of at least one CpG dinucleotide sequence of an Alu and of a Sat2 repetitive genomic sequence; and further determining a mean value based on the stutus, wherein the combination of repetitive genomic sequences provides a surrogate marker for global genomic 5-methylcytosine content, and wherein a quantitative measurement of global 5-methylcytosine content is provided, based on the mean value. Preferably, the quantitative real-time, bisulfite-based PCR assay comprises use of a MethyLight™ assay.

Further aspects provide for a methylation-independent method for detecting or measuring genomic DNA, comprising: obtaining a sample of genomic DNA comprising a repetitive sequence element; and amplifying and detecting the DNA of the repetitive sequence element using PCR primers and at least one labeled probe, wherein the primers and the probe are specific for the bisulfite-converted form of a sequence derived by replacing every CpG dinucleotide of the sequence of one strand of a consensus sequence of the repetitive DNA sequence with a CpA dinucleotide to simulate evolutionary deamination of the opposite strand of the consensus sequence, and wherein methylation-independent detection or measurement of genomic DNA is thereby afforded. In particular embodiments, the consensus repetitive DNA sequence corresponds to at least one consensus repetitive DNA sequence selected from the group consisting of Alu, LINE-1, and Chr1 centromeric Satα and juxtacentromeric Sat2 consensus repetitive DNA sequences. In certain aspects, the consensus repetitive DNA sequence corresponds to that of Alu. In particular embodiments, amplifying and detecting the DNA using PCR primers and at least one labeled probe, comprises use of a real-time PCR-based assay. Preferably, the real-time PCR-based assay comprises MethyLight™.

Yet further aspects provide a method for designing a methylation-independent assay for detecting or measuring genomic DNA, comprising: obtaining a consensus sequence of a repetitive DNA element; replacing every CpG dinucleotide of the sequence of a first strand of the consensus sequence of the repetitive DNA sequence with a CpA dinucleotide to provide an altered sequence of the strand that simulates evolutionary deamination of the opposite strand of the consensus sequence; and obtaining DNA amplification primers and at least one probe, wherein the primers and the probe are specific for the bisulfite-converted form of the altered sequence, wherein the amplification primers and the probe afford, at least in part, a methylation-independent assay for detecting or measuring genomic DNA. In particular aspects, the consensus repetitive DNA sequence corresponds to at least one consensus repetitive DNA sequence selected from the group consisting of Alu, LINE-1, and Chr1 centromeric Satα and juxtacentromeric Sat2 consensus repetitive DNA sequences. In certain aspects, the consensus repetitive DNA sequence corresponds to that of Alu. In particular aspects, the amplification primers and the probe are suitable for use in a real-time PCR-based assay. Preferably, the real-time PCR-based assay comprises MethyLight™.

Additional aspects provide an assay for determining an amount of genomic DNA, comprising: obtaining a test sample comprising genomic DNA; and determining, using a suitable quantitative methylation-independent methylation assay, the methylation status of at least one CpG dinucleotide sequence of at least one repetitive genomic sequence of the input genomic DNA, wherein the amount of input DNA is thereby determined. In particular aspects, the genomic DNA methylation assay comprises use of a real-time PCR-based assay. Preferably, the real-time PCR-based assay is MethyLight™. In certain embodiments, the at least one repetitive genomic sequence is selected from the group consisting of Alu, LINE-1, and Chr1 centromeric Satα and juxtacentromeric Sat2 repeat sequences.

Further aspects provide a method for distinguishing between evolutionary deamination and bisulfite-mediated deamination with respect to a reference or ancestral CpG dinucleotide sequence, comprising: obtaining a test genomic DNA sequence having first and second complementary strands, and having a dinucleotide sequence corresponding in position to that of a CpG dinucleotide of a corresponding reference or ancestral sequence; contacting the test genomic DNA sequence with a bisulfite reagent under conditions suitable to deaminate cytosine, but not 5-methylcytosine, to uracil to provide a bisulfite-converted DNA sequence; and determining, for either the first or the second bisulfite-converted DNA strand after polymerase-mediated amplification thereof in the presence of dNTPs, the dinucleotide sequence at the position corresponding to the reference or ancestral CpG position, wherein determining a TpA sequence at this position in the amplified strand confirms an evolutionary deamination event, reflecting the fact that an evolutionary cytosine deamination event of an ancestral CpG dinucleotide in one strand is memorialized as a complementary CpA dinucleotide sequence on the complementary DNA strand by virtue of subsequent DNA replication. In particular aspects, the method is used for designing a methylation-independent nucleic acid assay, particularly for nucleic acid assays based on repetitive sequences as disclosed herein.

BRIEF DESCRIPTION OF THE DRAWINGS

FIG. 1 shows, according to particular aspects of the present invention, an Alu consensus DNA sequence (SEQ ID NO:26) determined from the sequences of young and old individual Alu repeats. Old Alu sequences (Alu-J, SluSp, AluSx, AluSq and AluSc) (SEQ ID NOS:16-20, respectively) and young Alu sequences (AluY, AluSb2, AluYb8, AluYa5 and AluYa8) (SEQ ID NOS:21-25, respectively) were compared to generate an Alu consensus sequence (SEQ ID NO:26) for the purpose of designing an Alu-based MethyLight™ control reaction. Since the goal was to design a methylation-independent reaction of as many individual Alu repeats as possible, all CpG dinucleotides became a part of the consensus sequence. Old Alu sequences are the predominant form in human cells, and this is also reflected in the Alu consensus sequence. The continuous and dashed lines underneath the consensus sequence panels indicate the location of the MethyLight™ PCR amplicon locations within the consensus sequence for the Alu control reaction (ALU-C4), two reactions towards the methylated consensus sequence (ALU-M2 and ALU-M3) and one reaction towards the unmethylated Alu consensus sequence (ALU-U3).

DETAILED DESCRIPTION OF ASPECTS OF THE INVENTION

Figure 2:
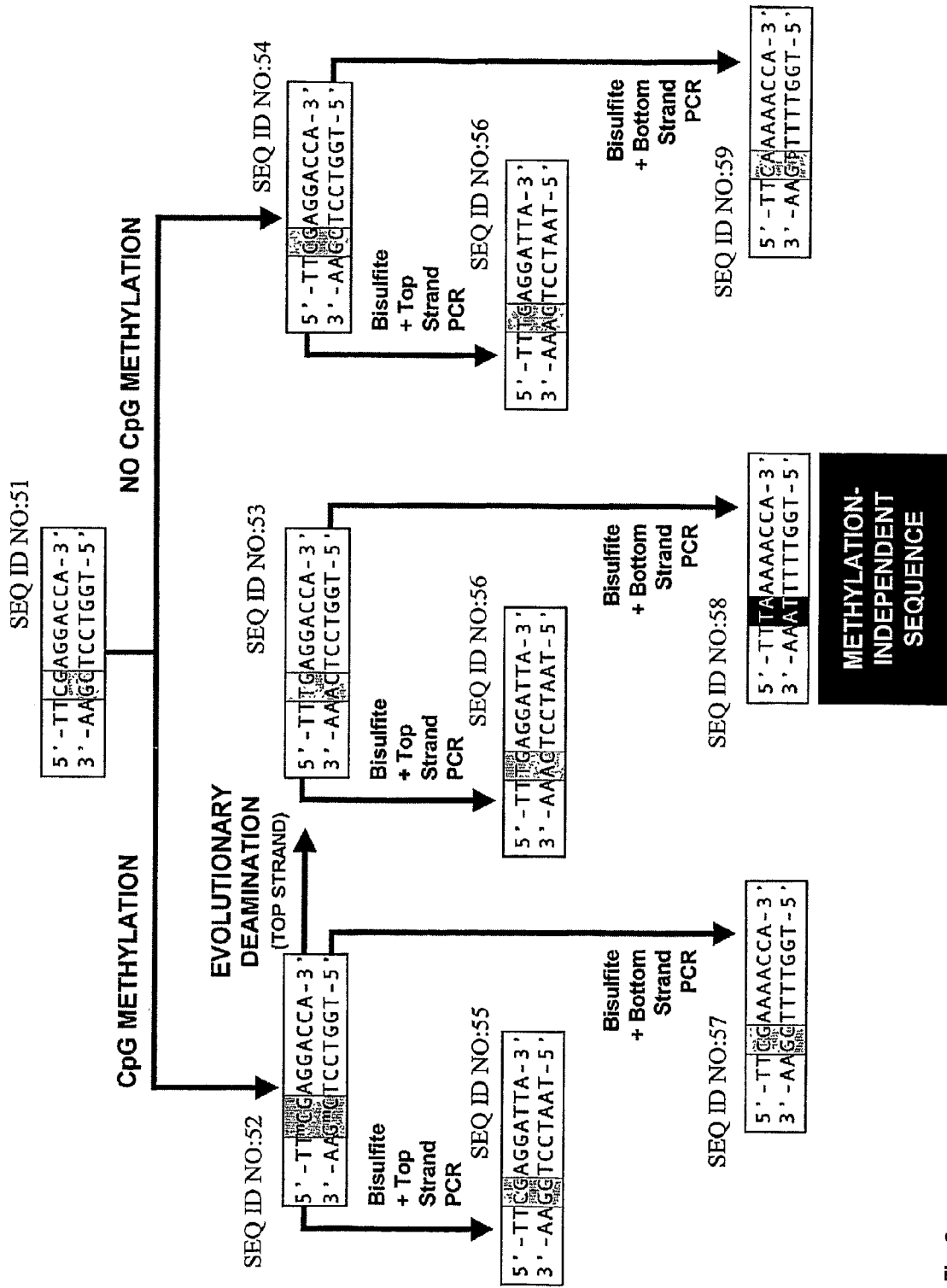
FIG. 2 shows, according to particular aspects of the present invention, a strategy for designing an Alu-based MethyLight control reaction against the Alu consensus DNA sequence in FIG. 1. Since CpGs in Alu repeats can either be methylated or unmethylated), one cannot distinguish if a CpG dinucleotide was subjected to evolutionary deamination of a methylated CpG or was an unmethylated CpG deaminated due to reaction with bisulfite, as both events result in a TpG after bisulfite-specific PCR. However, if the bisulfite PCR primers are designed for amplification of the strand opposite to that which was evolutionarily deaminated, a TpA sequence results (see *Methylation-Independent Sequence*, shaded in black), which is distinct from the PCR products from an unmethylated CpG (CpA or TpG) after bisulfite conversion.

Repetitive elements, such as Alu repeats, long interspersed nuclear elements (LINEs), as well as centromeric and pericentromeric repeat sequences, represent a substantial portion of the human genome, and most repetitive elements also contain a high level of CpG methylation in normal human postnatal somatic tissues. Loss of DNA methylation from these sequences might account for most of the global hypomethylation which characterizes a large percentage of human cancers whose global genomic methylation levels have been determined. However, the extent of global DNA methylation in cancer cells is often not determined because commonly used methods (e.g., HPLC, liquid chromatography/mass spectroscopy, restriction digestion and nearest neighbor analysis, chloracetaldehyde, SssI DNA methylase with labeled AdoMet, etc.) to quantitate changes in global DNA methylation are not routinely accessible, and generally require substantial amounts of fresh or frozen tissue. COBRA and pyrosequencing-based assays of Alu or LINE methylation (Yang et al. *Nucleic Acids Research* 32:e38, 2004), not only require post-PCR manipulation, but significantly have only been validated in the context of utility for tracking demethylation in particular cell lines treated with 5-aza-2'deoxycytidine (DAC), and have not been validated as assays for global methylation because they have not been directly compared to true measurements of global methylation, and thus no true/enabling correlation between repetitive element methylation and global methylation status has been established until the present disclosure.

Aspects of the present invention advance MethyLight™ assay technology, a quantitative, TaqMan-based real-time PCR system to analyze DNA methylation profiles, by extending it to the analysis of highly repeated DNA sequences. In particular aspects, MethyLight™ assays were designed and applied to examine the methylation levels of Alu, LINE-1, and Chr1 centromeric Satα and juxtacentromeric Sat2 repeat sequences. In particular aspects, repetitive element MethyLight™ measurements were evaluated on a panel of normal and tumor DNA samples for which accurate HPLC-based global DNA methylation measurements were available. These data indicate that methylation of either interspersed or tandem repeats has substantial utility as a surrogate marker for estimating global DNA methylation levels. More specifically, in particular aspects MethyLight™ reactions were developed for determining the methylation of Alu and LINE-1 consensus sequences and the chromosome 1 centromeric satellite alpha (satα) and juxtacentromeric satellite 2 (sat2) repeat sequences. These reactions were validated, after testing on methylated and unmethylated control DNAs, on a panel of normal and tumor DNA samples for which art-recognized HPLC-based global DNA methylation measurements had been performed. As disclosed herein, of all the MethyLight™ measurements, methylation of Alu repeats was most closely associated with global methylation levels, while methylation of sat2 and LINE-1 were also associated but to a lesser extent.

In particularly preferred aspects, mean PMR values for combinations of two or more repetitive elements were found to be highly correlative, and thus have substantially improved utility. For example, the mean PMR values of ALU-M2 and SAT2-M1 were found to be surprisingly highly correlative ($R^2$=0.7308, P<0.0001) with global DNA methylation measurements.

In additional aspects, the high Alu copy number was exploited to design an Alu-based MethyLight™ control reaction to sensitively determine input DNA levels for normalization in MethyLight™ assays. More specifically, the prevalence of genomic Alu repeats was exploited by designing a bisulfite-specific control reaction against the Alu consensus sequence to measure the levels of input DNA for methylation assays such as the MethyLight™ assay, which is a preferred quantitative, real-time PCR-based assay for determining DNA methylation levels.

Therefore, according to preferred embodiments of the present invention, the disclosed novel methods (e.g., MethyLight™ assays) are technological advancements based on real-time PCR and provide surrogate markers for global DNA methylation analyses, and have substantial utility for high-throughput and population-based studies. For example, because post-PCR manipulation is not required for the inventive methods, and only microscopic amounts of tissue are needed, these novel assays have substantial utility for high-throughput and population-based studies aimed at investigating genetic and dietary influences on global DNA methylation in human disease, including but not limited to, folate deficiency, MTHFR gene polymorphisms, etc.

Definitions

"DNMT" refers to DNA methyltransferase;
"HPLC" refers to high-performance liquid chromatography;
"LINE" refers to long interspersed nuclear elements;
"SINE" refers to short interspersed nuclear elements;
"sat2" refers to satellite 2 repeat sequences;
"satα" refers to satellite alpha repeat sequences;
"MGBNFQ" refers to minor groove binding non-fluorescent quencher;
"PBL-DNA" refers to peripheral blood leukocyte DNA;
"AdoMet" or "SAM" refers to S-adenosylmethionine;
"COBRA" refers to Combined bisulfite restriction analysis;
"WGA" refers to whole genome amplification;
"DAC" refers to 5-aza-2'deoxycytidine;
"K1KO" refers to DNMT1 knockout HCT116 cells;
"D3bKO" refers to DNMT3B knockout HCT116 cells; and
"DKO" refers to DNMT1 and DNMT3B double knockout HCT116 cells Overview of Particular Aspects:

Repetitive elements comprise nearly 45% of the human genome, with the one million Alu sequences alone occupying approximately 10% of the genome, and LINE-1 elements also representing a substantial portion of the genome. Since these interspersed repetitive elements as well as tandem repeated centromeric and juxtacentromeric repeats contain numerous CpG dinucleotides, the methylation status of these sequences is relevant to understanding global DNA methylation. It is generally thought that repetitive elements are heavily methylated in normal somatic tissues, but are methylated to a lesser extent in malignant tissues, driving the global genomic hypomethylation commonly found in human cancers.

Aspects of the present invention provide novel, quantitative high-throughput MethyLight™ reactions specific for methylated Alu, LINE-1, and the Sata and Sat2 repeats, as well as unmethylated versions of Alu, LINE-1 and Sata repeats. These reactions were evaluated and validated as described herein below on a panel of DNAs to test their methylation specificities. These samples included HCT116 colon cancer cells as well as HCT116 cells harboring gene-targeted disruptions of DNMTI, DNMT3B or both DNMT genes (Rhee et al., Nature 404:1003-1007, 2000; Rhee et al., Nature 416:552-556, 2002). In support of previous findings (Id), the instant results show that DNMTI-/- and DNMT3B-/- cells retained Alu methylation, but were hypomethylated in the HCT116 DKO cells. Additionally, Sat2 hypomethylation had been described for both the single and double knockout HCT116 cells when compared to wild-type HCT116 cells (Rhee et al., Nature 416:552-556, 2002). The presently disclosed inventive MethyLight™ data directed towards this repeat showed similar findings.

More evidence of the specificity of the novel MethyLight™-based Sat2 repetitive element reaction was shown herein with the analysis of cells from ICF patients. ICF cells exhibit hypomethylation of Sat2 repeats on chromosomes 1 and 16, however, global methylation is generally retained and Sata hypomethylation is found in only some patients. Sat2 sequences were also shown herein to be hypomethylated in ICF cells, while substantial levels of Alu and LINE-1 methylation remained. While DNMT3B is required for normal Sat2 methylation in vivo, both DNMT1 and DNMT3B cooperatively maintain genomic methylation.

More evidence of the specificity of the MethyLight™-based Sat2 repetitive element reaction was shown with the analysis of cells from ICF patients. ICF cells exhibit hypomethylation of Sat2 repeats on chromosomes 1 and 16, however, global methylation is generally retained and Satα hypomethylation is found in only some patients (Jeanpierre et al., *Hum. Mol. Genet.* 2:731-735, 1993; Tuck-Muller et al., *Cytogenet. Cell Genet.* 89:121-128, 2000; and Hassan et al., *Hum. Genet.* 109:452-462, 2001). According to particular aspects of the instant disclosure, Sat2 sequences were hypomethylated in ICF cells, while substantial levels of Alu and LINE-1 methylation remained. While DNMT3B is required for normal Sat2 methylation in vivo, both DNMT1 and DNMT3B cooperatively maintain genomic methylation (Rhee et al., Nature 416:552-556, 2002; Kim et al., *EMBO J.*, 21:4183-4195, 2002).

In further aspects, the MethyLight™ measurements for each repetitive element were also compared to global 5-methylcytosine measurements by HPLC for a panel of normal and tumor tissue samples. Of all the MethyLight™ reactions tested, the methylated Alu-M2 reaction was most closely correlated with genomic 5-methylcytosine content, although all four reactions targeting methylated Alu sequences exhibited a significant association with global DNA methylation. MethyLight™-based Sat2 and LINE-1 methylation levels were also significantly correlated to global DNA methylation.

Therefore, methylation of diverse repetitive elements has substantial utility as surrogate markers for genomic 5-methylcytosine content. Indeed, a composite measure combining ALU-M2 and SAT2-M1 PMR values yielded much better correlation with genomic 5-methylcytosine content (r=0.85) than either measure alone. In preferred embodiments this composite measure is used for MethyLight™-based estimates of genomic 5-methylcytosine content.

In additional aspects, individual MethyLight™ reactions specific for methylated Alu as well as those specific for LINE-1 and Sat2 repeats also gave statistically significant correlations (p<0.01) with the HPLC data. Moreover, a trend of increasing PMR values for the methylated repetitive element reactions with increasing HPLC-based 5-methylcytosine levels was noted; in addition, the MethyLight™ reactions specific towards unmethylated repetitive elements gave decreasing PUR values as HPLC-based 5-methylcytosine levels increased, as expected. The lower correlation coefficients may be due to a number of variables. First, the MethyLight™ reactions target fully methylated regions of the repetitive element, and partial methylation may be missed. Second, the use of bisulfite-converted DNA for MethyLight™ analyses and unconverted genomic DNA for HPLC studies may also contribute to lower correlation coefficients. Finally, MethyLight™-based PMR/PUR values are based on four independent PCR-based measurements: sample signals for the methylation and control reactions as well as the signals of methylation and control reactions for the SssI reference sample). It is possible that small changes in any of these 4 measurements from minor pipetting errors and minor variabilities in real-time PCR performance may be reflected in the final PMR/PUR values. This may also affect the relationship of MethyLight™ data with HPLC measurements.

A recent study from Yang, et al (*Nucleic Acids Res.* 32:e38, 2004) investigated whether Alu or LINE-1 methylation might possibly provide surrogate markers for determining global DNA methylation levels. That study used COBRA and pyrosequencing assays to determine Alu or LINE-1 methylation, but the results were limited and inconclusive, because they were not correlated or validated with any actual global DNA methylation measurements (e.g., such as the HPLC-based results used by applicants in the instant methods). Rather these authors allegedly 'validated' their assays only by looking at the methylation levels in particular lines before and after treatment with 5-aza-2'deoxycytidine (DAC), and a reduction their Alu measurement would be expected, regardless of whether their assay is a good surrogate for global DNA methylation or not. Additionally, both COBRA and pyrosequencing require extensive post-PCR manipulation, thereby substantially increasing the labor intensiveness of the assay, and introducing the potential for contamination of future reactions by PCR products. Additionally, while Yang et al., supra, teach only teach limited COBRA and pyrosequencing assays involving analysis use of a single type of repetitive element (i.e., either Alu or LINE-1, and do not teach or suggest combined analyses of two or more distinct types of repetitive elements, as instantly taught. Applicants' MethyLight™-based approach is the first to provide quantitative estimates of the degree of correlation between these repetitive element measurements and 5-methylcytosine content.

An important additional innovation of the present MethyLight™-based methylation-specific assays is that the accuracy of these assays is not affected by deamination at CpG dinucleotides, whether by evolution or by bisulfite conversion, since our methylation-specific reactions only recognize fully methylated, non-deaminated CpG dinucleotides. The Yang method relies on an indirect subtraction to distinguish between evolutionary and bisulfite-mediated deamination.

Therefore, according to preferred aspects of the present invention, the MethyLight™ assay is finished as soon as the PCR has been completed, requires no post-PCR processing, and can easily be applied to hundreds or thousands of samples. Moreover, the combined methylation levels of tow or more types of repeats (e.g., Alu and Sat2) was determined to give a better genomic coverage than any individual repeat type. These inventive repetitive element reactions represent advances in the MethyLight™ assay not only for determining the methylation of individual repetitive elements, but also in serving as markers for global DNA methylation measurements.

Pyrosequencing, COBRA and MethyLight™ provide different perspectives on DNA methylation determinations: pyrosequencing and COBRA are used to quantitatively measure methylation levels of individual CpGs within a given locus, while MethyLight™ assays measure the percentage of molecules in which all of the CpGs of a specific locus (usually between 4-10 CpGs) are either methylated or unmethylated. Yang, et al, supra, showed that Alu or LINE-1 methylation provides a marker for DAC-mediated demethylation in particular cell lines using COBRA and pyrosequencing-based assays, but is indefinite (as stated therein) with respect to whether any such assays could serve as surrogate markers for determining global methylation. By contrast, the instant MethyLight™ platform definitively establishes validated assays comprising the use of repetitive DNA elements as surrogate markers for global 5-methylcytosine content.

The measurements of repetitive element hypomethylation targeted by unmethylated MethyLight™ reactions were not found to be significantly correlated with 5-methylcytosine content, although there was a trend of increasing levels of unmethylated repeat sequences with decreasing 5-methylcytosine content. The poor correlation may be due to relatively low numbers of completely unmethylated repetitive elements in vivo. In addition, these reactions generated relatively low output fluorescence signals, and this may be due to difficulties in design and performance of MethyLight™ reactions specific for unmethylated sequences. These sequences have a higher A:T content than methylated sequences due to the fact that all unmethylated cytosines are converted to thymines after bisulfite conversion. This may reduce primer-template specificity and PCR efficiency.

The MethyLight™-based Sat2 methylation data disclosed herein below were significantly associated with HPLC-based global DNA methylation levels and also with Southern blot-based Sat2 hypomethylation scores. Therefore, in particular aspects, the Sat2 methylation analysis by MethyLight™ is a strong indicator of global DNA methylation measurements. This is in agreement with previous findings that the Southern blot-based Sat2 hypomethylation index is also statistically significantly associated with global DNA hypomethylation levels in numerous human cancer tissues (Qu, et al., *Mutat. Res.* 423:91-101, 1999; Ehrlich et al., *Cancer Genet. Cytogenet.* 141:97-105, 2003; Ehrlich et al., *Oncogene* 26:6694-6702, 2002; and Jackson et al., *Cancer Biol. Ther.*, 3:1225-1231, 2004). A statistically significant correlation between Satα methylation by MethyLight™ and global DNA methylation levels was not shown herein. Previously, a significant association between Southern blot-determined Satα hypomethylation and global DNA methylation was shown in ovarian cancers, Wilms tumors, and breast cancers (Qu, et al., *Mutat. Res.* 423:91-101, 1999; Ehrlich et al., *Cancer Genet. Cytogenet.* 141:97-105, 2003; and Jackson et al., *Cancer Biol. Ther.,* 3:1225-1231, 2004). The discrepancy between these sets of data may be due to inherent assay differences. The MethyLight™ reaction design is based on a short DNA sequence, and may not be specific towards the Chromosome 1 Satα sequence when compared to the hybridization probe used for the Southern blot assay. Moreover the relatively high C(t) value for the Satα MethyLight reaction indicates that a relatively small number of Satα repeats contribute to the MethyLight measurement.

In further aspects, Satα and Sat2 repeats were shown to be unmethylated in sperm. These data are consistent with previous findings of satellite hypomethylation in sperm, based on Southern blot assays (Narayan et al., *Int. J Cancer* 77:833-838, 1998; Widschwendter et al., *Cancer Res.* 64:4472-4480, 2004). However, the findings of Hassan, et al (Human Genet.

109:452-462, 2001) demonstrated that there was sporadic methylation of Sat2 sequences in sperm using bisulfite genomic sequencing. Partial Sat2 methylation may not be identified by the instant exemplary MethyLight™ assay embodiments, since the PCR reaction specifically targets sequences containing multiple fully methylated CpGs.

The findings disclosed herein provide further insight into DNA hypomethylation in human cancers. Hypomethylation of diverse classes of repetitive elements, such as interspersed and tandemly repeated sequences, occurs together with regional CpG island hypermethylation in cancer cells (Widschwendter et al., *Cancer Res.* 64:4472-4480, 2004; Ehrlich et al., *Oncogene* 26:6694-6702, 2002). DNA hypomethylation is not restricted to satellite sequences and other tandem DNA repeats (Ehrlich, M., *Oncogene* 21:5400-5413, 2002; Nishiyama et al., *Cancer Biol. Ther.* 4:440-448, 2005), but also includes the interspersed Alu and LINE elements. Repetitive element methylation, however, may be influenced by the local chromatin structure, especially for Alu and LINE-1 sequences, which are interspersed throughout the genome and can be embedded within genes. A study from Kondo & Issa (*J. Biol. Chem.*, 278:27658-27662, 2003) showed evidence of histone H3 lysine 9 methylation, a marker for inactive heterochromatin, at numerous Alu repeat sequences.

While, according to particular aspects disclosed herein, Alu methylation was most closely associated with global methylation levels, not all Alus are hypomethylated in human cancers. Alu sequences located upstream of the extensively methylated CDKN2A promoter were found to be hypermethylated in cancer cell lines (Weisenberger et al., *Mol Cancer Res.*, 2:62-72, 2004), and an Alu sequence located in intron 6 of TP53 showed extensive methylation (Id). In support of this, a recent study showed that NBL2, a tandem repeat found in acrocentric chromosomes, can become either hypermethylated or hypomethylated in human cancers (Nishiyama et al., *Cancer Biol. Ther.* 4:440-448, 2005).

Additional aspects of the present invention provide a novel strategy to design an Alu-based control reaction for measuring the levels of bisulfite-converted input DNA for MethyLight™ assays by which bisulfite and evolutionary deaminated sequences can be distinguished. In particular embodiments, the Alu-based control reactions show fluorescence above background levels at approximately 15 cycles earlier than, for example, the single copy COL2A1 control reaction, indicating an increased detection of four orders of magnitude (approximately 10,000 copies). This represents approximately 1% of total Alu content. Using human colon cancer cells, Yang et al (*Nucleic Acids Res.*, 32:e38, 2004) have deduced that a large number of CpGs in Alu and LINE-1 sequences are evolutionarily deaminated, consistent with the instant results in which a large number of deaminated Alu repeats were detected using the inventive control reaction.

Although the inventive Alu-based control reactions do not increase the sensitivity of the MethyLight™ methylation reactions and hence the sensitivity of methylation detection, it is nonetheless substantially useful for determining relative DNA amounts in specimens where the quantity and/or quality of DNA may be limited, such as formalin-fixed, paraffin-embedded tissues, free tumor DNA in plasma/serum, etc. Therefore, a methylation detection sensitivity threshold for such samples can be determined. More importantly, the inventive Alu control reactions are expected to be a more stable and reliable measure of input bisulfite-converted DNA levels than reaction towards a single-copy sequence when analyzing tumor samples with local amplifications or deletions, since single-copy genes may not always be present at diploid copy number levels in human cancers, where chromosomal alterations are frequent events. The high copy number of interspersed Alu repeats in the human genome makes it unlikely that cancer-related sequence abnormalities would substantially influence their PCR yield. The use of the Alu-based control reaction therefore results in a more stable determination of PMR/PUR values. Moreover, according to further aspects, Alu and other high copy repetitive element sequences have substantial utility in measuring changes in gene dosage, such as gene amplifications.

The design and application of MethyLight™ assays to measure repetitive element methylation represent novel and substantial technical advancements, particularly in those embodiments comprising the combined use of two or more of such elements (e.g., Alu plus Sat, etc.). Their use as surrogate markers for global DNA methylation makes them attractive in analyzing the effects of DNA methylation on, for example, human disease in population-based studies, etc.

EXAMPLE I

Materials and Methods

Design of the Alu-based MethyLight™ control reaction. The Alu-based control reaction was designed in silico based on a deaminated Alu consensus DNA sequence, in which we assumed that all CpGs on one strand underwent evolutionary deamination. The strategy is indicated with deamination of the top strand in FIG. 2 for simplicity, however, either the top or bottom strands can be chosen. In designing the control reaction, the CpGs on the bottom (opposite) strand of the consensus sequence were deaminated to TpGs in silico, and as a result, CpG dinucleotides on the top strand of the consensus sequence become CpA dinucleotides. These CpA dinucleotides will be converted to TpA dinucleotides upon bisulfite conversion and PCR, thereby generating a methylation-independent unique sequence. Using this deaminated and bisulfite-converted DNA sequence, we selected the PCR primer and probe sequences.

SssI methylation Assay. Peripheral blood leukocyte (PBL) DNA (Promega) was used as a substrate for SssI treatment. Briefly, PBL DNA (0.05 µg/µl) was incubated with SssI enzyme at a concentration of 1 unit/µg DNA (0.05 units/µl) and 0.16 mM S-adenosyl methionine (SAM) overnight at 37° C. A boost of SAM (to 0.20 mM) and SssI enzyme (to 0.065 units/µl) were added the following day and the reaction was allowed to proceed overnight at 37° C. The sample was stored at +4° C. and 18 µL (0.9 µg DNA) aliquots were removed for bisulfite conversion as described herein.

Whole Genome Amplification. To generate unmethylated DNA as control samples for testing the MethyLight™ reactions, sperm and PBL DNAs (10 ng each) were amplified with a whole genome amplification kit as described by the manufacturer (Molecular Staging; New Haven, Conn.). After amplification, the DNA was recovered by phenol-chloroform and ethanol precipitation, dissolved in water and stored at −20° C. A small aliquot (1-2 µg) was then bisulfite converted as described herein.

Bisulfite conversion and DNA recovery. DNA in an 18 µl volume was denatured at 100° C. for 10 minutes, then centrifuged briefly and chilled on ice. NaOH was added to a final volume of 0.3M in a 20 µl volume, and the sample was incubated at 42° C. for 20 min. To prepare the sodium bisulfite solution (preferably prepared on the day of use), 1.9 g sodium metabisulfite (Sigma) was first added to 3.2 ml 0.44 M NaOH and the mixture heated at 50° C. to dissolve the bisulfite. Hydroquinone (0.5 ml of a 1 M solution) was added, and 120

µl of this solution was added to each DNA sample. The reaction was allowed to proceed at 50° C. for 16 hours in the dark.

Following bisulfite conversion, the converted DNA was recovered using the Qiagen Viral RNA Mini Kit (Qiagen) according to manufacturer's specifications with the some changes. For: after loading the column with the supplied lysis buffer and 100% EtOH, the filtrate was re-loaded to increase DNA recovery. After washing with two supplied wash buffers, the DNA was eluted in 80 µl elution buffer (2×40 µl elutions). To desulphonate the sample, 50 µl of 0.2 M NaOH was added for 15 min, followed by neutralization with 10 µl of 1 M HCl. The supplied lysis buffer and EtOH was added to the desulphonated sample, and the bisulfite-converted DNA was then purified a second time. The eluted DNA sample was stored at −20° C. For example, buffer AVL+ carrier RNA (560 µl) was added to each sample, and after a 10 min incubation, 560 µl 100% EtOH was added. The resulting mixture was homogenized by vortexing for 15 sec, then the 1,260 µl solution was loaded onto a QIAamp™ spin column in 630 µl aliquots. To ensure that the loss of DNA was minimal, the filtrate was re-loaded. After washing with AW1 and AW2 buffers, the DNA was eluted in 80 µl elution buffer (2×40 µl elutions). To desulphonate the sample, 50 µl of 0.2 M NaOH was added for 15 min, followed by neutralization with 10 µl of 1 M HCl. To ensure the purity of the bisulfite-converted DNA sample, the eluted and desulphonated sample was recovered a second time with the Qiagen Viral RNA Mini Kit as described. The final eluate was then diluted as needed and stored at −20° C.

MethyLight™ reactions. The PCR primers and probes with Black Hole Quencher™ labeled probes (BHQ-1) were obtained from Biosearch Technologies (Novato Calif.). Probes with a minor groove binder non-fluorescent quencher (MGBNFQ) were obtained from Applied Biosystems. The sequences for the primers and probes are listed in TABLE I. The MethyLight™ PCR reactions utilized the TaqMan™ 1000 Reaction Gold Buffer A Pack (Applied Biosystems) and each reaction was performed in a 30 µl reaction volume with 200 µM dNTPs, 0.3 µM forward and reverse PCR primers, 0.1 µM probe, 3.5 mM $MgCl_2$, 0.01% Tween-20, 0.05% gelatin and 0.1 units Taq polymerase in a 96-well plate format. Plates were analyzed on an Opticon™ DNA Engine Continuous Fluorescence Detector (MJ Research/Bio-Rad) using the following PCR program: 95° C. for 10 min, then 50 cycles of 95° C. for 15 sec followed by 60° C. for 1 min. A standard curve specific for the Alu control reaction was performed on 1:25 serial dilutions of bisulfite converted, SssI-treated DNA for the methylated reactions and 1:25 serial dilutions of bisulfite converted DNA after whole genome amplification for the unmethylated MethyLight™ reactions.

Methylation Calculations. The MethyLight™ data specific for methylated repetitive elements were expressed as percent of methylated reference (PMR) values and were calculated similarly to a recent report (Widschwendter, M. et al. Cancer Res. 64:3807-3813, 2004), but with the following changes. DNA treated with M.SssI served as a methylated reference, and the Alu-based control reaction (ALU-C4 in TABLE I) was used as a control reaction to measure levels of input DNA to normalize the signal for each methylation reaction. The levels of unmethylated repetitive elements were expressed as percent of unmethylated reference (PUR) values, and were calculated similarly to PMR values except that bisulfite-converted, unmethylated human DNA obtained by whole-genome amplification, as described above, was used as an unmethylated reference for PUR determinations of each repetitive element.

Figure 4:
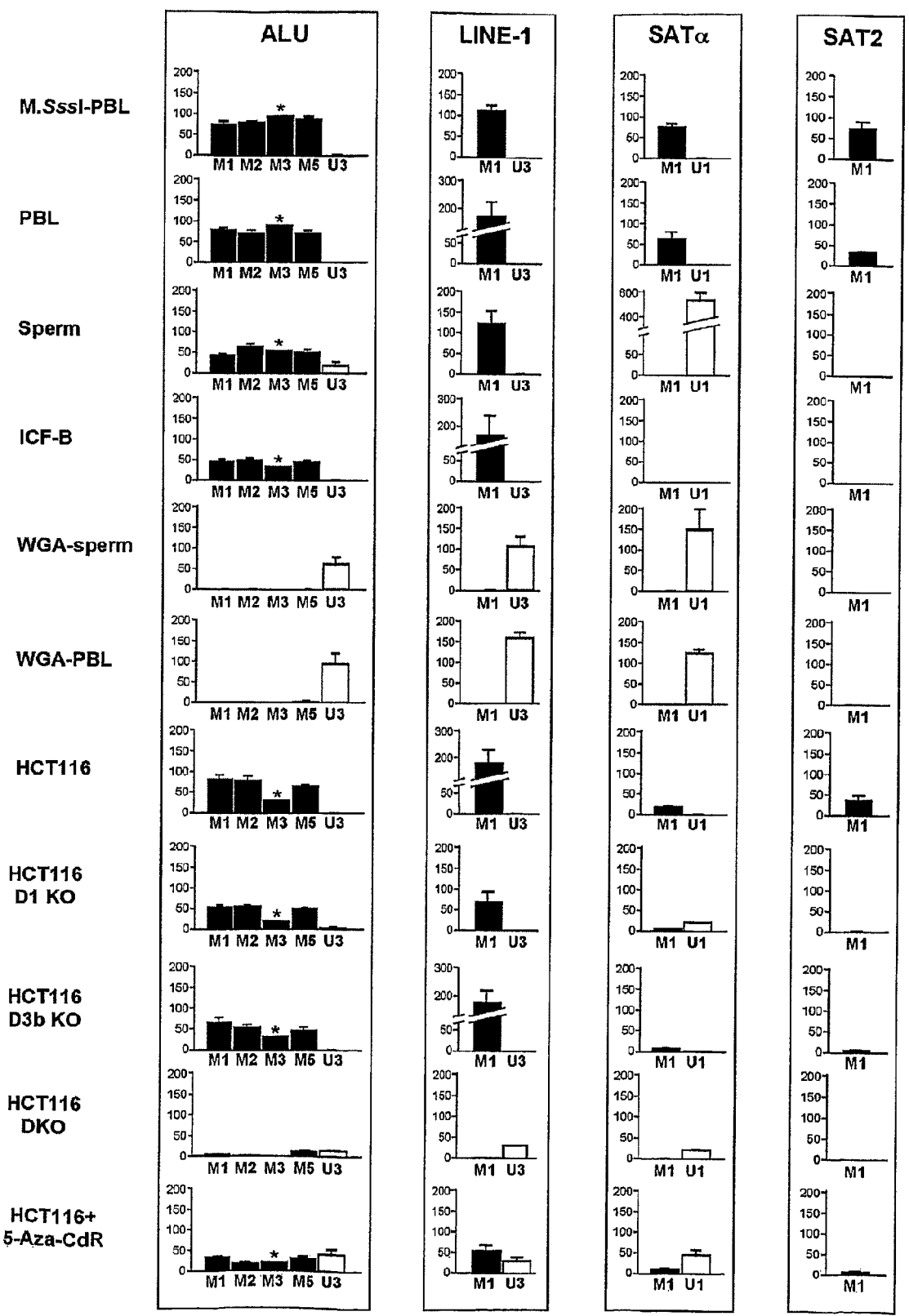
FIG. 4 shows, according to particular aspects of the present invention, evaluation of MethyLight™ reactions towards the methylated and unmethylated versions of Alu, LINE-1, Satα and Sat2 sequences on a panel of DNA samples. Levels of methylation are expressed as Percent of Methylated Reference (PMR) using DNA treated with M.SssI as a methylated reference. Levels of unmethylated DNA are expressed as Percent of Unmethylated Reference (PUR) in which a WGA-DNA sample was used as an unmethylated reference. Each value represents the mean of 3 methylation measurements, except for the ALU-M3B reaction, which is the average of 2 measurements. Error bars indicate the standard deviation of the mean and have been omitted for the ALU-M3 reaction. PMR or PUR values of less than 0.01 were detected due to cross reactivity of the methylated or unmethylated primers to either unmethylated or methylated template DNA, respectively.
Figure 5:
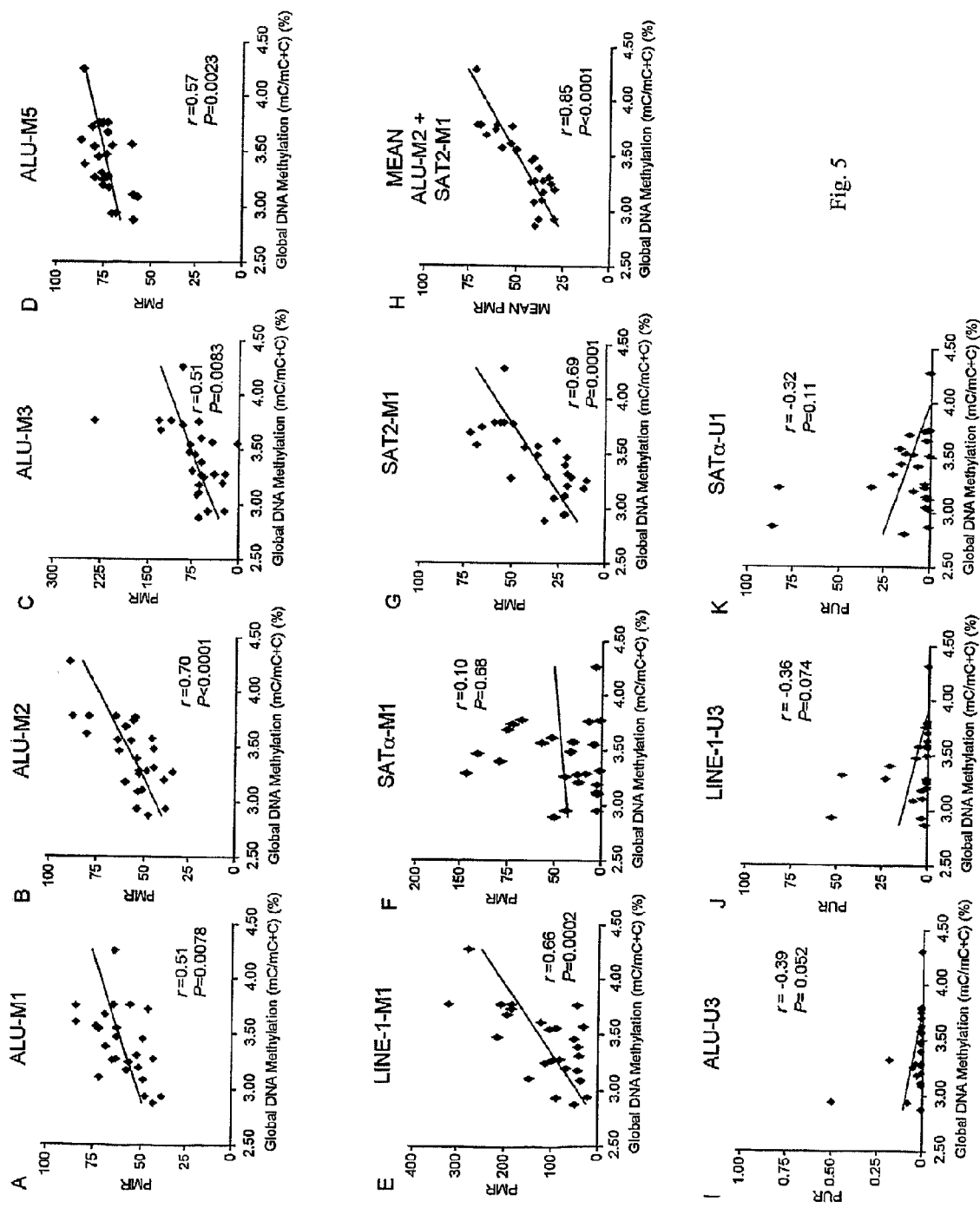
FIGS. 5A-5K show, according to particular aspects of the present invention, correlation of the PMR values of each repetitive element MethyLight™ reaction with HPLC-based measurements of global DNA methylation measurements for the samples described in TABLE 2 herein. The HPLC data represent the mean of 2-3 measurements and the MethyLight™ data represent the mean of 3 measurements. The MethyLight™ and HPLC-based methylation data were correlated using linear regression analysis for each repetitive element.

In analyzing the panel of DNAs described in FIG. 4, each MethyLight™ reaction was performed 3-6 times, except for ALU-M3, which was only analyzed in duplicate. The PMR/PUR values represent the mean values, and the error bars represent standard error of the mean. Standard error of the mean values were not included for the ALU-M3 reaction because we obtained only two PMR measurements for this reaction. In correlating MethyLight™ measurements to HPLC-based global 5-methylcytosine levels (FIG. 5), each MethyLight™ reaction was performed in triplicate, and the data shown is the mean PMR/PUR value. The data was plotted as PMR/PUR mean values for each repetitive element vs. HPLC-based global 5-methylcytosine measurements for each sample. The composite methylation measurements of Alu and Sat2 (FIG. 5H) were determined by obtaining the mean between the triplicate ALU-M2 and SAT2-M1 PMR values, and then plotting the composite mean PMR value vs. the HPLC-based global 5-methylcytosine measurement for each sample. Linear regression analyses were performed using GraphPad InStat™ version 3.0a for Macintosh (GraphPad™ Software, San Diego, Calif.).

HPLC measurements of global genomic 5-methycytosine content. The overall DNA 5-methylcytosine content was determined by high performance liquid chromatography (HPLC) on heat-denatured DNA digested to nucleosides. The global 5-methylcytosine content for each sample is listed herein in TABLE 2, and represents the mean value of 2-3 measurements (Ehrlich et al., Cancer Genet. Cytogenet. 141: 97-105, 2003). The average replicate percentage standard deviation for replicates was 2% (Ehrlich et al., Oncogene 26:6694-6702, 2002). Linear regression was used to determine a correlation between MethyLight™ based PMR values and HPLC-based global methylation measurements for each repetitive element. Global DNA methylation measurements in humans has been shown to be tissue-specific with a range of 3.43-4.26% of cytosine residues methylated in normal tissues (Ehrlich et al., Nucleic Acids Res. 10:2709-2721, 1982); Ehrlich et al., Oncogene 26:6694-6702, 2002). DNA samples were classified as hypomethylated if the global methylation was between 3.20-3.40% and substantially hypomethylated if the amount of global methylation was <3.20%. These designations were only included as an indication of global 5-methylcytosine content in various tissues and in cancer cells.

Southern Blot-based method of determining Chr1 Sat2 Hypomethylation. Chr1 Sat2 hypomethylation was determined by Southern blot analysis, comparison of band patterns in autoradiograms, and quantitation of Phosphorimager results as described previously (Widschwendter et al., Cancer Res. 64:4472-4480, 2004). The MethyLight™ PMR values were compared to the hypomethylation scores for each sample using ANOVA™.

EXAMPLE II

An Alu-Based, Methylation-Independent MethyLight™ Control Reaction was Developed that Detects Minute Quantities of Input DNA The MethyLight™ assay is a quantitative, TaqMan based, real-time PCR assay to measure DNA methylation profiles using bisulfite-converted DNA as a substrate. MethyLight™ is compatible with DNA samples derived from fresh tissue, cell lines, as well as formalin-fixed, paraffin-embedded tissues or bodily fluids such as plasma or serum where the amount of DNA available is usually limiting.

Each MethyLight-based methylation data poin, expressed as a percent of methylated reference value (PMR), involves the use of a CpG-independent, bisulfite-specific control reaction to measure input DNA levels. Preferably, the control reaction should be highly sensitive to accurately measure small amounts of DNA and should not detectably vary in its ability to be amplified from different DNA samples (e.g., different human DNA samples, including cancer tissues.

Control reactions amplifying the low- or single-copy genes MYOD1, ACTB and COL2A1 are known in the art (Widschwendter et al., *Cancer Res.* 64:4472-4480, 2004 (A); Widschwendter, M. et al. Cancer Res. 64:3807-3813, 2004 (B); Eads et al., Nucleic Acids Res. 28:e32, 2000; Eads et al., Cancer Res. 59:2302-2306, 1999). However, these single-copy genes may not always be reliable in human cancers, where chromosomal deletions, duplications and gene amplifications are frequent events. Therefore, an Alu-based MethyLight™ control reaction was developed to evaluate input DNA levels that would be both more sensitive in analyzing low amounts of input DNA, and at the same time would be less subject to local cancer-associated genetic alterations, compared to the single-copy control genes that have traditionally been used. The high copy number of Alu repeats, which are dispersed throughout the genome, makes it unlikely that copy number shifts at specific genomic loci would substantially influence their PCR product yield and also allows for sensitive detection of minute amounts of DNA. In addition, the presence of rare single-nucleotide polymophisms (SNPs) should not interfere with the PCR amplification of Alu control reaction, but may hinder the PCR amplification of single- or low-copy sequences. Recently, Stroun et al (*Ann. N.Y. Acad. Sci.,* 945:258-264, 2001), used an Alu-based real-time PCR reaction to analyze the amount of free DNA in plasma/serum of cancer patients and healthy controls.

Figure 1:
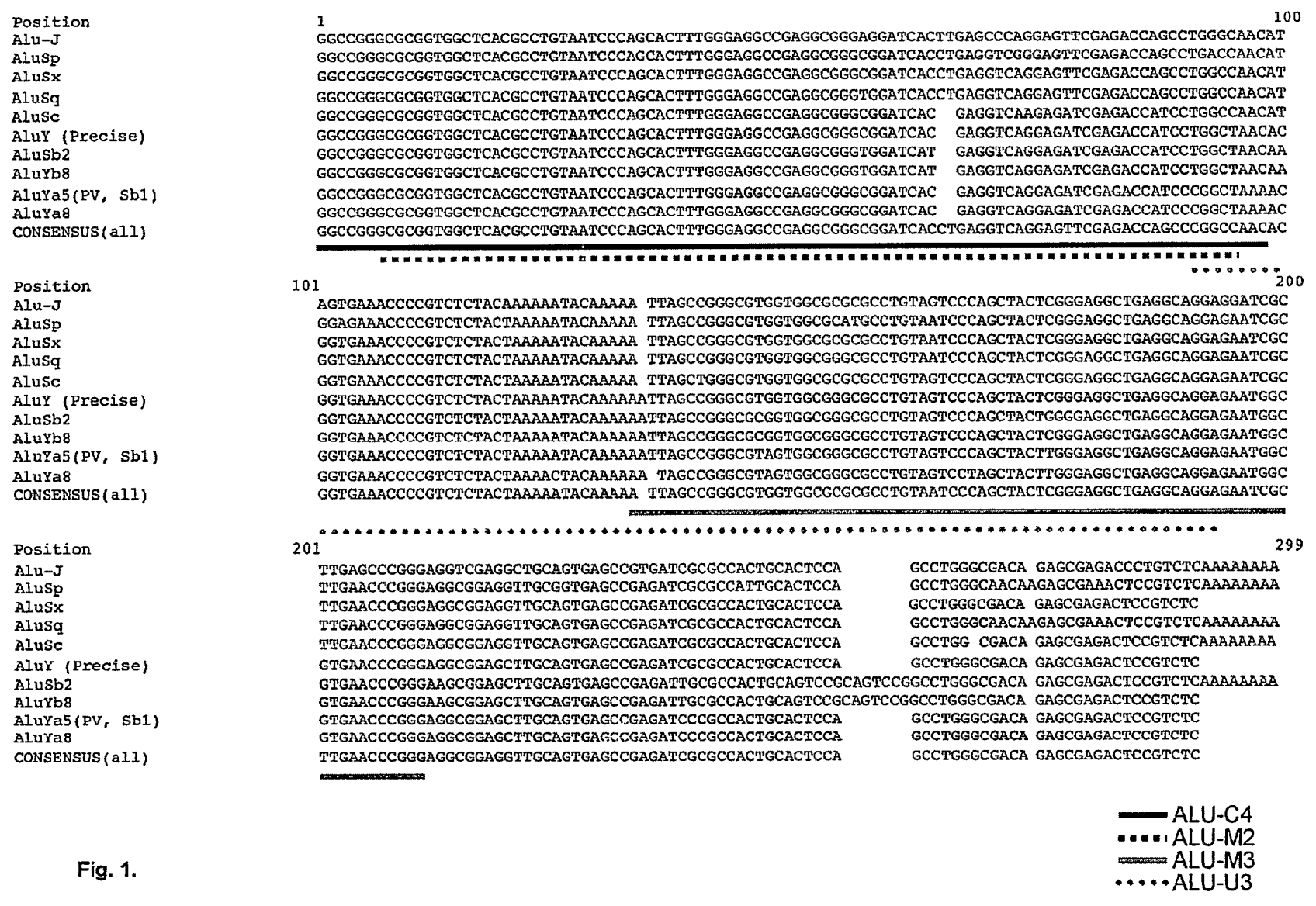

Alu repeats are highly heterogeneous due to the depletion of CpG dinucleotides by spontaneous evolutionary deamination, in which C-to-T transition mutations are generated. In order to develop a methylation-independent, Alu-based control reaction, an Alu consensus sequence was initially generated based on a panel of 'young' and 'old' individual Alu repeats subfamilies in which all CpG dinucleotides were identified as well as those that became evolutionarily deaminated to TpG (or CpA on the strand opposite of an evolutionary deamination event) in older Alu sequences (FIG. 1). However, a subregion in the consensus sequence could not be identified that was devoid of CpGs. The evolutionary deamination process was therefore exploited by applicants to design a control reaction toward Alu sequences in which all cytosines in a CpG context have been deaminated on one of the two DNA strands. These deaminated Alu sequences should be CpG methylation independent. Applicants reasoned that such strand-specifically deaminated Alu sequences should exist in the genome by chance, even though they were not present among the selected Alu sequences listed in FIG. 1.

The design of this control reaction is complicated because MethyLight™ reactions are specific for bisulfite-converted DNA. After bisulfite conversion, the two DNA strands are non-complimentary (FIG. 2), and the PCR primers are designed towards either the top or bottom DNA strands. Methylated CpGs are refractory to bisulfite and remain as CpG on both DNA strands, whereas an unmethylated CpG dinucleotide is deaminated to a TpG after bisulfite conversion. However, a TpG dinucleotide also results from the evolutionary deamination of a methylated CpG. Sequences deaminated during evolution can be distinguished from those resulting from bisulfite conversion if the bisulfite-PCR primers are specific for the DNA strand opposite to the evolutionarily deaminated DNA strand (FIG. 2, Methylation-Independent Sequence). This CpA containing strand will be converted to a distinct TpA sequence after bisulfite conversion.

Using this strategy, evolutionary deamination of the Alu consensus sequence was simulated in silico by first replacing every CpG dinucleotide with a CpA dinucleotide (representing the evolutionary deamination of the opposite strand of the consensus sequence), and then selected primers and a probe for the MethyLight™ control reaction specific for the bisulfite-converted form of this DNA sequence. The location of exemplary PCR amplicons and the respective primer/probe sequences are shown in TABLE 1, and the location of the PCR amplicon within the Alu consensus sequence is shown in FIG. 1. In particular aspects, to satisfy the PCR melting temperature requirements for the Alu control reaction, the probe contains a minor groove binding ("MGB") non-fluorescent quencher ("MGBNFQ"). The use of MGB probes in real-time PCR-based, DNA methylation analyses was recently reported for the purpose of improving PCR specificity (Zeschnigk et al., Nucleic Acids Res. 32:e125, 2004).

Figure 3:
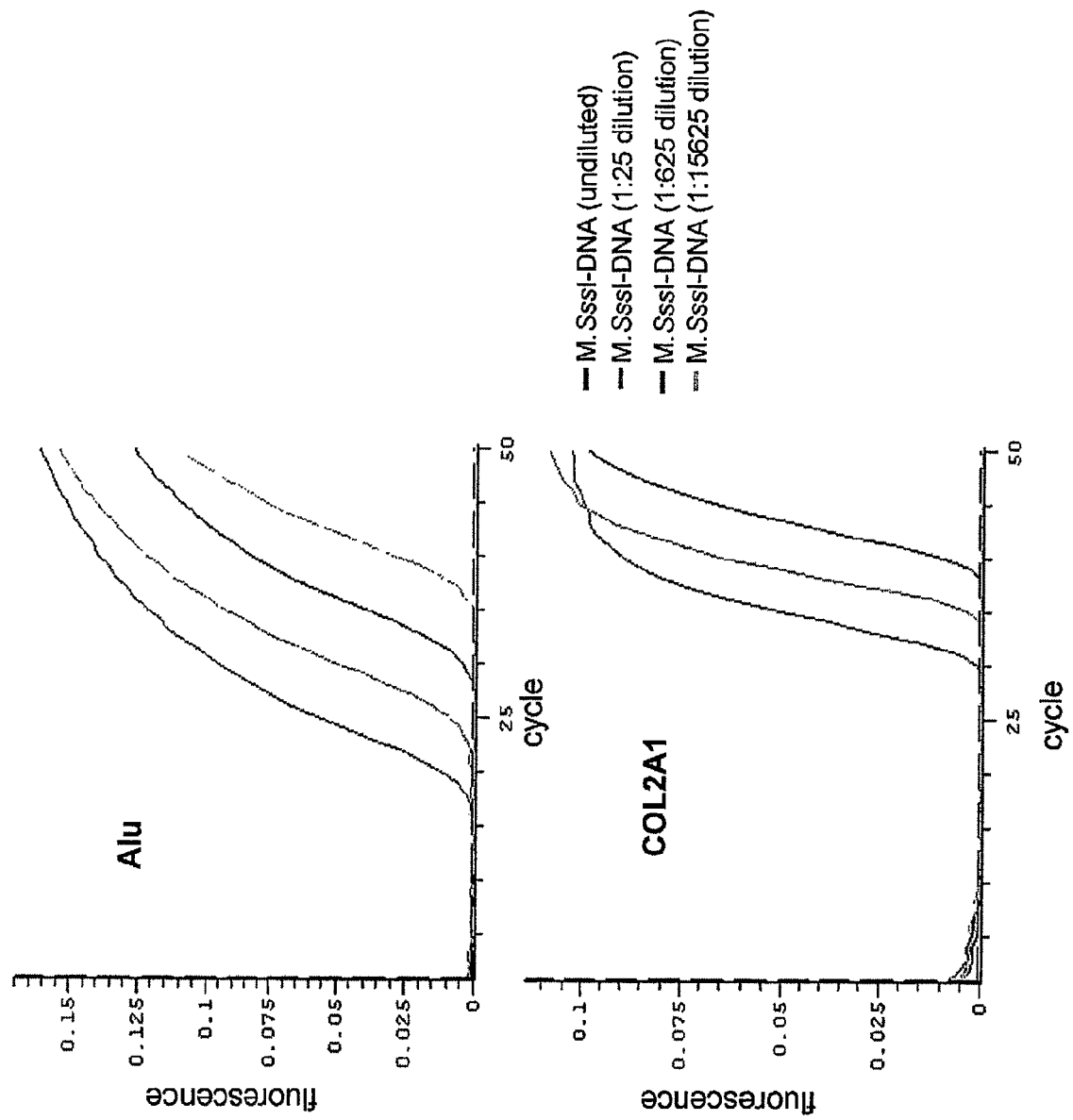
FIG. 3 shows, according to particular aspects of the present invention, evaluation of the performance of the Alu-based control reaction compared to a single-copy control reaction. Serial 1:25 dilutions of bisulfite-converted, SssI-treated DNA were used to compare the Alu and COL2A1 control reactions by real-time PCR. The fluorescence is plotted versus the PCR cycle number for both reactions and each sample dilution is indicated.

To assess whether the Alu-based MethyLight™ control reaction could detect a high number of evolutionarily deaminated Alu repeats, the threshold cycle (C(t) value) of this reaction was compared to the C(t) value of the single-copy COL2A1 control reaction using real-time PCR on 1:25 serial dilutions of bisulfite-converted, M.SssI-treated DNA (FIG. 3). The Alu reaction fluorescence was detected approximately 15 cycles earlier than the COL2A1 reaction on undiluted, bisulfite-converted M.SssI-DNA. The Alu reaction, after a 1:15,000 dilution, still could detect an appreciable amount of input DNA compared to the COL2A1 reaction, which at the same dilution, failed to amplify M.SssI-DNA (FIG. 3). To address the variability of the Alu control reaction, the cycle threshold (C(t)) values of the Alu and COL2A1 control reactions were compared on M.SssI-treated peripheral blood leukocyte (PBL) and HCT116 colon cancer cell line DNAs. The mean C(t) values for Alu and COL2A1 reactions on SssI DNA were 15.14±0.36 and 29.71±0.43, respectively, and the mean C(t) values on HCT116 DNA were 15.57±0.07 and 30.86±0.43, respectively. These data demonstrate not only the reproducibility of the Alu control reaction but also its high sensitivity. The greatly increased sensitivity for detecting input DNA in the methylation-independent reaction is especially useful when analyzing samples with limited amounts of DNA. However, this Alu-based control reaction does not increase the sensitivity of MethyLight™-based methylation detection, which is a function of the methylation-specific MethyLight™ reactions. Nonetheless, the availability of a highly sensitive control reaction allows determination of the methylation detection sensitivity threshold for difficult samples.

TABLE 1

Description repetitive element MethyLight reaction information.

| Reaction ID | GenBank Number | Amplicon Start | Amplicon End | Forward Primer Sequence 5' to 3' (SEQ ID NO:) | Reverse Primer Sequence 5' to 3' (SEQ ID NO:) | Probe Sequence 5' to 3'[a] (SEQ ID NO:) |
|---|---|---|---|---|---|---|
| ALU-C4 | Consensus Seq., FIG. 1 | 1 | 98 | GGTTAGGTATAGTGGTTTATATTTGTAATTTTAGTA (SEQ ID NO: 13) (SEQ ID NO:) | ATTAACTAAACTAATCTTAAACTCCTAACCTCA (SEQ ID NO: 14) | CCTACCTTAACCTCCC-MGB[b] (SEQ ID NO: 15) |

TABLE 1-continued

Description repetitive element MethyLight reaction information.

| Reaction ID | GenBank Number | Ampli-con Start | Ampli-con End | Forward Primer Sequence 5' to 3' (SEQ ID NO:) | Reverse Primer Sequence 5' to 3' (SEQ ID NO:) | Probe Sequence 5' to 3'[a] (SEQ ID NO:) |
|---|---|---|---|---|---|---|
| ALU-M1[c] | Y07755 (SEQ ID NO: 46) | 4359 | 5059 | ATTATGTTAGTTAGGATGGTTTCG ATTTT (SEQ ID NO: 28) | CAATCGACCGAACGCGA (SEQ ID NO: 29) | CCCAACACTTTAAAAAACCGAAAT AAATAAATCACGA (SEQ ID NO: 30) |
| ALU-M2 | Consensus Seq., FIG. 1 | 7 | 95 | GCGCGGTGGTTTACGTTT (SEQ ID NO: 31) | AACCGAACTAATCTCGAACTCC TAAC (SEQ ID NO: 32) | AAATAATCCGCCCGCCTCGACCT (SEQ ID NO: 33) |
| ALU-M3 | Consensus Seq., FIG. 1 | 133 | 210 | ATTAGTCGGGCGTGGTGG (SEQ ID NO: 1) | CCCGAATTCAAACGATTCTCC (SEQ ID NO: 2) | CGCGTTTGTAATTTTAGTTATTCG GGAGGTTG (SEQ ID NO: 3) |
| ALU-M5[d] | AC007256 SEQ ID NO: 47) | 156130 | 156221 | GGTATGATGGCGTATGTTTGTAAT TT (SEQ ID NO: 34) | CGACTCACCACAACTTCCACC (SEQ ID NO: 35) | AAACGATTCTCCTACCTCAACCTC CCGAA (SEQ ID NO: 36) |
| ALU-U3 | Consensus Seq., FIG. 1 | 91 | 192 | TGGTTAATATGGTGAAATTTTGTT TTTATT (SEQ ID NO: 37) | TCCTACCTCAACCTCCCAAATA ACT (SEQ ID NO: 38) | CAAACACACACCACCACACCCAAC TAATTT (SEQ ID NO: 39) |
| LINE-1-M1 | X52235 (SEQ ID NO: 48) | 251 | 331 | GGACGTATTTGGAAAATCGGG (SEQ ID NO: 4) | AATCTCGCGATACGCCGTT (SEQ ID NO: 5) | TCGAATATTGCGTTTTCGGATCGG TTT (SEQ ID NO: 6) |
| LINE-1-U3 | X52235 (SEQ ID NO: 48) | 110 | 210 | TTTATTAGGGAGTGTTAGATAGTG GGTG (SEQ ID NO: 40) | CCTTACACTTCCCAAATAAAAC AATACC (SEQ ID NO: 41) | CACCCTACTTCAACTCATACACAA TACACACACCC (SEQ ID NO: 42) |
| SATα-M1 | M38468 (SEQ ID NO: 49) | 139 | 260 | TGATGGAGTATTTTTAAAATATAC GTTTTGTAGT (SEQ ID NO: 10) | AATTCTAAAAATATTCCTCTTC AATTACGTAAA (SEQ ID NO: 11) | TATCCCGTTTCCAACGAA-MGB[b] (SEQ ID NO: 12) |
| SATα-U1 | M38468 (SEQ ID NO: 49) | 138 | 261 | TTGATGGAGTATTTTTAAAATATA TGTTTTGTAGT (SEQ ID NO: 43) | AAATTCTAAAAATATTCCTCTT CAATTACATAAA (SEQ ID NO: 44) | TTTATCCCATTTCCAACAAA-MGB[b] (SEQ ID NO: 45) |
| SAT2-M1 | X72623 (SEQ ID NO: 50) | 1074 | 1153 | TCGAATGGAATTAATATTTAACGG AAAA (SEQ ID NO: 7) | CCATTCGAATCCATTCGATAAT TCT (SEQ ID NO: 8) | CGATTCCATTCGATAATTCCGTT T-MGB[b] (SEQ ID NO: 9) |

[a] All probes contain a 6FAM fluorophore and a BHQ-1 probe unless otherwise noted.
[b] MGB refers to a Minor Groove Binder non-fluorescent quencher in the 3' terminus of the probe (MGBNFQ)
[c] This MethyLight reaction was designed towards an Alu sequence in the S100A2 gene.
[d] This MethyLight reaction was designed towards an Alu sequence in the CASP8 gene.

EXAMPLE III

Repetitive Element MethyLight™ Reactions were Developed and Validated

In addition to developing the Alu-based MethyLight™ control reaction, novel reactions to target methylated Alu and LINE-1 elements, as well as the chromosome 1 centromeric satellite alpha (Satα) and pericentromeric sat2 repeats (Sat2) were also developed (FIG. 4). MethyLight™ reactions specific for the unmethylated versions of Alu, LINE-1 and Sata sequences (FIG. 4) were also developed, however, a MethyLight™ reaction specific for unmethylated Sat2 repeats was not developed. The primers for the unmethylated reactions were designed by replacing CpG with TpG in the primers and probe. This design approach does not distinguish between unmethylated and evolutionarily deaminated CpGs in these repetitive elements. However, applicants assume that the fraction and genomic location of deaminated CpG dinucleotides are fairly constant in the human population, given the relatively recent evolutionary divergence of the human population, compared to the origin of Alu repeats, which predate the divergence of primates. Nevertheless, we acknowledge that a low level of inaccuracy in the measurements of unmethylated reactions may stem from this inability to discriminate between evolutionary and bisulfite-induced deamination. This problem does not arise for the methylation-specific reactions described below.

In particular aspects, four reactions were designed, directed towards methylated Alu sequences: the M1 reaction is designed towards an Alu repeat within the S100A2 gene; the M2 and M3 reactions are directed towards the consensus sequence (the locations of the ALU-M2 and ALU-M3 PCR amplicons are indicated in FIG. 1); and the M5 reaction is specific towards an Alu repeat located upstream of the CASP8 gene. The S100A2 Alu sequence is similar to AluSx and AluSq subfamilies, and the CASP8 Alu sequence is most similar to the AluSp subfamily. In an additional aspect, one reaction was designed, directed towards the unmethylated Alu consensus sequence.

Methylated and unmethylated reactions specific for the LINE-1 sequences were based on a LINE-1 consensus sequence (GenBank Accession Number X52235; SEQ ID NO:48). The Satα and Sat2 reactions were designed towards sequences specifically on chromosome 1 (GenBank Accession Numbers M38468 and X72623 (SEQ ID NOS:49 and 50), respectively), however, satellite-specific sequences on other chromosomes may also be detected and used. Therefore, these reactions were classified generically as Satα and Sat2. Similar to the Alu control reaction, the probes for the Sata and Sat2 reactions also contain a 3' MGBNFQ moiety to satisfy respective TaqMar™ probe melting temperature requirements (TABLE I).

The methylation specificities of the methylated and unmethylated Alu, LINE-1, Sata and Sat2 reactions were tested on a panel of bisulfate-converted DNA samples (FIG. 4). PBL DNA treated in vitro with the CpG methylase M.SssI (M.SssI-DNA) served as a methylated DNA template, and untreated PBL and sperm DNAs were also included. To prepare unmethylated DNA as a negative control for methylation, we used a strategy that takes advantage of the whole genome amplification (WGA) reaction used to amplify minute amounts of DNA. An approach similar to this has recently been described (Umetani et al., *Biochem. Biophys. Res. Commun.*, 329:219-223, 2005). WGA is based on extending random hexamers annealed to genomic DNA with the highly processive phi 29 DNA polymerase that contains both 5'-3' and 3'-5' exonuclease as well as strand displacement activities (Blanco et al., *J. Biol. Chem.* 264, 8935-8940, 1989; Dean, et al., *Proc. Natl. Acad. Sci. USA* 99:5261-5266, 2002). As genomic DNA is amplified by this polymerase, the DNA methylation will be lost. Sperm and PBL DNAs was amplified by WGA, followed by bisulfite conversion.

DNA from human cell lines that have been previously characterized with regards to repetitive element methylation was also included. ICF lymphoblastoid cell lines were included because they have extensive hypomethylation of chromosome 1 and 16 Sat2 sequences (Jeanpierre et al., *Hum. Mol. Genet.*, 2:731-735, 1993; Tuck-Muller et al., *Cytogenet. Cell Genet.*, 89:121-128, 2000; and Hassam et al., *Hum. Genet.* 109:452-462, 2001). Additionally analyzed were DNA from HCT116 human colon cancer cells, HCT116 cells containing DNMT1$^{-/-}$ (D1KO), DNMT3B$^{-/-}$ (D3bKO), DNMT1$^{-/-}$ and DNMT3B$^{-/-}$ cells (DKO) (Rhee et al., *Nature* 404:1003-1007, 2000; and Rhee et al., *Nature* 416:552-556, 2002) and HM116 cells after treatment with the DNA methylation inhibitor 5-aza-2'-deoxycytidine (5-Aza-CdR). Global DNA methylation is largely retained in the DNMT1$^{-/-}$ and DNMT3B$^{-/-}$ HCT116 cells, while DNA from the DKO HCT116 cells is almost completely hypomethylated. Alu sequences are detectably hypomethylated only in the DKO cells, while Sat2 sequences were hypomethylated in the single and the DKO cells (Rhee et al., *Nature*, 416:552-556, 2002). DNA from HCT116 cells after 5-Aza-CdR mediated DNA methylation inhibition should be hypomethylated relative to the untreated HCT116 cells.

The methylation specificity of each repetitive element MethyLight™ reaction was evaluated on the panel of 11 DNA samples (FIG. 4). The methylation values for the reactions directed towards methylated repetitive elements were expressed as PMR in which M.SssI-DNA was used as a methylated reference (Eads et al., *Cancer Res.* 61:3410-3418, 2001; Siegmund & Laird, *Methods* 27:170-178, 2002). For the unmethylated reactions, the amount of unmethylated DNA is expressed as a percent of unmethylated reference (PUR) in which a WGA-sperm sample was used as an unmethylated reference.

The results indicated that Alu, LINE-1, Sata and Sat2 repeats were highly methylated in M.SssI-PBL DNA as well as PBL-DNA (FIG. 4). Sperm DNA also showed substantial methylation of Alu and LINE-1 sequences. However, Sata and Sat2 sequences were hypomethylated in sperm relative to PBL-DNA (FIG. 4), consistent with previous reports (Narayan et al., *Int. J. Cancer* 77:833-838, 1998; Widschwendter et al., *Cancer Res.* 64:4472-4480, 2004). These results are also in agreement with previous reports of hypomethylation of Chr1 Sata and Chr1 Sat2 sequences in sperm (Jeanpierre et al., *Hum. Mol. Genet.*, 2:731-735, 1993; Tuck-Muller et al., *Cytogenet. Cell Genet.*, 89:121-128, 2000; and Hassam et al., *Hum. Genet.* 109:452-462, 2001). Substantial Alu and LINE-1 methylation was also detected in ICF cells, while Satα and Sat2 methylation was not detected. While Alu methylation and Sat2 hypomethylation in ICF cells is consistent with previously reported studies (Jeanpierre et al., *Hum. Mol. Genet.*, 2:731-735, 1993; Tuck-Muller et al., *Cytogenet. Cell Genet.*, 89:121-128, 2000; and Weisenberger et al., *Mol. Cancer Res.*, 2:62-72, 2004), unmethylated Sata DNA was not detected in the ICF sample. This may reflect the presence of either partially unmethylated or methylated Sata DNA in ICF cells, as the unmethylated MethyLight™ reactions were designed to recognize fully unmethylated target DNA sequences.

All four unmethylated reactions showed hypomethylation of the repetitive elements in both WGA-DNA samples, indicating that these samples are appropriate unmethylated DNA controls (FIG. 4). However, centromeric and telomeric regions of the genome are underrepresented in the WGA assay (Dean et al., *Proc. Natl. Acad. Sci. USA* 99:5261-5266, 2002). Although a decrease in Sata and Sat2 input levels was detected compared to the Alu and LINE-1 sequences in WGA-treated DNAs, there was still ample signal to accurately measure PMR and PUR values.

High levels of Alu and LINE-1 methylation in HCT116 cells was detected, while both Satα and Sat2 sequences were hypomethylated relative to M.SssI-DNA. The hypomethylation of satellite repeats in this cancer cell line is consistent with the very frequent hypomethylation of these sequences in human cancers (Ehrlich, M. *Oncogene* 21:5400-5413, 2002). Alu and LINE-1 methylation was similar or slightly reduced in the DIKO and D3bKO cells. Alu and LINE-1 repeats, as well as both satellite repeats were strongly hypomethylated in the HCT116 DKO cells, similar to previous findings by Southern blot analysis (Rhee et al., *Nature* 404:1003-1007, 2000; and Rhee et al., *Nature* 416:552-556, 2002). The HCT116 cells also showed the expected increase in Alu, LINE-1 Satα, and Sat2 hypomethylation after treatment with 5-Aza-CdR.

The present methylated-specific and unmethylated-specific reactions are designed to recognize fully methylated and fully unmethylated repetitive elements, respectively. However, due to polymorphisms among the repetitive elements, and due to variable levels of methylation of these repeats in human DNA samples, it is difficult to determine exactly how many repeat units in the genome are recognized by each of the inventive reactions. Nevertheless, a good comparative measure of the number of copies recognized by each reaction can be obtained by comparing the C(t) values of each reaction on its cognate optimal target DNA (M.SssI-treated DNA for methylated reactions, and WGA DNA for unmethylated reactions). For example, the ALU-M2 and SAT2-M1 reactions both had C(t) values more than ten cycles lower than the LINE-1-M1 and SATα-M1 reactions. Assuming an up to two-fold amplification with each PCR cycle, this suggests that the ALU-M2 and SAT2-M1 reactions recognize up to 1,000-fold more repeat elements than either the LINE-1-M1 or SATα-M1 reactions. According to preferred aspects, therefore, the ALU-M2 and SAT2-M1 reactions are superior surrogate measures of global genomic 5-methylcytosine content than either the LINE-1-M1 or SATα-M1 reactions.

EXAMPLE IV

Repetitive Element Methylation Levels were Correlated with Global Methylation Levels Using the MethyLight™ assay, each repetitive element reaction was tested on a panel of DNAs from normal tissues (e.g., liver, lung, kidney, spleen, thyroid and cerebellum) as well as ovarian carcinoma (OvCa) and Wilms tumor (WT) samples, all of which had been tested for global DNA methylation levels by HPLC (TABLE 2 below). Global DNA methylation levels in humans have been shown to be tissue-specific, with a range of 3.43-4.26% of cytosine residues methylated in normal tissues (Ehrlich et al., *Nucleic Acids Res.* 10:2709-2721, 1982; Ehrlich et al., *Oncogene* 26:6694-6702, 2002). DNA samples were classified as hypomethylated if the global methylation was between 3.20-3.40% and substantially hypomethylated if the amount of global methylation was ≤3.20%. However, these levels of hypomethylation were only used to better describe DNA hypomethylation in human cells and had no influence on the data analysis in this study.

The PMR values (from reactions aimed at methylated sequences) or PUR values (from reactions towards unmethylated sequences) were compared with HPLC-based global DNA methylation measurements for each sample. While the PMR values for all four methylated Alu reactions were significantly associated with global genomic 5-methylcytosine content (FIGS. 5A-5D), linear regression analysis showed that the ALU-M2 methylation reaction was most closely associated with global levels of DNA methylation as determined by HPLC (correlation coefficient, r=0.70, P<0.0001, FIG. 5B). ALU-M3, another Alu reaction based on the consensus DNA sequence, was also highly correlative with global methylation measurements (r=0.51, P=0.0083; FIG. 5C). However, the ALU-M2 fluorescence was greater than the Alu-M3 reaction, suggesting that the Alu-M2 reaction is superior not only in correlating Alu methylation to global measurements, but also in PCR reaction quality.

Methylation levels of LINE-1 and Sat2 sequences were also significantly associated with global 5-methylcytosine content (FIGS. 5E and 5G), but there was not a significant association of Sata methylation with global DNA methylation (FIG. 5F).

The ALU-M2 and SAT2-M1 reactions gave the best correlation with global 5-methylcytosine content, as applicants had anticipated from their relatively low C(t) values. Since these two reactions both recognize a relatively large number of repeat units, but represent quite distinct types of repetitive elements, applicants considered that their combined measurement could potentially provide a superior assessment of global DNA methylation across various human genomic DNA samples. Both measurements are expressed as normalized PMR values, so a composite measurement was compiled by calculating the mean PMR for the two reactions for each sample. This composite measure yielded a remarkable improvement in the correlation with HPLC measurements of 5-methylcytosine content (r=0.85, P<0.0001; FIG. 5H). In preferred embodiments, therefore, this composite measure is used for MethyLight™-based estimates of genomic 5-methylcytosine content.

The reactions directed towards unmethylated versions of Alu and LINE-1 sequences were of lesser significance when compared to global DNA methylation measurements (FIGS. 5I and 5J). Unmethylated Sata repeats were also not significantly correlated with HPLC-based global DNA methylation measurements (FIG. 5K). However, as expected, there was a clear trend of increased PUR measurements with decreasing global DNA methylation levels for all unmethylated repetitive element reactions.

TABLE 2

HPLC-based measurements of global 5-memylcytosine content in normal and cancer DNA Samples.

| Sample | Laird ID | Normal/Cancer | Global Methylation: mC/(mC + C) (%) |
|---|---|---|---|
| WT4 | 6027 | Cancer | 2.88 |
| OvCa E | 6020 | Cancer | 2.94 |
| WT31 | 6036 | Cancer | 2.94 |
| WT9 | 6030 | Cancer | 3.09 |
| OvCa 1 | 6021 | Cancer | 3.11 |
| WT14B | 6031 | Cancer | 3.18 |
| WT6 | 6028 | Cancer | 3.20 |
| WT29 | 6035 | Cancer | 3.25 |
| OvCa L | 6023 | Cancer | 3.27 |
| WT7A | 6029 | Cancer | 3.28 |
| WT24 | 6033 | Cancer | 3.28 |
| OvCa D | 6019 | Cancer | 3.31 |
| WT22 | 6032 | Cancer | 3.39 |
| WT 27 | 6034 | Cancer | 3.46 |
| OvCa B | 6018 | Cancer | 3.48 |
| Liver A | 6042 | Normal | 3.55 |
| OvCa J | 6022 | Cancer | 3.56 |
| OvCa Q | 6026 | Cancer | 3.57 |
| OvCa M | 6024 | Cancer | 3.61 |
| Lung C | 6046 | Normal | 3.68 |
| OvCa 0 | 6025 | Cancer | 3.73 |
| OvCa A | 6017 | Cancer | 3.76 |
| Kidney B | 6043 | Normal | 3.77 |
| Spleen C | 6045 | Normal | 3.77 |
| Thyroid B | 6044 | Normal | 3.77 |
| Cerebellum A | 6041 | Normal | 4.26 |

EXAMPLE V

Figure 6:
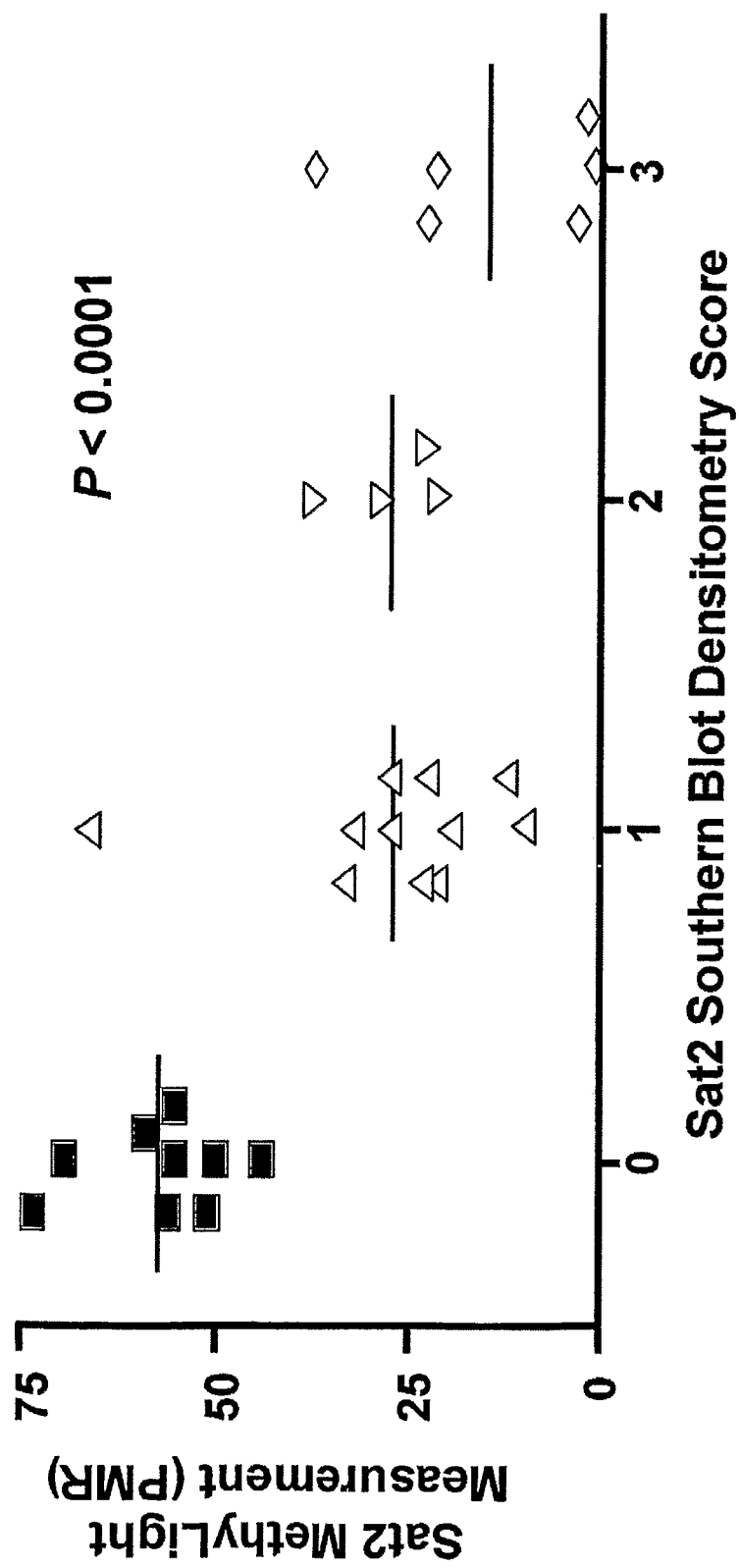
FIG. 6 shows, according to particular aspects of the present invention, MethyLight™ data (PMR) vs. Southern Blot-based Chr1 Sat2 hypomethylation densitometry scores. A score of 0, no hypomethylation; 1, small amounts of hypomethylation; 2, moderate hypomethylation; 3, strong hypomethylation on 7 normal tissues, two ICF cell lines, one control cell line and 20 cancer tissue samples (Wilms tumors and ovarian carcinomas). The data points are indicated by the squares (hypomethylation score=0, upward triangles (hypomethylation score=1), downward triangles (hypomethylation score=2) and diamonds (hypomethylation score=3). Mean PMR values are indicated by the horizontal bars. The significance of the association of both types of data after ANOVA analysis is shown.
Figure 7:
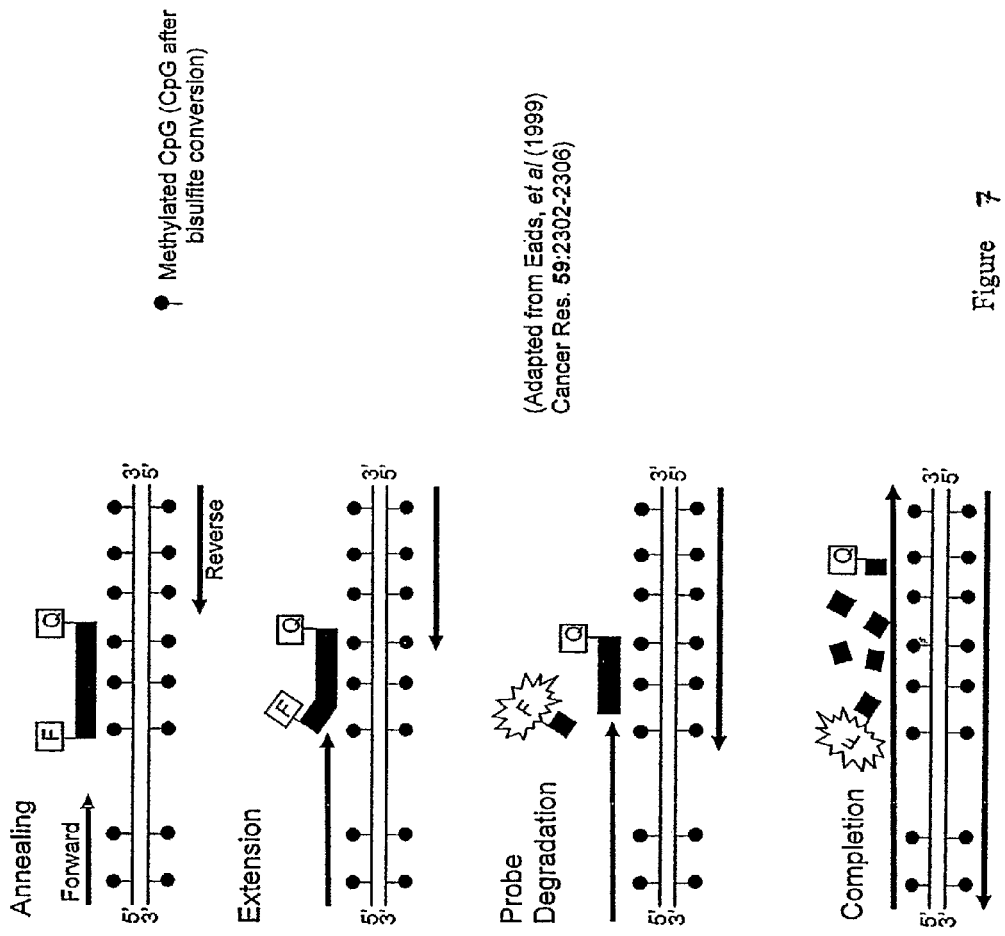
FIG. 7 illustrates the art-recognized MethyLight™ methylation assay.

A Correlation Between Sat2 MethyLight™ Measurements and Sat2 Southern Blot-Based Hypomethylation Score was Established A statistically significant relationship between Sat2 methylation and global DNA methylation levels was shown herein (FIG. 5G). Sat2 methylation had been previously determined for these samples using Southern blot analysis in which Sat2 hypomethylation was graded on a scale of 0 (methylated) to 3 (extensively hypomethylated) using quantitation of Phosphorimager data and evaluation of band patterns from autoradiograms (Widschwendter et al., *Cancer Res.* 64:4472-4480, 2004). The MethyLight™ PMR measurements were compared to the corresponding DNA hypomethylation scores from Southern blots for the same normal tissues, as well as ovarian carcinoma and Wilms tumor samples (FIG. 6). Two ICF cell line DNAs were also included, as these samples were previously shown to harbor Sat2 hypomethylation (Jeanpierre et al., *Hum. Mol. Genet.*, 2:731-735, 1993; and Hassam et al., *Hum. Genet.* 109:452-462, 2001). A statistically significant correlation between the Sat2 MethyLight™ PMR measurements and the Southern Blot-based hypomethylation score (p<0.0001) was found, indicating that the MethyLight™-based assay for Sat2 methylation measurements are highly consistent with the Southern blot based assay to determine Sat2 hypomethylation.

REFERENCES

Bird, A. (2002) DNA methylation patterns and epigenetic memory. *Genes Dev.*, 16, 6-21.

2. Laird, P. W. (2003) The power and the promise of DNA methylation markers. *Nature Rev. Cancer,* 3, 253-266.
3. Gardiner-Garden, M. and Frommer, M. (1987) CpG islands in vertebrate genomes. *J. Mol. Biol.,* 196, 261-282.
4. Takai, D. and Jones, P. A. (2002) Comprehensive analysis of CpG islands in human chromosomes 21 and 22. *Proc. Natl. Acad. Sci. USA,* 99, 3740-3745.
5. Jones, P. A. and Baylin, S. B. (2002) The fundamental role of epigenetic events in cancer. *Nature Rev. Genet.,* 3, 415-428.
6. Ehrlich, M. (2002) DNA methylation in cancer: too much, but also too little. *Oncogene,* 21, 5400-5413.
7. Gama-Sosa, M. A., Slagel, V. A., Trewyn, R. W., Oxenhandler, R., Kuo, K. C., Gehrke, C. W. and Ehrlich, M. (1983) The 5-methylcytosine content of DNA from human tumors. *Nucleic Acids Res.,* 11, 6883-6894.
8. Feinberg, A. P. and Vogelstein, B. (1983) Hypomethylation distinguishes genes of some human cancers from their normal counterparts. *Nature,* 301, 89-92.
9. Feinberg, A. P., Gehrke, C. W., Kuo, K. C. and Ehrlich, M. (1988) Reduced genomic 5-methylcytosine content in human colonic neoplasia. *Cancer Res.,* 48, 1159-1161.
10. De Smet, C., De Backer, O., Faraoni, I., Lurquin, C., Brasseur, F. and Boon, T. (1996) The activation of human gene MAGE-1 in tumor cells is correlated with genome-wide demethylation. *Proc. Natl. Acad. Sci. USA,* 93, 7149-7153.
11. Grunau, C., Sanchez, C., Ehrlich, M., van der Bruggen, P., Hindermann, W., Rodriguez, C., Krieger, S., Dubeau, L., Fiala, E. and De Sario, A. (2005) Frequent DNA hypomethylation in the human juxtacentromeric BAGE loci in cancer. *Genes Chromosom. Cancer,* 43, 11-24.
12. Kimura, F., Seifert, H. H., Florl, A. R., Santourlidis, S., Steinhoff, C., Swiatkowsli, S., Mahotka, C., Gerharz, C. D. and Schulz, W. A. (2003) Decrease of DNA methyltransferase 1 expression relative to cell proliferation in transitional cell carcinoma. *Int. J. Cancer,* 104, 568-578.
13. Florl, A. R., Steinhoff, C., Muller, M., Seifert, H. H., Hader, C., Engers, R., Ackermann, R. and Schulz, W. A. (2004) Coordinate hypermethylation at specific genes in prostate carcinoma precedes LINE-1 hypomethylation. *Br. J. Cancer,* 91, 985-994.
14. Chalitchagom, K., Shuangshoti, S., Hourpai, N., Kongruttanachok, N., Tangkijvanich, P., Thong-Ngam, D., Voravud, N., Sriuranpong, V. and Mutirangura, A. (2004) Distinctive pattern of LINE-1 methylation level in normal tissues and the association with carcinogenesis. *Oncogene,* 23, 8841-8846.
15. Narayan, A., Ji, W., Zhang, X. Y., Marrogi, A., Graff, J. R., Baylin, S. B. and Ehrlich, M. (1998) Hypomethylation of pericentromeric DNA in breast adenocarcinomas. *Int. J. Cancer,* 77, 833-838.
16. Lander, E. S., Linton, L. M., Birren, B., Nusbaum, C., Zody, M. C., Baldwin, J., Devon, K., Dewar, K., Doyle, M., FitzHugh, W. et al. (2001) Initial sequencing and analysis of the human genome. *Nature,* 409, 860-921.
17. Jordan, I. K., Rogozin, I. B., Glazko, G. V. and Koonin, E. V. (2003) Crigin of a substantial fraction of human regulatory sequences from transposable elements. *Trends Genet.,* 19, 68-72.
18. Weiner, A. M. (2002) SINEs and LINEs: the art of biting the hand that feeds you. *Curr. Opin. Cell. Biol.,* 14, 343-350.
19. Deininger, P. L., Moran, J. V., Batzer, M. A. and Kazazian, H. H. J. (2003) Mobile elements and mammalian genome evolution. *Curr. Opin. Genet. Dev.,* 13, 651-658.
20. Prak, E. T. and Kazazian, H. H. J. (2000) Mobile elements and the human genome. *Nature Rev. Genet.,* 1, 134-144.
21. Yang, A. S., Estecio, M. R. H., Doshi, K., Kondo, Y., Tajara, E. and Issa, J.-P. J. (2004) A simple method for estimating global DNA methylation using bisulfite PCR of repetitive DNA elements. *Nucleic Acids Res.,* 32, e38.
22. Gama-Sosa, M. A., Wang, R. Y., Kuo, K. C., Gehrke, C. W. and Ehrlich, M. (1983) The 5-methylcytosine content of highly repeated sequences in human DNA. *Nucleic Acids Res.,* 11, 3087-3095.
23. Schmid, C. W. (1991) Human Alu subfamilies and their methylation revealed by blot hybridization. *Nucleic Acids Res.,* 19, 5613-5617.
24. Kochanek, S., Renz, D. and Doerfler, W. (1993) DNA methylation in the Alu sequences of diploid and haploid primary human cells. *EMBO J.,* 12, 1141-1151.
25. Weisenberger, D. J., Velicescu, M., Cheng, J. C., Gonzales, F. A., Liang, G. and Jones, P. A. (2004) Role of the DNA methyltransferase variant DNMT3b3 in DNA methylation. *Mol. Cancer Res.,* 2, 62-72.
26. Lee, C., Wevrick, R., Fisher, R. B., Ferguson-Smith, M. A. and Lin, C. C. (1997) Human centromeric DNAs. *Hum. Genet.,* 100, 291-304.
27. Jeanpierre, M. (1994) Human satellites 2 and 3. *Ann. Genet.,* 37, 163-171.
28. Qu, G., Dubeau, L., Narayan, A., Yu, M. C. and Ehrlich, M. (1999) Satellite DNA hypomethylation vs. overall genomic hypomethylation in ovarian epithelial tumors of different malignant potential. *Mutat. Res.,* 423, 91-101.
29. Qu, G. Z., Grundy, P. E., Narayan, A. and Ehrlich, M. (1999) Frequent hypomethylation in Wilms tumors of pericentromeric DNA in chromosomes 1 and 16. *Cancer Genet. Cytogenet.,* 109, 34-39.
30. Ehrlich, M., Hopkins, N. E., Jiang, G., Dome, J. S., Yu, M. C., Woods, C. B., Tomlinson, G. E., Chintagumpala, M., Champagne, M., Dillerg, L. et al. (2003) Satellite DNA hypomethylation in karyotyped Wilms tumors. *Cancer Genet. Cytogenet.,* 141, 97-105.
31. Xu, G. L., Bestor, T. H., Bourc'his, D., Hsieh, C. L., Tommerup, N., Bugge, M., Hulten, M., Qu, X., Russo, J. and Viegas-Pequignot, E. (1999) Chromosome instability and immunodeficiency syndrome caused by mutations in a DNA methyltransferase gene. *Nature,* 402, 187-191.
32. Hansen, R. S., Wijmenga, C., Luo, P., Stanek, A. M., Canfield, T. K., Weemaes, C. M. and Gartler, S. M. (1999) The DNMT3B DNA methyltransferase gene is mutated in the ICF immunodeficiency syndrome. *Proc. Natl. Acad. Sci. USA,* 96, 14412-14417.
33. Ehrlich, M., Gama-Sosa, M. A., Huang, L. H., Midgett, R. M., Kuo, K. C., McCune, R. A. and Gehrke, C. (1982) Amount and distribution of 5-methylcytosine in human DNA from different types of tissues of cells. *Nucleic Acids Res.,* 10, 2709-2721.
34. Widschwendter, M., Jiang, G., Woods, C., Muller, H. M., Fiegl, H., Goebel, G., Marth, C., Muller-Holzner, E., Zeimet, A. G., Laird, P. W. et al. (2004) DNA hypomethylation and ovarian cancer biology. *Cancer Res.,* 64, 4472-4480.
35. Eads, C. A., Danenberg, K. D., Kawakami, K., Saltz, L. B., Blake, C., Shibata, D., Danenberg, P. V. and Laird, P. W. (2000) MethyLight: a high-throughput assay to measure DNA methylation. *Nucleic Acids Res.,* 28, e32.
36. Widschwendter, M., Siegmund, K. D., Muller, H. M., Fiegl, H., Marth, C., Muller-Holzner, E., Jones, P. A. and Laird, P. W. (2004) Association of breast cancer DNA methylation profiles with hormone receptor status and response to tamoxifen. *Cancer Res.,* 64, 3807-3813.

37. Ehrlich, M., Jiang, G., Fiala, E., Dome, J. S., Yu, M. C., Long, T. I., Youn, B., Sohn, O. S., Widschwendter, M., Tomlinson, G. E. et al. (2002) Hypomethylation and hypermethylation of DNA in Wilms tumors. *Oncogene*, 26, 6694-6702.
38. Eads, C. A., Danenberg, K. D., Kawakami, K., Saltz, L. B., Danenberg, P. V. and Laird, P. W. (1999) CpG island hypermethylation in human colorectal tumors is not associated with DNA methyltransferase overexpression. *Cancer Res.*, 59, 2302-2306.
39. Eads, C. A., Lord, R. V., Wickramasinghe, K., Long, T. I., Kurumboor, S. K., Bemstein, L., Peters, J. H., DeMeester, S. R., DeMeester, T. R., Skinner, K. A. et al. (2001) Epigenetic patterns in the progression of esophageal adenocarcinoma. *Cancer Res.*, 61, 3410-3418.
40. Siegmund, K. D. and Laird, P. W. (2002) Analysis of complex methylation data. *Methods*, 27, 170-178.
41. Stroun, M., Lyautey, J., Lederrey, C., Mulcahy, H. E. and Anker, P. (2001) Alu repeat sequences are present in increased proportions compared to a unique gene in plasma/serum DNA: evidence for a preferential release from viable cells? *Ann. N.Y. Acad. Sci.*, 945, 258-264.
42. Zeschnigk, M., Bohringer, S., Price, E. A., Onadim, Z., Masshofer, L. and Lohmann, D. R. (2004) A novel real-time PCR assay for quantitative analysis of methylated alleles (QAMA): analysis of the retinoblastoma locus. *Nucleic Acids Res.*, 32, e125.
43. Umetani, N., de Maat, M. F. G., Mori, T., Takeuchi, H. and Hoon, D. S. B. (2005) Synthesis of universal control DNA by nested whole genome amplification with phi29 DNA polymerase. *Biochem. Biophys. Res. Commun.*, 329, 219-223.
44. Garmendia, C., Bemad, A., Esteban, J. A., Blanco, L. and Salas, M. (1992) The bacteriophage phi 29 DNA polymerase, a proofreading enzyme. *J. Biol. Chem.*, 267, 2594-2599.
45. Blanco, L., Bemad, A., Lazaro, J. M., Martin, G., Garmendia, C. and Salas, M. (1989) Highly efficient DNA synthesis by the phage phi 29 DNA polymerase. Symmetrical mode of DNA replication. *J. Biol. Chem.*, 264, 8935-8940.
46. Dean, F. B., Hosono, S., Fang, L., Wu, X., Faruqi, A. F., Bray-Ward, P., Sun, Z., Zong, Q., Du, Y., Du, J. et al. (2002) Comprehensive human genome amplification using multiple displacement amplification. *Proc. Natl. Acad. Sci. USA*, 99, 5261-5266.
47. Jeanpierre, M., Turleau, C., Aurias, A., Prieur, M., Ledeist, F., Fischer, A. and Viegas-Pequignot, E. (1993) An embryonic-like methylation pattern of classical satellite DNA is observed in ICF syndrome. *Hum. Mol. Genet.*, 2, 731-735.
48. Tuck-Muller, C. M., Narayan, A., Tsien, F., Smeets, D. F., Sawyer, J., Fiala, E. S., Sohn, O. S. and Ehrlich, M. (2000) DNA hypomethylation and unusual chromosome instability in cell lines from ICF syndrome patients. *Cytogenet. Cell Genet.*, 89, 121-128.
49. Hassan, K. M., Norwood, T., Gimelli, G., Gartler, S. M. and Hansen, R. S. (2001) Satellite 2 methylation patterns in normal and ICF syndrome cells and association of hypomethylation with advanced replication. *Hum. Genet.*, 109, 452-462.
50. Rhee, I., Jair, K. W., Yen, R. W., Lengauer, C., Herman, J. G., Kinzler, K. W., Vogelstein, B., Baylin, S. B. and Schuebel, K. E. (2000) CpG methylation is maintained in human cancer cells lacking DNMT1. *Nature*, 404, 1003-1007.
51. Rhee, I., Bachman, K. E., Park, B. H., Jair, K. W., Yen, R. W., Schuebel, K. E., Cui, H., Feinberg, A. P., Lengauer, C., Kinzler, K. W. et al. (2002) DNMT1 and DNMT3b cooperate to silence genes in human cancer cells. *Nature*, 416, 552-556.
52. Kim, G. D., Ni, J., Kelesoglu, N., Roberts, R. J. and Pradhan, S. (2002) Co-operation and communication between the human maintenance and de novo DNA (cytosine-5) methyltransferases. *EMBO J.*, 21, 4183-4195.
53. Jackson, K., Yu, M. C., Arakawa, K., Fiala, E., Youn, B., Fiegl, H., Muller-Holzner, E., Widschwendter, M. and Ehrlich, M. (2004) DNA hypomethylation is prevalent even in low-grade breast tumors. *Cancer Biol. Ther.*, 3, 1225-1231.
54. Nishiyama, R., Qi, L., Tsumagri, K., Weissbecker, K., Dubeau, L., Champagne, M., Sikka, S., Nagai, H. and Ehrlich, M. (2005) A DNA repeat, NBL2, is hypermethylated in some cancers but hypomethylated in others. *Cancer Biol. Ther.*, 4, 440-448.
55. Kondo, Y. and Issa, J. P. (2003) Enrichment for histone H3 lysine 9 methylation at Alu repeats in human cells. *J. Biol. Chem.*, 278, 27658-27662.

The invention claimed is:

1. A high-throughput method for quantitative measurement of global genomic 5-methylcytosine content, comprising:
obtaining a test sample comprising genomic DNA from a human tissue sample; and
determining, using a quantitative real-time, bisulfite-based PCR assay, the methylation status of at least one CpG dinucleotide sequence of at least two repetitive genomic sequences selected from the group consisting of Alu, LINE-1, and Chr1 centromeric Satα and juxtacentromeric Sat2 repeat sequences, wherein the methylation status of at least one CpG dinucleotide sequence of the Alu or LINE-1 repeat sequence is determined, and wherein the determined methylation status of the at least two repetitive genomic sequence significantly correlates with global genomic 5-methylcytosine content, and wherein a quantitative measurement of global 5-methylcytosine content is thereby provided.

2. The method of claim 1, wherein the quantitative real-time, bisulfite-based PCR assay comprises the use of at least one labeled probe to detect the amplified DNA, and wherein the applied PCR primers and the at least one labeled probe specifically bind to bisulfite-converted DNA.

3. The method of claim 1, wherein the at least two repetitive genomic sequences is selected from the group consisting of Alu, Sat2 and LINE-1.

4. The method of claim 1, wherein one of the at least two repetitive genomic sequences is selected from the group consisting of Alu and Sat2.

5. The method of claim 1, wherein the global 5-methylcytosine content is deduced from the methylation status of at least one CpG dinucleotide sequence from each of Alu and juxtacentromeric Sat2 repeat sequences.

6. A high-throughput method for quantitative measurement of global genomic 5-methylcytosine content, comprising:
obtaining a test sample comprising genomic DNA; and
determining, using a quantitative real-time, bisulfite-based PCR assay, the methylation status of at least one CpG dinucleotide sequence of at least one repetitive genomic sequence selected from the group consisting of Alu and juxtacentromeric Sat2 repeat sequences; and
further determining a mean value of said methylation status of at least one CpG dinucleotide sequence, wherein the methylation status of a combination of repetitive genomic sequences significantly correlates with global genomic 5-methylcytosine content, and wherein a quantitative measurement of global 5-methylcytosine content is provided, based on the mean value.

7. The method of claim 6, wherein using the quantitative real-time, bisulfite-based PCR assay comprises use of at least one labeled probe to detect the amplified DNA, whereas the applied PCR primers and the at least one labeled probe specifically bind to bisulfite-converted DNA.

8. An assay for determining an amount of genomic DNA, comprising:
obtaining a test sample comprising genomic DNA from a human tissue sample; and determining, using a suitable quantitative methylation-independent methylation assay, the methylation status of at least one CpG dinucleotide sequence of at least two repetitive genomic sequences selected from the group consisting of Alu, LINE-1, and Chr1 centromeric Satα and juxtacentromeric Sat2 repeat sequences of the input genomic DNA, wherein the methylation status of at least one CpG dinucleotide sequence of the Alu or LINE-1 repeat sequence is determined, and wherein the amount of input DNA is thereby determined.

9. The genomic DNA methylation assay of claim 8, comprising use of a real-time PCR-based assay.

10. The genomic DNA methylation assay of claim 9, wherein the real-time PCR-based assay comprises the use of at least one labeled probe to detect the amplified DNA, whereas the applied PCR primers and the at least one labeled probe specifically bind to bisulfite-converted DNA.

11. The genomic DNA methylation assay of claim 8, wherein one of at least two repetitive genomic sequences is selected from the group consisting of Alu, and juxtacentromeric Sat2 repeat sequences.

* * * * *

UNITED STATES PATENT AND TRADEMARK OFFICE
CERTIFICATE OF CORRECTION

PATENT NO. : 8,642,263 B2  Page 1 of 1
APPLICATION NO. : 11/719033
DATED : February 4, 2014
INVENTOR(S) : Laird et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 480 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 59

<210> SEQ ID NO 1
<211> LENGTH: 18
<212> TYPE: DNA
<213> ORGANISM: Homo sapiens

<400> SEQUENCE: 1
attagtcggg cgtggtgg                                                 18

<210> SEQ ID NO 2
<211> LENGTH: 21
<212> TYPE: DNA
<213> ORGANISM: Homo sapiens

<400> SEQUENCE: 2
cccgaattca aacgattctc c                                             21
```

```
<210> SEQ ID NO 3
<211> LENGTH: 32
<212> TYPE: DNA
<213> ORGANISM: Homo sapiens

<400> SEQUENCE: 3
cgcgtttgta attttagtta ttcgggaggt tg                              32

<210> SEQ ID NO 4
<211> LENGTH: 21
<212> TYPE: DNA
<213> ORGANISM: Homo sapiens

<400> SEQUENCE: 4
ggacgtattt ggaaaatcgg g                                          21

<210> SEQ ID NO 5
<211> LENGTH: 19
<212> TYPE: DNA
<213> ORGANISM: Homo sapiens

<400> SEQUENCE: 5
aatctcgcga tacgccgtt                                             19

<210> SEQ ID NO 6
<211> LENGTH: 27
<212> TYPE: DNA
<213> ORGANISM: Homo sapiens

<400> SEQUENCE: 6
tcgaatattg cgttttcgga tcggttt                                    27

<210> SEQ ID NO 7
<211> LENGTH: 28
<212> TYPE: DNA
<213> ORGANISM: Homo sapiens

<400> SEQUENCE: 7
tcgaatggaa ttaatattta acggaaaa                                   28

<210> SEQ ID NO 8
<211> LENGTH: 25
<212> TYPE: DNA
<213> ORGANISM: Homo sapiens

<400> SEQUENCE: 8
ccattcgaat ccattcgata attct                                      25

<210> SEQ ID NO 9
<211> LENGTH: 24
<212> TYPE: DNA
<213> ORGANISM: Homo sapiens

<400> SEQUENCE: 9
cgattccatt cgataattcc gttt                                       24

<210> SEQ ID NO 10
<211> LENGTH: 34
<212> TYPE: DNA
<213> ORGANISM: Homo sapiens

<400> SEQUENCE: 10
tgatggagta ttttaaaat atacgttttg tagt                             34
```

```
<210> SEQ ID NO 11
<211> LENGTH: 33
<212> TYPE: DNA
<213> ORGANISM: Homo sapiens

<400> SEQUENCE: 11
aattctaaaa atattcctct tcaattacgt aaa                                    33

<210> SEQ ID NO 12
<211> LENGTH: 18
<212> TYPE: DNA
<213> ORGANISM: Homo sapiens

<400> SEQUENCE: 12
tatcccgttt ccaacgaa                                                     18

<210> SEQ ID NO 13
<211> LENGTH: 36
<212> TYPE: DNA
<213> ORGANISM: Homo sapiens

<400> SEQUENCE: 13
ggttaggtat agtggtttat atttgtaatt ttagta                                 36

<210> SEQ ID NO 14
<211> LENGTH: 33
<212> TYPE: DNA
<213> ORGANISM: Homo sapiens

<400> SEQUENCE: 14
attaactaaa ctaatcttaa actcctaacc tca                                    33

<210> SEQ ID NO 15
<211> LENGTH: 16
<212> TYPE: DNA
<213> ORGANISM: Homo sapiens

<400> SEQUENCE: 15
cctaccttaa cctccc                                                       16

<210> SEQ ID NO 16
<211> LENGTH: 290
<212> TYPE: DNA
<213> ORGANISM: Homo sapiens

<400> SEQUENCE: 16 ggcgggcgc ggtggctcac gcctgtaatc ccagcacttt gggaggccga ggcgggagga        60
tcacttgagc ccaggagttc gagaccagcc tgggcaacat agtgaaaccc cgtctctaca      120
aaaaatacaa aaattagccg ggcgtggtgg cgcgcgcctg tagtcccagc tactcgggag      180
gctgaggcag gaggatcgct tgagcccggg aggtcgaggc tgcagtgagc cgtgatcgcg      240
ccactgcact ccagcctggg cgacagagcg agaccctgtc tcaaaaaaaa                 290

<210> SEQ ID NO 17
<211> LENGTH: 291
<212> TYPE: DNA
<213> ORGANISM: Homo sapiens

<400> SEQUENCE: 17
ggccgggcgc ggtggctcac gcctgtaatc ccagcacttt gggaggccga ggcgggcgga       60
tcacctgagg tcgggagttc gagaccagcc tgaccaacat ggagaaaccc cgtctctact     120
aaaaatacaa aaattagccg ggcgtggtgg cgcatgcctg taatcccagc tactcgggag     180
```

-continued

```
gctgaggcag gagaatcgct tgaacccggg aggcggaggt tgcggtgagc cgagatcgcg      240
ccattgcact ccagcctggg caacaagagc gaaactccgt ctcaaaaaaa a              291

<210> SEQ ID NO 18
<211> LENGTH: 282
<212> TYPE: DNA
<213> ORGANISM: Homo sapiens

<400> SEQUENCE: 18
ggccgggcgc ggtggctcac gcctgtaatc ccagcacttt gggaggccga ggcgggcgga      60
tcacctgagg tcaggagttc gagaccagcc tggccaacat ggtgaaaccc cgtctctact     120
aaaaatacaa aaattagccg ggcgtggtgg cgcgcgcctg taatcccagc tactcgggag     180
gctgaggcag gagaatcgct tgaacccggg aggcggaggt tgcagtgagc cgagatcgcg     240
ccactgcact ccagcctggg cgacagagcg agactccgtc tc                        282

<210> SEQ ID NO 19
<211> LENGTH: 291
<212> TYPE: DNA
<213> ORGANISM: Homo sapiens

<400> SEQUENCE: 19
ggccgggcgc ggtggctcac gcctgtaatc ccagcacttt gggaggccga ggcgggtgga      60
tcacctgagg tcaggagttc gagaccagcc tggccaacat ggtgaaaccc cgtctctact     120
aaaaatacaa aaattagccg ggcgtggtgg cgggcgcctg taatcccagc tactcgggag     180
gctgaggcag gagaatcgct tgaacccggg aggcggaggt tgcagtgagc cgagatcgcg     240
ccactgcact ccagcctggg caacaagagc gaaactccgt ctcaaaaaaa a              291

<210> SEQ ID NO 20
<211> LENGTH: 287
<212> TYPE: DNA
<213> ORGANISM: Homo sapiens

<400> SEQUENCE: 20
ggccgggcgc ggtggctcac gcctgtaatc ccagcacttt gggaggccga ggcgggcgga      60
tcacgaggtc aagagatcga gaccatcctg gccaacatgg tgaaacccgt ctctactaa     120 aaatacaaaa attagctggg cgtggtggcg cgcgcctgta gtcccagcta ctcgggaggc    180
tgaggcagga gaatcgcttg aacccggag gcggaggttg cagtgagccg agatcgcgcc     240
actgcactcc agcctggcga cagagcgaga ctccgtctca aaaaaa                    287

<210> SEQ ID NO 21
<211> LENGTH: 281
<212> TYPE: DNA
<213> ORGANISM: Homo sapiens

<400> SEQUENCE: 21
ggccgggcgc ggtggctcac gcctgtaatc ccagcacttt gggaggccga ggcgggcgga      60
tcacgaggtc aggagatcga gaccatcctg gctaacacgg tgaaacccg tctctactaa     120 aaatacaaaa aattagccgg gcgtggtggc gggcgcctgt agtcccagct actcgggagg    180
ctgaggcagg agaatggcgt gaacccggga ggcgagctt gcagtgagcc gagatcgcgc     240
cactgcactc cagcctgggc gacagagcga gactccgtct c                         281

<210> SEQ ID NO 22
<211> LENGTH: 296
```

```
<212> TYPE: DNA
<213> ORGANISM: Homo sapiens

<400> SEQUENCE: 22
ggccgggcgc ggtggctcac gcctgtaatc ccagcacttt gggaggccga ggcgggtgga    60
tcatgaggtc aggagatcga gaccatcctg gctaacaagg tgaaacccog tctctactaa   120
aaatacaaaa aattagccgg gcgcggtggc gggcgcctgt agtcccagct actgggagg    180
ctgaggcagg agaatggcgt gaacccggga agcggagctt gcagtgagcc gagattgcgc   240
cactgcagtc cgcagtccgg cctgggcgac agagcgagac tccgtctcaa aaaaaa       296

<210> SEQ ID NO 23
<211> LENGTH: 288
<212> TYPE: DNA
<213> ORGANISM: Homo sapiens

<400> SEQUENCE: 23
ggccgggcgc ggtggctcac gcctgtaatc ccagcacttt gggaggccga ggcgggtgga    60
tcatgaggtc aggagatcga gaccatcctg gctaacaagg tgaaacccog tctctactaa   120
aaatacaaaa aattagccgg gcgcggtggc gggcgcctgt agtcccagct actcgggagg   180
ctgaggcagg agaatggcgt gaacccggga agcggagctt gcagtgagcc gagattgcgc   240
cactgcagtc cgcagtccgg cctgggcgac agagcgagac tccgtctc                288

<210> SEQ ID NO 24
<211> LENGTH: 281
<212> TYPE: DNA
<213> ORGANISM: Homo sapiens

<400> SEQUENCE: 24
ggccgggcgc ggtggctcac gcctgtaatc ccagcacttt gggaggccga ggcgggcgga    60
tcacgaggtc aggagatcga gaccatcccg gctaaaacgg tgaaacccog tctctactaa   120
aaatacaaaa aattagccgg gcgtagtggc gggcgcctgt agtcccagct acttgggagg   180
ctgaggcagg agaatggcgt gaacccggga gcggagctt gcagtgagcc gagatcccgc    240
cactgcactc cagcctgggc gacagagcga gactccgtct c                       281

<210> SEQ ID NO 25
<211> LENGTH: 280
<212> TYPE: DNA
<213> ORGANISM: Homo sapiens

<400> SEQUENCE: 25
ggccgggcgc ggtggctcac gcctgtaatc ccagcacttt gggaggccga ggcgggcgga    60
tcacgaggtc aggagatcga gaccatcccg gctaaaacgg tgaaacccog tctctactaa   120
aactacaaaa aatagccggg cgtagtggcg ggcgcctgta gtcctagcta cttgggaggc   180
tgaggcagga gaatggcgtg aacccgggag gcggagcttg cagtgagccg agatcccgcc   240
actgcactcc agcctgggcg acagagcgag actccgtctc                         280

<210> SEQ ID NO 26
<211> LENGTH: 282
<212> TYPE: DNA
<213> ORGANISM: artificial sequence
<220> FEATURE:
<223> OTHER INFORMATION: Alu consensus sequence

<400> SEQUENCE: 26
ggccgggcgc ggtggctcac gcctgtaatc ccagcacttt gggaggccga ggcgggcgga    60
```

```
tcacctgagg tcaggagttc gagaccagcc cggccaacac ggtgaaaccc cgtctctact    120
aaaaatacaa aaattagccg ggcgtggtgg cgcgcgcctg taatcccagc tactcgggag    180
gctgaggcag gagaatcgct tgaacccggg aggcggaggt tgcagtgagc cgagatcgcg    240
ccactgcact ccagcctggg cgacagagcg agactccgtc tc                      282
```

<210> SEQ ID NO 27
<211> LENGTH: 10
<212> TYPE: DNA
<213> ORGANISM: Homo sapiens

<400> SEQUENCE: 27

```
attccattcg                                                          10
```

<210> SEQ ID NO 28
<211> LENGTH: 29
<212> TYPE: DNA
<213> ORGANISM: artificial sequence
<220> FEATURE:
<223> OTHER INFORMATION: Alu-M1 forward primer, based on Alu sequence in
      S100A2 gene

<400> SEQUENCE: 28

```
attatgttag ttaggatggt ttcgatttt                                     29
```

<210> SEQ ID NO 29
<211> LENGTH: 17
<212> TYPE: DNA
<213> ORGANISM: artificial sequence
<220> FEATURE:
<223> OTHER INFORMATION: Alu-M1 reverse primer, based on Alu seqeunce in
      the S100A2 gene

<400> SEQUENCE: 29

```
caatcgaccg aacgcga                                                  17
```

<210> SEQ ID NO 30
<211> LENGTH: 37
<212> TYPE: DNA
<213> ORGANISM: artificial sequence
<220> FEATURE:
<223> OTHER INFORMATION: Alu-M1 probe sequence, based on Alu sequence in
      the S100A2 gene

<400> SEQUENCE: 30

```
cccaacactt taaaaaaccg aaataaataa atcacga                            37
```

<210> SEQ ID NO 31
<211> LENGTH: 18
<212> TYPE: DNA
<213> ORGANISM: artificial sequence
<220> FEATURE:
<223> OTHER INFORMATION: Alu-M2 forward primer, based on consensus
      sequence

<400> SEQUENCE: 31

```
gcgcggtggt ttacgttt                                                 18
```

<210> SEQ ID NO 32
<211> LENGTH: 26
<212> TYPE: DNA
<213> ORGANISM: artificial sequence
<220> FEATURE:
<223> OTHER INFORMATION: Alu-M2 reverse primer, based on consensus
      sequence -continued

```
<400> SEQUENCE: 32
aaccgaacta atctcgaact cctaac                                          26

<210> SEQ ID NO 33
<211> LENGTH: 23
<212> TYPE: DNA
<213> ORGANISM: artificial sequence
<220> FEATURE:
<223> OTHER INFORMATION: Alu-M2 probe sequence, based on consensus
      sequence

<400> SEQUENCE: 33
aaataatccg cccgcctcga cct                                             23

<210> SEQ ID NO 34
<211> LENGTH: 26
<212> TYPE: DNA
<213> ORGANISM: artificial sequence
<220> FEATURE:
<223> OTHER INFORMATION: Alu-M5 forward primer, based on Alu sequence in
      CASP8 gene

<400> SEQUENCE: 34
ggtatgatgg cgtatgtttg taattt                                          26

<210> SEQ ID NO 35
<211> LENGTH: 21
<212> TYPE: DNA
<213> ORGANISM: artificial sequence
<220> FEATURE:
<223> OTHER INFORMATION: Alu-M5 reverse primer, based on Alu sequence in
      CASP8 gene

<400> SEQUENCE: 35
cgactcacca caacttccac c                                               21

<210> SEQ ID NO 36
<211> LENGTH: 29
<212> TYPE: DNA
<213> ORGANISM: artificial sequence
<220> FEATURE:
<223> OTHER INFORMATION: Alu--M5 probe, based on Alu sequence in CASP8
      gene

<400> SEQUENCE: 36
aaacgattct cctacctcaa cctcccgaa                                       29

<210> SEQ ID NO 37
<211> LENGTH: 30
<212> TYPE: DNA
<213> ORGANISM: artificial sequence
<220> FEATURE:
<223> OTHER INFORMATION: Alu-U3 forward primer, based on consensus
      sequence

<400> SEQUENCE: 37
tggttaatat ggtgaaattt tgtttttatt                                      30

<210> SEQ ID NO 38
<211> LENGTH: 25
<212> TYPE: DNA
<213> ORGANISM: artificial sequence
<220> FEATURE:
<223> OTHER INFORMATION: Alu-U3 reverse primer, based on consensus
      sequence

<400> SEQUENCE: 38
```
tcctacctca acctcccaaa taact                                      25

<210> SEQ ID NO 39
<211> LENGTH: 30
<212> TYPE: DNA
<213> ORGANISM: artificial sequence
<220> FEATURE:
<223> OTHER INFORMATION: Alu-U3 probe, based on consensus sequence

<400> SEQUENCE: 39
caaacacaca ccaccacacc caactaattt                                 30

<210> SEQ ID NO 40
<211> LENGTH: 28
<212> TYPE: DNA
<213> ORGANISM: artificial sequence
<220> FEATURE:
<223> OTHER INFORMATION: LINE-1-U3 forward primer

<400> SEQUENCE: 40
tttattaggg agtgttagat agtgggtg                                   28

<210> SEQ ID NO 41
<211> LENGTH: 28
<212> TYPE: DNA
<213> ORGANISM: artificial sequence
<220> FEATURE:
<223> OTHER INFORMATION: LINE-1-U3 reverse primer

<400> SEQUENCE: 41
ccttacactt cccaaataaa acaatacc                                   28

<210> SEQ ID NO 42
<211> LENGTH: 35
<212> TYPE: DNA
<213> ORGANISM: artificial sequence
<220> FEATURE:
<223> OTHER INFORMATION: LINE-1-U3 probe

<400> SEQUENCE: 42
caccctactt caactcatac acaatacaca caccc                           35

<210> SEQ ID NO 43
<211> LENGTH: 35
<212> TYPE: DNA
<213> ORGANISM: artificial seqeunce
<220> FEATURE:
<223> OTHER INFORMATION: Sat alpha-U1 forward primer

<400> SEQUENCE: 43
ttgatggagt atttttaaaa tatatgttttt gtagt                          35

<210> SEQ ID NO 44
<211> LENGTH: 34
<212> TYPE: DNA
<213> ORGANISM: artificial sequence
<220> FEATURE:
<223> OTHER INFORMATION: Sat alpha-U1 reverse primer

<400> SEQUENCE: 44
aaattctaaa aatattcctc ttcaattaca taaa                            34

<210> SEQ ID NO 45
<211> LENGTH: 20
<212> TYPE: DNA
<213> ORGANISM: artificial sequence
<220> FEATURE:

<223> OTHER INFORMATION: Sat alpha-U1 probe

<400> SEQUENCE: 45
tttatcccat ttccaacaaa                                                      20

<210> SEQ ID NO 46
<211> LENGTH: 8670
<212> TYPE: DNA
<213> ORGANISM: Homo sapiens

<400> SEQUENCE: 46

| | | | | | |
|---|---|---|---|---|---|
| gagctcaaga | gttcaagacc | cgtctgggca | agatggcaaa | actccatcac | cacaaaagat | 60 |
| gcaaaaagat | gcgcacagtg | gcgcacacct | atagcccag | ttactgagga | ggttaatgtg | 120 |
| ggaggatcac | atgaggctgc | agtgagctgt | gatggtgcca | ctgtactcca | gccttggcga | 180 |
| cagtgagtct | atgtctcaaa | taagtaagta | aacaaaaatt | aaaagaatc | cagtccacag | 240 |
| ggcatttgaa | ggcaagagga | aaagatgcca | gaatcagaga | tggggagaag | atgggcttca | 300 |
| cgcacctgct | gaggttgaga | atgagacag | ataggctgag | tgtggggtgg | agagaggatg | 360 |
| ggcagagaga | ctgaggctgg | tctgaatgga | aatgaaatgt | tagggctctc | agggttatcg | 420 |
| gggaataatt | ggagcttcta | ggaaaggttt | aacgttgtga | ccacctgtgt | gcgtcatgcc | 480 |
| tccccacccc | ttactaattg | tgtgaatttg | gcagactttg | agtctcagtg | ttctcctctg | 540 |
| tgaagtgggg | tcatcttatt | ccaactcctg | ggattgttgt | gtgaattaaa | tggggtaatg | 600 |
| tacggagagc | acctgacgca | cagcgagtgc | ttcaaaattt | cagtctgcac | ccccagcaa | 660 |
| aggatatgca | cacgcccatt | gtgagtgaca | aatccaggat | gacctgaacc | caatgtgata | 720 |
| acgtgggtcc | tcgcatgctg | gtcatgctgc | cgggagacac | ttatggatcc | aattagtaca | 780 |
| acaggggaaa | taaattattt | aatgcatttt | gctaagacag | aataccctcag | aacttatttt | 840 |
| gtggggtggg | gcataataaa | gggggtcctt | ctgctgaaaa | cgtttaagct | caggttcgtg | 900 |
| gcaccactca | accaaggtcg | acagtcacac | agtaagccag | aggcaatgtc | aggacttaaa | 960 |
| ctaaacctgt | ggcccccaca | atgaggccat | ttctcttttcc | cctgaacggc | ctggggaaag | 1020 |
| ggggtgggtg | ggcagaactt | ggcagtggcc | aatccctcac | ttctgtcccc | tggttttctc | 1080 |
| ctgcccttat | ctctaggctt | gcattgattg | attgattgag | acagggtctt | gctctgtcgt | 1140 |
| ccaggctgga | gtgcagtggc | acgatcatgg | ctcactgcag | cctcaaactc | ctaggctcaa | 1200 |
| gtggtctttc | cgcctcctat | ctcccgagta | cccatatccc | taggctttta | aaatggcttc | 1260 |
| caggtatctg | gctgccgtct | cagacatcca | cctgggcttc | tgggcaggga | ctgtccggga | 1320 |
| aacctcatct | atgtgaagca | ggtgtgggtg | taggaaggcc | gcttggaaat | gaatcagcac | 1380 |
| tgtctcctgt | ttgagtcgta | agcagggcgc | cagagggtct | ggcggacaag | aaagggagga | 1440 |
| tgacaggagg | ccggcactgc | aatgacacgc | cttagccacc | agagggcacg | aagcagctgg | 1500 |
| gcaaaatccc | gcggggcccc | tggtggaaaa | tttctggcac | ctggagcccg | gagatggggt | 1560 |
| ggacggaatg | tgaggaccca | gcttcctgag | gctgggccgg | ggcagagtca | ctgctttgga | 1620 |
| tgtccgcagg | gcctgcttgt | gtcttgacta | ctctgccttt | gtagacagct | ggagaatgtg | 1680 |
| agagtgggat | tgggatcgga | ctctagggcc | attccgtaca | actctcctgc | cctgccgtgg | 1740 |
| gggagggagt | tgcccaaggt | tacgcagcaa | gttagtggca | aatgaatacg | attatcacca | 1800 |
| gtctcaggta | tatggccatt | tgatgggcgc | agtcgcagcc | tcagttcctg | agacagagac | 1860 |
| acctgattaa | ggacaggcct | tcaggagctg | acccgtagtga | cccgcggctc | tgctgctgtc | 1920 |
| tctgtttttc | tccctggctt | ttccatctga | ctgactcttt | gtcttcttcg | tctgcctgcc | 1980 |

```
tgtctccgtc tctgcccgct gggggtttg ctcaactccc tcactgggtc ctgggagccg    2040
cagtttcctg ctgtcactcc tcagggattt gtagctctct gaagctcttt tccgacccgt    2100
tgtctcggtt ccactcttgg gatccagagg agaggtgatt atttcgtagc atagtcagtg    2160
gtgtgatttc acggggtgag aaggactccc ttgctcctaa gcactcctcc agtgacccct    2220
gttgccatgt ggtagccgta agcactggtt ggcacctggt gtgggcgaga cccttacctc    2280
atgcagaaat gagtaagact ggtgagctca ctatgtgggg tgaggctgag agaaaacaag    2340
tacacaggtg attcagtcaa atcagaatt ctctaagtac acacgaaaag gcaaagggg    2400 gcgctttgta caggacagaa caggtagaca ctgaatccgg ttgggccctg gaaggctcc    2460 ctgcagtggc ctttgaaggg ggggttggat ttcagcagga tagagggcat gggcatgtgt    2520
gggcacgttc tgaacagagg ggtcagcgca agccgagggt cttggccaca ctagttgcat    2580
gtgccggtgt gtttaaggga cacgcagcag caggccgagt ctggagcgcc tcactgccag    2640 gcttttaaa aattttaat tttaattaa ttttatttta tttttacttt aagttctggc    2700
atacatgtgc agaatgtggt tgttacata ggtatacatg tgccatggtg gtttgctgca    2760
cctatcaacc catcatctag gttttaagcc ccgcatgcat caggtattag tcctaatgct    2820
ctccctcccc ttgcccccat ccttctcccc gcaactgccc acaggccctg gtatgtggtg    2880
ttcccttccc tgtgtccata tgttctcatt gttcaactcc cacttatgag tgagaacata    2940
ccgcctggct ttaagggaca gccatgggga tgcactgcag tttctgagca gggaaggccc    3000
tgtggaggcc cttagttaaa aggaaagaat ggctgtgaaa atcgatgcat gcgctccct    3060 tgtccctcac cctcagtgtg aagggttttt attccgagtt ctacttgaag taggcctcga    3120
tgggaagaca agtagcatga ggggttcaag tactgagggg agcaagggac actcggtggc    3180
tgtgccaagg tgtagaagag gacactgggg gccccaagac ctgacttcat gtacactgct    3240
caggctggcc cccaagtcac acggtgaccg ctaggaaggg accagcctgt tctcagtctg    3300
atcctacagc catgtcatta tccaaagctc ctcctggcag ggcctgtttg gggtctctgt    3360
gccagtgctt tccctgccag gctgggctgg ggcttccacc tactgctctg ggactgctgc    3420
tgccctggcc ctggggagg agggtgtgcc gctgagtcac tgcctgggca tctgggcctg    3480
gaacctcggg tgagtcactt agggctgagg tagaggggct gggggagggg aagaagctac    3540
tcgacagctg gagcagggag gggagctggg gccacaggaa gggcggtgcc ctgatgccca    3600
gacgggccgg gatagacaaa gggccaagga ggaaggggcc ctgggagggg gcagccctcc    3660
cttgggctgg ggtctgaatg gcacagtgtt tgcctttctc cgggtctggg gaggacatgt    3720 gtgtggggg cagtgagaga gggctgtggc tgagggctgt gcttcaggcc tggattctgg    3780
cttgggaagc tgtccagctg gtgttttcag ccttgggtag ggatgtaccc ctacccaccc    3840
acccagccct caagctggag aagaggaggc caaagttttc ctgttcagcc tttaactact    3900
cgggacttcc ttatgctccc cacagactgt ggcccagccc aactgcggct gtgtgtagag    3960
caaccccatt tctcactgct tccccatcct tccagacacc ttcctacaca gagggacctt    4020
cccaggtatt tctaagcaca cttagttacc tcattacctc attaagaggt attctggtgc    4080
tggccattaa aagtcactcc acttcatcca tgccctgaag tcagtcctgt ccttctcctc    4140
ctgatgtccc ccagctgcct cctctggccc ccagcttcct aaggtggccc caggttgctt    4200
ctctctcaca cacgggcg catgtatgta cacgagcact ggaccatgaa gtctcagcgt    4260
gtgctcacag cctctcacac aggagtgggc tgtgactcac aggcatgtca tgagaatgag    4320
gcctggcacc agtctccagg ccccagagca ggggttgcct cccctcaccc cggtccagga    4380
```

-continued

```
tgcccagtcc ccacgacacc tcccacttcc cactgtggcc tgggtgggct caggggctgc    4440
ccttgacctg gcctagagcc ctcccccagc tggtggtgga gctggcactc tctgggaggg    4500
agggggctgg gagggaatga gtgggaatgg caagaggcca gggtttggtg ggatcaggtt    4560
gaggcaggtt tggtttcctt aaaatgccaa gttgggggcc agtgggggccc acatataaat    4620
cctcaccctg ggagcctggc tgccttgctc tccttcctgg gtctgtctct gccacctggt    4680
ctggtgagta cctctgtcct gctgagggca gggtggggag gatccccgtg ggtctctgtc    4740
tttgtctcca cagttctctc attccagctt ccctggtggg atcaacctgg gcctctctgg    4800
gccttccccc ttggaagaac tctctgtgaa gtgctgaagt gttgactgaa gggtttttttt    4860
tttttttttt tttttttgag atggagtctc gctctgtcgc ccaggctgga gtacagtggt    4920
gtgatctcag ctcactgcaa actcccctc ccaggttcac gccatttccc tgcctcagcc    4980
tcccgagtag ctgggactgc aggcgcccac caccatgccc ggctaatttt tttgtatttt    5040
tagtagagat ggggttttcac catgttagcc aggatggtct cgatctcctg atctcgtgat    5100
ccacccatct cggcctccca aagtgctggg attacaggag taagccaccg cgcccggccg    5160
actgaagggt ttttctccag gttcctctgt gaggtctcag tgcaggggtt gctctgaggc    5220
cctcccctgg atatctcagt ctaggggccc ttctttgggg gtctaggcct aggagcagga    5280
ggtgtgcatg tgggcgttgc tgcaaaaaga atcctgagat tttttttttt tttttttttt    5340
ttgcaaagtc ctggattcta gcaggactaa ggtgcaagag gcagggtct caagactctg    5400
cctgggtcat ggccccaagc agcaaagctc tgcccctgc ctcggtgaag gcagggctgg    5460
catgatgggc ccagggcatg ccctgcctct ggcatagctc ctctggcctc accctgaaac    5520
ctgcctaacc tttccaggct ggtctgagta ttctcagagg ccttgccgct gaggtctgtc    5580
ccatcctgat cccaaggcaa tgaacatttc atatctttaa ttctaattcc aacaggatcc    5640
ttcctggtgg agagaatgtt aagttgcccc caccctatcc atgcccctgt ctgcctagag    5700
gctcaggggc cttcagggtg aggggagaca cattccccac cctctgggag ctcctagtct    5760
gagagaggaa acactcctgc ccaagggagc ttccagttag atggcagaga gagatgcctc    5820
tggcttcagg agtcccgagt ctaaggaggg aaacgactcc ttcagggagc ttcctgctcc    5880
taggctgtag ccatggctcc tgccagactg cacaggagcc cccatctgcc agccggtgca    5940
tgtggccctg ctccccagag cctgcgcaga tgccatcaaa atgggactct ggtcaccctg    6000
tcatttccct tctggcagac actaaaatgg ggagccctgc cctcaggggg gtgtcccaag    6060
tgccatcaga ggaggcttgg tgactcccag acacaaggga agcttagcg tctgccctca    6120
gggtgagatg gaggtatccc tccggcctca gggaaccaca gtctgagggg agatgcagcc    6180
cctgccttcc cattcagaga ggggttttgt gaggtggctt gggggcatag gcagaagtg    6240
gatcctacag gctgagctaa ggccccaaga gcctcagcag tgtacccatc acctggcacc    6300
tctgcagcca cagatccatg atgtgcagtt ctctggagca ggcgctggct gtgctggtca    6360
ctaccttcca caagtactcc tgccaagagg gcgacaagtt caagctgagt aaggggggaaa    6420
tgaaggaact tctgcacaag gagctgccca gctttgtggg ggtgagtggc acaggcctgt    6480
ggggggaggtc ctggtgtgag tgtggggggtg caggttaaat ctctccccca gttccgggtg    6540
cctgtcgatg caggtgccag ggtgggggccc agccctcccc cactttagct tcatggctcc    6600
actggagtgg aaatgaggcc cgagtgggag tgcttaatta atggctgttt cctgcaacat    6660
tccagagaac catgtgctgt gagggccttc cgagtccatc tgtttaatcc tgtcattgga    6720
acttgagaaa ccagagccca gaagggaaaa gtgattgtgtc caagatcaca cagcactggc    6780
```

```
acgttctctc tctctctttt cttttctttt ttttttttttg agatggagtt ccctcttgt   6840
tgcccaggct ggagtgcaat ggcacgatct cggctcactg caacctctgc ctccaggggt   6900
caagcaattc tcctgtctca gcctcctgag tagctgggac tacaggcgca tcccactacg   6960
cccagctaat ttttgtattt ttagtagaga cagggtttca ccatattggc caggctggtc   7020
tcgaactcct gacctcgtga tctacctgcc tcggcttccc aaagtgattt tgtatttt      7080
agtagagacg gggtttcatc atattggtca ggctggtctc gaactcctga cctcaggtga   7140
tctgccctcc tcggcctctg aaagtgctgg gcttacaggc gtgagcaccg tgcccggact   7200
ccttttttt tttttttttt ttgtggtggg gggacaagat ctcactctgt cacccaggct    7260
ggatcatagc tcactgtaat ctcgaactcc tgggctcaag caatcctccc aagtagttgg   7320
aactacagga gtattgtcac catgcctggc caatttttat tttttgtaga gatggagtct   7380
tgctatgttg tccaggctgg gcttgaactc ctgggttcaa gcaatcctcc cacctcggcc   7440
tcccaaagta ttggaattac agatgtgagc cactgtgctt gacctctttc catttttata   7500
tgccaaacta agaaagtatg ttagggatag aaaagccctg ctcagatata tagtctggga   7560
cattttgtgg agaaatgcat cgaccttcaa tttgtccctc accctcccta tactgactca    7620
ttggtgattc ccaaagttag gtgtcaggct ttgaacacat gaggcaggtc cttctttcct   7680
tggtttaatt ttgttttttgt ggctggttaa attttctaa ttatttcggc tagtattaaa   7740
aaagtgtttt tcagctgggt gcagtggcct atgcctgtaa tccccacagt gtgggaggct   7800
aaggcaggag gatctcttaa gcccaggagt tcgaccagcc tggcaacat agcaagactc     7860
catctctaca aaataaaaa taaaaattgg ccaggcatgg tggcatacgc ttgtagtccc    7920
agctacttgg gaggctaaag gtgggaggat tgctggagcc caggaggttg aggctgcagt   7980
gagttgtgat tgtgccactg cactccaacc tgggctaaca gagcaagacc ttgtcttaaa   8040
aaataaaaag tgttctttc tgaatctacc tggctggtgt tggggagcag caacttcggt    8100
ttcctcatca gcagaatggg gtgatgatac ctacctcgct gggctcctgt gggattcgag   8160
ctgatgcatg ctcagaggag catccagtgt cctccctgtg tccaggagga gggcacactg   8220
gagatgctca ccaatgagta tctgtctctc tccttactca ctgggccctc ttggtagctc   8280
ccagagcctc ctgcccacct tatacccagc tgcccagtgg ggagggagag ctggaaccaa   8340
cctgaatgtg tgagggtctg ggtgtttggt ggagctgggg ttggggctgg cttggtgatg   8400
agtgtatttc ctgtcacttt caggagaaag tggatgagga ggggctgaag aagctgatgg   8460
gcagcctgga tgagaacagt gaccagcagg tggacttcca ggagtatgct gttttcctgg   8520
cactcatcac tgtcatgtgc aatgacttct tccagggctg cccagaccga ccctgaagca   8580
gaactcttga cttcctgcca tggatctctt gggcccagga ctgttgatgc ctttgagttt   8640
tgtattcaat aaactttttt tgtctgttga                                    8670

<210> SEQ ID NO 47
<211> LENGTH: 181150
<212> TYPE: DNA
<213> ORGANISM: Homo sapiens

<400> SEQUENCE: 47
gaattctgtt ggtttagttt tgaattttaa accagacttg cattcctgga aaaactact     60
tggttatgat atattatctt ttttatatat gacaggttat atttactagt gttttgttag   120
ggagtgtgtg tatatgtgtg tgtgtgtctg tgtccttcct agtcccatta ataagggtta   180
ttggtttgta cttttttctt ttttcttttc ttttttttt ttttttttgc aatgtcttcg   240
```

```
ctttattttg atattgaggt aatactggcc ttgtaaaacg agttgtgaag tatgcctttc    300
tctgtgtttg gaaaaagttt gtgtggaatt ggtatcatct tattttttcat gtttttactt   360 tttaaactca tctgaatctt tacatttaac tgtgtagtta atgtggagtt acatttaact    420
ccacagataa cttataatgg ggtcttttct aaaaagaaaa tccagtctga tcatctgtac    480
tttctatttg cagtatttgg accatttaat tttaatgtaa ttatcacttt agttgagtct    540
actgtactcc tattttcttt ttctatttgt tccgtcttcc gttttttttct cattttcttt    600 ttttaaactt ttttttatttt aattctactg ttgacatatt agctataccct cttattttttc   660 tcactgcttg ctccaggttg caatacatac ctttaactta tcaaagccca tcttcaaata    720
acattatatt taataaagtg acactcttaa aacagtattc ttccatttcc ccctaccatt    780
ctacatatta ttattactat gccttttaca tctacatatg ttatatacat aatacattat    840
tacctttgct ttaaattgct aattatgaat taaataaatt atgaaaataa aaggcttatg    900
tattacccac agatttagca ttctattatt cttttgttg aatgaagttc ccattccata    960 tccttttgc ctgtttaact ttaacatttc ctgggatatg ggttagctgg caatgaatag    1020
ccatagtttt ctgcttgtgt gaaaaataaa attactttt ttttgagaaa gggtctcatt    1080
ctgttcccca ggctggagta cagtgacacg atcatggctc actgcagcct gaacctcttg    1140
ggctcaagtg atcctcccat ctcagcctcc tgagtagctt ggaccacagg catgtgcaaa    1200
cccagctaat ttttttcttct tccttttttt tttttttttt tttaatgtag agtcagggtt    1260
tcactatgtt gccaagctgg tcttgaactc ctgggctcaa gcagtccttt caccttgacc    1320
tcccaaagtg ctgggattac aggagtgagc taccacgcct ggcctatttc accttttttg    1380
aaagatgttt ttcactgaca catgattcta aattggcttt tgtccatgt gttttaatga    1440 tgctgttcca ttgtcatcta tcttgaaatg aataatttca tttcaagtga atgaaacttt    1500
aatgttcttt ttttcctatc tctctgcttt taggattttc ttctttatca ctggtttta    1560 gcaatttttgc tttgatgtgg ttttcttgt atttatactg catggagttg agattctttg    1620
aactatagac ttactgtatt aattaaactt ggaagacttc ggccaccatt ttttcaaata    1680
ttttttctgt ttctgcctct tctttcttct gggacttcag actgcttgat atgacacagc    1740
cactgatgtt ctgttcagtt ttctcccccc aatcttttttt tctctgtgct tcattttaga    1800
taatttctat tgctatgcct tcaagtttac tgttctttc ttctggagaa tatctaatct    1860
gtttatctta tctagtgagt ctttcatttt agatactgta ctctagttct atttgggttt    1920
ttaaaatgca ggcatatctt ctgtttctct ttccattacg ttcatatttt cccttaaat    1980 ctttgagcat attaaaaata gaggatataa aaaattgctg cttattaatt ctgttatttc    2040
tgtcatgacg ggtctgtttc tgttgactca tttccctcct ggttatggat tacattttgt    2100
ttatttttgc atatctagta attttgtatg gactggtgaa tattatgaat gttacattgt    2160
taggtgttta ggttttgttg tcttccttgg aaaagtgtta aaatttattt tggcaagact    2220
ttaagttatt tgctgataag gttaacccctt tgaggcttgt ttttcatctg taggtctaca    2280
gatcatactc tagaccaagc tctagtgtgc ttgattctag cactgattta attatcttac    2340
cggtaggcat gactgggaaa aaatggacat gaaggagaca tttggaggat aaaatggtag    2400
agaaggagtt gtcaagcctg ggcaagagta ataaatggaa cattatcaga atatggaagc    2460
aaggtggaag agctagtcta aagaatattt agcttaatct actaagcctg gattgtacac    2520
ttatttttaa tattacatt tggaagtagg gaattattct agtctagaag agatgctagg    2580
gactagtatc tcttgtaatg aatgtcactt ttgttcttca tctccactat accgttgaat    2640
```

```
acctaatagt ctgtttttag ctctgcatgt atttatagtc aacttctctt cctgagtatt    2700
aaaatgacaa tctctatgta atatatgtgt ggcaggaaaa atttggataa tcacatggaa    2760
cttgtaataa tagaatttgg atatatgttc aggtctccta tttaagagat ctgtaaggat    2820
tgagagctta tttagaacca tatttaaggt tttaaatctg cctcatctct atctcattgt    2880
ggtgatcaag ccactgcttc tccttctggg tgaataggga tgtctgatat tgccagcctc    2940
cttttattaa acttattaaa atgtcattgt gaagtcaagg tcaagtcgta ggaatttact    3000
ctcttaagga tttgtttttct taaccagtac tttgttgttc tttgccagag ctagagcatg    3060
tttcattata ctacccacaa aggaaatacc acatctcttt aaaagtgaga gggttgatat    3120
gacatcctgt actttcgcta ttttaagccc tagtatttta agcatgttaa cagaaataac    3180
tctccttttt tgtaaacagc taagtttggg aggtgttaaa tgatgggcag tactgggaac    3240
aggaagatag tggcagatac ataaaaacac aaaagctcag tttgttcaga gatggggtg    3300 ggggtgttat aggtgtgcaa gtgagagagt agtgatgtaa atagtattca gtgagtacct    3360
gtgatctgcc agatacc tg ggtgccttaa ttgcttattt tagttacttc ttactactgt    3420
tgtgtgtgat aaatgatctt tattttacaa atgagagaaa ttaaggctct gaaaggatga    3480
atcgtgtgtc taacaattag tagaggagtc agattcagaa gctacgtctg atgccaaaac    3540
ccatgatctt tctaatatta agagtgaaaa ataggacaat aagtagatta dacacctgga    3600
ggaattagga gatatgtagg actaatactg tatgttggag acatgatgtg taggaacttg    3660
ctttctagga caagttgtca gcctttgtcc tgtaaatggc agatagcaac aagaatgggt    3720
acagtgctgg ataggaagtc gagacccagg tctggtggtt ctagtgtcct cggcaagtta    3780
cccatcttta agtctcagtt tccttatcta ggaggcagga ttggatggtt tccgaaagtg    3840
tcttctacct ttaatactct gtaattattt agatactata gcaaccttat tttagcagtc    3900
ttgatttgat ctctaggtgt aaaaactcaa tagtaataca gtaataaaaa tagctgacaa    3960
taggtctttc agtcttttcc cccctccctt agtcttcgtc cccaatccct cccctcccta    4020 tcccttttccc tcctccagct gccacgtgtg aaggcagagc aggaacagcc tgtgtttagg    4080
ggggtgggga aaaagaggcc cagttctgcc cctcctggaa ggagagggaa aaggtaacta    4140
taactaccca atattgcagc catggagtcc atgtttaata aattgaagag tactgttaca    4200
gaagtaacag ctgatgtcac tagtgctgta atgagaaatc ctgtcactag agaatttgat    4260
gttggtcagc acattgccag tggtggcagt gggctagctt ggaagatttt taatggcaca    4320
aaaaagtcaa caaagcagtg gctgttttttg tctttgataa aaaatgattg acaaatatca    4380
aaaatttgaa aaggatcaaa taattgattc tctaaaatga ggagtccaac acttaactcg    4440
acttcaacac cctcgacttc ttactgtcca gcattcttta gaagaatcca gggattgctt    4500
ggtgttgtgt acagaaccag ttttttgcca gtttagccag tgttcttggt aactgggaaa    4560
atctcccttt ccctatatct ccagacatta aggattataa actttatgat gtagaaacca    4620
aatgtggttt gcttcaggtt tctaaaggat tgtcattctt gcatagcagt gtgaaaatgg    4680
tacatggaaa tattactcct gaaaatacaa ttttgaataa aagtggagcc tggaaaataa    4740
tgggttttga ttgttgtgta tcatcaacca atccttctga acaagagcct aaatttcctt    4800
gtaaagaatg ggacccaaat ttaccttcat tgtgtcttcc aaatcctgaa tatttgcctc    4860
ctgaatacat actttatgtg agctgtgaaa cagtcagtga tatatattct ttaggaactg    4920
ttatgtatgc tgtatttaat aaaaggaaac atatatttga aggcaataag caagacattt    4980
ataagagttt cagtaggcag ttggatcagt tgagttattt aggatctagt tcacttataa    5040
```

```
atatacctga ggaagttcgt gaacatgtaa ggctactgtt aaatgtaact ccaactgtaa    5100
gaccagatgc agatcaaatg acaaagattc ccttctttga tgatgttggt gcagtaacac    5160
tgcaatattt tgataccttta ttccaaagag ataatcttca gaaatcacag tttttcaacg    5220
gactgccaaa ggttctactg cccaagcatg tcattgtaca gagaattttg atttgacttc    5280
agaatttgta aaccctgaca tggtaccttt tgttttgccc agtgttctac tgatcgttga    5340
ggaatgcacc aaagaagaat atgtcacatt aattccacct gaacttggcc ctgtgtttaa    5400
gcagcaggag ccaatccaga ttttgttaat tttcctacaa aaaatggatt tgctactaac    5460
caaaacccct cccaatgaga taaagaacag tgttctaccc atggtttaca gagcactaga    5520
agctccttcc attcaatacc aggagctctg tctaaacatc attccaacct tgcaaatct    5580
tatagactac ccatcatgaa acatactttg ataccaagaa ttaaaaatgc ctgtctacaa    5640
atgtcttccc ttgctgttcc tgtaaattca ttagtgtgct taggaaagat tttggaatac    5700
ttggataagt ggttggtact tgatggtatc ctacccttct tacaacaaat tccatccaaa    5760
gagtctgcag tcctcatggg tatttaggc atttacaaat gtacttttac tcataagttg    5820
ggaatcacca aagagcagct gactggaaaa gtattgcctc atcttattcc cctgagtatt    5880
gaaaacaatc ttaatcagtt caattctttc atttccatca taaaagagat gctgaatagg    5940
ttggagtctg aacataagac taagctggag caacttcata taatgcaaga acaacagaaa    6000
tctttggaca taggaaatca aatgaatgtt tctgaggaga caaaagttac aaatattggg    6060
aatcagcaaa ttgacaaggt ttttagccac attggagcag accttctgac tggcagtgat    6120
tccgaaaata aagaggatgg gtttcagaat aaacataaaa gagcatcact tacacttgaa    6180
gaaaaacaaa aattagcaag agaacaagag caggcataga agttgaaagg ccagcagcct    6240
cttaaacccc aagtgtacac acctattgct gctgttaaac agactaagga cttgacagac    6300
acattgatgg ataatatgtc atctttgact agcctttctg ttagtacccc taaaccttct    6360
gcttcaagta cgttcacttc tgttccttcc atgggcattg acatgatgtt ttctacacca    6420
gttgataata caaagagaaa tttgacaaat ggcctaaatg tcaatatggg ctttcagact    6480
tcaggattca acatgcccgt tactacaaac cagaacttct acagtagtcc aagcacagtt    6540
ggagtgacca aaatgactct ggaacacctc ccactttgcc aaacttcagt gctttgaatg    6600
ttcctcctgc tggtgcgaag ccaacccaac aaagacccac agatatgtct gcccttaata    6660
atctctttgg ccctcagaaa cccaaagtta gcatgaacca attatcacaa cagaaaccaa    6720
atcagtggct taatcagttt gtacctcctc aagtttctcc agctacgggc agttcagtaa    6780
tgggaacaca gatgaacatg ataggacaat ctgcctttgg tatgcagggt aatccttttct    6840
tcaacccaca gaactttgca tagccaccaa ctgctatgac caatagcagt tcagctagca    6900
atgattttaa agatcttttt gggtgaggtg tctatttga aggattattt cagttccaat    6960
catgggtgag ctgatttaca tctttatgta gttggcttgg aggaactact tctatgggac    7020
agtgaatggt tctgtgacag aaaacatctg tgtccatgcc agcatagtag ttgtatggac    7080
ttctaaccag ttgagttttt ttaaagcact gaggattttt ttcctcttac caactcctct    7140
ccaggttttt tgttttttt ttttgagacg gagtcttgct ctgtcgccca ggctgaagtg    7200
cagtggcgcg atctcggctc actgcaagct ccgcctcagt ggcgggttca cgccattctc    7260
ctgcctcagc ctccctagta gctgggactg caggcgcccg ccaccacgcc cagctaattt    7320
ttttgtgtgt gtttctcgta gagacagggt ttcaccgtgt tagccaggat ggtctcgctc    7380
tcctgacctc gtgatccacc cgcctcggcc tcccagagtg ctgggattac aggcgtgagc    7440
```

```
caccgcgccc ggcccctctt caggttttta agacccaac ccttcccagt ctcaaagaga    7500
aaaaggacaa ctgagttatc ttgaatagct gaattttta atcaaatgtt tattttggct    7560
tgtgaatctt ggtgttattt aaaaaattga gttgatggtc attgcaagct catctatttt    7620
aagtaccaca tggtacacag tctaccttca caagtcatta gtgttcactt taatatgtaa    7680
aaaatcttga tgctgtattg atttgcttgc atttaagatg acagtgagaa atgataagc    7740 ataaagagat cagcttattt gcttttccg aggttacttt tcagatgaac taatgtttag    7800
tacaaagaga ctgagcaaat actacaaaat ttaacttgac ctacatttcg ttggctaacc    7860
atcttaaatg caaactaatc gttgtaaatt atattttagc atggtctgcc tcaaatggta    7920
atgtattttt ctgccttcac ttggatatat ttagagtcac tttggtatat gctgatttgt    7980
ttggatattt gacaaagcac tctgatgtga cttccctgac tactaacttc atatttcatt    8040
tcaaattcaa acttctgagg ttgcagcata tatgaattgt gttttcaaaa ggagatttgt    8100
aagaattaaa ctatatttaa taagtaaact tttgagattt ctgccgtatt ttttcaaatg    8160
taataaactt ctctctcaaa aaaaaaaaa gctgacattg atagagtgcc tccacagtgt    8220
gcaaggcgca ttgtactaaa tataagtatt tttcatgcat ttgtctcatt taattcatat    8280
aacctaggag gtaagtacct tctccatttt acagatgagg aaactgaggg ttagagttta    8340
ggtaacttac ccagtgtcac attgtggtat atgcagagtc aggactcaga ccaggactat    8400
cactgtacca tagtaaattt atgttatgtg aaggataggg aagattttt agaggaaact    8460 ttttcccctc ccctttccga tttccttcac ctcacatgtt ttgggattta gatgtaccac    8520
ttctttaaaa taaaaatgat aaaggactta tttcagtacc agtgctcagt aaaatttaat    8580 gcaatttta aaaaaattta atgactttga gaatatacta aaatgtaatt tttccagatt    8640
ttgaagaatc ctccacagaa ttcaattttt gtcattacag agcatatcat tttatccctt    8700
tggaactatt ttctgctggt tgcttttgtat tgcttttcc cccaggcatg taagttgaga    8760
tcagacctct ttcactttat ttttaaaaag tatatatcca attattctgt gtcaattaaa    8820 aatacttta aaaattcagc aggctgctgc tgcttcagag acacagacct cttttaaacc    8880
gtactaaata gattgatagg gagaaaatat gaaatttcta caaattctga actttaaaag    8940
catagttata aagacaggaa caacagacgg gcatatgtga gggatgagca tgggaagagg    9000
gagaggatca gaaaaaataa ctgttggatt actaggcctg gtacctgggt gatgaaataa    9060
tctgtacacc aaaccccccgt gacatgagtt tacctacata caaacctgc acatggaccc    9120 ctgaacctaa aataaaaact tttaaaaatt aaaaattaa aattaaaaa agcatagtt    9180 atagtcacta agcaatatat ttagatagta tgtaattcag atttgtggta tctgcatgtt    9240
ctcactcatg tggaagctga caagttgat ctgctagaag tagagagtag aatagtggtt    9300
actagaggct aggaagggta gcgggaagga gggatcagga gatgttagtt aacagataca    9360 aaattcagc tggataggtg gaataagttc tggtgttctt aagcaccata gggtggctat    9420
agttggcaat aatttgttgt atattttcaa atagataaaa ggtaggattt tgaatgtcct    9480
caatgcaaag aaatgataaa tgcttgaggt aaggaatgtg ctaattaccc taatttgatc    9540
attatacatt gtatacaggt gtcaaaatat cacatgtacc ccataaatat attcaattat    9600
tttgtgtcaa ttaaaaatac tttttagaaa ttactgtcaa aaaatgtatg ccatcatttt    9660
tactttagaa gttctcttac taaaagaaaa aaacctgga gaaaaaaaaa ctatactact    9720
aggatatact aataaaaatc agtggagaaa tgatcttgtc tagtatttct ttggttatcc    9780
tactttagaa aaactaattt tcatcaattt tctctgtagc ctagtaaaag ttgaaatata    9840
```

```
ttggattcat ttacatagac tctcctcttt agatgtctgc tccaatgagg atctccctga    9900
agttgagctg gtgagtctgc tagaagaaca actaccacag tataggctaa aagtagacac    9960
tctctttcta tatgaaaatc aagactggac tcagtctcca caccagcggc agcatgcatc   10020
tgatgctctc tctccagtcc ttgctgaaga gactttccgt tacatgagtg agtatttttt   10080
ttactctttt agtttgtgca ttaaagtaat gatcatgggt atcttggtat tgattttaaa   10140
agcactgatg tttagtagcc attgttcagt gtatacctac ttttatttga actgatttca   10200
caggaagaga taattctgtg ttatgtctga atgcagaaag tttgtcatcc ttatgactct   10260
cagtgtctag tgttgcaaac atacttagac gttttcgtta cttgatattt tcctcagact   10320
gagtagaaaa gggaactttt taaaaagcaa agtgatttaa aattttaata ttcctttata   10380
actgtcaaca tttattatcc cagtagtttg ttatcctaag ctatcagctt ttgactttta   10440
tctttattaa tatcgttggt aaacacagtc acaagaatta tgtcagcata acgaagcata   10500
gttcttaggt acataagtag ttttaataat gccaggagaa ataaatatac cctatatagt   10560
aatcttcatt atttaaggat tcctaagtga gagactgagc cagatttgtt ctgaaaatag   10620
gtctgtttta caccaagctg ttagaaaaga caaatgaatt tttaaacttt gaagtgtgga   10680
gacctttttg catttgatcc caaaaatctg cattaaggct gaaattactt ttctaaaaat   10740
tcatttggta aaaaatgttg tgtgcacagt agctgttaga atttataata aaagcttatg   10800
agttcaatac tgatatgttt gtgaaattcc tttaattaga attaagtagg tgattgcatc   10860
agatcctgga cattttccca gtgagtgctt tagtgtttta atgccagatt gtcgttggag   10920
aaggactatt gtgcaatact cattttcata gtaatcacta acttgttttc agcactagtt   10980
tcctagaatt ttttttctagt cgtttcttag aacttattac tgctcaaaaa aaattataaa   11040
cattgtttca gctgaaactg aaatatcaag aagcccagtg agtgttgtgg tgttttaatg   11100
ccagattgtt actggagaat gtctactgtg aaatactcat tttcatagta atcattaact   11160 tgctttagc accagtttcc tacaatttat ttctagtagt ttctgagaac ttaactgctc   11220
aaaaaaagta taaacattgt ttcagaaact aaaatatcaa gaagcccaaa tactattgtg   11280 ttttttgtcct taatatttct tttaaatagc taaattaagt taaattaagg ctccaaaggc   11340
tttcttgacg ttttagtttg agaatttgct tgcttgagat ttttctggaa aaacattttt   11400
agaaggaaca gtatttctta tttctagttc cctttgttca ttgagtgttt aaatttctga   11460
gaactttctt ttcttttctt tttttgaga cggagtctcg ttctgttgcc caggctggag   11520
tatagtggca cgatctcgcc tcactgcaac ctctgcccgc ccgggttca agcaattctc   11580 ctgcctcagc ctcctgagta gctgggatta taggcgggcg ccactatgct ggctaatttt   11640
tgtattttta gtagagacgg ggtttcacca tgttgattgg gctggtctcg aactcctgat   11700
cttgtgatct gcttgcctcg gcctcccaga gtgctgggat tacaggcgtg agccactgcg   11760
cccggcctaa attgctgaga actttcaaac tgaaatttca tctggataaa tttagtttgt   11820
cattattttg acaaagcgtc acagaaagtg ccctttagtt tatttgttct ttgtggaccc   11880
ctgcaatcaa tgtcacttga gaaattgtta gaaattcaca ttcttgggcc ccctactcca   11940
cctacaaaat tagaaactct aagggtgaga cagtcatagc tgcctgtgtt ttaaagagtc   12000
ttcctggtga tactgatgca cacacaagtt tgagaaccac tgatacaaag cattgccaac   12060
caaagcaaat ggccatttca cagtgacatt aattggagaa ttaaggaatc ggagagagtg   12120
tataattttg cagataaata tggtcataga aattattact tccaattggt aggtatactt   12180
ttcctcaggc tctgccctca aaaattatta acctgtactg gcagaaaaga acatatgact   12240
```

```
gatgaagttc aggaagcatt aaccataaac ccagtcatag aggttagcag atttattttt    12300
cccttagata agctctctcc ttcggttcca caagagaatt aagctataca ccctaagaca    12360
cttagcgttt atacagtgga ttaccttatc acccatgcat catgtactag ctttgtacaa    12420
ttcttgggag aattgagaaa attgtcattc aaatggtctg tagggcctga ttctcccctg    12480
gaatcctgtt gagaaagact gccctagatg gtgtgtatca tcagtttctc tcagtcattt    12540
tgaaggcaga aatgtttgct atatcgtagc agcaagggct gtggtcactg ctttagggtt    12600
aaaacctcaa gacctgcctg taggtgtcag gagctattgt agcttttact atgccatgtg    12660
ggcactgttt gtgtttcatt tctattttgt tgttgttttt gttggttttg tgtgtgggaaa   12720 gttggagagt gctgcaagat tagaattctt tttgaaattc tatagttgtg gtaaaaactt    12780
tagatcttga gaagggacat atgagagaac tatcaagcac catctcatgt aaatgacaga    12840
tattagaatg gattatcatt ggtgtttccc atcctgaaaa taatgtgaga ttgagctagt    12900
taatgtgaaa ttatgcaggg acagaacata agtaaggat tagtgaagtg cttatgtatg     12960
ttaaactccc accctgtatt ttcaggaaca ttagattctc caaacattac accaaaaatg    13020
ttgaacatta attaacaacc tctggaaacc aagttgcaaa attgttctgt aaaaatatct    13080
atcgtctccc tgatgtataa atacttttt agagagttag ggaagtctat gtctggaaat     13140
aagcaaggat cattgctaat ttctgtatca tttaacatat tttcaacaac gaaaactgac    13200
gggaaaatag gttttgatag gattgatttt aacaaagaca acctgcttgg ctacctctac    13260
attcctggct acagaattat ggtgaagaac tagtctgtgg tttttgaagc atttaattac    13320
aatgtctaaa tgccaagact ttaaacactt aagagttttg ccctgagtac ttttggaatc    13380
attccaagca gcatgtcttt atcaggagta ttgtgttaag gaagagaaga cagaactgat    13440
tccactgcag agagaaaaat ccattgttct tttccattgg aaaaggaaaa atccattgtt    13500
cctttctgtt ttgtgcctga catctttctg tgcaactgaa gaggcccagc ctttgtggat    13560
tggtagtatc taggttgcgc attcgacata agaatttgaa aattctgatt gcactatcta    13620 actttttttgc cataacaaat acttaggcat tttaaagttc attttgcttt tttgaaactt   13680
tttaacaaag gttcctgggt ttttgtgggt tttttttttt tttctgtttg gaaaataaca    13740
tttgttctat ggaaaactgg caaaacgctg aaagaaaac agatcagcca tagtccttac     13800
ccagagataa ccactattaa cattttaatg tatatccttt caggctctgt tgaatataga    13860
tatttataga tatgctcaca ctttaaaaag caaaattggg atctatgctg ttttattata    13920
taacatgcat tcacaggtgt atatgctggt atttcattag acaaggtctt ttttatgttc    13980
ttagtggggc tgcggtagaa acagcagcac agtggaaaga gctcattact ggactcttac    14040
atcatctgag ttttttctaa tgaccttgtg agatgagcgt tattatcatc tccatactaa    14100
aattccagct ttgccactaa tagctttctt cgtggtcttg aacatgccac ataatttctc    14160
tcagagaaga ttcctcatac aagaaagtga gatcattaaa ctagataact tcttaaggtt    14220
cagctttaaa tttttatgct gtgacagatg gtaagcattt ataggaaata ttttttcatt    14280
tttcctcact aaaacatatt ttattctaaa catttcttca ctgtattact gtgtccttca    14340
tttttttctt cccctttcat catatatgac ttgtggttca cagttgtttt tatatcctta    14400
acttactggt cttactccaa gttaaatctg ccacttcatc tttaactctg gtcagtcatg    14460
tcatgtgttt gttaaactcg ttgtataaaa actgatttta actgagccta taggatgcct    14520 gattttttgct ttgggtgtta accccagatt ggtggtttta attcctggct ccaggtcatt    14580
ttcaacacct gggaatcttc tgcatactac cagcgccaca gggctccctg aaattaatta    14640
```

```
aatcggaatc tggacttaag agccattgct ctatattaca tttgggttta caaccattgt   14700
ctggttttct gtaattagtt tagagcatgg atatattgat tttatatttt tcccataatt   14760
ttgttattga gaccagaagt aaaggagacc attcactgta agtatttgcc ttaattattt   14820
aatcctttgt tcccgctatg ctaccaaatt atattgtgtc tattccttag gcccaaaagt   14880
ctgcttccct tatcactgtg gttaaatcat tgttagtttc tctatttgta aatataaatt   14940
cttttggagt acaaatgttt atttctagct tttaagaaaa gtttttatat tttcagttta   15000
aatctttttt agttatctcc aataccatca agccagcact ttgttttact tttaactagg   15060
aataaggcta ttattaataa ttaagctata ggtaattccc agattcattt tagtcagtgg   15120
tgccagggag aaaataagct cagataaaag taaaacatat ctaatgatat cccttcatac   15180
tcagtcgtgg gcaccctaaa gtgttaagat gggactatgg aactatgaat tactgccaat   15240
tcagagaatt taaagtcaga atcatttcat acctaccagt tctgtttaag gagtagtaac   15300
tataaacagt tatatgatac gtagcagtta acgaatactt tattgcttag tagattatca   15360
tgtttgatcc tcttaataac ctcatgagat gtgttatcac ctccatattt attatctgaa   15420
tctcagaagg gttaagtgac ttgttccagc tcactaaaat ttatgaattc agcttttcta   15480
ctccaaagcc cctgtccttt tcacacttca aggcaaacta gttataataa aagagtctaa   15540
gtcaaacaca gaattatgtt ctgcagtaac gtatcatgtt caaagtcaaa agagccctct   15600
tttgttatgc attattaact ttaagatact gtttagtgtg actggaatca ttggagtcat   15660
atttgccctt ctcttttgaa ctaaattatc caggtacatt gacaattcct gaacttgtga   15720
agtgcagaaa tacagggctt gaattataca actaataatg tagcatacaa tttatttat   15780 agctgagacc tagatgggag aaagattttt atacaagtaa agggttttta attaagccta   15840
aaggaattat ggttcataac agaaccagaa aaagtccttc aaatcctgtt ccttgtttac   15900
attagctcac atggtagatg atcatagatg gttatgataa tcacagcaga attccaatta   15960
aattccttta taacagcata acccctcact gataccccctt agtaacttta atttagatta   16020
gactgtaaag caatcagtaa tttaatccat tctcccagcc aagattctca taagtgagtg   16080
gccaaacttc ctgtcttacc aggggaggag gagatagtca agatgtgact gccttttgat   16140
catttgatac tttcttaatt attgtgtggt atacacttcg tttgtaatga ttggactatt   16200
tcttgagtgt ctaatacatg aaacatttct ttttttttcac atatattttt attctcctga   16260 atgactttt gtaaaaggct ggggttttg ttgttgttat ctctcaattc ttattaatat   16320 ttaaatttt tcattattgc taaagcctat aaatagttgt ttttaactat attagttcta   16380
ggcacagaca gggtggagca gatgaccaaa acttacaatg acatcgacat ggttacacat   16440
ctcctggcag aggtaggaat atcttttctt tctccagtac aaaaaggtaa aacttgagga   16500
tcatttggaa tctatcaaat ttgcacatca aatggaaaat gttgtacgtg ctctgggtta   16560
ttttgtataa ggttgttgct actggaacaa ctgacatttc aaagtagaat gtttcctaaa   16620
gtttattatt gtaatgctat acaggatttt tagttattta tttatttaat ggtgttgact   16680 tgcctccccct tcctagaaaa gcattaatct taaaaaaaaa atcattttaa aataatgcct   16740
gctgttactt actctacagc agagctgccc attcagaaag cagtatcatt atcattgcaa   16800 atcaataacct gcagtttgga gcatctcccc tttttttactt ttagtttggg ctgtgatttg   16860
agctcacttt gtctatggca ttttaatat gtatagtgta tctcctctag ttggcaatca   16920
gtagaggtct cccttttgtac ctgtttcagt tgatcttatg gaagacagtc tttcttaac   16980 atatccttct cccctctccc cccagctctc cagaatgatt tctatgtatg ccatttagcg   17040
```

```
attatttaaa atgagcctta aaaatgtgga gataatccct ccatttcat  atgcctatgg   17100
agagaaagga tagaagctta atttatttta tataataatt actgtaagca gatcatatat   17160
aaggcagtga gatgtatatt gacagttttc tatcctatag aatacagtct tcaccactac   17220
cacacagatg gaattcctat gcccttgcga agtatcacta tctgcccaga aataataact   17280
ctgggtggaa gcctattgct tgacttttct acagacttcc ctgcattacc accagcttct   17340
tgagacttct ttcttctcta tactctaggc agaatcctgt ggcctcaaaa tttccagtct   17400
tttatctcct gttttatttc atatcatcat tcttgaacca gttgacaaca gagctcttgg   17460
ctgcacttcc ctctaagctg ctgaatgcac ataagctttg ccctaaatgg aactcttttt   17520
ttacatacgt acctgatcca tatcttaaat acctaattct gtatcattac catgcttgat   17580
acacaattgc tttcaacaaa tatttgttga gcttttactg tacagaccct atcctcattt   17640
ttaaagacta tgttgatttt ccaattcccc aaaattgtaa gtttaaagtt tgggttgcta   17700
gactcttaat ttactaggat gatcaataaa tctcacttga tatcaagaaa agagatgtcc   17760
tcttgcattt agaacagtgg tggtcatcca tttgaccaac gttttaaagc actacctgtg   17820
tgccagaccc tgtgtttatt cattttaatg aatgaatgaa tcttgatgct ttctaggacg   17880
ttgcttttga ttttaccaaa actgaccaca aaatttctga actgccattt aaccttgttt   17940
atactcaaag aaaaggtgta tttggtattt taacagaggg atcgtgatct ggaactcgct   18000
gctcgaattg gacaagctct cttaaagcgg aaccatgtct tatctgagca gaacgaatcc   18060
ctggaggagc aattgggaca agcctttgat caagtaagcc tttgatcaaa tgtctgcagt   18120
atgaaataat taggttttat gcaattgaaa atttattttc ctaggtgtcc ctgaaatgat   18180
ggcaatagat aaataacacc agtacttgtt cactttgttg gtgtccatta aactaatcag   18240
tagagaaatt aaatgttaat tgtacagagg agaactcacg taactacctt ggtcaactta   18300
aagtctatat taagtatctg taatacctgt ggcaccctgc ttagatatta aaactatcca   18360
tacccttttg tgtagacttt gtgtgtgatc ttatctgaaa tttattttta aaaaataggt   18420
acccaaatat gtgggtatct ttattcaaaa accaaacaaa ggaagaaagt aaaaagaaac   18480
tttgaaaata tatttattct atagcaataa acgtttgtag tgagaactga cttattatta   18540
acttggatgg ttacatttca aattttctgt aacttgttat ttttatctgg tttcgtttgt   18600
attttatgaa tgcattatgg atgatagcat ttgagccttt aggttgaaac tatttgttcc   18660
gagaactaaa atcagtactc ctaggaagac atgcacagtg atatacatct taaaattaca   18720
agcccttatg ataagagttt gaagtaggga tctattctga tactttgaag gttcttcagt   18780
tttgtcatgt tttcaactat gaatgtatta ttatcttacg tgaattttc  tcctatattc   18840
ctatcatata tatacaataa gaaaattagc ttttcttctc acctaggagg gaaaaaagct   18900
gtactgttga attaatgctc taaaattgta acttaggagg tatctgggt  ttgttattct   18960
cttttagta  cttgttgcgt tagtcagtaa aacctagcag ctgattttgt gattttcttt   19020
tgtgatgaaa ataattgtt  ccatgaatta gaagctatat tgctataaat aatgcaaaat   19080
aaagaacatg aaaatcaagc attttatatg gacaggttaa tcagctgcag catgagctat   19140
gcaagaaaga tgagttactt cgaatcgtct ccattgcttc tgaagaaagt gaaactgatt   19200
ccagctgttc tacacctctt cggttcaatg agtcctttag cttatctcaa gggttgctgc   19260
agttggaaat gctgcaagaa aagctcaagg aactggaaga agagaatatg gctcttcgat   19320
ccaaggtacg ttcaacctaa ttgccatttt cctttacttt aaaggctata aagttcaggt   19380
ccaggtacta ttgaggtgaa atatggcata agtaaggatt tgctattggc attccaatta   19440
```

```
gagagtcgtg acaaggagc tgtatttttc ttgccttcca ctgttcttag atcccactga   19500
aaagtggata gtagcaggtt gacagtacaa tagtgaaagt cacaggatag aaaatgtatc   19560
ttgtggagtt tacgcaagta actaagtagt tacaactgtg ataactttta cacaagtaac   19620
taagtagtta caactgtgat aagaactatc tcagaaaatc acaatattct gtgaacttgt   19680
atagtatggg catcaaggaa gtcctactta agcaaggatc attttagcca aggccaggga   19740
tgagccaggt agagatgtat gaacaggttg ttgggttttt cctttgtaa gtgatgaaat   19800 ttagtcttca aatgagaatt aaaggttttt gtagttattt ctataaaatc actagaaggt   19860
attgtcacat actgatttt ttcttgaagg cttgtcacat aaagacagaa actgttacct   19920
atgaagaaaa ggaacaacag cttgtcagcg actgtgttaa agaacttcgt gagtattaac   19980
atattctctt ttgtaccttt ttggacaatt ctttggtagg gtatctccac ctcggaagtt   20040
agatcactgg tttcagtaga agcatctcaa gaaacaattt taaatggtta ctgaaaatct   20100
tagaatatca cattgagcct acaaccctaa ataagatacc atatgtattt ttaagaaata   20160
tatttgtttc aaattgcaat tatcattaca gacctatgtt ttgtaagtaa gttatagcat   20220
gttagagtga aaggaaccaa agctctcata ttgttgatga ggaaatagtc ctgtagagga   20280
agatgatatg ccaaagtcag aaaactggta agtggcagag ccagggctta aatgatggca   20340
taaaacctaa caatcaatga gtataaagtg ccagttatgt ttctttaaag gaatgtgttt   20400
tagtttgagg taatgttaac caatttttta aaacaagtca gttggaaaaa gattggcttc   20460
actggagaaa gataaattta atttctccat aaatacaaca gttgtccctt acctgcagtt   20520
tcacttctca ttgtttctgt taaccgtggc caactgcagt ctgaaaatat aaatcaaac   20580 attccagaaa taacaattc atgagtttca atcgcgaac cattctgagt agcgtgatga   20640
aatgttgtgc catcctactc catacttccc aggatatgaa tcatccgttt gtccagtatc   20700
tccacgcagt atatactacc tgccttcagt cacttagtaa ccatctctta gtagccgtca   20760
gttaccaggt caactatcgc aatattgcag tacttgtgtt caggtaaccc ttattatact   20820
tagtaatggc cccaaagtgt gctgatatat tgttataatt attttattat tagttattaa   20880
tctcttactg tgcctaattt ataaattaag ctttatcatc ggtatttatt tgtaggaaaa   20940
cacataatat atacagtata gagttcagta ctatctgtgg tttcaggtac ccactgcagg   21000
tcgtggaatg tattcccgac agataagagg ggactactgt atatagcctt ttacattgaa   21060
aacaatgata tgaaaatatc acatcaattc atttgggcta tgggcttcaa aatgtgatat   21120 cttagaaatag cagaatacta gagaaccgga aggaatgtaa attgaatttt ctcctccacc   21180
atgaaaacat taccccacctt ttacacttta aaatacagga aatgacttgc ccaagagctc   21240
tcagatccag atctcctgcc tgtgtatcgc catcctttga aatattagag gctatctgtc   21300
aattttaaaa tagctttaca tgacactgag aagtagcttt tctgcttgta tttacatgtc   21360 aaattttca tatgagatag agagtgaata aattcctagt ggaattctaa aggctctatt   21420
ttatgtgcat gtaagaaggc caggctataa caattgctct agaggcttta ctcagtttgc   21480
cacatatccc tgaaagggt atgccagaaa gtctgtctcc tacagaagca tttccgtagc   21540
tttatcacat tctgttatag attgtgactg ttccattctg gaaatgttcc tttgttagat   21600
ttgttaagat taattttcat tgcttgtggg attttatgtc cctaaagagt tctcaaagaa   21660
atgaatgaga ttatctcttt gcacttgccc tcctttcagc cttcttttcct tcataaagaa   21720 aaagattgag caaatatcgt tttcataaag aaaacgattg aagcaaaacc tttagcctgc   21780
ttgcctttat aagtcgtctc tcttttttagc ttcattgtct cctattctgt tcccagcatt   21840
```

```
tgcctatttc agaagaactt ttattttct ctattggttt ctctggattt ttttttatgt    21900
ttaagaaaaa tctattcacg acagtccagt gcttgttata aaacaagatt tagctcacaa    21960
gtcatagttt gccaactcct tctctacatt tgtattaatt taaaaaaatt tttttgctt    22020 ccaaggtgaa acaaatgctc agatgtccag aatgactgaa gaattgtcag ggaagagtga    22080
tgagctgatt cgataccaag aagagctttc ctctcttttg tcacagattg tagaccttca    22140
gcacaaactt aaagaagtag gtttattcat tcattcaaca gatatttgtt aagcactcac    22200
atagtatctt gcaccatgct aagtgctaga tacaataaac aaaataaaca ttgtccctgc    22260
ccttttaaaa tgccctaatc tgattgctgt tttaatcatc tttatgtcat ataagatatc    22320
atgaataaat actttcaagt cattatttct ctttgtaaaa tggggttagt gcttcctcag    22380
aaagtggtgt aaattattga ctcatgccca ttgtcctctg aacaccttga tagattttgt    22440
attcgaatgc ctatcttatt tagcttttga aaggttagct ttttgtaggc tttaagatga    22500 tacccccagag agaaattctt cacatgtctt tataagaaag agaatagcta tattttactt    22560
ggaaaggctt cacatgtctt ttttaatatg ttgttagcat gtgattgaga aggaagaact    22620
aaaacttcac ctgcaagctt ccaaagatgc ccaacggcaa ctgacaatgg aggtaatgaa    22680
atctttatct tgtgtaattc aggaggggaa agagtgacta gtttctttca tcttcatgaa    22740
taagaattat taaaggggaa ttaccagatt taaaaaacaa caacaaaagg ttaagatgat    22800
attatgagat ctaagaagta aagcattttg gctggttgtg gtggctcacg cctgtaatcc    22860
cagcactttg ggaggccgag gtgggtggat cacctgaggt caggagttca agaccagcct    22920
ggccaacatg gtgaaacccc atcactaata aaaatacaaa agttagctgg gcatggtggt    22980
gggcatctgt aatcccagct acccaggagg cgaagcagga gaatcactgg aacccaggag    23040
gtagagattg cagtgggccc agatgtgcca ctgcattcca gcctgggcaa caaagcaaga    23100
cttcgtctca aaaaaaaaaa aagaaagaaa aagaataaag cattttaaaa gtcctgtccc    23160
taaaactagt aacgtggtaa catccttctt gattaatagg gaaaacctca actttataag    23220
attctttagg agtatatcac tcttttacca gctgacctaa actagctcaa cagttttaa    23280 aataagataa gttctagtag taaatctttg tgcaggtgtg tcaggagaag aagcaaaaaa    23340
tctcttactt tctatctaca taaaattta tttattaaat ataacttagt gattctttag    23400
catgcattag tatcacctgg agccaagcac agtagctcat gcctgtcatc ccagcacttt    23460
gggaggccaa ggtgggagga tggcttgagc ccaggaattt gagaccagcc tgtacaacat    23520
aaggaaacct tcgtctctac aaaacaatca aaaacttagc taggtgtagt ggtgcacgcc    23580
tgtggtcccc gctatttgag aggctgaggt agaaggatca cttaagccca gaagattgag    23640
actgtagtga gccataatca caccactgca ctcaaccctg gcaacagag tgatatcttg    23700 taggagggag ggggaaagaa tcacctcgga gagcaagttt taaatggcga tttccaggca    23760
ccatcccaag agcttctact tcaagtggtc tggagtgaga gcctagaatc tgcatttta    23820 ataagcatct tcaaccctgg tgattctgat gaactggggc atatactgca cttgaagaaa    23880
ttttacagtt aaaatatact ctgaaaatta tgtactcttt tatcagatgt gtatatctag    23940
ttgtaaagaa ggttctgaaa caaggcacga agatctactt gtttaggagg attgagcaca    24000
ctgacattgt atataacact ttgtaggctc ttgatcttgt cacttacaga cttcagagtg    24060
atgtttaaaa agattaatat tatactaaac ctaacttgac tgtagctgtt atacttcctc    24120
tgttaagtgt atgaagcatt caatattaaa ttgacagttc tggtagtcta gctacgtttc    24180
agactttcag gaagtcacat ccgtgtataa ttttggccaa gacacccctc cctaattctg    24240
```

```
gtagctcaat atatatatat acgcttcttg cttagtttgt tttagtctttt gtattgaaat   24300 gatattcata aagttagcta gccctctggg taaaatcaat acttatccca aaaggtttcg   24360 ggttttttt cctaatgtt gttttgggaa ggcaataaag tacactacca tcctttcttt    24420
tagctgcacg agttacaaga caggaatatg gagtgtctag gaatgttaca tgaatcccaa   24480
gaagaaataa aggaacttcg tagtagatct ggccctactg ctcatctcta cttctcccaa   24540
tcatatggag cttttactgg ggtaagcaac taagaaagat gctatgtatt taagaaattt   24600
tgtttaagat tagtttgtcc taaaagtttg atggtttatg atggtataaa acatctggag   24660
aagagatttt ttccttgttt ctggactcca attattgatt taggccctaa tttgtatatt   24720
gacatcttcc ttaatactct tatttattct aacaggtgac tttccagata tattgtatca   24780
ataatacata agatgagccc taaggaaatt cagtttagga ctgtgtacca tagaactagt   24840
taaacttggg tcatcctacc ctaggcccac agcctgccac ttacttaagt ggtgctttga   24900
atatctaaaa cctcttttcaa taaatcttga gtctcctgat atttttaact tgttagaatg   24960
taagcttcat gagaacaaga ttcatctttg tttgattcat ttataaatgg tattttgta    25020 ttaaaaaatt aataaaaact tctgagttta tattagaatt tgtaatgttg gttcaaagag   25080
ttgttttaac aatctgattc ttaaacttct gtgcaatcct gtgaactttt ttaaaagact   25140
gaaactatac attttagtag attttcttaa aaatagggag gcataatttt gttttttatg   25200
tttgaaataa ttttaaactt agagtaaagt tccaagagta gtataaagaa tttttgtata   25260
tccctcacat cgattcttca gttttttaaca tattattgct tttgccatat cattcaatct   25320
ctctttctct ttcttccccc ctgggctatt ttaacagtaa gttgctgata taccttatta   25380
ccccgtagta cttaagtgtg tatttactaa aaacgaggac atttggacac tcttaaggac   25440
actgtcctac ataaacgcac tacaaccatc agcatcagga agttgatgtt tatgcagtat   25500
tatcatctaa tccacagagc ccattccaaat ttttccagtt gtctcactaa tgtccttcaa   25560
aggatacatt gaattttgtt gtttccatct gggacagttc ttctgtcttt atttctcttt   25620
cgtgactttt gtaggatgtc ctcagtttag gattgtctga tgcatcctca tgattagatt   25680
ccagtaatgc attcttggca gaaatcatgc catattctca gagcatggtt tcaagaggtg   25740
cataatgtct gtttagccca ttgcaggtgg tattaattaa ctttgatctc ttggttaagg   25800
taatctgctg gtttttttcca ctgtaaagtt aacggtaatt aacagttaat taaattaaca   25860
ctactaattc accgtgtagt gatgaaaatc ggcagatact accccaacca agtgatcaaa   25920
gtaaacattt tatgagagat actttgagac taagtatcct gttcctcatc aaactattac   25980
ccactagttt tagcacccat tgatggttct tatctggcag agttattaca gtgatgactg   26040
ccaaatggtg atttttcaaat ttcatcattt ttcaacattt attaattggc attttttcttt  26100 tgtaagttag tgcattcctg tcccatttat ttgttcattt gttcacttag gtatgtcatg   26160
gactcatgga tttctatttt attcaataga ttacaagcta ttgttgtata ttcaatctgt   26220
atgtaggata ttcagattgt cctagatatg atcagtagga tctcctttaa gctgatcttg   26280
tactttttgt ctcagccctg gaatcagcca tttctccaaa gagctctggt tacttttatt   26340
gaagaattgt atttcgaatc caagatctgg gtgttaggtg tgcccattga ttgctactag   26400
agtattgtgg cttctagtcc ctctcagcag gtaggactag gaaatatatg tatttcatac   26460
ctatacctat actatatatg tgtatatata tgttttcatc catatatata taaatatata   26520
taatcatgag ttcacaccat tgcctccaat tccagtcatc ctcagctgag tcccactgag   26580
catgtcaccc atattagttg agtcctcacc cctgaccaga ggaagaggaa gcttgctttt   26640
```

```
tttttaaatg attttaatg ttataaaagc tatgcatgtt tattacagaa aagttggaaa    26700
ttacagaaaa gcaaaaagca atcgttaaat accattaaat tccaccctcc acagaatcac    26760
tgtcaacact agatttagtc ctcatccctg actgggggga agaggaagct tgcttgttct    26820 ttttttaag tgatttttta atattataaa agctatacat tgttttttgt tggtatttt      26880 gttttactt ttttttttt tttttgaga cggagtctcg ctctgtcacc cagactggag      26940
tgcagtggtg cgatctcagc tcactgaaag ctctgcctcc cgggttcacg tcattctcct    27000
gcctcagcct cccgagtagc tgggactaca ggcgcccgcc agcacacccg gctaatttt    27060 tttttttt tgtatttttt tgtatttta gtagagacag ggtttcacca tgttagccag      27120
gatggtctcg atctcctgac ctcgtgatcc acccaccttg gcctcccaaa gtgctgggat    27180
tacaggtgtg agccaccgca cccggccagc tatacatgat tattatagaa aagctagaaa    27240
ttacagaaaa gcaaaaaaa aattgttaaa taccattaaa tctcaccctc cacagcatca    27300
ctgtcaacac tgggtttatg gcctttcaga ccttttgttt ttgtgtgcct gcacatatat    27360
tttctattta tcatatcagc ttttccact actttcctat ttgaaaagat tatgaaaagg    27420
tagttggttc ttatttaaaa gttatatttc cagaatgtct ttttcccct gaatgttagc    27480 cttgactatt tccttgtatt ttattataaa accaaaagta taggattgta gagactctgt    27540
taatttaagg gcaacaatca ctttagaaat ctcaaactct ttttcttagg aatctttggc    27600
agctgagatt gaggggacta tgcgtaaaaa gctgagtttg gatgaggaat cttctctctt    27660
taaacaaaag taagtacagg tcacatgtgt tgttactcaa tcattggaat agaaattaaa    27720
aagaagccac aatccaaagt ggcaagtatt acgagattca gtagtaattt gcttactatt    27780
cagtgttttc ctcacagtgt cctttttttg tgagagagtt ctcttgtttg aaagcttatt    27840
ttctgatgat ttctcctaaa tagctcctca gggtggcttt atttctgatg gactgcacat    27900
acattctctt ctctagatgc tttagtggct agcagtgata taacgaaca cttcctttt    27960 tgacagagcc caacagaagc gggtatttga taccgtcagg attgccaatg acacacgggg    28020
ccgctctatc tcattcccag ctctgttacc cattccaggc tccaaccgtt caagtgtcat    28080
catgacagca aaacctttg agtctggtct tcagcaaaca gaggacaaat cactcctgaa    28140
ccaggggagc agctcagagg aggttgcagg gtaggaatcc gatgataaca gtgattctgc    28200
atttcttttc acattgccgc accagattca catacgcaca ttccagcatt actctactgt    28260
cccaagaagg ttctggaact gtcagttttc cttcacttat gatgccttgt atcattattc    28320
atgagacaga tcatgccaaa gtcaaatttt tttgaatctg tttggtcact agcatgaata    28380
catcggatga cacctttctca taatccgtgc tcataatctc aaccgctttg gtgatttta    28440 ggataaatgt aagtttgaat acatcttgag gaccatcgag gtgctgtcga ttttctgttt    28500
attaaacttt ggattttttt ttcattcctt ttattaattc agtacattga attctatata    28560
actagaaggt aaacaacttt actgaaaagt gagctgaaag cttttgcaaga tagatgtttg    28620 gcaccaaagg gaaatgtttc ctaacataaa aattcatcac actaggttc agttgcattg    28680 cctggtctgt cctgggcagt gttctgcacc cacagcagct ttgtgtccta ctgcctcact    28740
gtcacacaat tatcttagga gaagatctga aacacattta tgtggattta taccccagta    28800
tcccagagta cccacaactc agcttgctga tcttccattt gatatcaatt ataagatagc    28860
ttccagtttc aaaagtgttg aagtcaaaaa atgggcatca gacaactata aaaatgcagt    28920
attatataca aattttgttg tttccttta aatgttctgc agtgttgatg ggtgattctg    28980
tgacccaaag caaattttt tcatattta atatttta aattattatg ttttgtaact    29040
```

```
gatagtatgc cttagtttaa tccgtagcgt ttttttcctt ctttatgata cataaaataa   29100
tggtacctct tgcaatctat gatacagatt cagcaaaata taatatttac tttcgtgacc   29160
acctaatatg aatttataga tggttgaatg tgtagtttca taaattaaat gaaatagaaa   29220
attcagaaaa cacagaatat caataaagta ttatcttgcc tttcaagtca tttgcaatga   29280
tctgtaaaaa tgatatatag tgttgttggt gattttggtt tgttgttatt acttctatat   29340
tccaggtatc taggaaaata tcatgttttt aatatcagtc tcttgaatgc ttaccattat   29400
agaaaggaga ggtctgggtc atgctgatga tcctcaagat ctaatcagtg aacgcgattt   29460
tcctatagga gctcccagaa gatgggccaa ccaggaccct caggagatag tgatttggct   29520
acagcactgc atcgccttag cttgcgtcga caaaactatt taagtgagaa gcagttcttt   29580
gctgaagaat ggcagcggaa gatccaggtt ctggcagacc agaaggaagg agttagtggc   29640
tgtgtcaccc cgacagagag ccttgcctct ctctgcacca cccagtcaga gatcacagac   29700
ctcagcagtg ccagttgcct tcgaggtttt atgccagaaa aattacaaat tgtcaagccc   29760
cttgaaggta ataaatcagt aagggccctt actaagccat gtgacttact ggaagttcct   29820
ttccctggaa ttgagatttg tgtcttaatt ataggaacat tatgtgcaga tgatcttttt   29880
atcccttaat cttgctgttt gggtggcaag actgtagtac tttgtggaaa attaatgaat   29940
gaagagagtt gcattctctg aatcatcagc cagcagttct cttctgatgt tttttaatat   30000
aaacgtgagc agggaagagg agtaatcttt ttctgtcctt tgctaaggaa tatcattgac   30060
agcagtttcc atggttagat gaataagata tgataaatga taatgatcta gagataataa   30120
ttcatctcca ccttcctttt caaaagagtt ttttacccaa aagtataatt gacttagagg   30180
tgtgtgtgta cctgtatttt tccttttttc agtttagttt ctatactctc ctaagaaaga   30240
gcttgaattc aaaataaatt ccttcatttt ctggaacaat gacaatcatt gaatgattct   30300
ctgatattat cctaaaagag ttctgcatta aatgaaattt tgagtgtgta acttataaag   30360
acccctcaaa ctcaaagatt ttataactta gttgtattca ttaatgatca gtgcagatat   30420
ttgttggagt tgccattttt aggatgaaat gactacagtg acataattag acattgcatc   30480
tggtgcaatt acttgggatg atcattcacc agggttctgt agcctggaac cagtagaaca   30540
tatcctcctt ttcattatct tcttcatttt cctattctcc ctgggagcct ggcttttgac   30600
tttcaccttc ataggcatag ttccaggcca gagaagtatt gacttttttg tcacctggga   30660
aaatacagcc cacctcttag gcacgtatct tccatcactg cctcagcagc taagctcctt   30720
tcctattaag ggtgtctcct tgggtttttt ttcacccctt taggtgtcct ccttaactat   30780
taaaacagat tatgactcat acctttgaca tcttgtcatc ttccactgaa aactttaatt   30840
tgcagctttt accaaattat taacaccaaa taaatagttt tattgctgtc attattgtta   30900
ttacacatat aattttagct tgtgttttaa gatttgtggg aaatgtaaaa catgcctttc   30960
cccttccttt gttttgcata ttcaggatca caaactctgt atcactggca gcagcttgct   31020
caaccaaact tgggaaccat ccttgatcca cgaccaggtg tcattactaa aggctttacc   31080
cagttgcccg gggatgctat ttatcacatc tcagatttag aagaggatga agaggagggt   31140
attactttc aggttcagca acctcttgaa gtggaagaga aactttcaac atccaagcca   31200
gtaacaggga tcttcctgcc acccattact tcagcaggtg gaccagttac aggtgagaag   31260
agtgtctggt tgaatatggt ataataacca gaagtacttt gcattctgac ttactagaca   31320
gtcagctggc tacctctgct cactggaggg tacttaatct tgcatatcag ataatgaaaa   31380
tctatagcat tagtggcatt cctaattctc tccactttat cttagccagc ctgcgttagt   31440
```

```
agattgggta gagagctgga tgaattcaag tcagtggttc acaaaccttt tgggctcaga    31500
aactctttat actctaaaaa atcattgaga attccagaga gcctatctgt gcaggttata    31560
tctattgaca tttaatatat cataaatcaa aactgaaaaa ccataaaaat atgtattaac    31620
tcatttaaaa taattgtgtt acacaaatat gtttaatgaa aaatagctaa ttttttttaca   31680 tagtgagaaa aacagttgtt caagtctcta attttttgact taatacaaaa tagctttatt   31740
ctcattatca gcatctgcct tcagtctatt gcaatatgtt gtttcagttg aacaatatga    31800
aggaaatgca gccaggcaca acatgcagt tggaaagagt gttttaatag tcttttcaga     31860
tatgtgtagc tattttttga tattacacta aaactaggta agtagtagtt tcttgaacgt    31920
ttgtagcaat gtgagatctg aaaccctaac aatgaacttt tcattacttt gttaacatta    31980
aaatgcattg gtcaggctgg gtgtggtagc tcacacctgt aatcccagca ctttgggaga    32040
tcgaggtggg cagtcacctg aggtcaggag tttgagacca gcctggccaa catggtgaaa    32100
ccctgtctct actaaaaaaa aaaaaaaatt aaattaaatg cattggtcgt atcctacatt    32160
ttgaatatat ctttgagcca tgcttgattt ttaagatcat gcgttggtca tttagaaaat    32220
gttgattggt tcatggagtt atgcagattt tccaaatatt ggcacatttt attacgtaaa    32280
aatattaaaa tcatattaat atcaccacct actcatcaga aaagtcttca aggatgttca    32340
tgctttcagt ggtggatacg agttttccaa aactcacttt ttcttgaaag ctcacatttt    32400
gttagctgtt tttcttgaag gacaggctca cttcattcat ttttaacatg tctgtctttc    32460
acccaagtct gaattactat agtttgtctg ttagttcttt caagtaaaaa tggtattcca    32520
tgagaaaatt tcaaatcagt tgcacaagtg ttttcctcta gataaccact gtatctcagt    32580
gtgcagcaag agtgcttaat acatccttcc cattttttcat cacacagaac aggaaaaaga   32640
ctcaacggcc aagatccaaa atttaataga taattttttac tgctacttca aggacattct   32700
taagtgaata tggcttttta aaaaatacca agtgcataac aataaagaag actagtacaa    32760
cttggtgata ttgccttgtt ttgtgctgag gagccatcaa ttttgccttc cattgctttt    32820
gcaccagcag tgcaaatgtc aacccagtca aaagaaaag gcctctgtct taccattact     32880
atgaaagtag ctttgacatg tagactccca cagagtctgc agaccacact ttgagaacca    32940
ctagagtaga taaatttggc tgaatcattt ggatactaga tcttgatttt tttaatgtat    33000
tttttcagtt ttctcatttc taatctttgt ttatgccttt tgctttacag ttttaaagta    33060
ttggattcac ctatatacta accagttgat actagtacaa tctttatgta tatttatttc    33120
atttccagat ttggggattt ttaatacaaa aggtacttga taaatgctat attattaata    33180
aataatgatg agcttttttac attattaatc tagactttca atcttgtatt tgctccctaa   33240
aaatctattt cagttgcaac cgccaaccca ggaaagtgcc tgtcgtgcac aaactcaaca    33300
ttcactttca ccacctgtag aatattacat ccctctgaca tcactcaggt tacccccagg    33360
taagagtgcc tgggaaatct ggggcctcac ttctttcctc agctatattt tcatgaattt    33420 cttttttaaaa ttaccttcat tttaattcc agaatgttaa ttaatgttct gtgataatgt    33480
gtctttagaa tattttcaca ttgcattttc tcatttgatt attaaaaaag taggcagggc    33540
aagtgagtat gtattgtgta gagtaaactg aggcatggaa ggttgaggtg actggtccta    33600
gggcagacaa ctaataaata acgcagctgg ggcaatatac ccagagttag ccaaactgca    33660
agatttacag ggccagtcct ctgcacaagc tcaccttcac ttctgacaac acctgcaagt    33720
gcagagggtt cccaaaacca ctttcaggtt cagcaatttg ctagaagatc tcacagaact    33780
cacagcaagt tgttatactt gtggctactg tattacaagg aacgaataca ggttaaaatt    33840
```

```
atccaaagga agaaaggcat agggcagagt cttggagaat tctacacgtg tccttaggat    33900
tcattactct cctggtattg atatgtggca gtacacacag aatattacca accagggaag    33960
ttcacccaag tattagtgtt tacagtctgt attgaggctt cattgtgtag gtatgattga    34020
ttgaactcag ttcaacagag ttgaactcag tcttctggcc aactgatact gcatgactca    34080
aaggccctac cctaaatcac gtggttggtc tttttggcat ggccattcct caccctaaga    34140
ctactgggtg tggcctggct caccctaaga tttagtgtga tcagcctcca ctctagccaa    34200
agacactcct attagttgtg acatagattg cctccaagga gcagagggca aaggccagac    34260
ctctctgggc aaggccaaat tatttactac ataggctaga acttgaatat tctaatatat    34320
agtcccttat taagccatat tgatgccatt tctatcctaa caattcccaa aaggatctaa    34380
ggtagctttt aaagatatgt agaacatgta acagtgtaca gttactgatg tgtttgttgc    34440
ctgttccttt atatttacca aagataacta ctataattac tttaagtgca ttaaataata    34500
atgttaacta gaagtagaaa agaaagatgt tgcaaagggg aatcaagagt aaggatataa    34560
aatgggtaaa aaaaataaag ctagtgtgca aattgtacca taaagtctta tgttagccat    34620
gttagcttgc taaggttagc catgtatttg agtcttaact ttctagctgc cagtgtggag    34680
ggaaataaga ttatgatcca ccatgtctat aaaatagaaa caaatggatt atttacggaa    34740
gcatttggat gatatccact aaagatccca ataaagtctg taacaaaaaa aatctgcatt    34800
ttttctaca ttgttcttat agtcatcaag ataacaagtt ttacaaaatt ggttcttgag    34860
gagactctta atacaggttg atgccattat atgaagtgta cagtttgggt aaggacaggc    34920
agttctagag tctagtagaa atagggagat ttagagactg gaatacaat atatagactg    34980
ttccatatca gaggctttta gttggactgg tttgaccagg gagtcaaact catttgaatt    35040
ttgctgttcc tatacaagtt ggtgcttag aaagtttgtt aatttaagc ttacattttg    35100
ttcataatct ttaaaatttt tgatatcttg atatttaata tattgagtat tttatgttga    35160
agtgaaagtt gatctattaa atactggtaa catttgtttt gcagggaaat tggctaaaga    35220
agtaccatct ctatttcatc actgtttcct caagtacatg attcgttagt ttttcttttc    35280
gactaagcat agaataagaa ttttctcatt tgattattat aaaagtaggc aaggcaagta    35340
tgtattgtgt aaagtaaacc gaggcatgga aggttgaggt gactggtcct agggcagaca    35400
actaataacc cagctggggc tatatacccg gagttagcca aactgcaaga tttacagggc    35460
cagtcctctg cacaagctca ccttcacttc tgtatattca gtagtattac tgaatactga    35520
agtaatactg aagaagtatt actgaatagt tgtcgaagct attagttatt tttaatttcc    35580
taaaaacaca tgtttcaggt caaggttgag aaaaaattca tcctatggat attttttatac    35640
cattattgtt tgaaattaac atttcttgag aaaatgaaat ttaacaatta gaagttttta    35700
tttctcaatg aaataaaatt aaaagattaa aagaaagaa acttctccca gaagagtttt    35760
catgtttaat tgtgaaagat tgtatttttt taaaagttgg taaactgttt acccatggat    35820
tattgtctca atgtatctca ctttatggaa tggatatatg aataaacatt ctaaattact    35880
ttccttaatc ttcaaatttc tttgccttct atcataaaat ttaactgtat ttctacagat    35940
gtacatttta gagttaaaat ttaagagtaa agttatctaa gagtacagca ataccttca    36000
tatcccactg aaaagaaata tctttttaata agttaattac taagttatga attacaaata    36060
attaatcatt gaagtatcat gtcaaaattt tcattcccca gatctgttcc acagcataca    36120
gttacggatg tgtttgttgc ctgttacttt atatttacca aggataacta ctataatttc    36180
tttaaatgcc agcttggagc ttgctttta ttcttaaaca ctgtctccca cttttttttt    36240
```

```
ttttttttaa gctctgggtt cccttcatta tcctgtggaa gtagcggtag cagttcatcc    36300
aacacggctg tgaattctcc tgccttgtcc tatagactca gcattggtga gtccatcacc    36360
aaccgacgag attccactac aaccttcagt agcaccatga gcttggccaa acttctacaa    36420
gagcgaggca tctctgccaa agtgtaccac agcccaattt cagagaaccc cctccagcct    36480
ctccctaaat ccctggctat cccttccaca ccaccaaatt caccatctca ctcaccttgc    36540
ccttctcctt tacccttga gcctcgagtg catctctctg aaaattttt ggcctctcga     36600 ccagctgaga cattcctcca ggagatgtat ggcttgagac cctcccggaa ccctcctgat    36660
gttggccagt tgaagatgaa cttagtggac aggctgaaga gactgggat agccagagtg     36720 gtcaagaacc ctggtgccca agagaatgga agatgccagg aggcagaaat tggtcctcaa    36780
aaaccagatt ctgctgttta tttaaattca ggtagcagtt tattaggtgg actaaggagg    36840
aatcagagtc ttccagtcat aatgggtagc tttgctgccc cagtttgcac atcctcaccc    36900
aaaatgggtg tcctgaagga ggactgaggt tcagcagtta actgaccttt tatacaagtt    36960
agcacatgaa ggatagatat gcactgaaac atgtggtctg gtctgacttg agagaaaagg    37020
aatgttgcac aagggttgtg aatgtgaaag ggggaatgga ggaatggaaa taaaattggg    37080
atgagcccta atggaggaag tcgggcaaat tgaaagtata aatgaatggg ccatgagtgt    37140
tcagagggag aaaagaaagg tttaatatac tccttcagtt gagttttctt gtcttgaaca    37200
taaaaagtga atacaaataa attcagtaat actaaaacat acagagatac tgaacttgct    37260
ggcacattta cttctggtaa gcataaagca gagagaaccc aggttagaag gatgggaaga    37320
gaaaaggagc agttttattg cttatagaaa gccgttctga ggggttggtg gggtaagctc    37380
agtctattac tgagacaata gtgagatggc ttatatgttt cccctgttaa tatctggtta    37440
aattatgtat ccatcaaatg gtatgctcgc agcattagca aaattaggag tttcatcttt    37500
ttcattgaat cacaggtgga gactcctatt tccttctg tttcaggcc tttgagcccc      37560 tgggagccca ataccactc aattattttg tatttatgat taataaaagt tcattttta     37620 aatttgtatt tttatacaac ctccaaaaaa aaaacaact gggtagaggg tgggagggat    37680
ttacttttaa gaggcaaaat gtgagtaaat tgaaccaag aaaacttgtt tttagaatat    37740
ttcgtctgaa taagtacagt agccaaggaa tacaaacata attgcatgtt tttaaaaatt   37800
ccttggaggc tggaaggggt taagccagaa gtgcaatcaa taggaattag ggaatgttgt    37860
atatttatat atgtaaactt ttttgtaag aaaagttggt gacaactaaa ccaacttttt     37920
ccaaagtgcg ctatgcatat ttttaatgaa agatgacatg tatttgcaca aaaattctca    37980
ggcacattaa attattgtaa actgaagtaa aacccgggtg cttgctttga gattgtggtt    38040
ttttcttcct aatgtaaaat aaaataaaac acatctgcct tcttgatatt tatagaatta    38100
gagaataaac ttttaatgg gggagtcaaa gcttttctt tttctctaag gttctttttt      38160
tttattcaaa ctgtatgaaa tggcaaagtg aggctctggg gttagatttc agcattcagc    38220
agttgacaca ggctaagaaa tggaaagaag tagatctgtt ttttctcaat gttgctgagc    38280
aaagtctgct tctcatcaga tgacgtggct ttgtctagac agcacgcagt tcagaaagaa    38340
atgtctttat acaaaagaca tgatagagaa agatgagag aggggactaa ttattttgtt     38400
tatgaaaatg gcaagtaaat tacttgatct ttttggtgct taatttgcaa atgttttgtt    38460
cctttgtcct gacttaaagg cagttttctg aagaactctt gactcttgct cctatggttc    38520
ccataggcac acctattccc aggccaagga gagtccttcc tctccccttt tgaggcatcc    38580
ccgccatccc cccacttaga gctatgtgct caaaaagcca acatgaatgc agtggtaaaa    38640
```

```
atttgttagt tccttatact ttttagaatc tctcaataaa attttctaa ataaattcca   38700
caaaaacaaa gggtgaagat ggtctctccc tttcgttccc cttcactcag ttgtgctgag   38760
gtcaatagag tgtagagttt cagaaaggat tccagcaggt ttatatgtga atataagtgt   38820
ccctgaatgg ggcaggcatt aaatagaaga atccctgctg tttaaatttc ccgcatattc   38880
caattcactt ttaaaaaata ccatttgaat ttgtatttca taaagtgact ctggggtgct   38940
tactttagtc aattcttaaa attttttatt tgttccctaa gaaagtaatt actgtttctg   39000
ttgcctggac agttacagtt tccaggaaac atcaggaagt aggaaactgt agggccagag   39060
agtagtacaa cgttaaattg tccgatttat gtgtattact taaagctata aattgaacta   39120
gatcttgccg tgctctgtat tgagtataat ttgtatactt ttttataatt aatgactaaa   39180
tgatcacttt ggaggcaggg tggtgggggt gtattagcag ccaaataagc acatctgatc   39240
aaaaagaacc aggcttagat ttttttttaag tacattgatg ttgatgttcc accagaaaca   39300
ccttaagtgt atactgttgt gtaatgtctc tagaaaggaa tcctgtctta aaactggggtt  39360
ttgctgtttt ttgaagtttc tacctaaaat cattttggt atatcctgat aatctctata    39420
atactagaat tgtctgcaaa atatagtaag aagaattgga gcctaatagc tgattcctcc   39480
caatttatct gttatgtttt gtcactattc acattttagt cttttctacg ataaaaattg   39540
tatgtgtact ttcatgccag tataggaaac ctcaatcttt ttttttttttc gcctttaaga  39600
aggttttcag tgattatacc tcaggtattt ctgagtgtcc tattgtctaa taggagaaat   39660
atcttcccga gctcagaatt aaaagttctc ctaaattatg aagatcccaa atcttatgta   39720
aataaccta ggcatgagtc cttagggaga agttaatgac cattgttaaa gtgctttttt    39780
agaaaatgtt gtgctgtatg ttcttgattt gacataaatg aatagacttt ggcaaggggag  39840
gaaataagtt aaaaggcagc ttacaagagc ctattcccta taagggtat aattttacac    39900
agtactcaaa gcttgttatc ttttctgacc attttagtac agaattagta cttggtggtt   39960
actaacatca acttgtgaca tctagaacta gggctcttag tgtttagtgg gccacttctc   40020
tgatgtcaga tgcatgcaga cctgtactcc acatgcaacc caacagcagt gcagtgtgat   40080
aactgagcgg tcgcatggca gaggacatcc ccctcagagt gggcacaagt gccctctagg   40140
gcagccaggg gaatactatt gttcgatacc tgggatttga cttttgtcaaa cagctctttg  40200
tgcccctatc tttgttttgt caaatgtaga tcagttaata aacatgagta gcttgaattt   40260
tcatttgtct ccctgtgtct ttgtcacagc tgtctgcaca ggtaatcctg tactaaatct   40320
tttctgttat gttttttggtt agaaaacaac ctctacttgt caaaccaaca catacacaag  40380
aaaccactaa tagtaataat aaacagatct taatgtattt tcctagatat tttttaaaat   40440
agcatagaca gtatctatgt ataccataat acttccttag caaaagtaac agcaacataa   40500
aaataaaatc taaagtcatt gatatgcaga taccaagttt gagaagattc gggaaatatg   40560
aagcagttct tttcctgtag tccacagttt tctgttgatg ctcttagcta tttaaaagtt   40620
atttccaaga agctaaattt gaacattgtt agactctaac agaaaaggtc ttttgatact   40680
ttgtcttctt cacaatttaa tttctttttt ttttataatt tccatttttta ttttagattc  40740
tgggatatat gtgcagggtt gttacctgga tatgttccat gaggctgagg cttagagtat   40800
gatagatcct gttacccaga tacagagtat agcatccaat acatagtttt tcaacccttt   40860
ccccccctcca tccctgctgt aatagccccc agtttctatt gttgccatct ttatgtcctt  40920
gagtagccag tgtttacctc ccacttgtaa gtgagaacat gcagtatttg gttttctgtt   40980
tctgtgttaa tttgcttagg ataatgacct ctacctacat gcatgttgcc atgaaggaca   41040
```

```
tgatttcagg gttttttatg gctgcatact attccatggt gtatatatac aacattttcc   41100
ttatccagtc caccactgat ggacacttgg gttgattcca tgtctttgct attgtgaata   41160
atgctgcgat gaacatgaat gcatgtatct ttttgtagaa tgatttattt tctttggat    41220
gtatacccaa tagtggaatt actgggttga atggtagttc tgatttaatt tctttgagaa   41280
atctccaaac tgccttccaa agtggctgag ctaatttaca ttcccaccaa cggtgtacga   41340
gcattccctt ttctccacag cctcgctagt atctgttttt tgtttatttt gttcattatg   41400
agacagagtc ttgctctgtc acccaggctt gagtgcagtc gtgcaatcat ggctcactgc   41460
aacctcaacc tcctgtgctc aatcgatcct cccacctcaa cttcccaagt agctggaagt   41520
gcaggtgtgt tccataaagt ccagttaatt tttgtatttt ttgcagagat agggactcac   41580
catgctgccc aggctggtct caaattcctg aactcaagcg attctcctgc cttggcctct   41640
gaaagtgctg ggattacaga catgagccac tgcatctggc acatattatt attactatta   41700
ttatacttta agttctgcgg tacatggcaa aacatgcagg tttgttgcat aggtatacac   41760
atgccatggt ggtttgctgc acccatcaac ccgtcatcta cgttaggtat ttctcctaat   41820
gctgtccctc ccctaggcac ccccacccc caacaggcc ctggtgtgtg atggtcccct    41880
ccctgtgtcc atgtgttctc attgatcaac tccacttata agtgagaaca tgcagtgttt   41940
ggttttctgt tcttgtgtta gtttgctgag aatgatggtt tctagctgca tccatgtccc   42000
tgcaaaggaa acgaactcat cctttttatg gctgcatagt attccatggt gtatatgtgc   42060
cacattttct ttatccagtc tatcattgat gggcatttgg gttggttcca agtctttgct   42120
attgtgaaca gtgctgcaat aaacatacgt gtgcatgtgt ctttatagta gaatgattta   42180
taatcttttg ggtatatatc caataatggg attgctgggt caaatgatat ttctagttct   42240
agattcttga ggaattgcca cactgtcttc cacagtggtt gaactaattt atactcccac   42300
caacagtgta aaagcatttc tatttctcca cattctctcc agcatctgtt gtttcctgac   42360
tttttaatca ttgccattct aactggagtg agatggtatc tcattgtggt tttgatttcc   42420
atttctctta atgaccagtg atgaggtttt tttttcatat gtttgctggc tgcataaatg   42480
ccttcttttg agaagtgtct gttcatatcc tttgcccact ttttgatggg gttgtttgtt   42540
tttttgttgt aaatttttt aagttctttg tagagtctgg atattagccc tttgtcagat   42600
ggatagattg caaaaatttt ctctcattct ctaggttgcc tgttctctct gatggtagtt   42660
tctttggctg tgcagaagct ctttagttta attagatccc atttgtctat tttgacttt    42720
gctgccattg cttttggtgt tttagtcatg aagtctttgc ccatgcctat gttctaaatg   42780
gtattgccta ggttttcttg tagggttttt atggttttag ggcttatgtt taagtcttta   42840
atccatcttg agttaatttt tgtatgaggt gtaaggaagg gatacagttt cagctttctg   42900
catatggcta gccagtttcc ccagcaccat tttattaaat agggaatcct ttccccattg   42960
cttgtttttg tcaggtttgt caaagatcag atggctgtag atgtgtggtg ttaattctga   43020
gggctctgtt ctgttccctt ggtctatata tctgttttgg taccagtacc atgctgtttt   43080
cgttactgta gtcttgtagt atagtttgaa gtcaggtagc gtgatgcctc cagctttgtt   43140
cttttgctt aggattgtct tggctatgca ggctcttttt tggttccgta tgaaatttaa   43200
agtagtttt tccaattctg tgaaggaagt cagtggtagc ttgatgggga tagcatcaaa   43260
tctataaatt actttgggca gtatggccat tttcacggta ttgattcttc ctatccatga   43320
gcatggaacg ttttccact tgtttgtgtc ctctcatttc cttgagcagt ggttgcagt     43380
tctccctgaa gagatcctca catcccttgt aagttggatt cctaggtatt ttattctctt   43440
```

```
tgtagcaatt gtgaatggga gttcactcat gatttggctc tctgtttgtc tgttattggt    43500
gtataggaat gcttgtattt ttgcacatta attttgtatc ctgagacttt gctgaagttg    43560
cttatcagct taaaggagat ttggggctga gacgatgggg ttttctaaat atacaatcat    43620
gtcacctgcg aacaaagaca gtttgacttc ctcttttcct aattgaatac cctttatttc    43680
tttctcttgc ctgattgccc tggccagaac ttccaatact atgttgaata ggagtggtgg    43740
gaaagggcat ccttgtcttc tgccagtttt caaagggaat gcttctagtt tttgcccatt    43800
cagtgtgata ttggctgtgg gtttgtcata aatagctctt attattttga gaaatgttcc    43860
gtcaatacct agtttattga gagtttttaa catgaagggc tgttgaattt tgttgaaggc    43920
cttttctgca tccattgaga taatcatgtg gttttgtca ttggttctgt ttatgtgatg    43980
gattacgttt attgatttat gaatgttgaa ccagccttgc atcccaggga tgaagccgct    44040
tgatcatgga ggataagctt tttgatatgg tgctggattc tgtttgccag tattttattg    44100
aggattttag cgtcaatgtt catcagggat attggcctaa aatttcttt ttttgttgtg    44160

tcttagccag gtttggtat caggatgatg ctggcctcat aaaatgagtt agggaggatt    44220
ccctctattg tttggaatag tttcagaagg aatggtacca gctcctcttt gtacctctgg    44280

tagatttcgg ctgtgaatcc atctggtcct gggtgttttt ttggttggta ggctattaat    44340

tgctgcctca atttcagaac ctcttatcag tctattcagg gatttgactt cttcctggtt    44400

tagtcttggg agggtgtatg tgtccaggaa tttgtccatt tcttctagat tttctaattt    44460 aтттттcaтag aggtgtttat agtattctct gatggtagtt tgtatttctg tgggatcagt    44520
ggtgatatcc cctttatcat tttttattac atctatttga ttcttctctc ttttcttctt    44580

tattagtctt gctagcagtc таттaaттттт gttgatcttt tcaaaaacca gctcctggat    44640

tcattgattt tttgaagggt ттттттgтgтc tctgtctcct tcagttctgc tctgatctta    44700
gtaatttctt gtcttatgat agcttttgaa tgtgtttgct cttgcttctc tagttctttt    44760
aattgtgatt tagggtgttg aтттттagaтc tttcctgctt tctcttgtgg gcatttagtg    44820
ctataaattt ccctctacgc actactttaa atgtgtccca gagattgtgg tatgctgtgt    44880
ctttgtgtca ctggtttcaa agaacatctt tgttctgtc ttaattttgt tatttaccca    44940
gtagtcattc aggagcaagt tgttcagttt ccatgtagtt gtgccgttt tagtgagttt    45000 cttattcctg agttctaatt tgattgcact gtggtctggg acactgttat agtttccttt    45060
cttttgcatt tgctgaggac тgтттттacтт ccaattatgt ggtcaattt agaataagtg    45120 cgatgtggtc ctgagaagaa tatatattct gttgctttgg ggtggagagt tctgtagatg    45180

tctattaggt ctgcttggtg cagagctgag ttcaagtcct ggatatcctt gttaattttc    45240

tgtttcattg atctgtctaa tattgacagt ggtgtgttaa aggctcccac tattattctg    45300

tgggagtcta agtcttttt taggtctcta agacttgctt tatgaagctg gctgctcctt    45360

tattggatgc atatatattt aggatagtta gctcttcttg ttgcattgat ccтттттacca    45420

ttatgtaatt cccttctttg tctcttttga tctttgttga tttaaagtct gtttatcaa    45480 agactaggat tgcaacccct gctttttttt ttgcttccca tttgcttggt aaatattcct    45540
ctatcccttt attttgagcc tatgtgtgtc tttgcatgtg agatgggtct cctgaataca    45600
gcacaccgat gggtcttgac tctttatgca atttgccagt ctgtgtcttt taatttgggc    45660
attcagccca tttacattta aggttaatat tgttatgtgt caatttgatc ctgctattat    45720
gatgctagct ggttatttt g cctattagtt gatgcagttt cttcatagtg acgatggcct    45780

ttacagtttg gtatgttttt gcagaggctg gtagtggttt tcctttcca tgtttagtat    45840
```

```
ttccttcagg agctcttgta aggcaggctt ggtggtgaca aaatctctca gcatttgctt    45900
gtctgtaaag gattttattt ctccttcgct aatgaagctt agtttggctg aatatgaatt    45960
tctgggttga aaatactttt cgttaagaat gttgaatatt ggccccccct ctcttctgtc    46020
ttgtagggtt tctgctgaga gatccactgt tagtctgatg agcttccctt tgtgggtaac    46080
ccaaactttc tctctggctg cccttaacat ttttccttc atttcaactt tggtgaatct     46140
gacgattatg tatcttgggg ttgctcttct cgaggagtat ctttgtggtg ttctctgtat    46200
ttcctgaatt tgaatgttgg cctgccttgc taggttgggg aagttctcct ggataaatg     46260
ctgaagagtg tttccaactt ggttccattc tccctgtcac tttcaggtac accaatcaaa    46320
tgtagatttg gtcttttcac atagtcccat atttctcgga ggctttgttc gtttcttttc    46380
cctcttttc tctaatcttg tcttctcact ttatttcatt gagttgatct tcaatctctg     46440
atatcctttc ttctgcttga tcgattcagc tattgatacc tgtgtatgct tctcgaagtt    46500
cttgtgctgt gtttttcacc tccatcaggt cattatgtt cttctctgaa ctggttattc     46560
taattagcaa ttcatctaac ctttttttcaa ggttcttagc ttccttgcat tgggttagaa   46620
catgctcctt tagctcggag gagtttgtta ttacccacct tctgaagcct acttctgtca    46680
attcatcaaa ctcactctcc gtccagtttt gttcccttgc tggcaagaag ttgtgatcct    46740
ttgtaggaga ataggcattc tggttttggg agttttcagc ctttttgcac tggtttctcc    46800
ccatcttcgt ggatttatct acctttgatc tttgaagtcg gtgatcttcg gaggacgtct    46860
ctgagaggac atccttttg ttgatgttga tattattcct ttctgtttgt tagttttcct    46920
tataacagtc agtcagaccc ctctgtttca ggtctactgg agtttgttgg aggtccactc    46980
cagaccctgt ttgcctgggt atcaccagca gaggctgcat aacagcaaag attgctgcct    47040
gttccttcct ctggaagctt tgtccaaaag gggcacctgc caggtgccag ccagagctct    47100
cctgtgtgag gtgatagatg catggtcggc ccctactggg aggtgtctcc cagtcaggat    47160
acacggggt cagggaccca cttgaggagg cagtctgtcc cgtatcagag ttggaacgct     47220
gtactggaag atccgctgct ctcttcagag ctgccaggca gggacattta tgtctgctga    47280
agctgcgccc ctaaccgacc ttcccccagg tgctctgtcc caggaaggtg gggatttat     47340
ctgcaagtcc ctgacgggct gctgcctttt tttcagagat gcgctgccca gagaggaggg    47400
attctagaga ggcggtctgg ctgcagcggc cttgctgagc tgtggtgggc tccacccagt    47460
tcaaacttcc cagcagcttt gtttacactg tgagggtaaa accgcctacc aaagcctcag    47520
caatggcgga taccctccc ctgcaccaag ctcgaccatc ccaggtcgat ctcagactgc     47580
tgtgctggca gcaagaattt caagcctgta gatctcagct gcagggctc tttggggtg     47640
ggacccgcca agccagacca cttggctccc tggcttcagc ccgctttcca gaggagtgag    47700
ctgttctatc tcactggtgt tccaggtgcc actggggtat tgaaaaacaa acaaaacaa     47760
aacaaaactc ctgcagctag cttgatgtct gcccaaatgg ccacccagtt ttgtgctgga    47820
aacccagggc cctggtggca taggcaccag agggaatctc ctgatctgtg ggctgtgaag    47880
agcgtgggaa aagcacggta tctggctgg agtgcacggt acagtcccta atggcttccc    47940
ttggctagga gagggagttc ccaacccctt gggcttcccg ggtaaggcaa cgccctaccc    48000
tgcttcagct caccctcgtt ggcctgcgcc cactgttcaa ccagtcccaa tgagatgaac    48060
caggtacctc agttggaaat gcggaaatca cccaccttct gcattgatct cactgggagc    48120
tgtagactgg agctgttcct attcagccat cttgccagg gcttccacat atcttatttt     48180
ttgactttt aatgatagcc attctgactg gtgtgagatg ttatattcac agtggttttg     48240
```

```
attttcattt ctcttacgat tagtgatgtt gagcatttt  tcatgtttgt tgtccacttg  48300
tatgttttct tttgagaagt gtttgttcat gtgttttgac cattttaaaa tgggtttatt  48360
aagttttgc  ccattcagtt gtttaagttc cttatagatc ctggatatta gacctttgtc  48420
agatgcatag tttgcaaata attttctcac attatatagg ttgtctgttt actatcgagg  48480
gcttagtcat aaattctttc ccaaggccca tgtccaaaat aatgtttcct aggtttcttc  48540
taggattctt acagtttgag gtcttatatt taaatcatta atccatcttt gatttttata  48600
tatggtgaaa ggtaagggtc cagtttcatt cttctgcata tggctggcca gctgtcccaa  48660
caccatttat tgaataggga gtccttttcc cactgcttat ttttgttgac tttgtcaaag  48720
atcaaatggc tgtaggtgtg tggctttatt tctggattcg gtattctgtt tcactgatct  48780
atgtttttgt accaatacaa tgccatttg  gttactgtag ctttgtagtg tagttttgaag  48840
tcaggtaatg agatgcctcc agcttttctc tttttgctta ggattgcttt ggctatttag  48900
gctccttttt gattccatat gaattttaga atgctttttt tctagttctg tgaaaaatga  48960
tattggtagt ttgataagaa tagttttcac tctgtacatt gtttgggca  gtatggccat  49020
tgtaatgata ttgagtattc ctatccatta tcataaaata ttttccatt  tgtgtcatct  49080
gtgatttatt tcagcagtgt tttacagttc ttcttgtagc tgtcttttcac ctccctgatt  49140
agatgtattc ctaggtattg tgtgtatgtt tgtgtggctg ttgtaagtgg aattgtgttc  49200
ttgattctgc tctcagcttg aatgttattg ctgtatagaa atgctactga ttttgtatc  49260
ctgaaactta ctgaagtcgt ttatcagttc caggagcctt ttggcagagt ctacggtttt  49320
ctaggtatac agtcatcatc agcaaagaga aatggtttag cttagttttcc tatttggatg  49380
ccttttgttt ctttctcttg cctgattgct ctggcaaaat cttccagtac agttttgaat  49440
aggagtggta aaaatgggca tctttgtctt gttgctgttc gcaatggaaa tgcttcctat  49500
atttgcctgt tcactatgat gttgattgtg gatttgtcat agatggctct cattatttg  49560
agataatttc ctgtgatgcc tagtatcttg agacattta  tcaggaaggg atgttggatt  49620
ttatcaaaag ccttttctgc atctactgag atgatcatat gatttttttt ttttttttt  49680
tttttttgag acagagtctc acactatcac ccaggctgga gtgcagtggt gcaatctcgg  49740
ttcactgcaa cctccacctc tagagttcaa acgattttcc tgcctcagcc tcctgagtag  49800
ctgtggttac aggtgtgtgc caccatgccc agctaatttt tgtaatttta gtagagacag  49860
gttttcacat gttgcccaag ctggtttcaa actcctgacc tcaggtgatc cacctgcctc  49920
agcttcccaa agtgctggga ttacaggcat gagccaccct acccggcctg attttgttt  49980
ttaattcaat tctttttata tggtgaatca catttgttga tttgcatatg tttaaccaac  50040
cttgcattcc aagaatgaag cctacttgat tatggtgaat tagttttttg atgtgctgtt  50100
ggattcagtt tattagtatt ttgttcagga ttttttgtgtc tatgttcata gggattactg  50160
gcctttagtt ttcttttttc attgtgtctt tgcccagttt tgggattaga atgataccaa  50220
aactggcttc atacaatgag ttagggagaa gtccttcctt agtttttttt aatagtttca  50280
gtagagttgg tatcaactct tctttgtata tctggtagaa tttggctgtg aattcttctg  50340
gtctgggcct ttttttggtg gttaaatttt ttattactga ttcaatttg  gaacttaatg  50400
ttagtctatt caggctttcg atttcttctt gatttaatct tgggaagttg tgtgtttccg  50460
ggaatttatc catttcctct aggtttctag ttttttgtgca tagaggtgtt cataataatc  50520
tctgaggatc ttttgtattt ctctcagtta taatgtcacc tctgtccttt ctgactaggc  50580
ttacttggat cttctttttct ttgttaattt agctagcagt ctatcagtct tgtttatttt  50640
```

```
tttcaaagaa ccaacttttg gtttcattga ttctttgtat ggattttggg gtctcaattt    50700
cattcagtgc tgctctgact tatttctttt cttt gctggc tttgggatta gtttgttct    50760 ttcctgtttc ctctatgtgt gatgttagat cattaattta agatcttt ct aacttttga    50820 ggtaggtgtt tactgctata aactttcctc ttaaatattg cttttgctgt atcccagaga    50880
ttttgatata ttgtttctgt tttcattaat ttcaaagaat ttttttattt ctaccttaat    50940
tccattgttt acccaaaagt gattcaggag caagttgttt attttccatg tacttatgtg    51000
gttttgaaca gtcttcttga tactgatttc tattttt att ccactgtggt ctgagagtat    51060
ggttgttatg attttgattt ttttttt aaa tttcttaaaa cttactttat gaccaagcat    51120
gtggtcaatc ttggagtctg ttctgtgtgc agatgagagg aatgtatatt ctgtggttga    51180
tgggtggaat attcagtaga tgtctattag gcccaattgg tcaagtgttg aagttaagtc    51240
tagaatttct ttgttgtttt ctgcctcagt gatctctcta atgctgtcaa tgtggtgttg    51300
aagtccccca ctactattgt gtggctaagt ctttttgtag gtctagaagt acctgtttta    51360
tgaatctggt tgctctattg ttggctgtat atatatttag ggtagttaag tcttcttgtt    51420
gaattaactc tttatcgttt gtccttttct ttactgttgt tggttaaaag tgtgttttat    51480
ctgatatatg aatagcaacc cctacccatt ttttgttttc tgtttgcatg gtaaatcttt    51540
ttccaaccct ttactttgag cctatggatg ttattaatgt gtgacaatgg tcagtcgaag    51600
gtagcaaatg gatggctttt gtttttttat ccaacttgcc accctgtgcc ttttaagtga    51660
ggtgtttaaa ccatttacat tcaaggttaa tattgatatg caaggtttg attctatcat    51720 gagattgtta gctggttgtt ttgcaatttc tgtggtgtgg ttgctttata ggatctgtgg    51780
gctatgttct taaaagtgtg tttctgtgat agcacatatc attctatcgt ctccgtgttt    51840
tgaactcctt taagaatctt ttgtacagct gatctggtgg taacatattc ccttagctct    51900
tgcttatcta gaaaatatt tctttctcct ttgcttatga agcttaattt ggagggatat    51960
gacattcttg gctggaattt cttgtcttta aaaatgccga aaaaagactt ccaatctccc    52020
ctggcacgta aggtttctgc tgagaagtcc attgttagcc tgatgcatta tctttgtaca    52080
caatccgacc ttttttctcta gctgccttta aaatgttttc tcctgggcgc ggtggctcac    52140
acctgtaatc ccagcacttt gggaggccaa ggtcagcaga tcacttgagg tcaggagttc    52200
aagaccaacc tgaccaacat ggcaaaaccc ggtctctact aaaaatataa aaattagctg    52260
gccgtggtgg tatgcacctg tagtcgcagc tactcaggaa gctgaggcta agaatcgtt    52320 tgagcccagg aggaggaggc tgcagtgagc caagataatg ccactgcact ccagcctgag    52380
tgacagagtg agactccatc ttgaaaaata tatatatata tattttcttt agcattgacc    52440
ttggacagtc tggtggctat ataccttggt gatgctcatg ttgtatggta tcttgcaggt    52500
gttctctgga tttcttgtat ctggatgtct acctctagca agattaagga aacttttttg    52560
aattattccc tcaaatatgt tttccaggtt gttcactttt ttccttctca ggaatgccag    52620
taattcacag gtttggttgt tttacataat cccatatttc tcaaagcctt tgttcacctt    52680
taaaaattat tttttcctta tttttgtgta actgagttag ctcaaaagat cagtcttcaa    52740
gctctgaaat tctttcttct gctaggtcca gactattgat aaagctttca attgtatttt    52800
gaaattccct gagtgagttt ttcaacttca gaagctctga ttgatttctt tataagatgt    52860
ttatctcttg cttcatttcc tggattgctt tagaagtttt gtgttgttga ttttta acct    52920 tgacttggat ctcattgatc ttccttgtaa tccatgcttt gaattatta tccgttcttt    52980 ctgagtttct attttggcta tagaccattg ctggagagca agtttgatcc tttggtggtg    53040
```

```
tcactatatt gagattttc atggtgccag aattctcgca ctgattcctt ctcatctgga    53100
gatgctggca tttaatttt atagtattt catataggtt aggattattt attttcctt     53160 ctgtccctat aatattattg gggttttttt tctttcctt tcccttttcc cctctcta    53220 gggagtgtga ctataaagaa tgctgggtag ggtcttttgg ctttgcttct ataaccctat    53280
tcacttctgt cagcaggttt tatactgggc tgtgcagttc aacctacaaa ccagtagatg    53340
gtgctaatag gtaagagcct gctatggcca atgtgactga gtatatactt gatccttgtt    53400 tatgggaaa agctctgtta cctcaggcaa tgagctgatt catgggtgc atagtggtct     53460 gagctccctg ctcagacaca gggagggagg ggccaaaatg agcagagctg actaggcag     53520 gtccaactac aggtcccctg atggcaggta caagtaccag cactgaggga gaatgcagtg    53580
ggtagccact accaagcacc cagagatgct tgggaaattt cctcgacccc aagttccctg    53640
caaagggatg ggggcggctt aaactaatcc agtagagtga ctgctccaga tgcctggagc    53700
tctatctagg catggagccc cactgcacca ggatctatgc acaggaaggg tgaggtgctc    53760
aggctgctgt tccaggcaag tgagtgctct aaatgcctag agatctgcct gagcatggag    53820
gagagagggc cccccatacc aagacctctg cgtaggaggg tttgggtgac tcagactgct    53880
gatcgaggaa aatgggtgct ccgaatgcct gatgatctgc ctggtcatgg agcagagagg    53940
gccttgctgc accatgatct atgtcttgga atggggaggg gcagcggctc aggctgctga    54000
accagatgag caagtgcacc taatgcctag agatctgccg gggtgcaaaa tggagagggc    54060
tttcccacac ccagatctct gcacaggaaa ggtagggcac tcaggctgct agtccatgtg    54120
agcaggtgct ccaaatgcct ggagatctgc ctagagttgg agtggagagg gcacccttgc    54180
accacaatct atacacagga aaggtaggac aactcaggct gctgatccaa ggaagggggt    54240
gctccagata cctggagatc tgcctgggtg tggagcagag agagccacgc tgtaccacaa    54300
tctatgtcca tgaagggtga ggcagctcag gctgctggtc cagacaagca agtgctccaa    54360
atgcctggat ttctgcctga gggtggagca gagggctctg ctgcaccaca atctcagggg    54420
agcaggctgg gtcaccctgc aatgacatat gcagactagt tccaggttac caagctagcc    54480
ctggctgcaa gtctcatcac acaggagaaa ctgcagctgt agcagctctc ctcccacctc    54540
aggcctgcaa agcgggagag cacaatccct gcacctacta ctgaggctct ttgcacagtt    54600
ctggctatgg agactcctac cctaagccag agcaggtgct ccaattgctg acccaagact    54660
aaaatgcctg tgtggccaca ctgctaggtc accaaagaat gcctggatta aaaatggcac    54720
cctgctttca gtcctgagtc tgggaaaatg tttgcagctt ttctctatgt cttttcctca    54780
cagtgtttcc aagccgcttc cccaagttag ctccagagct tgcgagaaac aaagtgctct    54840
ccctcagcct gggttgcctg gatcccaagt ggaaaggtga gtcatagagg gaggctgtct    54900
gcctctccca tgtactaggg cttcactcat ttttatcagc tgcatgccat cactggggct    54960
gtttgtccac attctcctcc ctggcatctg gggtgtcctt cacaattcta gtggattccc    55020
attttccttt ttggataaaa acccacagag atgatcttta cacactatct tgctatttcc    55080
aaggagccaa ggcacactga aagactctaa tctgccatct tggaaaaaaa aaagaaactg    55140 ttttttaaa aaaactcagt atccatttag aattatgacc atcttgtgag aaatgaagct    55200
tgagactcta ctttgatatc aaatttagtg ctattctcat catctttaat tgtgttttct    55260
ttcacaaatg actactagtg gatgtgttta agtccaaaaa accttctgat gaggtttaag    55320
atttggggct ttaagcatcc tgttgacttc tattgttagt ttcactatat taaatttgag    55380
ttaggctaat agtaagtttt attttctgt ttttcattag tttttatgag ttaagggcca    55440
```

```
aaataccaca aaattttcaa atgagcaaat gttactgtgc aaattcagaa aagatgctga    55500
aatacaactg ttggctggca ggtcatggtg ccagcaatag catgaagtgt tttgttcttt    55560
agtttaagaa gttatgaaga aagcaccccg aaggtgttat gagatgatga aaaatacaga    55620
aaacccaaat atataaaaat caaagtattg tttcacaaaa tttgatcgtc ttgccttctc    55680
agaaaaatca ctaagttgtt caaaagcaag attttcacat cacattcaaa cattatgata    55740
ggccagaaaa tgctatggag tattttaatt tcatataatt cactaccact tctatggctg    55800 ttttttaccat ctctcaaaca atctttagat ctatccagta atatgaagag ttggtaccag    55860
gcttcatgtt ccatctagat ctacatatat ataaatgtaa gggtactcag gatgcatatt    55920
gcacaatgtt cttcagccac catatgtagc tcttgcaaat accattcctg tatgcgaata    55980
cctgtggaat tgcaaattaa ggcattaaaa gaagcaaaaa atgggtgctc agcaccactg    56040
gaaaatatat ttcattatgc acaaatcttg cattcatgct atctgagagg ttttgacagg    56100
ttacctttcc tcttacctta ctgctgctgc cccagtcttt cctgcactcc aaagcagtgt    56160
ctgtgtctga tctcagcagc agcatcaccc acaaaccttt acagtatttg ggcacagtca    56220
tcttttgttt tgaaggtaaa gggtaaaaga tgtggtgaag cattccctga gacctgaatg    56280
tggttaatga tgagagtgaa tctttagggt tatggttcct gctgtttcag agctgagctc    56340
cagatcaagg gcccgtgtgt ttttgttttt gtttttgttt tcttcctctt ctgagatgga    56400
gtcttgctct atcatccagg cttgaatgca gtggcacgat cttggctcac tgcaacctcc    56460
gcctcctggg tttgtacaat tcttccacct caacctcccg agtagctggg actacaagca    56520
tgcaccacca cacccagcta atttttttat ttttagtaga cgggggttt caccatgttg    56580 accaggctgt tcttaaactc ctgacctcag ttgatccacc caccttggcc tctcaaagtg    56640
ctggaattac aggcatgagc cactgcaccc agcccgggcc cacgtattct tgaacaaatg    56700
taggtttctg tgtgtgcctg tcctatgcag agccctctaa agcccagggc tcagaacagt    56760
ggcccctctt tctaggtgca agggtagcac tacaggcttt cacgggattc ctgtggctac    56820
ctggtcgggt ctattcagga tgatccatgg gagttagcat agcaccactc taaagtcaga    56880
tgttgaaagc caaagatcaa agagagttga gcaagtgagc aagttggaga taattacaag    56940
cttcttaaga gaacactgtc ttttccacac tgggagtgtt ctcatagagc cacaaatagc    57000
gctccacaga tggaaagcct ccgaatgctc ccagctgacc atgtttgcca cttcgtgaat    57060
gctgcagcat cacacaagag gatatctatt tccccaagcc ctgtgcagac caatttttgat    57120 aatattgctg tcagaattaa gttgcagttt ctctcattca ttttttcaact tatactttgt    57180 tttactattg gtggcctcct ccacctctgt tccaaatagt aagacacttt gctttaggcg    57240
aagttactga gaatgccagc acttccccaa tttcatccaa gagaagagca cttaacactt    57300
agcccctaaa caccttcatt tccttctcct cagctgtttt ggaactggcg aagctttact    57360
catgtccaaa aagatgaaag gagaatgggg atacccaagt agtagtaatt agtgctgagc    57420
ctttgccaag tcgagtggct ggggtattcc ttcagcactt acttcctctg tatctctgtt    57480
tttagccatg cttcactcaa gacccaaatc ctgctgcttt tttttttttaa tcataagaaa    57540 ggatttaaat ataaaatttt acacattaaa cacactcaaa gtaaatattc aatctctgga    57600
tggagacaga ttgtctagat gactaataga gtctatcaat tcttctctaa gttatttccc    57660 tcctttaat ctttgaaagt ctctcttcat ctagcctgtt catggtgctc agagttgaag    57720
cagccatagt gcaaccaaga cgcttccctc catcaacaca ccgaggctgg cataacagag    57780
agatggaaag agcccagttc tccaaggaca ttgctgaatc tttgcaccaa ctctgatagc    57840
```

```
actgcctcca gactctattt catgaggtta ataaacctct ttgatgtaag ccacttgcaa   57900
tcaagcaaca ggtctatgca ttttaactac acatggccca cactgagaaa tcttgtcgta   57960
aatactggtg tcctcagagc tctgttctag accctcttct ctccttacac aatactctct   58020
ctatatgtga tctcactcgc tcccttggct tggaatagta tccactctga agactcctaa   58080
atctgcttct aggccagaat cttcctctga acttctaaaa tatgtaagaa actctaacag   58140
acgtcaccac ttgtctatta gtctccctgc acctcaacat atccaaaact gaactaataa   58200
tctgctccct agaacctgtt tatccctcca cactttccta tctcaataaa tggcaccacg   58260
gtcaactcaa ttgctcgagc tggaaagcca ggaatcatca ccttctcctt ttcgctcatc   58320
ccagcatcca gtcaatcacc aagttctatc atgtcttctc tccatcccca ctgctgctcc   58380
tcagtcaggg ccatcgtcag gtcccatgac gaccactgcc acagactttt acctggtttt   58440
cctggccctt ccaattgctt ccctatattg cagtcagaat gatctttctg atatgtagat   58500
ctagtcagat ctcttctctg tttaacactg ctgcctgact cactggacta gaagagtaac   58560
tcctgctatg aactcccact gcttctggca agtctcaata tgagtcattg tggctgcatg   58620
gtgacttaca cctgtaatcc cagcactttg ggaggccgaa gcaggaggat cacttgaatt   58680
caggagtaca agaccagcct ggacaacata gcaaggcctc atgtatacta aaagtcaaaa   58740
aaattagctg gcggccgggc gcagtggct cacgcctgta atcccagcac tttgggaggc   58800
cgaggcgggc ggatcacgag gtcaggagat cgagaccatc ccggctaaaa cggtgaaacc   58860
ccgtctctac taaaaataca aaaaattag ccgggcgtag tggcgggcgc ctgtagtccc   58920
agctacttgg gaggctgagg caggagaatg gcgtgaaccc gggaggcgga gcttgcagtg   58980
agccgagatc ccgccactgc actccagcct gggtgacaga gcgagactcc gtctcaaaaa   59040
aaaaaaaaa aaaaaaatt agctgggcat ggtgctgtgc acctgtgtag tcccatctac   59100
ttgggagtct gaggcagaag gatcgcttga gtccaggagg tcaaggctgc agtgagctat   59160
gcatgcagcc tgcactgcca ctgccactgc accgcagcct gggtaacaga gtgagctact   59220
gtctcaaagg aaaaaaaaat taattatgct tttattgagc ttttttattg tctgttttct   59280
cattggtctc taagttgtat tgagtataag aactgaggta tatccccaca cctagcaata   59340
gtgcctggca cacagtagac aacaaatgtg aagttgagtg aatagatgaa tttataacaa   59400
tattttgtaa gctaggggtt gtgacccacc aggatcatga aatcaatcta gtggattata   59460
atcagcttta atttaaagaa gaaaagaaa tagaagagaa tagcaaataa taagagtatt   59520
atttcatgaa attttttat tacaaaattt gtaaaatgta tttcttataa tgagtggcag   59580
taaaactaaa atgaaagcca ctgggttgta ataagcaagt acttttttct atagtaagaa   59640
aaagcagctt tatttaaaaa aaaaaatcgg aaaaccttgt gactgcaaaa gattcctgcc   59700
ttggggatt tttactttca cagatttcaa agccttaaac tcgagggaaa aaagtgtcta   59760
gagttttagg tttctgtgag tagatcacag aggaattaaa aatccatcac agatcctgcc   59820
tggtaactat tgccatagac caatgaagcc taaaagtgct gttgaattct atttcctctg   59880
aagatatatc ttaaactttt ttgtcccatg actgatgacg aaagtggaaa tccagtgtta   59940
aaagtatgaa ttctttgctg ttgagggtgg tcactgattt gtgtcttgga gaatttaatt   60000
ggctgtttct cccaaccttc tctcttgaag aaaagagccc tgagccaatg aggagctact   60060
gttctgtgtc catagcaaca aaataaacaa actttggcct gccatctccc aagggcaaac   60120
ctcacaactc aggcccaagt cacaggaatc tgaatggtgg ggtgaccttc tcctctagtt   60180
taatttcatt gcaatactga gaaacttcaa ctgttttgtc tttagaaggg aaattcatgt   60240
```

```
ttgtgccagg ccagcctttg taaaagcctt tgattggatt cactagaagt ctgtcttccc   60300
gcagtacata tactgtgaat tttctccttc ggcatttcaa ccacttggaa tggccactaa   60360
agtggctttt gatctaaagt aaactctgat tctgtgttga tggggaacca tttctctcta   60420
acatggtggt ttctttaaga tgtttgactt gggccacatg agaataacag atctttgggc   60480
agtccaaggt aagctctttg gaaaagatgt tttatattat tttttctact gattattaat   60540
actaaccagt aacttctctg aagcctctgc cggctcactg gtgactattg ttagggcaag   60600
cctcaggtaa aatcatcagg tagaagtgca ggaaagggaa aaaggggga gaaaaatcc    60660 ttacacacac tcacacaccc ctctataatt agagctatat gatgtcaagc cactgtaaat   60720
gcagatctat ctgtgatgac atggaaatat caactagata tcctgttaca caaaagaac    60780 aagatgcaac attgtgtgca agtatgctc tcacttatgc aaataattta aaaaatctat    60840
tatgcttctc tacaggttaa gttctatatg caaaacattt aaggttatat gcactcacaa   60900
catttctgga aggatgcccc aaaaatctgt tagaagtagt tcccacttaa gaagctatga   60960
gaagtcaagg gctgattta gctactgaaa tattaaaata ctgccatata ggcagggcac   61020
ggtagctcac acctgtaatc ccagcacttt gggaggctga gatgggtgga tcacctgaag   61080
tcaggagttt gagaccagcc tggccaatat ggtgaaaccc catcgttata aaaatacaaa   61140
aattagccag gcatggtggc gggtgcctgt aattccagct actggggaag ctgaggcagg   61200
agaatcgctt gaacctcgga ggtagaggtt gcagtgagcc aagaccacac cattgcactc   61260
cagcctaggc aacaagagca aaactccgtc tcaaaacaat aataataata ataaaatac    61320 tgtcatattg attggtagat gaccattgtc caagccccctt gcatgtcctc cttgccacct   61380
tggttgtccc aactcctccc ctggcacccc cagaccacct catgattcag caactaaggg   61440
gttaatgcct ggcatggagg tgggagtgag atctcccagg accctgttcc aaccctggtt   61500
gattattcaa tagccttgtc ttactggttg ttaaatattt tgagtatcac tcccatgggt   61560
gttcaaagaa aaaggccttt attttatttt tatttattta tttattttt agagacaggg    61620 tcttgtgctg tcacccaggc tgaaatgcag tggtgtggtc ctagctcact gcaacttcaa   61680
actcctggcc tcaagtgatc ctcccgcacc acctgccaag tggctgggac tacaggcaca   61740
ctccaccata ctaggctatt tttaaaattt tttgtagata cagagtctcg atatgtttcc   61800
caggctggtc tcaaactcct agcctcaagc gactctccca cctcagtctc tcaaagtgtt   61860
gggattacag acatgtgcca ccacacctgt gaggccttct tttttttttt tcttaagagc   61920
aaaagaatat ataccaagac attgtttatc atgggaaaga ggaaaaggaa acaactacac   61980
attcatcaaa gatcattgaa aatctatgta aaactccact gagtgattgt atcacccata   62040
caatttacct ctgctttctg gcttttgaat gcaaatgttt aatgttattt ataatatggt   62100
aatgacgatt acaacatttt ggcagtttca tctgtgaatc tcttttctct tgttttttgt   62160
tttttgtttt attcatttat ttattgagac agagtcttgt tctgtcatcc aggctggagt   62220
gcagtggtga gatctcggct cactgcaacc tccacctccc aggttcaagt gattctcctg   62280
ccttagcctc ccgagtagct gggattacag gcatgtgcca ccatgcctgg ctaatttttg   62340
tgtttttagt agagacgggg tttcgccctg ttggctaggc tggtctcgaa ctcctggcgt   62400
caagtgatcc tctcgccttg gcctcccaaa gtgctggaat tacaggcatc agccaccata   62460
ccatcttttt ctctttgttg agctagcccc aaccaccatg atgagctgat tacaaccact   62520
aagtttacta gtcaggtaag aaatattcat caaatgcccg ttgtggacaa gccactttgc   62580
aaggcttagt ggaggtgttg aggcacagag agcactccat agtggagtcc tggccttcaa   62640
```

```
gaagagagaa ggcagttgct agaagtgggc ctgccttagc ctctcacttc ttgccccatg   62700
gactcctgct aaatctccca agttcagggt tggctccttt cgtacaggaa gcagatacaa   62760
ggttctaagc agaagcagtt tcttttttgc tactgttgta gccttctttc agactctcac   62820
ctgaattcca gccccttgta gcatcatctt cccacctggg cactcgatcc catctgcttc   62880
tctgacctca tctccttgac ttggccctaa caggccccca aacccagtgg agtatggaca   62940
gttataaatg gcggccctgt cacctgctct tcaggccttt gctgtttagc cagtctcctg   63000
gactcctttc tagccctgga ctcctttcta gccctgacct ctattgcaga agactcccta   63060
gtcccaggcc tctggcccag ccaacccctg cacacgctgc cttctcttcc aaggccaggtc   63120 tcttgccttt gctccactgc tcacttagct ctctttctgc cgactcctct gctgactgca   63180
agctccctga gggcaaggtc caaccagcat ctagcacagg actcacagca cgagcctcta   63240
aagatttgta ctgttaaagc agcagttaca agtgagtgag ttttagtatc ctcatatgta   63300
aaacagattc aaccttaagg tcctctgtag ctcttaaggt cattagacac catcagtggg   63360
tttctcaagc atcagtcgtg ttggagacaa aggttgattt cattttttca gcaggttctt   63420
aagcaaatgt attccagtgt aatattgaaa actaatcata gacttagaca tttgagttaa   63480
atctgctatc actttaatgc ttctgttagg ccattgattc ttataacatt tttggcattt   63540 gttttatta ctaatgaaat atccactgac atggctgggc acagtggctc atgcctgtaa   63600
tcccagcact ttgggaggcc gaggcaggag aatcccttga ccaggagt gcaagatcag   63660 cctgatcaac atggcgaaac ccagtctcta ctaaaaatac aaaacttagc caggcatagt   63720
ggtgggcact tgtaggaggc tggaggccta cacctcagg aggctgaggc gggagaatcg   63780
cttgaaccca ggaagcagac gttgtagtga gccaagattg tgccactgca ctccagcctg   63840
ggtgacagag tgagactctg aaaagaaaaa agaaagaaa agaagaaaag agaaagaaa   63900 tatccactga catcatttaa aaatcaacta atgttaaaaa ttcattaagg aaaagtctca   63960
atttctgccc catccctga cctgtcagtt ctacttctca atgtgctcct agaggcaatt   64020
attttcaact ctgctatcta tttctttgga attttattta cctcatactt ccaagtaatt   64080
tgtctgtgct ccgtatgtta atttttcttt ctggtacagc agatgaggat ttggctctta   64140
tacatcccca ttccactcat tcttcccatg tagtcacagt tcacttttg gctaagtcac   64200 tattaagtat ttacatttga tacatatgag tgtgtgccat actatgatta tgtttacttt   64260
ctcattcaat attttttaac ctggagtaat tgcacatttt attttcttag gtttctatgt   64320
ttctattgcc aatctctcac ccacactccc aaatgctctg gttctggttg ctctgtaaca   64380
aagttaccac aaatgtagtg gctcaagcaa caatcttaca attctgaaag tcaaagtcca   64440
aaatgagcct cactgagcta aaatcaagag gtcggcagag ctgcattcct tccgaggct   64500 ccagggggaa ttcgtttcct tgccttttcc agcttctaga tgctgccccg attccttggc   64560
tcctggacct tttcctcaat cactcctact tcttcctcca ttatcacatc ttctctgact   64620
gataattcag gttaatcttt ctatctcaag atctttcatt taatcacagc tgcttttgcc   64680
atgtaaggta acatagtcac actttccagg gattaggaca tgcggtatag ggaaagggac   64740
agtattcatc ctaccatgtg ctcctacaca tctaccagct gcctgtcaat atcatcaggt   64800
aatctaccag ttccaagtcc tgcaccctct gggacctctg atgtgtgaat tggctccatc   64860
ttgttcatac cctgtctttg caggcacata ggctatagtg agctatggag agagccctag   64920
ttactatgcc aaacatgtac ggacatccct tgtgcaatct tgtctcctct cccattttct   64980
tgctcttgtg gaactaaatc tctttttaatg ctgtactcta attttagttg gattctggaa   65040
```

```
aagaaagaag ataagccagt gtggtcaagc caccatgttt atctgatagt tttctttcat   65100
caagattctc ataatagggg ttttgttttt tgggagccag ggaaggagtt tccactctgt   65160
aattcaagaa ggtgaccagg aatgagaaac gaggagattc atttgcactg tagctcaagc   65220
agcagaacta attttccagg aagttctgtg cagaacttgc tgtgggaatt tctcttccct   65280
tcagtgagaa ctggtgtggc ctgctggaaa ggaaggagct tgggagtcaa agagatttgt   65340 gtttgttttcc agctctgcaa cttgctgccg ccgtgacttc tctgagtctc agtagcttca   65400
tctatagtat cagcataaca ataattgagc agttttacct ggctcacagc aaggactcgg   65460
ctatggcaaa ttttattta ttttaattat tttgttttat tttatttgt atcttatttt     65520 attttttgag acgaagtctc actcttcacc caggctggag tgcagtggca caatctcagc   65580
tcactgcaac ctctgcctcc caggttcaag caatcctccc acctcagcct cctgagtagc   65640
tgggactata ggtgtgtgcc accatgccca gctaattttt gtattttcag tagagacggg   65700
gtttcaccat gttggccagg ctggtctcaa actcctgacc tcaagtgatc catccacctc   65760
ggcctcccaa agtgctggga ttacaggcgt gagccaccat gcccagccag ttatggcaaa   65820
gtttaaattg ctttcaagtc aagtctactg agtagaaagg gatgagctgt taacctatag   65880
tcaagaccct gcaccagatc aacagcttct ggaatctacc attgttcttt gggtcctccc   65940
tgggttcttc ccaattcttc tgtattttg ctttgattct aaatggttta accttctgct    66000
gttgtttttc aatttcagca agagcctcct gatctagcag ccaagactcc ccctgacctt   66060
tggccatgta ccccaaccct ctcatctact gcacctgctg ggaccctgg aacttgggac    66120 cacggaagct aatcaagacc cctcaactac cacgcaagaa ctccacaggg agttccaagt   66180
aagaattatc tgggatgggg taggcacagg gaccttggga tccatttgta gcctcatttc   66240
tctcacaaga tttctaaaac agcaagtgtg gcaggaaaat cccaggtggg ccagaaagcc   66300
tcgctttccc cagcttccct gccagctggt tggctgcacc ctcatcttgc cagccctgcc   66360
tggggtttgt gccatttaa atgaggaagt ctcagtgttg gtgcaacggc aaagtgcagc    66420
ttccaaccaa agggccctga tgcagctgc cgccttcatg tgggataaag agctttggga    66480 atcggggac aaactcttcc tgggacagtg aacaagtgcc agggcttgg gcctgagttt     66540 taaaggcctc agatttaaa gattccagct atcagatcat gcattccaat tttgggtcac    66600
tatagggatg tacttaatct gggagtgtta aaaagggttt ccgaatttcc aatgttcttg   66660
ttttagttat ttgtttttca ctttcaggct aactcctctt gtaccagctc caaaaaatca   66720
caattacctc caaccaacaa aacctgttgt ttccccaaag taagtattgt tttgttttgt   66780
tttgtttttg agatggagtc tcactctgtt gcccaggcta gagtgcagtg gtgtaacctt   66840
ggctcactgc aacctctgcc tcccagtctc aagcgattct cctgcctcag cctctcgagt   66900
agctgggaat acaggtgtgc gcgccaccat gcctggctac ttttttgtat tttagtagag   66960
acggggtttc accacattgc ccaggtggt cttgaactcc tgaactcagg caatccaccc    67020
gcctgagcct cccaaagtgt tgggattaca ggtgtgagcc actgcaccaa gcagtttgtt   67080
tgtttgagat ggagtcttgc tctgtcaccc aggctggagc gcagtggtgc atcttggct    67140 cattccaacc tccacctccc tggttcaaac gattctcctg ccttagcctc ctgagtagct   67200
gggattacag gcaccatta ccatgcccac gtaattttg tatttgtagt aacgacgggg    67260
tttcaccatg ttggccaggc tggtctggaa ctcctgacct taagtgacca gccctcctca   67320
gccttcaaag tgctgggatt acagtcgtga gccactgtgc ctggcctaa gtatttttat   67380 gtccatgagg cagaaatggt ttcaggcatg tgaataaaat aatctccctc tcacctggcc   67440
```

```
tgacttgaac taattgatgc cagggatgtt agagaattgc cagaatcgac cttgatttct   67500
tgcaaacctc agatcctaca tgtagatttt ggggtcctct gcatccacag cttccaaagt   67560
cattgcattg tttgattcaa agtcactgta tccactgctc tccacagggg tgcccccagt   67620
aactgtcttc tgccctggag cccaaagctt gatgtgtgct attgtcacag agccttggcg   67680
accctcccgt gcatttaggg tggtgactca ctctttagct gattactgtc ctgtgtctaa   67740
gattttctat gggttgcatc ttggttttaa tcacaaatta aaattttttac tcgcatttta   67800 caagcttaga aatgtacctt agtttttaggt cttttgtatga atctttgtat tccattaatt   67860
tttttggaaa atatttattg accacctatt atttattagg cactgtttca ggtgctggga   67920
aaagagccag aaacacaata aagtctccac tctcctggca cttatattct agtggggaag   67980
gaaggggaag aggaccataa actagttatt acatccgagg ttggcaagtg ctacatagaa   68040
aaaagatgca ggcaaagcag gtaggggctg tgacggtggg gatactttac gtagagaggt   68100
cagggcaagt gcctgtgtaa agggggcaaa aggagcctca atgatgcctg ggcaagcac   68160 tcttggcaga gggaccagca agtccaaagg ccctggggtg ggaacttgct tggcatgtct   68220
gacctcttcc aggaaggcag aagccagtgt ggcatgagcg gagcgagtga gcagggagtg   68280
gtgggagatg agctcaaaga aggtaacaag gtgatgggtg tggtgggcag gacagtgacc   68340
ccctcccaag gacgtctaca ccctaatacc cagagactgt gaatatgtta cttgccaaag   68400
aggaattaag gctgcagatg gaattaaggt tgctaatcag ctgaccttca gttggagaga   68460
ttatcctgga ttatcccaga tcccatgtaa tcacaaaggt ccttctttgt atgtgaaaga   68520
ggaggtcaca gtgtcagagt cagagaagga gctgtgacaa cagaagcaga ggttggagtg   68580
atgcaattgc tgctggcttt ggagctggag ggaaaggcca ctgtgaacat atacacatat   68640
gtggtattca ttttatatat agcatatata aagatttgaa tgaaaacaa gtttaacttc   68700 aacatttgta tcttaatggg atacatttca ttttctggaa catttgttta tatagaatgt   68760
ttcattctcc aataaagaga gttccacaca gttccctgaa ctgagtgtgt gtgtgcccgt   68820
ttgtgtgtaa gggggtggtg ggggggtgtca cctgactcac agagccttga ctcagggaga   68880
atatgtaggg gtccctctag ctggtttatg ctcctccaaa acagaagttg ccccaacatc   68940
ataagacaag tcttttgcct ccttgggcag gaccttttca tgagcacccc tactttgggg   69000
ccctcaggag cccggcttca gtgagttccc caactatcct agggatcccc taagaaggtc   69060
aggtcagaga gcagaagtca gatggtggcg gcctcagggt tcagctccta agctttgaac   69120
ttctctttgc tgtctggttg ctttctgagc atgtctttct cttgcagaat gaaaatccat   69180
tcagcaaggc aagaagagac taataaatca tttttatgtga gtaaaggcag gagagggcgg   69240
tgggactaaa atttattgag tgcctactat gtgcaagcat gggccctta cattttata   69300 cttaccttgt cgaatcttca caaagatcct gggaggaggt gctgttaata ttgcacatta   69360
tgcacggcag gtaagtggaa gaaccacgac ttgaactcag ctcagctaga ttccagagtg   69420
ggcatttaat tgccactctc tcctgccttg cacaagacaa acagagtgtc tcagagaaac   69480
tggacatgac agctagtcca ggccagtgaa cagctcatgc ctagatgcag gaagtgctct   69540
gctgacctag ggaactaacg aaagctgggg agaggctgcc gggaccctc aggggagcag   69600 gggcgggagg gcactggaga aggtgatgag aaccaaactc gaaggctctt gacgcctgcc   69660
tgggagtgtg ggcccgaccc ttctggtgtc tgggagcctt tactggtctg acgcaggcac   69720
aggaccaagt aagagttaca tttcagaaaa agcacccttt ggtgggatgt aatcggtaca   69780
ttttactgtt ttctgtgttt atctagtttc ttttctttct tttttttgtt ttgtttttta   69840
```

```
gttttaggtc tttgtatgaa tctttgtatt ccattaatttt ttttggaaaaa tatttattga   69900 ccacctatta tttattaggc actgtttcag gtgctgggaa aagagccagg gaaaagagcc   69960
atgcagtcct ttaatggtta gggaaaaaaa tatacaagca aaaatataat tgccctctag   70020
gtagagagga ggatgaactg tggggggagc aagactgaag gcagagaggc cagagcccaa   70080
gagaaagatg atggtggcct ggggccgtca ggcagggtg tggagagagg agggtgactc    70140
acagagacat gaaggaggtg acaacagcag ggatcaaggg gctgcagcat gtgctgcgca   70200
gctctcagag ccccagcctt gccctggtcc aggccagcag aggccctgcc caggtttctg   70260
acttggcgtc taatgggaaa aggaggagga aatgacatt tgtttgcaac cgtcctagtc    70320 atttctcat atgttgtttt gtttttccct cacaaaagcc ctttgagaaa gagttattaa    70380
ccccactttc tgataaggaa actgaggcac agagatgctg gatggctact gtctggtggc   70440
agagccaaga tttactcagg cctctgtgat tccaaaaccc gagcagttgc cgcatgccca   70500
cctcctctgg gctctggcca cgagggtgaa cacaagtcgg gggcagggc atcagtggct    70560 tggtttggcg cagagcttga gaggccccta gggacaccca ggagcctgct aagcatcaga   70620
tttgagtcgg agagatgtga gaatgagcta taatgggtga agggcccaga agggcttggg   70680
ctgtggagtc ccaggtccct gttttttaaga tgtgagtgag gcaataagag aagatttgga  70740
aaaatctcag cactccaagt ctgccatttt atcttacttt cccttgatgc ctaggaagtg   70800
atcaacgtgt cacctggcta tcaacttgtt cggaatcggg aacagatttc tgtcaccta    70860 ggggatgaga tgtttgatag gaaaaagcgg tgggaatcgg agatcccgga caaaggcaga   70920
ttttccaggt aatgctgttg cagcaacatg cagctgcttg gggctactcc cacccagctc   70980
agcccggcct cagggacaag ccaaagccgc tatgcccaca cccaggccac tggtccctgc   71040
tctggagggg ccgcaagggc acctccctcc tcgcccctgc ttcctgatga tgcatctctc    71100
cacatctgcc tctctgctct gatcccatcc gtgagcagat ccaaggggca ggatgaagat   71160
tgggagttat gtgattgatc ccaaaggata gcaattgttc gtggggtgag aatagatag   71220 aatagccata aattagtctg aatttgaggc atgcaaatta agtaaagtga gggtttctgg   71280
gtggctggag tgcacttttt ttttttgagac agagtctctc tctgccaccc aggctggagt   71340
ttagtggcac gatctcagct cactgcaact tctgcctccc aggtttaagc tattctcacg   71400
cctcaacctc ttgagtagct aggattacag gcttgcacca tgacgcccgg ctaatattta   71460
tagctttagt agagatggga ttttgccata ttagccaggc tgttctcaaa ctcctgacct   71520
caggtaatcc tctggcctca gcctcccaaa gtgctgggat tataggcgtg agccactgcg   71580
cccagcctct ttttcattat gtccaaaaat actactcagc tcatgccccc gggagatgca   71640
gtgtggaagg ttctggcctg actctaaccc attagcacag ctgtcctgtc tgtcttcagg   71700
ctccacccac tctctgtcct ccaatgccat atcaagtata tctccatgtc tttctttttt   71760
cattaacaga tgcagattca tctctacatc ttttcattct acccttaat ctcttattca    71820 tatcttcttc tctgatatcc tgcccatgtt caggcatctt acttcttaac tgcactactg   71880
aatggctctc caagtgcctc ttccctcagg ctgattttgc tgtaagaatt atttttcaa    71940 cacacaagtc taaaagacca acaatagaaa acacacacac acatacacac acacacac    72000 acacacacac acacacacaa tcatctacct atctgctagt gtattggcag aattcaacca   72060
aaccgttagc agtggttaca tctggggaag ggattcaggt tgagggtgag tctgaaggcc   72120
cctcaagtag aatgaggcca tgccatggag tctccctgat ctgacctggc ccagagggcc   72180
acccaggggc caggggcatt caccctgctt atcttgtctt cccacccagg ggcattcagc   72240
```

```
ctctgctttc ttttccctgc ttatccacag ccctctgcag gaagagaatg ggtcatgcac    72300
ctatagtcaa gctagcaccg acagccacct cttggcctca caaggaagtt gtcaccagtt    72360
gtgcacaata aaatatgata acctgtgctt gttgtattcc ctggtaaagt tgtgggtgtt    72420
gtttgtattg aagattgtgt tcaaaagata ggggctccct attattcaac tttctcaagc    72480
cttttctttc tcttacccct gaactgtctc ctcctgtatc tcctctcttg ttttatcagc    72540
ccacattctc tctgtgctca gttagacatg caaagtggtt ggccaaagag gtcaaagcat    72600
cttgcattga ggacttcctc tcagctccac tgcacatggc accacctgct gccttgtcac    72660
tctagcccaa ccagacagag ctaaataatt tacagatacc atggcagcct tagacccaga    72720
aacacagaaa accatgacct gtgctgaaag ccactctctt aaatacccct cttagtcccat   72780 ctctggccca atccttgtct gtggttcaca gccagcatca atcctattgc acatcttcta    72840
atttcctaat cctctgaact tcgtcctctg tttcaactat cattaccaaa tcaaggtcaa    72900
actctaataa atttctgaca tattcttatt ttccttctat tcggtagggc accaaaccat    72960
cctgttcaag tctagtgagc ttacccacaa gagccagatc tgagcctcaa ctgccctata    73020
gccaaatgcc ttctgtaaga ccaccccctat ccctccaccc ccaccccata atgatagagc    73080
aggtgcagaa catggccagc tctcaccagg ccagctctca ccatgccaga gtcagtcatg    73140
ctcaggggcc tgaatggcat ggaatggtaa gctttgtgga tgatagaaga attacttctc    73200
ctacaggacc aacatcattt ctgacctaga agagcaaatc tcagagctga cagcaataat    73260
tgaacaaatg aacagagacc accagtctgc ccagaaattg gtgagtgacc ttacattagc    73320
taacatcttc atggacaaaa taaaattaat attttttgaat cacctatgtg ccaggcaaaa    73380
tgccaagcac tttactcata tgagccatgt tgtccaggtg acaggaccct aaagattgga    73440
ctgtgtcact cagtagtatt tctctgacat cttatctgt aattccaaga actcaagttc     73500
ttccacaaag cttaactcat ttatttccag gagctctcca agtacctctg tgtgtgtgca    73560
gtgacactgt cctcctcaca ctagggtgca cttgttgttt tctgtctggc ctttgtggtg    73620
caattaagtt tcagagcttg tgaggctctc actaacgaca ccagcgcact taatgtgcag    73680
ggcttactct ctgactgtta aagctgccca cacatcagaa tctgcagatg tcatttgaca    73740
ctctttgtga ttcctgagga tttcagtgac accttttag cttttaccat ctgtttcatc     73800
tggtgacttc ttcctcacct caaacaggtg tgcctgttgg cctggcctgg agtgacagcc    73860
agtgctgtgt tcagaaatat cctccccagg gttgttgaac cccacccccat ctgtgaagtt   73920 ttacttccca gaaggcagcc tctcaccctc tgatatgccc cagatgtgtc tgaatcctac    73980
agtgacccag cttatgactc aggctgggtc ctatcctgag accacccctcc tccgcctgcc   74040 aactattgat tcattacctt atttatctga aaacactgcc aggtttatgg tctccttcta    74100
tagaaaggaa aatgagactc agggaagtta acaatttgc atacaatctc tcaactgaac     74160
agtggtagat cattggacaa aatgaacatt ttaagtcata ggcacagatc ctgctgaaga    74220
catatttaga gactatttcc atgaagggat cctagactgt gttactgaaa atactgccac    74280
ttgtgaagat gctatttgtt gtgtggccct gtggaaggga gtagtgttgg ctgacgctgg    74340
gctgttctct gtctgtcaga gtggctctgc tgaccacttg ttgtgtgaca cagtccctgg    74400
cttctcccca gtagtcagag aggtacaagg acaagcccta aacccttgtc ctagctgaca    74460
gtggtcaccg actgatttga agtattgatt tatcctgaga cactggccag aggatctgac    74520
atgttagaat gaagtatcac ctgaaagtga gcaaatcctg cctgctagaa tggaactata    74580
ctgtcaacaa ggattaacac tagatttttaa gttcctcgaa ggcaagatct gagtcttagt    74640
```

```
cctccttggc tcttccaagc caagccttt  gttcaataaa tgattgctca attggattac    74700
atatccaaaa atctgaaggc catgatgtaa cagaaatgac gatctagcac aggagaccag    74760
acctacccaa aaaaaatagt cagtgaaaga gatgcaccaa cattatgaac tgaataagta    74820
caaaacaaca tagagcaagg cacaaattgt tctgttccct tattaataat gtgctctctg    74880
gcactgcaga gcacagtgga agaggggtgg aaggggggct gtgccccatg aattggaagg    74940
cggctgtgcc ccataaattg gaaggctttt cagaaggtgc agatcagaat gggacagggt    75000
cctcagtcct gtgttgtaga tgctgattt  gtttccagct ctccagtgaa atggatctcc    75060
gctgtgctga gatgaaacag aactttgaaa acaagaacag gtacactttc tggcatggac    75120
ccttgtgtgt gttgatggct ctaagggtcc cgcatccttt gcaggatttt agttcactgg    75180
gacttcaaat agttctaaat ggagttgggg gatgaagggt gggggagatg aacaagacac    75240
gtgtctttga agagcagaat ggcttgattc aaagccacta aaataaacca caagaaagt     75300
tattactgct tttacattt  atcatccaat cctttcattt caattataat ctccctttt     75360
gttggttact gagaagagtc atttttgttc tctatgagat ttctgtgata ataactgtt     75420
gttctcagcc aaggctcctc ctccaccatc tcctcgttct tctcttcctc ctcctctttt    75480
tctttgtctc acctctactc tccctggctg ctaggtcagg gcctcagcaa aataggaaga    75540
aagtataaga gaatcaggag caaagtcaaa tcaagagaaa attgaaagga gtccaaatac    75600
agaaagacag agaatagaac atggttacca tggtccggta ggaggaagaa aatggggaga    75660
tattgatcaa atcatacaat gttgcaaata tgtagggtga acaagtttat attgtttaca    75720
aagatataat gtaaaaaatg agagctatag ttaataataa tgtatgatat taagaactgt    75780
tgctaaatga gtttatagct gttctcacca cagagggaaa atggttaact aagtgaaatg    75840
atggatatgt taatttgttc cactctagta aacttttac  tatatgtata tagtaatctc    75900
cactattata accatttgtg tatatatata tatacataca tataaactct acctatatat    75960
atatgcttgt gtagtgtgag tgtatatata tagtaaaaat tatgtgtaat atatatagta    76020
taatggttac tatagtagag atgcatatat atatgattta tatatatata tatatatgaa    76080
tcttatgaca tcatgttgta tacctcaaat atacacaata aaatttattt ttaaaggagt    76140
tttcttatgt gtatgggtga agataatcct acatccccctt tcaggctact tgctgcacac   76200
cagagcagcc ttagaaatcc tggtggagag atagcactct tagttgagtc atagccattt    76260
acacatttat ttatctatag actttatctg ttagagcagt tttaggttta cagcaaaaat    76320
gaggagaaag tacagagagt tcctgtgcac ctgctcctaa tcaaattcaa tcaaattaaa    76380
ctcaaagatg agtacaccaa gacacataat aatcaaacta tcaaaaatca aagacaaagc    76440
aaaaattctg agagcatcag aaggtaagaa acacgtcaca tacaaaggag tgccaataca    76500
attgtaattt cttaacagaa accctgcagg ccaggagtca gtgtgatgat gtattaaaag    76560
tgctgaagga aaaaactgcc taccaagaat accttagcaa agctgtcttc cccagttgag    76620
ggagaaatag aaactttccc aaacaaaaat taagggagtt cattaccact atgcctgcct    76680
tacagaaatt gcaaaggaa  gttttaaaaa cggaaacaga aagctgctaa taacatgaaa    76740
catatgaatg cacaacactc aatggtataa gcaaaataga gccatactca gaatacttta    76800
ggactgtgat gatgggatgt aagacaattt tatcccaata tgagagtaaa aacacaaaac    76860
tattaataac aactatagct aaaataaatt ttcaatgata aatcatatta taaaatgata    76920
tcaattctga catcaaaaac aaaatgttag ggagggagta aaactgttga gttattgctt    76980
gcaactaaac ttgttgtcag cttgaaatag cttattacaa gaacaagata ttctaactaa    77040
```

```
gtgtcatggt aaccacaaag ataaaaatct ttagcagtag cacaacacaa aaatagaaat    77100
gattcaaagc atacactaca aaaaacatca aaccacaaaa gaagagacca agagaggaag    77160
aaagaatcta caaaacaaca aaacaaaaat taacaaaatg gcagtagtaa gttcttacct    77220
attaataatt accttgaatg taaatggatt aaattctctg attaaaaaaa atagaatgcg    77280
tgaatggatt tttttaaaaac aagaaccaac tatacgctgc ctacaagaga ctcatgtcac    77340
ctgtaaggca catgagcact cctcccaggg tctgagatta agcccactca acctgccgct    77400
accaccattg ctggcaccta tctgcatgca ccacctatgg gcctgaggac aagaccaccc    77460
aacttctcat agccattgcc aataccagtg agtaccactt gggtgctaga ggggttgtccc   77520 actattgcta ctgccatcag ccacaacaca cccactgcca atgggtccgt gaacctacct    77580
acctgcccag cccatagctg ccattcctga cacctgaaaa aaacactaaa aggcccaaga    77640
attggcctgc ctgaacccac taatacttaa tgccagcata tgccaccctg gggcccaaag    77700
ataggcacac ttataagatt agaataaaac tagaaatcaa taacaagaaa aactttggaa    77760
actatacaaa cgcatggaaa ttaaacagca ttctcctgaa tgaccaatag aacaatgaag    77820
aaattaagat ggaaataaaa aaaatttctt gaaacaaaaa aaaattgaaa tacaatatac    77880
caaagcctgt gggatacagc aaaagcagtg ctaagaggga agtttatagc aataaacacc    77940
tacatcaaaa aagtagaaag atttcaaata aacaatctaa taatgcacct gaaggaattg    78000
gaaaaccaag cccaaaatta gtagaagaaa agaagtaata aaaatcagac cagaactaaa    78060
cgaaatagaa actaaaaaaa caatacaaag ggtcagcaaa aaaacagatt cttcaaaaaa    78120
ataaaccaaa ttgataaacc agtagctaga ctaaccaaaa aaagacaaga gaagacccaa    78180
ataaaatcag aaatgaaaaa agagacatta caactgttgc cacagaaata caagaaatca    78240
tcagagacta ttatgaacaa ctataactaa cactaacaaa ctaaaaaatc tagcaaaaat    78300
agataaattc ctgaaaagat aaaatctaac aagatgaatc aggaagaaat tgaaaattat    78360
tcaagaccaa taatgagtag caaggttgaa tcagtaataa aaagtctccc aacaaagaaa    78420
agcccaggac caaatggatt cactatcaaa ttctaccaaa catataaagg agaactaata    78480
gtaatcctcc ttaaactatt caaaaaaatt tgaagaggag gaaattctcc cttacttatt    78540
ctgtgaggcc agcattacct taataccaaa gtcagatgac aatacaacaa caggaaaaag    78600
aaaaccacgg atcaatatct ctgatgaaca cagatgcaaa aatcttcaat gaaatactag    78660
caaaccaaat ccaacaatac atcaaaaata taatacacca tgaccgagtg ggacttatat    78720
cagaaatgca aggatggttc agcttatgaa aatcaataaa catgatatat aacatcaaca    78780
gaatgaagga caaaaatcat gtgatcatcc caatagatgc agaaaaagca tttcataata    78840
gtcaacattg cttcatgatt aaaaaataaa acctttcaac aagctagata tagaagaaac    78900
atacctcaac ataacaaagg ctgtatatga cagatctgca gctatcatca tactgaacag    78960 ggaaagttg aaaactttc ctctaagaat tggaacaaga taaggatggc tacttttacc     79020
gctcctattc aatatagtac tggaagtcct agccagagca atcccgcaaa agaaaaaat    79080 aaaaggcatc caaattggaa agaggaagc caaatgatct ctctttgccg aaaaacataa    79140
tcttatatat gaaaatcaca aaaaaactcc atccaaaaac tcttagaact aataaattca    79200
gtaaagttgc agaatataaa atcaacatac aaatatcagt tgcatttctg tacaccaaca    79260
gtgaaatagc caaaagagaa atcaataagg caataacatt tacactggct acaaagcata    79320
aaataaaata tctaggaata aatttaacca aaaaggtgaa agacctttag aaggaaaact    79380
gcaaaacaca gatgtaataa attgaagagg acacaaacaa atggaaagac atttcaccca    79440
```

```
tgcttatgga ctggaagaat taagatcgcc aaaatggcca tgctgcccaa tgcaatccct    79500
aaattaccaa tgtcactttt cacagaaata gaaaaaataa ttctaaagtt catatggaac    79560
aaaagatgag ccagaatagc caaagcaatc ctgtggggaa aaaaaatctg gagttatcac    79620
attacctgac ttcaaaatat attacaagac caggcatggt gactcacacc tgtaatccca    79680
gcactttggg aggccaaggc gagaggatgg cttgtgtcca ggagtttcag actagcctgc    79740
acaacatagc gagacaccgt ctacacaaaa gattaaaaat tagccaggta ttatggagtg    79800
tgcctggagt cctagctact tgggaggctg aggtgggagg atcacttgag cccagatggt    79860
caaggctgca gtgagctatg atcatgctac tgcactccaa ctgcactcct tgatatagat    79920
caaggctatc ataaccaaaa tggcaaggta ttagtataaa aatagacata taaacataaa    79980
gcatggaaca gaatagagaa tccagaaata aattcatgta attacagcca actgatcttt    80040
gacaatgctg tcaagaacat acactgggaa cagggcaccc tcttcaataa atgatgctgg    80100
gaaaactgaa taaccatatg cagaagggtg aaactagacc cctatctctc atcatgtaca    80160
aaaatgaact caagatggat taaagtctta aatgtaagat ccaaagctat aaaaatacta    80220
gaagaaaacc tagggaaaag tcttcaggac atcggtctag gcaaagattt tatgaccaag    80280
actttgaaag cacaggcaac aaaaacaaaa aaagacaaat gagactatat taaactaaaa    80340
agcttctaca cgcaaaagaa accatcaaca gagtgaagag acattctctt aaatgggaga    80400
aaatatttgc aaactactca tttgacagag gactcaaaca attcaacagt aaaacaaaca    80460
caaattcatt aaaaatgggt aaaggacatc tttcttaaaa gacatttctt aaaagaagac    80520
atttcttaaa agaagacata cgaatagcca acaagtatgt gttcaacatc actaatcatc    80580
agggaaatat agagcaaaaa cacaataaga tatcatctta caccagttag aatggctatt    80640
ataaaaagac aaaaaataac atatattgac aaagatgtgg agaaaaggga actcttatat    80700
actgttggtg gaaatgtaaa ttagtacagc cattatggaa aacactacag agatttctca    80760
aaaaattaaa aatatgaacc agcaattcaa ctactggata tttcttcaaa ggatgtggag    80820
aataggaaat gctatacact attggtgggg atgttaatta gttcagccac tgtggaaagc    80880
agtttggaga tttctcaaag aacttgagac agaactacca tttgacccag caatcccatt    80940
attgggtgta ttgtactcaa aggaatgtaa atcattctac caaaaagaca catgcatacg    81000
tttgttcatc acatcactat tcacaataac aaagatatgg atcaacttag atgcccatca    81060
gtggtggact ggataaagaa aatgtggtat atatacacca tacaatacta cacagccata    81120
aaaaagaaca aaatcatgtc ctttgcagca acatggatgc agctgaaggc cattatccta    81180
agtgaattaa cacaggaaca gaaaaccaaa tactgcatat tttcacttat aagtgggagc    81240
taaacattgt gtacacatag atacaaagaa gagagcaata gacggtgggg cctacttgaa    81300
ggtggaggtt gggaggagag tgagggttca agaacaacct atcaggtact atgctcacta    81360
cctgagcaat gaaatcattt gtacaccaaa ccccagtgat gtacaattta cctatgcaac    81420
aaatatatac atgtacatgt acccctaaac ctaaaataaa aacggaaaaa gaaaaaaatt    81480
agtagtattt ctatatacta tctaaaaaag aaattaagaa gacaattcta tttatgacag    81540
cttaaaaaat aagatagcta ggaataaatt taaccaagga agtggaagat ttctacactg    81600
aaaattatgg agcatcggta aaagaaattg aagaagcagc aaataaatgg aaagatattc    81660
catgttcatg gattggaaga attaatattg tttaaatgat catgctaccc aaagcattac    81720
acagatttaa tgcaatccct attaaaatac caaaaatgtt cttcacaaaa atagaacaaa    81780
taatcttaaa attcatatgg acccacaaag tccccaaata gccaaaatga tcctgagcaa    81840
```

```
aaataacaaa gctaaaggca cgtgatttta aatgatacta caaagctata gtaacccaaa    81900
cagcatgata ctggcataaa aaacagaca catagaccaa tggaacagaa tagaggccta    81960
taaataaatt tatacaccca tagccaactg attttgaca aaggtgccaa gaacacacac    82020
tgggaaaaaa gatagccttt tcaataaatg cttttagtc aaattaaaag aagtagataa    82080
aacagagatc tcaaagaagc taatattaca cctcacaaaa ctaggaaaga agaacgaaat    82140
aagcccaaag tatgctgaag aaagaaaata ataaagatca aagcagaaat aaatgaaata    82200
gagtctagaa aaacaatata aaaatcaatg aagctaagag ttgttttttg aaaagataaa    82260
agcaacaaac ctttagctaa actaagaata aaatagagaa gactcaaata aataagatca    82320
gaaatgaaag aggagacatt acaactgata tgacaaatac aaaggatcgt aagagactac    82380
tgtgaacatt tatatggcaa tgaattggat aatctagaag aaactgataa atttctagac    82440
acataaaacc tgccaagact taatcataaa aacaatagaa aatctgaaca gaccaataaa    82500
gatgatattg aataagtaat aaaaagccta ccatccaaaa aaaacccaga cctggtgcct    82560
ttactgctta attctacctg acatttaaaa taagaactaa catcaattct tctcagattc    82620
ttctaaaaaa gtgaagaggt ggaaggactt tcacatgatt ttttttttag ctttttttt    82680 tttttttagg cagagtttca ctcttgttgc ccaggctgga gtgcaatggt gcgatcttgg    82740
ctcaccacaa ccaccacctc ctgagttcaa gcgattctcc tgcctcagcc tcctgagtag    82800
ctgggattac aggcatgcac caccacgcct ggctaatttt gtattttag tagagatggg    82860 gtttctccat gttgctcagg ctggtcttga gctcccaacc tcaagtgatc tgcctgcctc    82920
ggcctcccaa agtgctgaga ttacaggcat gagccaacgc acccagcctg ttcacactat    82980
ttttatgagg ccaggattac tctgatacca agtcagacaa gaacattata agaaaataaa    83040
attacaggcc aaaatcctta aatgaactta gatacaaaaa tccttaatta aatattagca    83100
aacagaattc agcaacatat tgaaaggatc atccaccatg atccagtgag actgatcccc    83160
tgggatgcaa gaacggttgg acacacacaa atcaataaat gtgataccto acattaatag    83220 aatgaaggac aaaaccgtat gaacagacac ttctcaaaag aagacattta tgcagccaaa    83280
agaccatgaa aaaatgctca tcttcactgg ccatcagaga aatgcaaatc aaaaccacaa    83340
tgagatacca tctcacacca gttagaatgg cgatcattaa aaagtcagga aacaacaggt    83400
gctggagagg ctgtggagaa ataggaagag ttttacactg ttggtaggac tgtaaattag    83460
ttcaaccatt gtggaagtca gtgagtcagt gtggtgattc ctcagggatc tagaactaga    83520
aataccattt gatccagcca tcccattact gggtatatac ccaaaggatt ataaatcatg    83580
ctgctataaa gacacatgca cacgtatgtt tattgtggca ctattcacaa tagcaaagac    83640
ttggaaccaa cccaaatgtc caactatgat agactggatt aagaaaatgt ggcacatata    83700
caccatggaa tactatgcag ccataaaaaa tgatgagttt gtgtcctttg tagggacatg    83760
ggtgaagctg gaaaccatca ttctcagcaa actatcgcaa ggacaaaaaa ccaaacactg    83820
catgttctca ctcataggtg ggaattgaac aacgagaaca catggacaca ggaagggaa    83880 catcacactc tggggactgt tatggggtgg gggaggggg gaggtatagc atttggagat    83940
atacctaatg ctaaatgacg agttactggg tgcagcacac caacatggca catgtataca    84000
tatgtaacta acctgcacat tatgtacatg taccctaaaa aagtataata aaaagtaaat    84060
aaataaataa atccaattaa aaaatgggta agggacctga atagacattt ctcaaaagaa    84120
gacatacaaa tggccaacag acatatgaaa aaatgctcaa tattgctaat cattagggaa    84180
atgcaaatta aaaccatagt gagttattat ctcacatgga tcagaatagc tattatcaag    84240
```

```
aaggcgaaag ataacaagtg ttgaagatgt ggagaaaagg gaacacttac aaagtgttag   84300
tgggattgta aattagtatg gccattatgg aaaactgtat agaggttgct caaaaaacta   84360
aaaatagtaa taccatatga tccagcaatc ccacttccga gtgcttaccc aaaatatttg   84420
aaatcagttt gttgagatgt ctgtattccc atgttcaatt cagtactatt aacaacatcc   84480
aagttatgga atcaacttaa gtgtccatca gttgatcaat ggataaagaa aatgtggtat   84540
atacataaaa tggaatacta ttcagccttt aaaagaagg aaattctggc atttgtgaca    84600
acatggatgg aactggagag cattatgcta aataaaataa accgggcaca ggaagacaaa   84660
taccacatat tctcacttat atgtgggatc tgaaacaatc aaactcatag aaacagcgag   84720
taaaatggtg gttaaagaga ctaggggtg gggggaatag ggagatgatg gtcaaagggt    84780
acaaaatctc aattaggcag gagaaatatg ggattttctt agatctattg cacagagtag   84840
taaatatagt taataataga gtattggaca tttcaaaatt gctaagaata aatttcaaat   84900
gttctcactg aaaaaacttt taggctgggc gcagtggctc acgcctgtaa tctcagcact   84960
ttgggaggct gaggtgggtg gatcacctga ggtcacgagt tcaagaccag cctggccaac   85020
atggtgaaaa cccatctctg caaaaataca aaaattggtt ggacataatg gcaggtgctt   85080
gtaatcccag ctactcagga agctgaggtg agagaatcgc ttgagcccag gaggcgaagg   85140
ttgcagtgag ccgagattgc gccattgcac tccagcctgg gggacagagc cagagactac   85200
gtctgaaaaa aaaaagaaa aaactttaaa gtatttcagg tgatgactat gttaactagt    85260
ttggtttcat tattccacat tgtattcata aatcataaca tcactttta ccccataaat    85320 atatataatt ataagttatc aatttataat taaaaaaaga aatcctggtg gagagacagc   85380
actcttagct gaggcataaa cttttatgta cttattcatt tatttataaa ctttatttt    85440 tagagtagtt ttagagtttt aggtttacag caacattgag gggaaagtat aaaagatttc   85500
ccatatactt actgccccct cacacacata gcttccccca ttatcaatat ccccaaaagt   85560
ggtaacattt gttataatca atgaacctat attgacacat cattatcacc cagagttcat   85620
agttgacatt agagttcact cttggtactg tacattcaat gagtttggac aaatgtgtaa   85680
tgacatgtat ccactattct agtgtcataa caatagtttc actgccctaa aaatctgctt   85740
cgctctgcct attcatccta cctcccatcc ctaaccttgg gcaaacactg atctctttac   85800
tgtctccata gtttgacctt tttcagaatg tcatatagtt ggaatcatac cctatgtagc   85860 cttttaaat tggcttcctt cacttagtaa tatgctttaa aggttcctcc atgtctttc    85920 atgcttgata gctcatatgg actcatttta atactcatca taaacactgc caacattgct   85980
tcctggaatg gaggctggag agaacttggg ttctaaaatt atcctgggtg gcaatgcagc   86040
ccatagtttc ccgagcaagc tatagacaag actgtgctga ctattagagg ggaatctgtg   86100
gtcatgctgg ctccattcaa aacaatgatg gtagaaaagg gtcccctcac cctttctgga   86160
tagatgccag gataatgctt caggaagtga aggcccagg ctgagtatgg tagctcacgc    86220
ctgtaatccc agcacttcgg gaggtcaacg caggaggatt gcttgagtcc aggagtattt   86280
tgaaaccagc ctggacacca tagcaagacc ccgtctctac aaaaaattaa aaaattagat   86340
gagcatggtg gcacatgcct gtgttcccaa ctacttggga ggttaaggtg ggaagatcac   86400
ttgagcctgg gaggttgagg ctgcagtgag ctgtgaccat gccaccacac tcactctggg   86460
caacagaggg agactctgac tcaaaaaaaa aaaaaaaga tttaaaaatt ttaaaaataa    86520
aaaagtgaga acctcacttc ctgtgggagg gtggagggta ggatcagatc agggtaacag   86580
ctcagctctg gacttctttt tactaatgat tgtggccttc tcctgggtc ccacagggag    86640
```

```
ctcaaagagg cccatgaagc agaactcagt gagttggaga acaactacaa agcagccttg   86700
aaggcagaga agttggctgc ccaagagaag ctaggtactg ctgggacctg ggagaatgac   86760
cctggatgaa ggtccaggca atggcatttc taataagctt ctagggtgat ttccaaggca   86820
cacaaaggtt ttactacctt ggtgatgagt ttggggtggg gaaggtgtgc agaagaactc   86880
acatttgaat ttgaaaatgt gcatatcaga agactaatga tgatcctgtt gttttccttt   86940
tatccagagg agatgggaaa agaatacaag tatttgaaga atatgtttcg tacgtatcag   87000
gtgagataca cagctccctg ttggattaca agagaaggaa ggctcattcc tggctaacat   87060
tgggataaat ctagagcttt tgtccagaaa ataatgtcct gagattccca gcatccttag   87120
acctaagtgg cactagctgc acccagggg aggatgaacc caatggcttc catgcatgac   87180
aagtcaggca cccaaatcct gaagagcact actgaaaaat atgtttgtga ttacaaaagt   87240
aatagcttct cattttttgt aatggagcaa aaagaaatat caccacccaa agacaacccc   87300
tgttaatatt tgtactttgt tagaactgca gttgagatca tactgtatat tgtataacat   87360
ctatatattt tttatatgtt ctttatcaag catataagaa acttttccct cctttataat   87420
gacttgatat tatcctaatg aaattgccat tgggttctaa aattttactg ttcccctatt   87480
attgggcatt tgagttgttt ccaattgctt gctgtaacag ataataccac tttgaatatc   87540
tttgattcta gaagtagagt gcttggtcaa aaggaatgaa ctttaaaaaa agtcaacttt   87600
cattttagat tcagggggata catgtacaag ttattgtgtg atgctgaggt ttgggatatg   87660
aatgatctca ttacccagct ggtgagcata gtacccaata gttattccac ccttccccct   87720
cttcctctct cccaatagcc cccagtgtct acaagaacac gtggcacttg gttttctgtt   87780
cctgtgttaa ttggctttag gataatagcc tctagagcca tccatgtttc tatgaaggac   87840
atgattttgt tctttttat ggctgcatag tattccatgg tatatgtacc acattttgtt   87900
tatccagtcc actgtcagtg ggtacttagg ttgattccat gtctttgcta ttgtgaattg   87960
tctgtgatta acatacaaga gaaggtgtct ttttggtaga aaaatttatt ttcttttgga   88020 tatatacccca gtaatgggat tgctgagtca aatggtagtt ctgttttaag ttctttgaga   88080
atttccaagc tgcttttccac cggcaatgaa ctaatttaca ttcctaccaa cggtgtataa   88140
gcattccctt ttcctccaa cctcaccagc atctgttgtt ttttggcttt ttaataataa   88200
ccattctaat gtgtgtgggc tggtatctca ttatggtttt tgatttgcat ttctctgatg   88260
attagtgaca tgaagcatt tttatgtttt ctgaccactg tatgtcttct tgttttttac   88320
acactattac attctatta tgacaagaaa tatttacatg attggaaaaa gtaaaaattg   88380
gaggacaaaa agcagattag tatttaccat gggctggact gggactgggg aaggggctta   88440
ctacaaaggg acaggagaga attactggag atgtagtggt ggttccgtaa ctatccgttt   88500
gtcaaacaca ttaaaagtat actgaacaag gcacatttt actcaattaa actgacatta   88560 aaaaagaag tgaaaagaa gaaattccat ttagaatgtt gaaaaactgt agatttagtt   88620
ctagaattct ggggctctat aacttatttc aaaatatagg ttttcagccc attttaact   88680 tatcaaatct ttattcagaa atccaaagtt tatatttaaa aatagctcat ttaaatttga   88740
ccataggccg gtgctgtggc tgatgcctgt aatcccagca ctttgggagg ccgaggcagg   88800
cagatcacct gaggtcagga ttttgagacc agcctggcca acatggcaaa accctgtctc   88860
tactgaaaat acgaaaatta gtcggacatg gtggcacaca cctgtaatcc cagctactca   88920
ggaaactgag gcgggagaat cgcttgaacc tgggaggcag aggttgcagt gagccgagat   88980
cgtgccactg cactctagcc tgggcaacag agcaagactc tgtctcaaaa aatatatata   89040
```

-continued

```
aataaataaa ataaaaaaga aataaatttg accctaaagc taacacatgt aaaaattata    89100
taaaagaaaa gaaaattgtt ccaacttttt tactttgggg tttttaaaaa agttttattt    89160
caatagcttt ggggatacaa atggttttt tgttacctgg atgaattata tagtggtgaa     89220
ttctgagact ttagtgcacc catcatctaa gtagtgtata ttgtacctaa tgtgtagttt    89280 tgttttttt ttatcacaag ccactctccc acctcccct tctgagtctc taaagttcat      89340
taatgaatat gcctttgcat attcatgact tagctcccac ttttaagtga catcatacag    89400
tttttggttt tccactcctg tgttactttg tttagaataa tggcctccag ctccatccaa    89460
gttgctgcaa aagacatttc attccttta atgactgagt agcagtctat ggtgtatata     89520
tgccacattt tatttatcca ctcattagtc aacgggcact taggttggtt ccacatcttt    89580
gcaactgtga attgtgctgc tataaacata cgtgtacaag tgtcttttc tgtaatgact     89640 cattttcctt tcggtagaga tcaagtagtg ggattgctag attgaatggt aaatctactt    89700
ttagctcttt aagaaatctc catactcttt tccaaaaggt tgtactaatt tacattccca    89760
ccagcagtat ataagcactc cctttccc acatccacac caaaatatat gtttttta       89820 cttttaata atgaccattc ttgcaggagt aaggtggtat ctcattgtgg ttttaatttg     89880
catttccctg atgattagtg atattgagca cttttcatg tttgttggcc atttgtatat     89940
cttcttttga gaaatatcta ttcatgtcat ttgcccactt tttaatggga ttatttgttt    90000
ttttcttgct gatttgtttg aattccttgt agattttgat tactagtcct ttgtcagatg    90060
catagtttgc aaatattttc tcccattctg tgggttgtct gtttattatt tcttttgctg    90120
tacagaagct ttttagttta attaggttct atttatttat ttttggttt gttgcatttg     90180 cttttgggt cttagtcatg aattatttgc ctaagccaat gactggaaga gtttttctaa     90240
tgtcttctag aatttttata gtttcgggtc tcatatttaa gtctttgatc catcttgagt    90300
tgatttttgt ataaggtgag aaatatggat ccagtttcat ttttctacat gtggcttgcc    90360
cattctccca gcaccactta ttaaataaag tatcattccc caatttatgt ttttgtttgc    90420
tttgtcaaag ataagttggc tatacatatt tggcttcatt tctgggtttt ctgttctgtt    90480
tccttggcct atgtgcctac ttttataccA gtaccatgct gttttggtaa ctatagcctt    90540
gtagtataat ctgaagtcta gtaatgtgat acctccagat tgttctttt tgcttagtat     90600 tgctttggct attctggctc ttttttggtt ccatatgaat tttagaactt ttttctaat     90660 tctgtgaaaa ataatgttga tattttgatg ggaattgcac tggatctgta atgcaagatt    90720
actttgggca gtatggtcat tttcacaacg ttgattcttc caatccatga gcatagaatg    90780
catttccatt tgtttgtata acctattact tctttcagct gtgttttata gttctccttg    90840
tagagatctt tcacctcctt ggttaagtac attcctaagt atttatttt tttgtagctg     90900 ttgtaaaagg gtatcagttc tttttttgat tctcagcttg gtcgttgtta gcgtatagca    90960
gtgctactga tatgtgtaca ctgattttgt aaactgagac ttcactgaat tcgtttatca    91020
aatcttagag tctttggagg agtctttagg attttctagg tatacaatta tataatcttc    91080
aaacagcaat agtttgactt cttctttcc aatttggacg ccctttattt ctttctcctg     91140
tctaattgct ctagctagga cttccagaac tatgttgaat gagagtggtg aaagtgaagg    91200
tggccatctt gtcttgttcc ggttctcaag gggaatgctt tcaactttt tccattcagt     91260 atgatgttgg ctgtgggttt gtcacatatg gcttttatta ttgaggtagg tcccttctat    91320
gcctagtttg ttaggagttt taattatgaa ggatgctgga ttttattaaa tgcttttcct    91380
gaatctattg agatgatcat gtgttttttg ttttcaattc tgtttatgtg atgtatcaca    91440
```

```
tttattgact tgtgtgtgtt aaaccatccc tgcctccctg ggacaaaatc cacttgaatt    91500 atcttttga tgtgctattg gggtcggtta gctagtattt tgttgaggat ttttgcatct    91560
atgttcaaca tcagtgaaat tggtctgtag ttttttttat tgttgtgtt ctttcctgat    91620 ttggatatca gggcgatact ggctgcatag aatgatttag agaggattcc ctcttctca    91680 atctttcgga attgtttcag taggattgta ccaattcttc attgaacatc tggtggaatt    91740
cagctgtgaa tccatctagt cctgggcttt ttttgttgtt cttggcaatt tgaaattac    91800 tgattcaatc ttgctgcttg ttattcacct gttcagggtt tctgtttctt cctgatttaa    91860
tacaggagag ttgtacgttt ccaggaattt gtctatttcc tctaggtttt ccagtttgta    91920
tgcaaaaagg cgttcatagt agcctcaagt gatcttttgt atctctgtgg ttctgtgggt    91980
tgtaatgtct ccaatttcat ttctaattga gcttatttag atcttctctt ctttacttgt    92040
ttaatctttt cttcttttct tggctaatct agtctatttt attttttcaa agaaccagct    92100
ttttgtttca ttgatctttt tatatttttt gtttgaattt cagttagttc tgctctgatg    92160
ttcattattt cttttcttct atctttggac ttcgtttttt ttgtttctcc agttccttgc    92220
agtgtgacat tgtcaatttg tgctctttca gactttttga tgcaggcgtt tagcactata    92280
aactttccta gcactgcttt tgctgtatcc cagaggtttt tttagttttt agttttttga    92340
gacagtctca ctctgtcaac caggctggag tgcggtggca ctatcttggc tcactgcaag    92400
ctctgcctcc caagttcaag caattctcgc acctcagcct cccaagtagc tgagactgag    92460
actacaggcg cctgttacca cacccagcta atttttgtat ttttagtaaa gatgggttt    92520 caccatgttg gccagcctgg tctcaaactc ctggcctcaa gtgatccacc tgtttggcct    92580
cccaaagtgc tagaattaca ggcatgagcc accgaacccc acctatccca gaggttttga    92640
taacttgtgt cattatgatt caattcaaaa attttttaaa tttccatctt gatttcactg    92700
tttaccccag atatcattca ggaatggatt attttatttc catgtatctg tatagttttg    92760
aggattccct ttgaaattga tttttagttt tattctgcta tggcctgaga agatacttca    92820
taggatttca atttttaaaa attaattgag acttgttttg tgacctatca tatggcctat    92880
cttagagact gttctatgta ccaatgagaa gaacatacat tctacagttc ttgggtagaa    92940
tgttctgtaa atagctgtta tgttcatttg ttttagcatg tcatttaagt ccatttttc    93000 tctgttggcc ttctgtctca aagacttgtc tagtgctgtc agtggtatat taaagtatcc    93060
caccattact gtgttgctgt ctatctcatt tcttaggtct agtagtaatt gttttatgaa    93120
tctgcaagct ccagtgttag atgcatgtaa atttaggatt gtaatatctt cttgttggat    93180
tgatcctttt atcattatat tgaccatctt tgtcttgtct tactgttgtt gctttgaagt    93240
ttgtttcgtc tgatataaga atagctactc ctgcttgctt ttggtgtcca tttgcatgga    93300
atatcttttt ccacccttt cccttgagtt tatttgaatc ctttcatgtt aggtgagtct    93360
cttgaagaca gcagatattt ggattgtgat ttttgttatc cattctgtca ttctgtatttt    93420 tttaagtgga gcgtttaggc catttacatt caacattaat attgagatgt gaagtactct    93480
tctcttcatc atgttaattg ttatgtatat agcttttctt ttttcattct gttattgctt    93540
tatagacttc atgagtttta agctttcaag agattctatt ttggtgcgta tttggctttt    93600
gtttcaatgt ttaaaactcc ttttagccca ccttctttc ttttctttcc ttccttcctt    93660
ccttactttt ttttttttt tttttgatag agtctggctc tgttgcccag gctggagtgc    93720
aatgttgcaa tcttggctca ctgcaaactc tgtctcctgg gttcaagaga ttctcatgcc    93780
tcagcctccc aagtagctga gattacaagc atgcacaatc acacctggct aatttttgta    93840
```

```
tttttttagta aagacagggt tttgccatgt ggccaggctg gtagcatttc ttgtagtttg   93900
gtttgctagt gacaaattcc ctcagcattt gtttatctga aaatgactttt tatttctcct   93960 tcaattacaa aacctagctt tacaggatac agaattcttg gctgacagtt ttttctgtt    94020 taaggagatt gaagataaga ccccaatacc ttctggcttg taaggtttct gctgagaagt   94080
ctgctgttat tcagataggt tttcctttat agcttacctg atgcttttgt cttactgctc   94140
ttagaattat ttccttcatg ttgagtttag atagcctgat gactatatgc cttggtgaag   94200 atcttttttgc aattaatttc ccaggagttc tttgagcttc ttggatttgg atatctagat  94260
ctctagccac gccagaaagg ttttcctcaa ttattccctg aaataagttt ccagacttg    94320 ttattttctc ttcttcctct ggaacaccag ttattcttag gtttggctgt ttaacataat   94380
cccatatttc ttgaagactt tgttcatttc tttttattct ttttttcttta ttttttgtctg  94440 attgggttag tttaaaaacc ttgtcttcaa gctctgaaat tctttcttct acttgttcta   94500
gtctattgtt aaagctttct gctgcatttt gtattccctta agtgtgtctt tcatttctag  94560
aaattcttat tgttttttct tgataaatatc tatatctcta gaaaattttt cattcatatc  94620
ctgaaatgct ttttaaattt ataatagttt tcatcttttct ctgaaatctc cttgagtagc  94680
ttaataattg accttctgaa ttccttatct ggtattttaa agagttcgtc ctactttgga   94740
tccattgctg gagagctagt gttatctttt gagggtgtta tagaaccctg tttttttcata  94800 ttaccagagt tccttttctg gttcctcctc atttgggtag attatttctt ctaattatcc   94860
ttgaattgat gtttgatttg actgtgtttc tttttgtgtt tgtttttttaa tttctttttt  94920 ccacttaagg atgtgactttt aatgcttatc atattatggc ctaatttggt ttttggtgct  94980
ttcaggggtg aagactctgt aatagttcct tggttataga gagtttttttt atgtggcttt  95040 cttagatgct ggttgtagta gcaatgtgct tggtatatta gcaagatcac tgtctcctat  95100
ggggctgtaa tgataagagg tctcttaaag cttatctcat tccccgtgtgg catgcccttt  95160 tttatttacg cattttcgtc cagttttttt tttcttttttt tttttttgagg ctgaatctca  95220 ctctgttgcc caggctggag tgcagtgtca tgatctcact gcaatctccg cctcctgggt   95280
tcaagtgatt cttgtgcctc agcctcccaa gtagctggga ttacaggtgc ctgccaccac   95340
acccaactaa ttttttgtatt tttagtagag acagggtttc accatattgg ccgggctggt  95400
ctcgaacccc tgacctcaag tgatccaccc gcctcagcct cccaaagttt tgggattaca   95460
ggcatgagcc actgcacccg gccttttctc cagtgttttta tttactagtt tgatggttcc   95520
agcttcaggc cagtaggggaa ggtgtccctg ggtaggaatc agctgtggct aaagcaggtg   95580
ggtaaatgca atacccagtg atgggcagag gtctcagcct tgacagaggt ggctggagga   95640
gtgagttgca atgaggtctt acctggggta agggttggag ccacctcagc tccctgcca   95700 ggttagcagg aaagttatcc ctctcaaaca cactcctgtt tcagtgctcc agcttttcat   95760
ctccagacag ccacctcttt tcatctgcag gaatttttgat gttccaaata gagaaaaatt  95820
gtgaacgtct ctcatacaag cttgaaccta gagggtgccc ctcctatggg gatgcagtca   95880
ccctgatgtc ttccagaaag actgtctata gttgcactca caccaagctc caatgggaga   95940
agctccaact gtgcctgcag tggtagacaa tgggtggggg ggttgtctgt ctgttgggtt  96000
agagctgaag acttttcctg ctgagcccag cactgcaact gtgcctctgc tgaaagaaac  96060
ttcccactag cagaaagatc tggttcttaa gtcctgctgt ctggattatt ttctcccaca   96120
gggtgttctc ttgatgtggt gcactccctg ttccccctagg atcaggggga tcccactcct  96180
aagggaacag ggtctctggg tctagctgtc cagtgaaggt accacacccc aggctggtgc   96240
```

```
tagggaatat ctgcaaggga tccagtgatg tgacctctct tcaagtctcc caacagtggg    96300
tagcagcacc agttctaatg ggcgtggcag ggtaatagac tctgtgagag tccttggtta    96360
ttgatagcct tagtgtgttg gctttctcga acactggttt tagtagtaat gaactggtca    96420
tgtggacaaa ctcaggacct cctggttagc cagaatggtg caggcagtgg tgatagctga    96480
gattacacag ccatcttctt cctaggtgcg ttgttattct accaggagat gctgtaatgg    96540
actgtgttgg ttggcctcca gccaagaggt gatgcttaca aaagggaacc agctgcaata    96600
gtagcaatag gacttttgct tgctttatgt tgtccagagg ggttactctg gtttctcagg    96660
caatgagtgg ggctatatag cccccaagag tttctgtcct ttgtgttaaa ctaccagggc    96720
aggtgacggg gcaaagcagg gtgagggttg gttcagtgg gcttgcgctc tgagtctccc    96780
tgtgcagggc aagcagcagc ccctgtggaa gccaggggat gggagtggtt ctcaggccac    96840
tgggttgatg ttccaaaagg cagtgttgct ggctttgcca cacagaaggg tttgtgcaga    96900
gtgaggagaa gcaggtggct gtgagccca cacagatccc atgcacttgg caagacagat    96960
gcactcccac agtgttccac tggcagcagc aagctaagtt ccagttagcc tgcactcaga    97020
acttgcaact gtcccgagtc atatacgttc cctgcagaga tagcaatcac ggctttcagg    97080
ccaagcccct ccctgtccac tgcaaagcca ggcacccagt tcctgcactg gcagctcctg    97140
cactcatggc tgcagcccac ttttcactct cctccaccct ggccctggcc aagggagttc    97200
atccgcacct aaggttatat catgaaaccc agttggaggc ttctttcaac ctgcgaccac    97260
tgcctgaact ttttggctgt cctccacagg gttccccgtg aggaacagta agaaatggct    97320
tccctctctc catgctgaaa tctgggagtg tgtgcaagaa tcttcctgcc actgctccca    97380
cttttatatt ccacatccct ccccaagtca gttcctgtgc tgcatagggt tagggctttc    97440
tcccatggtc tggactttca gggtccacag tgggggtgtg tattccagga gtaatgtagg    97500
gtgagtcccc cttctcacac tctgggaact cacagccctt tgcctgattc acagtgtaac    97560
ctgcagcctc ctgcttcctt caaagggtct gtagattcct ttggttttcc tgttcagttt    97620
ctgcattgct ccttgaaaaa agttcagtgt gaatctctac aactattttg tttttcaag    97680 tgggagaagt atgctagcaa tgcctctaat ctgccatttt ggaaaaacac aaacaaactt    97740
ctgtcttctt ttgagaagtg tctgttcatg tcttttgccc actttttaat ggggttgttt    97800
tttgcttgtt caattgttta agttacttat agattctgga tattagatat ttgtcagatg    97860
cgtagtttgt gaatattttc tctttttttg taggttgcct gtttactttg ttgacgggtt    97920
tttttgctgt gcagaagctc tttagtttaa ttaggtccca cttgtcaatt tttgtttttg    97980
ttgcagttgc ttttgaggac ttagtcataa attctttccc aaggccagtg ttcagaatgg    98040
tgtttcctag gttttcttct aggattctta gagtttgagt tcttatgttt aaatctttaa    98100
ggcatcttgg gttgattttt gtatatggtg aaaggtaggg gcccagtttt attttctgc    98160 atatggctag ccagctatcc cagcatcatt tattgaatag ggaactcctt ccccaccact    98220 tgttttgtc tactttgttg aagatcagat ggatgtaggt gtgcagcttt atttctgagt    98280
ttgctattct gttccattga tctatgtgtc tgttttgta tcagtaccaa gctgttttgg    98340
ttactgtagc cttatatttt tttaaattt tttatttcta tgggttatta ggaaacagga    98400
ggtgtttggt tacatgagta agtactttag tggtgatttg tgagattttg gtgtgccat    98460 cacccgagca gtatacactg cactcaattt gtagtctttt atccctcacc cccttcccac    98520
tctttccccc tgagtcccca aaatccattg tgttattctt atgcctttgc atcctcatag    98580
cttagcttcc acttatgagt gagaacatac gatgtttggt tttccattcc tgagttactt    98640
```

```
cacttagaat aagtctccaa tctcatccaa gttgtgttga tgccattaat tcattacttt   98700
ttatgactga gtagtattct atcatatata tatggaattt ctgaatcaaa tggtagttct   98760
acttttagtt ctttaaagaa tctctatgct gttttccata gcagttgtac tagtttacat   98820
tcccaccagc agtgtagaag tgttctctgt tcaccacatc catgccaaca tgtattttt    98880 ttttattttt tgattatggc cattcttgta ggagtaaggt ggtatctcat tgtggttttg   98940
atttgcattt ccctgatcat tagtgatgtt gagcactttt tcatatgttt gttggccatt   99000
tgtatatctt cttttgagaa ttgtctattc atgtccttag cccactttt gatgggttat    99060 ttgtttttc ttgctaattt gttttagttt gttgtagatt ctggatatta gtcctttgtc    99120
agatgtatag attgtgaaga ttttctccca ctctgtgggt tgtctgtttg ctctgatgac   99180
tgttcttttt gccatgcaaa agctctttag tttaattaag tcccagccat ttatctttgt   99240
ttttattaca tttgcttttg tgttcttggt aatgaaatcc ttgcctaagc caatgtctag   99300
aagggttttt ctgatgttat cttctagaat ttttatattt tcaggtctta gatttaagtc   99360
cttgatccat cttgagttta ttttttgtgta agatgagaga tgaggatcca gtttcattct   99420
cctacatgtg gctagccaat tatcccagca ccatttgttg aataagatgt gctttcccca   99480
cttatatttt gtgtttgctt agtcaaagat cagttggctg taagtatttg ggtttatttc   99540
tgagttcact gttctgttcc attggtctat gtgcctatat ttataccagt accatggtgt   99600
tttggtgact atggccatat aatatagttt gaaatcaggt aatgtgatgc ctccagattt   99660
gttaggtttt ttgcttttg attttttgtt tgcttgtttt gctttgtttt gttttgctta   99720
gtcttgcttt ggctatgtgg gttctttttt ggttccatat ggatttaagg agttttttt    99780 ctagttctgt gaaaaacgat ggtggtattt tgatgggaat tgcattaaat ttgtagattg   99840
cttttggcag tatgatcttt ttcacaatat tgattctacc catcagtgag catgggatgt   99900 gttccattt gtttgtgtca tctatgattt ctttagcagt gttttatagt tttccttgta    99960
caggtcttac aactccttgg ttaggtatag tccaaacatt ttattttct tttgcagcta   100020 ttgtaaaagg ggttgagttc ttgatttgat tttcaccta gtcgctgtca gtgtatagca   100080
gagctactga tttgtgcaca ttaattttgt atctggaaac tttactgaat tctttttatca 100140 gttctaggag cttttgggag gaatctttag ggttttgtag gtatacaatt atatcatcag  100200
caaacagcaa tagtttgact tcctctttac tgatttgggt gcccttatt tctctctctt   100260 gtctgattgc tctggctagg acttccagta ctatgttgaa gaggagtggt gagagtgggc  100320
atccttgtca tgttccagtc ctcagtggga atgcttccaa cttttcccca ttcagtatga  100380
ttttggctgt gggtttgtca tagatggctt ttattacatt gaggtatggc ccttgtatgc  100440
tagttttgct gagagtttta atcataaagc atgctggatt tgtcaaatg cttttttccgc   100500 atctattgaa atgatcatgt gattttatt tttaattctt tttatgttgt gtatcacatt    100560
tattgacttg agtatgttaa gcctatatcc ctggtatgaa acccacttga ttatggtgga  100620 ttatctttt gatatgttgt tggattcagt tagccagtat tttgttaagg attttgcat    100680 ctatgttcat caaggatatt ggtctgtagt tttcttttt ggttatgtct tttcctgttt    100740
ttagtattag ggtgatactg gcttcataca atgatttagg gaggattccc tctttatctt   100800
gtggaatagt gttaatagga ttggtaccaa tccttctttg aatgtctggt agagttctgc  100860
tgtgaatcca tctagtcctg gactttttg tgtaggtaat tttttaatta tcattccaat    100920
ctcactgctt gttattggtc tgttcggggt atctaattct tcctgattta agctaggagg  100980
gttgtatctt tccaggaatt tatctgtctc ctctaggttt tctagtttat gcacgtaaag  101040
```

```
gtgttcacag tagccttgaa tgatctcttg tatttctgtg gtgtcagttg taatatctcc  101100
cttttcattt ctaattaagc ttatttggat tttctctctt cttggttaat cttgctaatg  101160
atctatcaat tttatttatc ttttcaaaga accagctttt tgtttcattt atcttttgta  101220
ttttttgttt gtttgtttgt ttgatttcat tcagttctgc tctgatcttg gttatttcct  101280
ttcttctgct gggtttgtgt ttggtttgtt cttgtttctc tagttccttg aggtgtgacc  101340
ttatattgtc tgttttttgct cttcagact tttttatata agtgtttagg gcttttagct  101400
ttcctctttg cactgccttt gctgtatccc agaggttttg ataggtttta tgtcactgtt  101460
gtcattcagt ttgaagaatt tttttaaatt tccatcttga tttcattgtt gactcaataa  101520
tcattcagga acaggttatt taatttccat gtatttgcat ggttttgaac attccttttg  101580
gagttgattt ccagttttat tccactgtgg tctgagagaa tgcttgatat aatttcaatt  101640
ttaaatttat tgaggcttgt tttgtggcct atcatatggt ctatctggga gaaagttcca  101700
tatgctgttg aataaatgta tattctgggg ttgttggata gaatgttctg taaatatctc  101760
ttaagtccat ttgttccagg gtatatttta aatctattgt ttctttgtta actttctgtc  101820
ttcttgacct gtctagtgct gtcagtggag taatgaagtc cgccactatc attgtgttgc  101880
tgtctatctc attttttagg tctaggagta attgttttat aaatttggga gctccagtgt  101940
taggtgcata tatatttagg attgtgatat tttcctgttg gagaaggcct tttaccatta  102000
tataatgtcc ctctttgtct ttttttaactg ctgttgcttt aaagtttgtc ttgtctgatg  102060
taagaatagc tactcctgct agcttttggt gtccatttgc atggaatgtc ttttccacc  102120
cctttcctta agtttatgag ttcttatgtg ttaggtgagt caactgaagg cagcagatag  102180
ttgattggtg aattcttacc cattcagcaa ttctgtatct tttaagtaga gcatttaggc  102240
catttatatt caatgttagt attgagatgt gaggtaccat tccattcatt gtgctatttg  102300
tttcctgtat gccttgggtt tttttgtttt tgtttttgtt tttgcttttt tttgtattat  102360
aggtcctgtg agatttatgc tttaaagagg ttctgttttg atgtgtttcc aggatttgtt  102420
tcaagattta gagctccttt tagcagtttt tgtagtgctg ccttggtagt ggcaagttct  102480
tttagcattt gtttgcctga aaaagactgt atctttcctt catttatgaa gcttggtttt  102540
gcttggtaca aaattcttgg ctgataattg ttttgtttaa ggaggctgaa gatagggccc  102600
taatcctttc ttgcttgtaa ggtttctgct gagaaatctg ctgttagtct gataggtttt  102660
cctttacagg ttacctggtg cttttgcctc acagctctta agattctttc cttcatctta  102720
actttagata acctgatgac aatgtgccta ggctatgatc ttttttgtgat aaatttctca  102780
agtgttcttt gagcttcttg tatttggata tctaggtctc tagcaagggt ggggaagttt  102840
ccctcaatta ttgcacaaat gtgtttccaa acttttagat ttctcttctt cctcaggaac  102900
accaattatt tttacatttg gttgtttaac atcccagact ccttggaggc tttgttcata  102960
ttttcttatt cttttttctt tgtctttgtt ggattgggtt aattcaaaaa ccttgtcttc  103020
aggctctgag ttctttcttg tgcttgctca attctattgc tgagacgtac cagagcattt  103080
tgcatttcta taagtgtgtc cattgtttcc tgaagttttg tttttttattt atgttatttc  103140
attgaagatt tctcccctca tttcttgtat cattttttt taaatttcct taaattgggc  103200
tttgcctttc tctgttgctt ccttgatgag ttctttgtca ggtagatcag gggtttcttc  103260
ttggtttaga tccacatctg gtaagctagt gtgatttgt gggggatgtt aaagaacctt  103320
gtttttttcat attaccagag ttggttttct tgttccttct catttgggta ggttctgtca  103380
gagggaagat ctagggctca aggctgttgt tcagattctt ttgtcctatg gcgtgttctc  103440
```

```
ttgatgtagt actctccccc ttttcctagg gatgtgcctt cctgagagcc caagctgtag 103500
tgattgttat ctcttttag gatctagaca tccagcagtc ctaccaggtt ccaggctggt 103560
attgggggtt gtctgcacag agtcctgtga tgtgaaccat ctgtgggtct ctcagctgtg 103620
gataccagta cctgctctgg tagaggtagc aggggagtga gatggactct gtgagggtcc 103680
ttagttttgg tcatttaatg cactattttt gtgctggttg gcctcctgcc aggagatgat 103740
gctttcaaga cagcatcagc tgtggtagta tggggaggat caggcggtgg gtggggccct 103800
agaactccca agagtatatg cctttgtct tcagctacca gggtgagtag gaaaggacca 103860
tcaggttggg gcagggctag gcgtgtctga gctcagactc ttcttgggcg agtcttgctg 103920
cagctgctgt ggggatggag gtgtggttcc caggtaaatg gaattatgtt cccaggagga 103980
ttatggctac ttctgctgtg tcgtgcaggt tgtcagggaa gtaggggtaa actggcagtc 104040
acagacctca cccagctccc acgaaaccca gaagatcaat ctcactccca ccatgccccc 104100
aacccagtag taccaagtct gtttccaggc agtgggcaaa caggactgag aacttgcccc 104160
aggctaccag cctcccagct gcaaaagcaa gtagtgcttt tgtgcttccc tgcctgtgga 104220
gtctgcacac cagattcatg ccttcccca agttctggcc aggagatttc ctattcagtt 104280
ggaattgtta gaaaattcag ctggagtttt ccttctccct gtgatgtttt ctgagttcct 104340
ctggcagtcc tccccaggta gccctgtgag acaagtcaga aatggcatcc ctgggaaccc 104400
agagagccca cagggctttt cctgctactt cctttacccc tatatttcac ttggttctct 104460
aaattgactc agctccaggt aaggtcagaa tcttctccca tgatctagac cttcaggttc 104520
cccagtgagg ttgtgtgttt gaaggtggac aatccccctt tcctacttcc acagtttggg 104580
cactcacagt atttggggca tctcccgggt cctacgggag caatccactt ccttcagagg 104640
gtctgtggat tctcttggct ttcctgaatt attcctgcag tagttctgga gcaaaagttc 104700
acgatgcaag actccacatg ctgctctgtc catccgagtg ggagctgcag tctagtcctg 104760
cttcccgtcc accatctctg tagccttata ttagtagtat attttgaagt caggtaatga 104820
gatgcctcca gctttgttct ttttgcttag gattgctttg gctatttaga ctctttttg 104880 gttccatatg aattttacaa taatttttt ctaattctgt gaaaaatgat gttggtagtt 104940
tgacaggaat agcatttaat ctcttaattg ctttaagtag tgtggccatc ttaatgatat 105000
tgactcttct aatccatgag catggaatgt tttccattt gtttgtgttg tctctgattt 105060
ctttcagcag caatttatag ttctccttt acctccttgg ttagctatat tttagggat 105120 tttattcttt ttgtgtctat agtgaatggg attacgttat tgatttggct ctcaccttgg 105180
acattattgg tgtatagaaa tgctacttat ttttgtaca ttgattttgt atcctgaaac 105240
tttactgaac ttgttatca gttccaggag ccttttggca gattcttaa agttttctag 105300 gtatgcaatt atgttatcag tgaacagaaa aatttgactt cttcttttcc tatttggatg 105360
ccttttattt ctttctcttg cctaatggct ctggctagta cttccagtgc tatgttgaat 105420
aagagaggtg agagtgggca tccttgtctt gtgctagttc tcaagggtaa tgcttccagc 105480
ttttgcccat tcagtaggat tttggctgtg ggtttgtcat agatggctct tattatttg 105540 aagtaagttc ctttgataac ctaatttgct gagagttttt atcatgaagg gatgttggat 105600
tttatcaaag gcttttttcca tgtctattga gatgatcata tgggttttct ttctaattct 105660
gtttatgtgg tgaatcacat ttatggattc acgtatgttg aaccaacctt gcattgtgag 105720
aatgaagcct acttgatcat ggtgaattaa cttttttt tttttttg agtcagtgtc 105780 tcattctgtc acctgggctg gagtgcagca gcacaatcac agctcattga agcctcaacc 105840
```

```
tcctgggctg gagtgatcct cacacctcag cctcctaaat agctgggacc actacaccta  105900 gctaatttt  tatttttct  gtagatgtgg  ggtctcatat catgttgctt aaactcctgg  105960
gctcaagcaa ttctcctgac tcaacctccc atagtgctgg gataacaggt atgagccacc  106020
gtgcctggcc atgaattaac ttttcatgt  gtagctggat tcaatttgca agtattttgt  106080
tgagcatttt tttcagtcta tgttcatagg gatattggcc tgtagtttct ttttgtctt   106140 tgccaggttt tggtataagg ataatgccag cttcatagaa taagttaggg aggagtcccc  106200
cctcctcatt tttttggaat agtttcagta gaattggtac cagttcttct ctgtactttt  106260
ggtagaattt ggctgtgaat ctttctggtc ccaggatttt tttttttttt tagtgttaga  106320 ttatttatt  actgaatcaa tttcaaaact caatattgtc tatttggggt ttcaattgct  106380
tcttgattca atctttggag gttgtgtttc caggaattta tccatttcct ctagattttc  106440
ttgtttgtat gcatacagat gttcataatg atctctgagg ttcttttata tttctgtggg  106500
attagttgta atgtcacctt tgtccttct  aaatgtgctt atttggatcg tcgttttttt  106560
ctttgctaat gtagctagca ctctatcggt cttgcatttc cttcaaaga  tccaactttt  106620 tgtttcattg attctttgta tgggttttg  aattttgatt ccattcagtt ctgttctgat  106680
tttagttatt tctttcttc  tcctagcttt ggggttagtt cttgttttgg aatgaacatt  106740
tttaaggcct ttaatatata tggccaaatt gccatccaaa aagaatgtat cactctgcac  106800
tgccacaagc aaagcatgga gtgctcccgt catctcagaa taaacccat  ccatttaatc  106860 agctcatttg atgaaggccc aggaaaacaa agttagggca tgattcttac taggtagatg  106920
aagagagtta agagatggct agtggggcgg gaaaggactg aagcctcaag ccttcatcct  106980
gtttaattgt gaagtatagt gaccaactag ttctagttgg cctgagactt tccaggtttt  107040
agcactgaga gtccagagtc ccaggaaacc cctaagtgtc aggcagacaa ggacacttgg  107100
tcgctctatc aaaagttaaa caccagtacc acctctaaag ttctatttac cacttacaat  107160
ttcagttttg agcctgtgtc taaaactcat ttttttaaga tactccttgg tatattcagg  107220
gaaaacatca tagaacagag cctaagacgt gtgagtggta aatagaatag gtcgggtgtg  107280
aatccttctg ctaacctgaa aaataaggca gtcagcgtcc ttggaccta  ctagtgtcat  107340 ccaggtccag ggccttcccc ctcctaggat tccatgttca tgaaatctga gccaagcaac  107400
agtattggta ttagattagg cttatttaac ctcaaccaca aaagaaagtt agatttgctg  107460
agaaaaagtg gacattctct gaaaaacatc cccttatttt ctaagtgttc aaattaacta  107520 ctaggtatt  cctttcttct tctttttttt ttttttttt  ttttgagaca gagtctcact  107580
ctgtcaccag gctggagtgc agtggcgtga tctcggctca ctgcaacctc tgccttctag  107640
gttcaagcga gtcctgcc  tcagcctccc aagtagctgg gactacaggt gtgtgccacc  107700
acgcccagct aatttttgta ttttagtag  agatggggtt tcaccatgtt ggccaggatg  107760
gtcttgacct cttgacctg  tgatctgcct gcctccacct cccaaagtgc tgggattaca  107820
ggtgtgagcc actgcgcccg gcctcctttc ttcttgtgct attgaagagg gatttgtgat  107880 ttaggggag  ctaacatatg atccttcaac atggagaact ctacctttct tcaaaggaag  107940
ctcagttcta gtgggcaaa  cactgtgcat agtttgccct tgacctttgg gttccataag  108000
ctctctgttg ggctggctg  gaatttactt ctcaccagtc acccatggag gacccactca  108060
gtgagggccc caggtaaggg aagatgcaca gaacatggtg atgggccctg ccactgtgc  108120 aatgccaaga ggagtcctcc ctgagttgag tttacagcc  tctccaggtc accttcattt  108180
taggactctt ttcttcatgg tgcctttgta cctccccagg acagtattta tgatgaaatg  108240
```

```
gaagagaagt ggtcaaaaca gaaggcgaaa tggaagaagg atgagaagtt cgagcgagaa    108300
aatatcctgc tacagcaaag tgagtacaga aactctagct tttttgatga caagtgcatt    108360
aaaaaactgc catgaagttt ggtcttgact tgaggaaggt ggccttgggc ttaccaaggg    108420
tgatgggcca catgctagat acctgaatgg aaggtgccca gagttttcat gaaagcaaaa    108480
tgacaacaag ggtagggtct tttttgaagt tcaggcatct gatctaagag agtctaagcc    108540
tgtaccttct gaaactcatt tggtccaagt ttgcccatga tggctggaac aaatgttaga    108600
atccctgtag ggagtgcaga cttattatct agaaacagat gaacccaaag ttccaagagt    108660
tctttagtta aatgtgaaa tgttcacttg catgtgggca gggggcagat aggaacaaca    108720
caatccatta tactgagagc ttctatattc ccacgtcttc cagaaggaag tcacacttgg    108780
taaatatttt taatatttcc aacaattaac acagagcttg caccatacaa agtattctat    108840
aggtgcacct cccaccccca ttggacttgt tcataaaagg aaaaagaag agaatttgta    108900 gagactactc caggcctaga agactagttg aggtaggagt gggacctcta cagacctatt    108960
ccgcattcca cgccaaccac atttatttca gatttagttg attttaacaa attactcatt    109020
taaatgcaga tactccatgg gaaaattaat tcacattctg gtgggcactc tggactgcca    109080
gaaggtaata tgaagacccc ggagttaagg ctggggaacg ggaggggag ctgctcctgt    109140 ctggggcttt acctagaatt ctagtgcaat agaacccaag tcatatccca gattctagct    109200
actcatacga ctctcatccc atgttgctaa agtctaagta aagatgtaac cgccagtttt    109260
ggaagaccag aattcagctg ctcaccatcc agctcagtca gaggcttacg ctgtcagacc    109320
agagactccc tgtccatccc cagaattgca acactgaaat ctgtgtttcc ctccacccct    109380
ccttcctctt gtttgataat ggggctctac tggcaggttt cctgcccagg aaaagagctg    109440
aagcctacct ctaccccagc actaagtaca ggatgaattt tattgctggc aaagtaatgt    109500
tagccaagag ctttatttta agataaggat atccatgata gcatagtggt tacatcagca    109560
gagggaatgg acaaaataaa aagcaacaga ttcaaaataa actacacaca aaagaaccag    109620
agatgttggt ggtaaatccc atatgactaa tgtgattgag acaaccacc gtgctcacct    109680 caccctcaag caccttcagg tgagtgtcag aggccaaaca ccaggctgca atgaccttga    109740
gtctgacaca gtctggaatt gcttttatct ttagatattc tgggtttctc attgcacctg    109800
ctttccccat ctttacacat atatgtgctt tcctgtcact tccacagaaa aaagatgac    109860 caaaaattc gaaatggagt caggagaaga agataagaaa ataaatgaat cctgcagtgc    109920
tgtctttgag aacttcattc aagagaagga ggtaactcag cccaaagcac cttggtgatt    109980
gaatgggtag tccaggtggt acacccaagt ccccaggtgt gcctccataa ttaggtgatc    110040
tttttgtctt tctgggcata atcctcctct cccagctttc tggaaatgta tgcaaataga    110100
ctgacagtct tgctgtcctt tagctgggca atcttcccac aggctagaca gtcttatcaa    110160
agggttctta gaacaaaaat tttaattaac tggaaataac agaatgctaa acatgcgaaa    110220
actgaaattc cttattttgc caaaatccca tctctgaata tccttttcat tcctcactgt    110280
agctgttata gctgtagtgc tattactggg cgctagggca ggtacaggtt taactttatg    110340
ggaacttgcc aaaacttatt ttccaaagta gttgtaccat ttttttcttg catcttagat    110400
atattggaat tctagttgct gtatatcctc cacaacaatt agttttgcta gtcctttaat    110460
tttggccatt ccagtgggca tgaagtggta cttcattatg gttttagttt ccctgatgac    110520
taattatgtt gggcattttc tcatatgctt attggtccat tcatatatgt tcttccataa    110580
agtgcctgtt caagtctttt cccatttgaa aaagtaggag gtgcttacat ttttattttt    110640
```

```
gatatgtagg agtactttta tattgtggat acaagttttt tttgccagat atacatgttg   110700
taaatattgt ctgtcagcct gtggtttgcc tcttcatttt attaatgata tatttcgata   110760
tacagaagct ttaaattttg atgaaaggca atgatcattt ttttactttt atggttacag   110820
attttttgtgt cctctctata aaatcattgc ctattccaag gtcatgaaga tattctattt   110880
tttagaagct ttaaaatttt agcttctatg attctctgat ctattttgaa taattttgt   110940
gtatgaagtg aagtgtaaga gtcatgggtc attttttgtct tatggatatt cagttgtccc   111000
agcatcattc tttaaaaata ctttcctttc cccattgagt tgccttagtg tttgatacag   111060
tttagatttg tgtccctgcc caaatctcat gtcaaattgt aatctccaat gttggagaag   111120
ggggtctggt gggaggtgat tggatgatgg ggacagattc tccccctttc tgttctcgtg   111180
atagtgagtg agctctcaaa agatcaggtt gtagcacctc cccttctct ctctttcttt   111240
tgttccagct atgtaagaca ggcctccttc ctctttacct tctgccatga ttgtaagttt   111300
cctgaggcct ccccagccat gcttgcagaa atgtgagcca attaaacctc ttttctttct   111360
tttttttttt attctttttt taatttatta tactttaagt tccagggtac atgtgcacaa   111420
cgtgccagtg tgttaaatat gtatacatgt gccatgttgg tgtgctgcac ccattaactc   111480
atcatttaca ttaagtatat ctcctaatgc tatccttccc ccctcccccc acccacaac    111540
tggccctggt gtgtggtgtt ccccaacctg tgtccaagtg ttctcattgt tcatttccta   111600
cctacgaatg agaacacacg gtgtttggtt ttctgtcctt gcaatagttt gctcagaatg   111660
ttggtttcca acttcatcca tgtccctaca aaggacatga gctcatccat tattatggct   111720
gcatagtatt ccatggtgta tatgtgccac attttcttaa tccagtctat cattgatgga   111780
cattttggtt ggttccaagt ctttgctatt gtgaatagtg ccacaataaa catacgtgtg   111840
catgtgtctt tatagcagca tgatttataa tcctttgggt atatacccag taatgggatg   111900
gctgtgtcaa atgggatttc tagttctaga cccttgagga atcgccacac tgtcttccac   111960
aatggttgaa ctagtttaca gtcccaccaa cagtgtaaaa gtgttcctat ttctccacat   112020
cctctccagc acctgttgtt tcctgacttt ttaatgatcg ccattctaac tggtgtgaga   112080
tggcatctca ttgtcgtttt gatttgcatt tctctgatgg ccagtgatga tgaacatttt   112140
ttcgtgtgtc tgttggctgc ataaatgtct tcttttgaga agtgtctgtt catatccttc   112200
gcccacttgt tgatggggtt gtttgatttt ttcttgtaaa tttgtttaag ttcttagtag   112260
attgtggata ttagcccttt gtcagatggg tagattgcaa aaattttctc ccattctgta   112320
ggttgcatgt tcactctgat ggtagtttct ttcgctgtgc agaagctctt tagattattt   112380
agatcccatt tgtcaatttt ggcttttgtt gccattgctt ttggtgtttt agacatgaag   112440
tccttgccca tgcctatgtc ctgaatggta ttgcctaggt ttccctctag ggttttatg    112500
gtttaggtc tgacatttaa gtctttaatc catcttgaat taattttgt ataagatgta    112560
aggaagggat ccagtttcag cttttctacat atggctagcc agttttccaa gcaccattta   112620
ttaaataggg agtactttcc ccatttcttg tttttgtcag gtttgtcaaa gatcagattg   112680
ttgtagatgc gtggtattat ttttgagggc tctgttctgt tccattggtc tatatctatg   112740
ttttggtacc agtaccatgc tgttttggtt actgtagcct tgtagtatag tttgaagtca   112800
ggtagtgtga tgcctccagc tttgttcttt tggcttagga ttgtcttggc aatacaggct   112860
cttttatggt tccaaatgaa ccataaaagt agttttttcc aattctatga agaaagtcat   112920
tggtagctta atggggatgg cattgaatct gtaaattacc ttgggcagta tggccatttt   112980
cacgatattg attcttccta tccatgagca tggaatgttc ttccatttgt ttgcatcctc   113040
```

```
ttttatttcg ttgagcagtg atttgtagtt ctccttgaag aggtccttca catcccttgt    113100
aagttggatt cctaggtatt ttattctctt tgaagcaatt gtgaatggga gttcactcat    113160
gatttggctc tctgtttgtc tgttattggt gtataggaat gcttgtgatt tttgcacatt    113220
gattttgtat cctgagactt tgctgaagtt gcttatcagc ttaaggagat tttgggcaga    113280
gatgatgggg ttttctagat atacaattca tgtcatctgc aaacagggac aatttgactt    113340
cctcttttcc taattgaata ccctttattt ccttctcctg cctcattgcc ctggccagaa    113400
cttccaacac tatgttgaat aggagtggtg agagaaggca tccatgtctt tgccagtttt    113460
tcaaagggaa tgcttccagt ttttgcccat tcagtatgat attggctgtg ggtttgtcat    113520
aggtagctct tattattttg agatacgtcc catcaatacc taatttattg agagttttta    113580
gcatgaatgg ttttcgaatt ttgttgaagg ccttttctgc atctattgag ataatcatgt    113640 ggttttgtc tttggtactg ttgatatgat ggattacgtt tattgatttg cgtatgttga    113700
accagccttg catcccaggg atgaagccca cttgatcatg gtggataagc tctttgatgt    113760
gatcctggat tcagtttgcc agtattttat tgaggatttt tgcatcgatg ttcatcaggg    113820
atattggtct aaaattctct ttttttgttg tgtctctgcc aggctttggt atcaggatga    113880
tgctggcctc ataaaatgag ttagggaaga ttccctcttt ttctattgat tgcaatagtt    113940
tcaaaggaat ggtaccagct cctccttgta cctctggtag aattcggctg tgaatccgtc    114000
tggtgctgga cttttttgg ttggtaggct tttaattatt gcctcaattt cagagcctgt    114060
tattggtcta ttcacggatt caacttcttc ctggttaagt cttgggaggg tgtatgtgtc    114120
caggaattta tccatttctt ctagattttc tagtttattt gcatagagtt gtttatagta    114180
ttctctgatg gtagtttgta tctctgtggg atcggtggtg atatcccctt tatcattttt    114240
tattgcgtct atttgattct tctctctttt cttcttatt agtcttgcta gcggtctatc    114300
aattttgttg atcttttcaa aaaaccagct cctggattca ttgatttttt gaagggtttt    114360
tgtgtctcta tctccttcag ttctgctctg atcttagtta tttcttgcct tctgctagct    114420
tttgaatgtg tttgcccttg cttgtctagt tcttttaatt gtgatgttag ggtgtcaatt    114480
ttagatcttt cctgctttcc cttgtgggca tttagtgcta taaatttccc tctacacact    114540
gctttaaatg tgtcccagag agtctggtat gttgtgtctt tgttctcatt ggtttcgaag    114600
aacatcttta tttctgcctt cattttgtta tgtacccagt agtcattcag gagcaggttt    114660
ttcagtttcc atgtagttgt gctgtttga gtgagttctt aatcctgagt tctagtttga    114720
ttgcactgtg gtctgagaga cggttgttg tgatttctgt tcttttacat ttgctgagga    114780
gtgctttact tccaactatg tggtcaattt tggaatacgt gtgatgtggt gctgagaaga    114840
atgtatattc tgttgatttg gggtggagag ttctgtagat gtctattagg tccacttggt    114900
gcagagctga gttcaattcc tggatatcct tgttaacttt ctgtctcgtg gaactgtcta    114960
atgttgacag tggggtatta aagtctccca ttattattgt gtgggaatct aagtttcttt    115020
gtaggtctct aaggacttac tttatgaatc tggctgctcc tgtattgggt gcatatgtat    115080
ttaggatagt tagctcttct tgttgaattg atcccttac cattatataa tggccttctt    115140
tgtctctttt gatctttgct ggtttaaagt ctgttttatc agagactagg attgcaaccc    115200
ctgccttttt ttgttttcca ttttttgtt agatcttact ccatccttt attttgagcc    115260 tctgtgtgtc tctgcacgtg agatgggtct cctgcataca gcacactggt gggtcttgac    115320
tatccaattt gccagtctgt gtctttaat tggagcattt agcccattta catttaaggt    115380
taatattgtt atgtgtgaat ttgatcctct cgatatgatg ttacctggtt atctgttcat    115440
```

```
tagttgatgc agtttcttcc tggcattgat ggactttaca atttggcatg tttttgcagt   115500
ggctggtacc ggttgttcct ttccatgttt agtgcttcct tcaggagctc ttgaaagaca   115560
ggcctggtgg tgacaaaatc tctcagaatt tgcttctctg taaaggattt tatgtctcct   115620
tcacttatga agcttagttt agctggatat gaaatcctgg gttgaaaatt cttttctta   115680 agaatgttga atattggccc ccactctctt ctggcttgta gatagagttt ctgccgagag   115740
atccactgtt agtctgatgg gcttcccttt gtgggtaacc caacctttct ctctggctgc   115800
ccttaacatt ttttccttca tttcaacttt ggtgaatctg acaattatgt gtcttggagt   115860
tgctcttctc gaggagtatc tttgtggcat tctctgtatt tcctgaattt gaatgttggc   115920
ctgccttgct aggttgggga agttctcctg gataatatcc tgcagagtgt tttccaactt   115980
ggttccattc tccctgtcac tttcaggtac accaatcaga cgtagatttg gtcttttcac   116040
atagtcccat atttcttgga ggctttgttc atttcttttt actctttttt ctctaaactt   116100
ctcttcttgc ttcatttcat tcatttgatc ttcaatcact gatacccttt cttccacttg   116160
atcgaatcag ctactgaagc ttgtgcgtgc atcacatagt tcttgtgcca tgattttcag   116220
ctccatcagg tcatttaagg acttctctac actgtttttt ctagttagtc attcatccaa   116280 tctttttca aggtttttag cttgtttgtg atgggttcga acatcctcct ttaacttgga   116340
gaagcttgtt attactgatc atctgaagcc ttcttctctc aactcgtcaa ttcattctct   116400
gtccagcttt gttccattgc tggtgaggag ctgcattcct ttggaggaga agagtcgctc   116460
tgatttttaa aattttcagc tattctgctc tggtttcccc ccatctttgt ggttttatct   116520 accttttggtg tttgatgatg gtgatgtaca gatgaggttt tggtgtggat gtcctttctg   116580
tttgttagtt ttccttctaa cagtcaggac cctcagctgc aggtctgttg gagtttgctg   116640
gaggtccact ccagaccctg tttgcctggg tatcaccagg agaggctgta gaactgcaga   116700
tactgcagaa cagcaaatgt tgctgcctga tcgtttctct gaaagcttca tctcagaggg   116760
gcacccagct gtatgagttg tcagttggcc cctactgggc ggtgcctccc agttaggctt   116820
ctcgggggtc agggacccac ttgaggaggc agtctgtcca ttctcagatc tcagactcca   116880
tgctggcaga accactactc tcttcaaagc tgtcagacag ggatgtttaa gtctgcagaa   116940
gtttctgctg cctttttgttg agctatgccc tgcccccaga agtggaatct acagaggcag   117000
gcaggcctcc ttgagctgtg gtgggctcca cccaattcga gctttccagc cgcttttgttt   117060 acctactcaa gcttcagcaa tagcaggcgc ccatccccca gcctcactgc tgccttgcca   117120
ttcaatctca gactgctgtg ctagcagtga gcaaagctcc gtgggcgtgg gaccctccca   117180
gccatgcatg ggatataatc tcctggtgtg ccatttgcta agactgttgg aaaagcacag   117240
tattagggtg ggagtgaccc gattttccag gtgccgtctg tcacggcttc ccttggctag   117300
gaaagggaat tatctgaccc ctcgcgcttc ccaggtgagg cggtgcccca ccctgtttcg   117360
gctcccggtc cgtggcctgc acccactgtc ctgcacccac tgtctgacaa gcccagtga   117420 gatgaacctg gtacctcagt tggaaatgca gaaatcacct gtcttctgca tcactcatgc   117480
tgggagctat agactggagg tgttcctatt tggccatctt ggaaactccc cctaaacctc   117540
ttttctttat aaattaccca gtctctcagg tagttcttca tagaaatgtg agatcagact   117600
aatatagtgt ctttgctgta tttggggtgt taggactctc cgttctgttt gactattttt   117660
ccatacttag gtcaacaaca cattgtcttg actactgaag tttgaaatcg ggtagcaaag   117720
gttatctagc tttgctattg tttttcaaga ttattttgcc tttccacatg ctttgtatttt   117780 ttacataaat gttagaacta gcttgtcaat ttagaattag cttatcaagg aagtttgctg   117840
```

```
atattttgac tgggatttca ttgaatataa agatcaatct gtggcgagat taattcttaa   117900
gagtattgaa tctatccact gacttaagaa aagcttttga tgaaaatata atttctttta   117960
atatttgtca gtgagataag gttgaacata attaagattt tcattaactt caacaagtca   118020
tgtcactagt ttataatgtg tgcttcatta tagcagtgtc taagctttgg tgaatattat   118080
attcctgaat cctagtctgg cttttcttaac tccctagaag atgtgccaga accacagtgc   118140
taaccttttc ccaataaaat tgttttagg agctcttgaa acaacatcaa agtgacacct   118200
tgcaattaga agagctgaga aaaaccaaag aggtaagctt tttcatcctt tcctgtggac   118260
ttggtatatt acaaatacac caataaaata acaagctgtc agtataatgg aatcaatgat   118320
aatttcccca aagccaataa gaaatggaag acctaaagct gagtttactg gattcaataa   118380
gttaaaaaga attttttgaaa ttatctgtaa aataaagcca gtgggtcttt ttaaagtctg   118440
atttgaacaa atagatcagc aatatactat gtgatcttca atgttgaatg actttcattt   118500
ctagcaaggt tcaaaccaca aatgatcttt cagttataaa acaccaagtt cttccctttg   118560
agctctgaaa agtataaaac tgtctccttt gaaactctgt caccaagccc ctccttaagc   118620
tctgaatgta cctcacacat gataacttcc tcagggactc tattctgggg caaattatgg   118680
cagtctgtgg gagacaactg aagaggagcc gttcaaatcc acaaggtgat gtgtgattct   118740
tccatcactg aaaatttgac ttggatccag aatggacacg tttgagaaaa cattagtcat   118800
tataaaggca ttgtaaatga attctatctt agagcccagg cagggcttca gcattatgga   118860
aaggcaaaca gactgtggtg tcctacaagt tcaagaaatg ggctttggag aagatatac   118920 ccagtgtatt ataataacta ttttcatgag cttgtctacg aattctgtca tttgtgtcat   118980
gtctgggcct gtttctcttc attgattttt ctcctcattt atggtcatat ttccttgttt   119040
gcatgcctgg taagtttggc ttggatgtca gtcattttgg tgtttacctt gttgggtgct   119100
gaatattttt atattccttt agatattctt aagctttgcc ctgggatgca gttaagttgc   119160
ctggaaacag tttgatcctt tcaagccttg cttttaagc ttcgttgggc agaactaaag   119220
cagtctttag tgtggaacta attttcccca ctattgaggt aatacccctct gagtacttga   119280 caccacaccc tctgtatgag aaggattttc tactctgcct ggtgggacca tgaactattc   119340
ccagccttgt gttggccctg gggattgttc cacctgctcc ttgctgatgt ttccttcctc   119400
taaccttgtc tctttctatt tcttccctac atcactccac cccagaggca cttgcctcct   119460
tgctgttccc ttaacaggcc aggatgttcc tacctggggg tctttgatgt tctctcttcc   119520
tgaaaagctc tttcccggat atccacatga ctaacttcct ttcctcctcc tgttctttat   119580
tcaaatgcca ccttctcaga aggtgcccga tttaagggct ccgctccctg cccaacactt   119640
gcttttctcc aaatgggatg ccactggagg tttttgagga gagtatca tttgggaaaa   119700 taactgtggc agcaatgtga aggagaatct gaagaggcaa aatgatggga ggcagaacct   119760
attagaaggg tcacctcccc tttacacctc aacctgactt ctgctccaat cccagccatg   119820
gaaactgttc ttgttaaaat cacaagtaaa ttccgagttg ccaaatccaa ggaatgcttc   119880
acctcactgg acatgagcag tatcaggtgc gattgatcat tctctccttg caacattcac   119940
ctgtcttagc tttcatgggc ttctggtgtt tccttcacct cattggtcac accttctcaa   120000
tctcctttac tagaactaga actctgctta aaacccttca atggcaccc actgttctcc   120060 cacctacttt ctaagtcctg gagtattttg aggcttgttc ccaggcccca cttatcttct   120120
ttatctcccg tttctccttt ggtgagctca tctgttcaca cagatgtaaa agccatctct   120180
gtactgataa cttggtttga tacctccagc cttgcctctc tcctgagctc caggcttgta   120240
```

```
catccaactg cccatttgac atttcaacat aggtgacata cagacacctc aaaattaaca   120300
tgcccagttc cacactctca atttccacc agagatttag cccccaaatt gtcaactccc   120360
tcagctgttc taagcctaga cctgaagtca tccttgattt cttctttcct ttcactctcc   120420
caaattcaac ccagcagcct cagccaatcc tctataacat aatccaaatt catccacgtc   120480
cctccaactc tgttgtcacc ttaccctagt ccattatttc tcacctacac gactgtagta   120540
ttctcctcct tagttccgtt gctttccctc ttgcccttcc aatccatccc catggagcat   120600
aatgtaaaca gtaagatacg tgcattcact tctctgctta aaaccttca gtaggtcccc   120660 attgttctta ggttaccttg tcctctcagg tgccaccaga cttccctgta tttcctcacc   120720
atggccctct atccttacta tctctattcc agccatattg gtgttccttt gggtcctcaa   120780
acagaatgag aattttgcat ttttttttatt atactgtaag ttttagggta catgtgcata   120840
atgtacaggt ttgttacata tgtatacatg tgccatgttg gtgtgctgca cccagtaact   120900
cgtcatttaa cattaggtat atctcctaat gctatccctc cccctcccc caccccaca    120960 acaggccccg gtgtgtgatg ttccccttcc tgtgtccatg tgttctcatt gttcaattcc   121020
cacctctgag caagaacatg tggtgtttgg tttttttgtcc ttgccatagt ttgctcagaa   121080
tgatggtttc cagcttcatc catgtcccta ccaaggacat gagctcatca ttttttatgg   121140
ctgcatagta ttccatggta tatatgtgcc acattttctt aatccagtct atcattgttc   121200
gacatttggg ttggttccaa gtctttgcta ttgtgagtag tgccgcaata aacatacgtg   121260
tgcatgtgtc tttatagcag catgatttat aatcctttgg gtatataccc agtaatggga   121320
tggctgggcc aaatgggatt tctagttcta gatccctgag gaatcgccac actgacttcc   121380
acaatggttg aactagttta cagtcccacc aacagtgtaa aagtgttcct gtttctccac   121440
atcctctcca gcacctgttg tttcctgact ttttaatgat cgccattcta actggtgtga   121500
gatggtatct cattgtggtt tgatttgcat ttctctgatg gccagtgatg atgaacattt   121560
tttcatgtgt cttttggctg cataaatgtc ttcttttgag aagtgtctgt tcatatcctt   121620
tgcccacttg ttcatggggt tgtttgtttt tttcttgtaa atttgtttga gttcattgta   121680
gattctggaa tattaaccct ttgtcagatg agtaggttgc aaaaattttc tctcattctg   121740
taggttgctt gttcactctg atggtagttt cttttgctgt gcaaaagctc tttagtttaa   121800
ttagatccca tttgccaatt taggcttttg ttgccattgc ttttggtgtt ttagacatga   121860
agtccttgcc catgcctatg tcctgaatgg tattgcctag attttcttct aggtttttta   121920
tggttttagg tctaacattt aagtctttaa tccatcttga attaatttt gtataaggtg   121980 taaggaaggg atccagtttc agctttctac atatgactag ccagttttcc aagcaccatt   122040
tattaaataa ggaatccttt cccatttct tgtttttgtc agatttgtca aagatcagat   122100
agtgtagata tatggcatta tttctgaggg ctctgttctg ttccattggt ctatatctct   122160
gttttggtac cagtaccatg ctgttttggt tactgtagac ttgtagtata gtttgaagtc   122220
aggtagcgag atgcctccag ctttgttctt tggcttagga ttgacttggc aatgcgggct   122280
cttttttggt tccagatgaa ctttaaagta gttttttcca attctgtgaa gaaaatcatt   122340
ggtagcttga tggggatggc attgaatcta taaattacct tgagcattat ggccattttc   122400
acgatgttga ttcttcctat ccatgagcat ggaatgttct tccatttgtt tgtatcctct   122460
tttatttcgt tgagcagtgg tcaacgaaga ggtccttcac atcccttgtg agttggattc   122520
ctaggtattt tattctcttt gaagcaattg tgaatgggag ttcactcatg atttggctct   122580
ctgtttgtct gttattggtg tataggaatg cttgtgattt ttgcacattg attttgtatc   122640
```

```
ctgagactttt gctgaagttg cttatcagct taaggagatt ttgggcagag atgatggggt   122700
tttctagata tacaatcatg tcatctgcaa acagggacaa tttgacttcc tcttttccta   122760
attgaatacc ctttatttcc ttctcctgcc tcattgccct ggccagaact tccaacacta   122820
tgttgaatgg gagtggtgag agagggcatc cctgtctttt gccagttttc aaagggaatg   122880
cttccagttt ttgcccattc agtatgatat tggctgtggg tttgtcatag atagctctta   122940
ttattttgag attcgtccca ccaataccta atttattgag agttttttagc atgaacggtt   123000 ttcgaatttt gttgaaggcc ttttctgcat ctattgagat aatcatgtgg tttttgtcat   123060
tggttcggtt tatatgctgg attacattta ttgatttgcg tatgttgaac cagccttgca   123120
tcccagggat gaagcccact tgatcatggt ggataagctt tttgatgtgc tgctatattt   123180
ggtttgccag tattttattg aggattttttg catcgatgtt catcagggat attggtctaa   123240
aattctcttt ttttgttgtg tctctgccag gctttggtat caggatgatg ctggcctcat   123300
aaaatgagtt agggaggatt ccctctttttt ctattgattg caatagtttc aaaggaatgg   123360
taccagctcc tccttgtacc tctggtagaa ttcggctgtg aatccatctg gtcctggact   123420 tttttttggtt agtaagctat taattattgc ctcaatttca gagcctgtta ttggtctatt   123480
cagggattca acttcttcct ggtttagtct tgggagtgtg tatgtgtcca ggaatttatc   123540
catttcttct agatttttcta gtttatttgc atagaggtgt ttatagtact ctctgatggt   123600
agtttgtagt tctgtgggat cggtggtgat atcccctta tcgttttttt ttgcgtctat   123660
ttgattcttc tctcttttct tctttattag tcttgctagc attctattaa ttttgttgat   123720
cttttcaaaa aaccagctcc tggattcatt gattttttga agggttttttt gtgtctctat   123780 ctccttcagt tctgctctga tcttagttat ttccttgcctt ctgctagctt ttgaatgtgt   123840
ttgctcttgc ttctctagtt cttttaattg tgatgttagg gtgtcaattt tagatctttc   123900
ctgctttctc ttgtgggcat ttagtgccat aaatttcccc tacacactgc tttaaatgtg   123960
tcccagagat tctggtatgt tgtgtctttg ttctcattgg ttttgaagaa catctttatt   124020
tctgccttca tttcattatg tacccagtag tcattcagga gcaggttgtt cagtttccat   124080
gtagttgtgt ggttttgagt gagtttctta atcttgagtt ctagtttgat tgcactgtgg   124140
tctgagagac ggtttgttgt gatttctgtt cttttacatt tgctgaggag tgctttactt   124200
ccaactatgt ggtcaatttt ggaatatgtg cgatgtggtg ctgagaagaa tgtatattct   124260
gttcatttgg ggtggagagt tctgtagatg tctattaggt ctgcttggtg cagagctgag   124320
ttcaattcct ggatatcctt gttaactttc tgtctcgtgg agctgtctaa tgttgacagt   124380
ggggtgttaa agtctcccat tattattgtg tgggagtcta agtcttttttg taggtctcta   124440 aggacttact ttatgaatct ggctgctcct gtattgggtg catatatatt taggatagtt   124500
agctcttctt gttgaattaa tcccttttacc attatataat ggccttctttt gtctctttttg   124560 atctttgtta attgaaagtc tgttttatca gagactagta ttgcaacccc tgcctttttt   124620
tgttttccat ttgcttggta gatcttcctc catccctta ttttgagcct ctgtgtgtct   124680
ctgcatgtaa ggtgggtttc ctgaatacag cacactgatg ggtcttgact atccaatttg   124740
ccagtctgtg tcttttaatt ggagcattta gcccatttac atttaaggtt aatattgtta   124800
tgtgtgaatt tgatcctgtc attctgatgt tagctggtta ttttgctcgt tagttgatgc   124860
agtttcttcc tagcctcgat ggtctttaca atttgacatg tttttgcagt ggctggtacc   124920
ggttgttcct ttccatgttt agtgtttcct tcaggagctc ttttaaggca ggcctggtgt   124980
gaccaaatct ctcagcattt gcttgtctgt aaagtatttt atttctcctt caatcatgaa   125040
```

```
gcttagtttg actggatatg aaattctggg ttgaaaattc ttttctttaa gaatgttgaa   125100
tattggccct cactctcttc tggcttgtag agtttctgct gacagatctg ctgttagtct   125160
gatgggcttc cctttgtggg taacccgagc tttctctctg gctgcccttta acatttttc   125220 cttcatttca attttggtga atctgacagt tatgtgtctt ggagttgctc ttctcgagga   125280
gtatctttat gctgttctct gtatttcctg aatctgattg ttggcctgcc ttgctcggtt   125340
ggggaagttc tcctggataa tatcctgcag agtgttttcc aacttggttc cattctccct   125400
gtcactttca ggtacaccaa tcagacgtag atttggtctt ttcacatagt cccatatttc   125460
ttggaggctt tgttcatttc ttcttattct ttttttttcta aacttctctt cttgcttcat   125520
ttcattcatt tgatcttcca tcactgatac ccttctcttcc agttgatcga atcggctact   125580
gaggcttgtg catttgtcac atacttcttg tgccatggtt ttcagctcca tcaggtcctt   125640
taaggacttc tctgcattgg ttattctagt tagccattcg tctaatcttt tttcaaggtt   125700
tttaacttct tggccatgag ttcgaacttt ctcctttagc tcggagtagt ttgatcatct   125760
gaagccttct tctctcaact cgtcaaagtc attctccatc cagctttgtt ctgttgctgg   125820
cgaggagctg cattcctttg gaggaggaga ggcactctga tttttagaat tttcagtttt   125880
tctgctctgt ttttttcccca tctttgtggt tttatctacc tttggtcttt gatgacagtg   125940
acgtacagat ggggttttgg tgtggatatc ctttctgttt gttagttttc cttctaacag   126000
tcaggaccct cagctgcagg tctgttggag tttgctggag gtccactcta gaccctgttt   126060
gcctgggtat cagcagcgga ggctgcagaa cagcagatat tggtgaacag caaatgttgc   126120
tgtctgattg ttcctctgaa agttttgtct cagaggagta cccagccgtg tgatgtgtca   126180
gtctgcccct actgggggt gcctcccagt taggctactc aggggtcagg gacccacttg   126240
aggaggcagt ctgtccattc tcagatctca agctgcgtgc tgggagaacc attactctct   126300
tcaagctgtc agacagggac atttaagtct gcagaggttt ctgctgcctt ttgtttggtt   126360
atgcctgccc ccagaggtgg agtctacaga ggcaggcagg cctccttgag ctgcggtggg   126420
ctccacccag ttcgagcttc ctggccactt tgtttaccta ctcaatcctc agcaatggtg   126480
ggcgcccctc caccagcctc actgccacct cgcagtttga tctcagactg ctgtgctagc   126540
aatgagcaag ctccgtggg cgtaggacct tatgagccag gcatgggata caatcttctg   126600
gtgtgccgtt tgctaagact gttggaaaat gcagtattag ggtgggagtg acctgatttt   126660
ccaggtgcca tctgtcaccc ctttccttgg ctaggaaagg gaattccctg accccttgca   126720
cttcccggat gatgtgatgc ctcgccctgc ttcggctcat gctcagtgca ctgcacccac   126780
tgtactgcac ccactgtctg acaatcccca gtgagatgaa cacgatacct cagttggaaa   126840
tgcagaaatc atacgtcttc tgcatcgctc acgctgggag ctgtagactg gagctgttcc   126900
tattcggctg tcttggctcc acccctgagc attttgcatt ctaaggacct tgcacaggc   126960 ttctattcat tctttagtgg aagtttgtgt gtttgtttca agaagctact ttttagagca   127020
gttttaggtt tacagaaaaa ttgagcagaa agtacagaga gttcccatat actacccac   127080 cccaccctac cccaccacta gtttccttta ttattagtat cttgcattgg gatggcacat   127140
tagttgcaat tgatgagcca atgtggatgc attcttatta actaaagtcc atagtttaca   127200
tgagggttct ctcttttgtgt tgtacattct gtgggttttg cctaatatgt catgtcatgt   127260
atccaccatt atagtgtcat acagaatagt ttcactgctc taaaagtgcc ctctatccca   127320
cctattcatc cctcccttcc cctccaaatc cctagaaacc actaatcttt tttctctctc   127380
tatagttttg ccttttccag agtgtcatat aattggaatc ggtagtaggt atttaataaa   127440
```

```
gacttgctta gtgaatgaat aactgattgc cattagaacc attcatatga gctctggtga   127500
ggctgaagag aaggatatag atgggtgaga cagagaggag gcaggactga cagggtgtga   127560
gtggccatga gtgatgcaaa agtagctcag gttgctccct ttcatcatag tccaggtgcc   127620
ctggagaaga gaccaaataa atagacattg gcatgatgtc ctgcaacagc ttcttcttat   127680
gcaggtcatg caggaagaat tgcatgcaca agcccttatc ctagagtcac tgaacacaaa   127740
cctctactat acccagttgg aactccagaa agaggtgagt ccctactgga gtggggatgg   127800
gggttggggg aagaacccag gtctccatcc agctctgcca tatagctctg ccctggatgg   127860
ctctgggttg gggaagatgg ctattaaaat gtatgtcttt cagaaagcta tagtgggaaa   127920
tctggagaaa atgcttcaaa ccaagtttgc tgaaactgaa gaaaagtata agcacaccat   127980
acagatcctg acgaagaga acattcatct gaagtgcggc tgctgctgaa aaagacatag   128040
ctgagttctc tttaggagtg ggaaggagtt tgagtgagga atgggttagg aagatagacc   128100
aactgctccc tagttatgtc aaggcacagg tgttttcggg agggaggtat gtcactctag   128160
gccagtgaca caaagccaga tagttcactt gaggtggagt ggagatgtgt ctatacttct   128220
cccattcacc tgtgtccttg tttctatgca aaacaacaca ggacatttgt cttccagttt   128280
ctgagtttgc tcagttctat gactgagggt ggtttttaaa tccatctccc ctgggagtct   128340
gatggtcttg ccattacatg cagctgcttc tggttcctat ggaaatcacc tttggatcag   128400
aaggtgtact gttacctgaa gctgcatctt aaatcattaa aataaatttt ggtcaatact   128460
ttaatagaag aaagttattt attgcattga tttagtagaa aattcctcgt ataggacttt   128520
agtcacctga acaccatacc tcactaaatt caaaaccact gcaagtaatg agtgagagac   128580
tgctgtggtg aaggaacgaa ggcacatttc tctccctgca ctccaaatat cctatacccc   128640
ttctagcttt tgagttgaca ttgatacatc tttcctttct ttttacaggc aaaagataat   128700
ttctaagaat gaagaaattt gtgaaggatg ttctgggaga ttggcctcta ttactgtttc   128760
taaggatgat tctgacactg tgcaagatgg tagcaagaaa ggacaagaat cataaacaaa   128820
aagttgctct gcattgttga agatggttgg cacaccattt ctgtaggccc aggaaactcc   128880
tgggagggtt ttcttgagaa aatgcatata atgagtttag ttcttgggtt gctctgactc   128940
tctgaatgtc tgaaaatgtt tgaattcgca tctgaatttc acagcttatc acggactctt   129000
cactgaaaaa tgatgctctc catactggga gctgagcttt ctctgagttt tgtactattt   129060
ttcttctacc ttgacgtatt tcgttagaaa gaaactgatt tgaaggcctt cttcatattg   129120 aactttact atatttggga ggtgtacctt tgtcccctgg ggcatttagg tagcaaaaaa   129180
agatgatgtg ttgatttac tctaaaatat ttttctctca cacccatgcc ccctacttcc   129240
ctacctctca atcatgttcc ctaacctatg acttaggaag ggtttctgat gattcttacc   129300
acctcctctg gaccatcacc agaattcaga cacccacagt gcaggcaaca taaataagtg   129360
aagtgggcta gacataagga aaacaattgc ccaagcacag tgataagtgg caaccaacag   129420
cagcctcagt agaggggctt gggcagggct ggggcacagc ggatggggaa gagtgaccca   129480
cagagcactg tccatctga agaaggtgct tctcagacct ttgccatgca aaagcatgag   129540
gtcaatattg tcagatagta tgattttta aaagaagtta ttctggtttt tatgtgatat   129600
ctcctaattt ttaaacattg acaacaaatt ttaaaaatac aactgtgtgt gccgatcatg   129660
ggagactcaa gtagaacatg tctgtagtcc agatgttttc cacctgtgag atgtcattgg   129720
cagaaaccaa aaccaaacac aaaaaatctc caaggagcaa taagatcaaa ttatatttta   129780
ttctattaaa aaatgttttt gaaaaaagat acttaaattt taaagataac ttaattccta   129840
```

```
atgatttaaa ataatccaag cagagatgaa agagcaaatg caaatgcata aaaagacccc    129900
agagcattgt tagcaaaaag caaatatagt tagccaagca tatatatatc ataaaagcaa    129960
taagaaggca taaagcaagt ttggggagag cttatttaaa acttgtaaaa atcatttgaa    130020 ttttttaaaag atttcaaaca aattttgttt tattaaaaaa aaaattttt ttgagacggg    130080 gtcttgttct gtcacccaag cttgagtgca gcggtgtgaa catggctcac tgcagccttg    130140
acctcttggg ttcaagcaat cctcccacct caacctccca aagtgctggg attatagaca    130200
tgagccacca tacgtggcta cttctaatt ttttaatgt ggtagtgtgg aatttagctt     130260
tgaaagagaa ttaaagttaa tagaatatta acagtgggct tatagttgat agataacaat    130320
ctgaatcata agccctctat attcatagct ggattttgta cgtgtctggt atttattgcc    130380
accagctaaa aacattccca aagccttaag cataagagaa aggagacagt gttattgttg    130440
ttaatatcct atttaacttt agctcttata aaaagtgca aacaattaa taaagtagaa      130500 aatctagaaa attagtaaat aaacatagtg ttatatctaa atagtaccat cggccaggcg    130560
cggtggctca cgcctgtaat cccagcactt tgggaggccg aggtgggtgg atcacgaggt    130620
caggagatca gaccaccct ggctaacaca gtgaaaccct gtctctacta aaaatatttt     130680
taaaaaatta gccaggtgtg gtggcgggcc cctgtagtcc cagctactcg ggaggctgag    130740
gcaggagaat ggcctgaacc cgggaggcgg agcttgcggt gagccgagat cacgccactg    130800
cactccagcc tgggcgacag agcgagattc tgtctcaaaa aaacaaaaca aacaaaaca    130860 aacaaaatag caccatcaat cagaagggaa gacaagtttt tttcttagtg tgaaagtagg    130920
ctgaggcatc tgtttcccca tgttttttctt gtcatccttg ttgcttactt catagttcac   130980
ttcagtcagg atggtgagaa tatcatcgcc tctgaaatac atcacataat attgtgactg    131040
tctgtggggg aaagcaactg atgaactgtc tcctctgctg tgctcagaga tagttctgta    131100
gttctttctc tcaaaatatc agtcatttga aacaataagg tgcgaaacca agacctaccc    131160
cagctttcct ggtaaatggg ttgtctcaga gcttaataac ttacttttgg tttattcagg    131220
aactcttttg accatcagaa acctcggtgt cagtattaga gttggtttct ttctctcctg    131280
acctgtgtgt ctctcactct tctccacgtt acttggctcc ccattgcttc aatgccccc     131340 aatactctct gcctcgaatt gacatcgcat ctgcggattc atctttgatg caattaaact    131400
taaggcaagt gaaagtataa cgtctcctgc agctactccc accttcttct caccaggatc    131460
tcttagcatt tttgttaggc aacctcttct tctaccttgg tagctagccg cggaaaccttt   131520 gcaggattca tgatctaagt tacgaaatct aagttagatt catgatctaa gttacggaa     131580 attctcactc ttcatatact caaaacatga aatacagggc tagaaggaac ctgctattta    131640
tctcccataa tgcaccaaga ggttttgagg atggtttgct attatagaac ttttgacaga    131700
gttggaggat gtttaaacat tgaattgggt tactgccttc ttggaagatt ccaaaacta     131760 gttgaattgg ctcagtcatg ttttggccta aagacagaga gctggagtat atgactttcc    131820
tatcctttcc tgctctgtga taccctgatt gtcctttgag gtgctgaata aaggaataaa    131880
gcatctcagc ttttccatct ataaactaag gatgttaaca cttgccactc tcccactttg    131940
taactgacct gggaaatgca gctatgtgat ctacagctag acatttagag ttgaacggaa    132000
accactcccc ttggacagtt ctctgacctg ttaatgtgat ctaaatcaca tagcactttc    132060
taataggctc tgaatatgag tagatagtag tgtgatggag tagggggga aggtagtgta    132120 acagtgagga gggctgagta ggcaaaactt accgaggaca tcgctctctc aggctctggc   132180
aaagtgactg gatgtaccag gttccctctg cagggtttcg gtaggaaaca cagttattca   132240
```

```
cagtggccat ccccagcaga aagtcagcct catccgggat atatctcgtt tgaggtgatg    132300
ataaatccat ttctaaatag ggttgctcct ctgaatcagt ctcaacaggt atacctttct    132360
ggtagttatc ccctgacaa gcctgaataa aaaacacttt gggttttcca gcaagggaag     132420
ggcacttcaa accagtgaac tgagatgtca gctcatagat gggggcctcc tgtccatcag    132480
tgccatagat gatgcccttg tctccatggg agaggataca gcagatgaag cagtccatgt    132540
tactgtggtc catgagttgg tagattttca aaatctcata gatttgctct actgtgcagt    132600
catcgtgggg cttgatctca aaatgaagct cttcaaaggt cgtggtcaaa gccctgaaa     132660 agtgaaattt gaacagtcac gttataccac agtaattcac agaccacagc tggagagcac    132720
agtgggcata acattgatag ataagaattt gacccctctc cctctccctc tcccgtctc     132780 cctctccctc tccctctccc cgtctccctc tccctctcat gccgagccaa agctggacgg    132840
tactgctgcc atctcggctc actgcaacct ccctgcctga ttctcctgcc tcagcctgcc    132900
gagtgcctgc gattgcaggc gcgcgccgcc acgcctgact ggttttcgtt ttttttttgg    132960
tggagatggg gtttcgctgt gttggccggg ctggtctcca gctcctaacc gcgagtgatc    133020
cgccagcctc ggcctcccga ggtgccggga ttgcagatgg agtctcgttc actcagtgct    133080
caatggtgcc caggctggag tgcagtggcg tgatctcggc ttgctacaac cacctcccag    133140
ccgcctgcct tggcctccca aagagccgag attgcagcct ctgccccggcc gccacgccgt    133200 ctgggaagtg aggagcgtct ctgcttggcc acccatcgtc tgggatatga ggagcccctc    133260
tgcctggctg cccagtgtgg aaagtgagga gcgtctctgc ccggccgcca tcccatctag    133320
gaagcgagaa gcgcctcttc cccgccgcca tcccatctag gaagtgagga gcgtctctgc    133380
ccggccgccc atcgtctgag atgtggggag cacctctgcc ccaccgccct gtctgggatg    133440
tgaggagcgc ctctgctggg ccgcaaccct gtctgggagg tgaggagtgt ctctgcccgg    133500
ccgctccgtc tgagaagtga ggaaaccctc tgcctggcaa ccgccccgtc tgagaagtga    133560
ggagcccctc cgtctggcaa ccaccccgtc tgggaagtga ggagcgtctc cgcccggcag    133620
ccaccccgtc cgggagggag gtggggggggg tcagccccc gcccggccag ccgccccgtc     133680
cgggaggtga ggggctcctc tgcccggccg ccccactgg gaagtgagga gccctctgc      133740 ccggccagcc gccccgtccg ggaggaggc ggggggggt ggtcggccat ccgccccgtc       133800
cgggaggtga gggcgcctc tgcccggccg ccccactgg gaagtgagga ccctctgcc        133860 cggccagccg ccccgtccgg gaggaggtg gggggtcag ccccccgccc ggccagccgc       133920
cccgtccggg aggtgagggg ctcctctgcc cggccgcccc tactgggaag tgaggagccc    133980
ctctgcccgg ccagtcgccc cgtccaggag ggaggtgggg gggtcaaccc ccgcccggc      134040 cagccgccca gtccgggagg gaggtggggg gtcagccccc cgcctggcca gccgcccgt      134100 ccgggaggtg aggggcgcct ctgcccggcc gccctactg ggaagtgagg agccctctg       134160 cccggccagt cgccccgtcc aggagggagg tgggggttca accccccgcc cggccagccg    134220
cccagtccgg gaggaggtg gggggtcagc ccccgcctg gccagccgcc ccgtccagga      134280
ggtgaggggc gcctctgccc ggccgcccct actgggaagt gaggagcccc tctgcccggc    134340
cagccgcccc gccaggagg gaggtggggg ggtcagcccc ccgccggcc agccgccccg      134400 tccgggaggg ggagggggg gtcagccccc tgcccggcca gccgcccgt ccggagggga       134460 ggtggggggg gtcagccccc gcccggcca gccgcccgt ccgggaggga ggtgggggga      134520 tcagcccct gcctggccag ccgcccgtc cgggaggtga gggcgcctc tgcccggccg        134580 cccctactgg gaagtgagga gccctctgc ccggccagcc gccccgtccg ggagggaggt     134640
```

```
gggggggtca gcccccctcc cggccggctg ccccgtccgg gaggtgaggg gcgcctctgc   134700
cgggccgccc ctactgggaa gtgaggaccc ctctgcccgg ccagccgccc catccgggag   134760
ggaggtgggg ggaacagccc cccgcccggc cagccgccct atccaggagg tgagggcgc    134820
ctctgcccgg ccgcccctac tgggaagtga ggagcccctc tgcctggcca gccgcccgt    134880
ccgggagggc ggtgggggg tcagccccccc gcccggccag ccgccccatc tgggaggtga   134940
ggggcgcttc tgccgggccg ccctactgg gaagtgagga gccctctgc ccggccacga    135000
ccccgtctgg gaggtgtgcc cagcggctca ttggggatgg gccatgatga caatggcggt   135060
tttgtggaat agaaaggcgg gaagggtggg gaaaaaattg agaaatcgga tggttgccgg   135120
gtctgtgtgg atagaagtag acatgggaga cttttcattt tgttctgtac taagaaaaat   135180
tcttctgcct tgggatcctg ttgatctgtg accttatccc caaccctgtg ctctctgaaa   135240
catgtgctgt gtccactcag ggttaaatgg attaagggcg gtgcaagatg tgctttgtta   135300
aacagatgct tgaaggcagc atgctcgtta agagtcatca ccactcccta atcttaagta   135360
cccagggaca caaacactgc ggaaggccgc agggtcctct gcctaggaaa accagagacc   135420
tttgttcact tgtttatctg ctgaccttcc ctccactatt gtcctgtgac cctgccaaat   135480
cccctctgc gagaaacacc caagaatgat caataaaaaa aaaaaaaaa aaaaagaat    135540
ttgaaccaga aattcaagag caaaaccctc tatattcgta gctggattct gcaggcttct   135600
aatatttatt gccaccagct aaaacattc tcaaaccctg aagcaaatga aaaggagag    135660
agtgttattg ttggtctgtt ttctctagta aactagttta caagatgggt aagctatcat   135720
ttaggcttac tactgaacca attttaaaaa tgattatatt atttacataa tcagaaaaaa   135780
acaaaacaat ttttgaataa aagatccaac ttattttatc ctaaaccttc tcaaaattat   135840
ttatgtatag caaaataaaa gatatgaatt aataagatag aactagaaga ccttatacaa   135900
aaggttatcc cctctctatc cctccccatt acctagtcac attccatgaa ggcaaccact   135960
ttcagttttt aaccactttt ttccacattg agctccattt tgtaatgaat ttgggtacac   136020
tgctaattac tcatttataa attttagact ttcgcattga gttcttatta tggagaataa   136080
gcatttgggc tcttactcaa ttatttacaa gttttggttg aatccatagt aatatttta   136140
ttttttttaat tttttttaga aaaggtctca ctctgtcacc caggctacag tgcagtgtca   136200
caatctcagc tcactgcaac ttctgcccccc caagttcaag caattctcct gcctcagcct   136260
cccaagcagg tgggactaca ggcacgcacc accacaccca gctaattttt gtattttag    136320
tagagacagg gtttcgccat gttagccagg ttggtcacaa actcccagcc tcaagtgacc   136380
cacccacctt ggcctcccaa agtgctggga ttgtaggcat gagccaccac ctccggccca   136440
tagtaatatt tctattatta agactatgta aacataatgt tctttcatta tgtttccttt   136500
cttattaacc ttttgcctt tcctggaact tgtaattgta ttattttttc atctgctttg   136560
tttcctatat gcttaacact gttttttctc caagtgctca atggatctgg ccaaaatctt   136620
tcaacatttt caggctactt gtctgactca tttttatttc ttcctggaaa actttccatc   136680
cagagcactg catccttctg ctgtaatacc aactggctgt tccataggcc agatgaattt   136740
ctcttctcct gggacatctc tctgtctctt ccatagtagg ttccctgttt cctccatcta   136800
tgacttcctc tttcttatca gtttccttg ctggagcata accatgagaa gtacattttt   136860
tgagcccctg tatgagtctt tagtttatag agttctattt ccaaaagcat ttttcctcag   136920
aattctgaag gcctttcttc acagtctttt agctttcagt gttgctagag agaagacttt   136980
ccatttctga tactttacat atttggctta cttttttctc tttccagaag cttctagggt   137040
```

```
atgatatgtt tggaagtgaa tcttaatcca ttatacccctt tcaatctgga gattgcgtca  137100
tttcgttctt ggaaagttcc atttcccctt tctctgtcct ttctttctgg aactcttatt  137160
gtcaaaaatt ggacatcctt gatttagctt caaattttct tatctttcac tcctattttc  137220 tattttgtc ttttatcct acttcctag actttatct ctactttat gaattttca  137280 ttttggtgct caaatttta atttcaagg agacttgctt gttctgtccc ttttcataa  137340 catcttgttc tttcatggac ctttaactaa ctctctaaga atactaaata ccaatattaa  137400
gcattaaaaa aggttgcttt tttctcaaca ttatctttt ttcattcata ttctgtttca  137460 tgttttctt gttgtttgca ttgcctctca tttatctagt aatttattta tttatttgag  137520
atggagtctt gctctgtcac ccaggctgga gtgcagtggt acgatctcag ctcactgcaa  137580
cttccacctc ccaggttcaa gtgattcttc tgcctcagcc tctgtagtag ctggggttac  137640
aggcacctgc caccatgcct ggctaatttt tgtatttta gtagagatgg gtttcacca  137700 tgttggtcag gctgggcttg aactcctgac ctcaggcgat tcgcctgcct cggcctccca  137760
aagtgctgga ttttcacgcc accgtaccaa gctacctctc tttcgtatta gagcctttct  137820
tcaaatgcct gctgaccttt ggttgtccat tcataaattg actaattagt ccattaaaaa  137880
gtcgactgaa agctctgtgt ttgtggatgt ggcttgttct ctgagggatt tcatagcaag  137940
atgattggtt ggggacctga tcatttcatt aggaaacctc cagatgtcat tatctgtatg  138000 tatttagct agagctttca gcttctccag aggtaagtct gtatctgctg ccagtgtctt  138060
ggaaccaagt tggtttagag atctgactcc atgccaccag caggttttct tcagtctctc  138120
tgtgttcagt aaaatgcttc attgcttcct ttgctgggcc tggcacaccg aagtgtagag  138180
cctctctggt tcaatttat gagaaaacaa acttcctgtt ccttatgatg gtagaataag  138240
aatagttgct ggctctatga gaggaaggta tgaatcagag gattgtatag gcttatatag  138300
gctttcaaag aatcttcctg ttttctgctc attgcctcac ctacactttg tacttccaat  138360
tgctgaattt ttccaggatt ctgtggggt aaataggctt gcctcctttc cgtgttcccc  138420
tctgtaatca gtgaggttgt agcttttctct gttaagtcaa ttacctcgac tctttttttt  138480
caactccccc aaattgttgg aaaccttttca ttagctattg tctcctttcc tgttctcttg  138540
atccttgttg gattattcct tttttattcc ttctccagca ttttgtccct gtcagcacat  138600
cagagctaaa cataagtcat cagtcaaaag gcagtctcag ccaggtgcag tggctcacac  138660
ctgtaatccc agcactttgg taggccgagg cgagtggatc acctgaggtc aggagttcaa  138720
gaacagcctg accaacatgg tgaaacccca tctctactaa atacaattaa ctgggtatgg  138780
tggcacatgc ctgtaatccc agctacttgg gaggctgagg caggagaatc acttgaacct  138840
gggaggcaga ggttgcggtg agccaagatc atgttattgc actgcagcct gggcaacaga  138900
gtgagactct gcctcaaaaa aaaaaaaag aaaaaataca gtctagcatt aggaatagaa  138960
aaaaataact gaaatgcaat aggcccttgt tgatttggaa gcactttggc aagactaata  139020
cagtgtgttg gttctgtgaa aaaaattctg atcctttgga aatgtggaat gttgattaaa  139080
aaaatgactg taaagcaagt ctgaaggcac tgaagcagga cagaagggag tctctcagga  139140
gaaatgactt ctgcagctgg gtctcctact tttactcatt cagcataaaa cataagaaca  139200
ggaacagaaa aagcaggaca cacagactcg aatgcctacc agagactagt caatcatggg  139260
ccagttataa gaaaatgagc tgccagaaat agaagcaaat gttattttaa tagaaatgtt  139320
ttaattttaa aagaatacaa atcaagggtc caaaatatt ttttcaatac caagcgcata  139380
gtgacgaatg atgtaatcaa tggacttaat ctctgtgcct tttaaaggc ttagatttgc  139440
```

```
ttaaataaac aaatcaaatg ttagcaggga ccaggtacag gtggctgaca cctgtaattc    139500
cagcactttg ggaggccgag gcaggcggat cacttgaggt caggagttca agaccagcct    139560
ggccaatatg gcaaaacccc atctctacta aaaatacaaa aattagccat gtgtggtggt    139620
gtgtgcctgt agtcccagct acttgggagg ctgaggcagg agaatcactt gaaccaggga    139680
ggtggaggct gcagtgagct gagatcacac cactgcactc cagcctgggc aacagagtga    139740
gactttgtct caaaaaaaaa aaaaaaatgt taataggggc cattacagac tcctgatgat    139800
tataatcagt ctacattaat tttctaaact tacctccatt tgcaaaacaa atcaataatt    139860
gatgttatgc ctgataaaca ctatttccaa aagttctttg atcaaatcaa aattattaat    139920
ctctcaatgg tgatggatga ttttttatttt ttgttgttgt agtcacttttt tatattcaca    139980 tactacaaat tgttttttca tttaacttgt aagttcttga tcttagctta atttggctga    140040
gcaaaagaat tgctaaccag tttaatattt aatacttgaa aatgctattt ctgttaagaa    140100
cccacaattt ctgctgcact taacagccca acctgtaaaa atgcagcctc tataagaact    140160
ttgataccac agcaatttca tcgcctaata cattccacag aagcgctatg catttagctg    140220
aattcaaaac aaagcttatt actgcttttc attatgtctt ttagtaagat ttgatatttt    140280
atatttatac atacattact tttatttaaa aaattaattt ttaaaaaaag caggaaactg    140340
ataaatgtat aagaatgttc tttacctcca cagggaaata tgtttaaatc cattttcttg    140400
aaacatggcc cttttggtat agcttttgtt ctctcccttt tgatttaaaa aaaaataggc    140460
ataagaaata ttttactttt ctcttttggg ttctactgta cctgcatcca agtgtgttcc    140520
attcctgtcc ctaatgctgt gaagtttggg cactttctcc cgtgcttttg caaaattgtg    140580
attgttgatg atcagacagt atccccgagg tttgcttttc atttggtaaa ctttgtccaa    140640
agtctggaaa acaaaaaccc aacccaggag ctgactctgt gggtcaaaca ctagagatgt    140700
aaacaaacaa ctccctagta agaggacttg cttttccattg caccacccca actcggggtc    140760
gtttcctcga agaactagtt tctacctatt tccttcacac aggacctctc agacttctgc    140820
cccatcgttg taaagtcagt gtcccaatac ctgggcctcc tgagcacttt gcacatatat    140880
taatattgtt gtcatcacat tgtattattg tttgttctca tttctgcttc ccatactata    140940
cagaagactc cttgaggttc ataacatctg tgccagggac tacggtgtat aacttgtga     141000 gagctcaatc aagagtcact gaatgaatga atgtctttgg ctgcccccac gccatgactt    141060
gtgattctct tggctgtcta ctgaactcat ctgtgcttcg tggctaacag ctgagggtct    141120
cccattcatg cattgcacag tgtggtccca ggattttaaa ggtgatggct aacccagct     141180 ctcaggacca cggtggctgc tgggaagaga tgggctggtc agggaggtcc tggctacact    141240
gtaggttatg gtatccaaac tgtagtacct gatagtactg gccagggatg gcgctgtgtc    141300
ctattcattc tcctagggct gtttcagtac cgagaaactc agcatttagt tggaggtctg    141360
cgtagcccct tgaggtggag aaaaggactc caggctagga agcccaattc ctgcctctac    141420
ttcaccttat gactttgggc aaataacctg ttatcttaat atgttaactc taagatatta    141480
aatatttgat taagtttgta ccaagtatgt taagtttta ttatttacag ttgtgttcta     141540
agtatttatt aagcatatta agtgtattta ctgagatact aagacactaa gatttggcca    141600
ggcacggtgg ctagtaccta taatcccaga cttttgggagg ccaaggcagg aggattgctt   141660
gaggccagga gttcgagacc tggcttggca acgtagcaag acccctgtct caataaaaca    141720
ttaaaaaagg aaaaagatac taagatttac taagatatta agacagtgtt tttagctctt    141780
cagtggggac aatgcttgta gcatgctata ctgtttagaa agtaccacat tacttgggtt    141840
```

```
aatccttgac tttcagatga aagaggtctg gtaattttct caggagccca cactagtgaa   141900
taatctctct caagcctact tcagatattc aggatttcct cttcttccta ccatgaggag   141960
gagcagatcg tctaataagt caggatgtat ttggtggatt gttgattaca taaagagaag   142020
ttattatgcc taaaaattac atgtttctgc tggttcactg agacaaaaac acagagatgg   142080
ctagattgtg agagtttgct gcttacacct catcaccaag gagaagcatt tttgaaacat   142140
taagctaaag gaaaaggctt ggcttttttcc attcctgcta gactcttttct ccaaaccact   142200
cccccatcca ggctggcacg gctgctagaa gatttggtag gaggcttatt accccctcca   142260
ccctccaact attccagtat cttcatctcg ggtcttaaaa taaaattcaa atgtatagaa   142320
aactgaagga gtcacatttt aaaaattaag tcacatttttt aacttttttt gtgtgaattt   142380
tttctacagt tctcaaaatt ttcagtaagt ttctgcccct tgtcagttta tctggcagca   142440
aaaaaaaaaa aaagctaaca aattaaataa ctagaatctg taatgtaaaa aaaaggattt   142500
ggaggtttcc gtctacctgt gattcactat cctgttctct tggagagtcc gagattgtca   142560
ttaccccaca caactcctcc cctgcaaaca acgaagagac acatctagaa tgagacatgg   142620
caggaaaggt acactggtaa tgaaatatgt agcacatagg acaacataag gtctttttta   142680
agatgaaaat tcaagctggg aacagggggct cacgccggta atcccagcac tttgggaggc   142740
caagatgggc agatcacttg aggtcaggag ttcaagacca gcctggccaa catggtgaaa   142800
ccctgtctct actaaaagta caaaaaaatt agccgggcgt ggtggtagcc acctgtagtc   142860
ccagctactc aggaggctga ggcaggagaa tcacttgaac ttgggaggta gtggttgcag   142920
tgagctgaga tcgcactact gcactccagc ctgggcaaca gagtgagact ctgtctcaaa   142980
taaataaatg aaataaaatg aaaattcaca gactgccatg aatataatct cctttcaagc   143040
cagagagatt ctgcaagcag ggcaattaac atgcttctgg aaacacaaga tcaagttgtc   143100
tcctcgccaa agaaaaaaac ataccaagaa atgccataat tttatattgc tccacatggc   143160
caggttgaat ttttgtggta tttgtgagat actcattaat aaagccacta gctcaggatg   143220
aattaatgat ttagtacttt actccttaaa gtattcttaa ggccttaggc tcagcaggca   143280
gagggggaaag ggaaggacag cctgcataga cattaatctt taaaatacat ttgagtgatc   143340
caaaatgtat tttacacaca cacaccacaa agagccaacg taaaaataca ataaaaatat   143400
tcataatatg aatggagtga tggtgttctt ggacttgtaa aaatttctct gaatttaaaa   143460
taatcttcaa ttagtgtata taattttttct aatcagaaag aatactttat taattgccta   143520
tagtcccagc actttgggag gcccaggtag gtggatggct tgagctcagg agttcaagat   143580
cagcctgggc aacatagcga aaccccatct ctacaagaca tacaaaaatt agccgggcat   143640
ggtggcttgt gcctgtggtc ccagctactc agggggttga ggcaagagga tcatctgagt   143700
ccaggaggtc gaggctgttg tgagccaaga ttgcatcact gcattctagc ctgggggaca   143760
aagtgagaca ctgtctcaaa aaaaaaaaaa gactatttga ttaatcaaaa ttttgaagga   143820
gatcgttgag agctctctct cttggttcag cctcgcttat caggtagaaa aagtgaaagg   143880
aagttgaaag gagtgactta gtgtagaagg tgttgaaaga gaaagtgact taaccaagaa   143940
aattatgaaa cataatttaa atccagctac tcagtgcata acatgagcag cacgtcaagg   144000
agaaaaaaaa agccacatag aaaaaatgat gttaaattac ttactactga ctaactctgc   144060
acctatttca aacttgccag cttgggctac aggtcttagg agagcaggtg cggccgggcg   144120
cagtggctca tgcctgtaat cccagcactt tgggaggcca aggcaggcag accacctgag   144180
gtcaggagtt tgagactagc caggccaata tagtaaaacc ccatctctaa taaaaataca   144240
```

```
aaattagcta ggcgtggtgg tgcacgcacc tgtaatccca gcttctcagg aggctgaggc    144300
aggagaattg cttgaacctg ggaggcggag attgcagtga gccgagatgg tgccactgct    144360
ctccagcctg ggaaacaaag taaaactgtc tcacaaaaaa aaaaaaaaaa agaaaaagta    144420
gagcaggcac gttaagatgt gcatgtggta gaaggctgtg gggaggacac atgcaggtac    144480
cagatagtaa attaactaaa tcttgaaaat gtatctccaa gcattaccat ttgaaaattc    144540
atcaggactt ccttcaaggc tgctgcttct ctctgaatta aaggggaaa ccccaaacaa    144600 tatttgatta gaaacaactg tgatatggag cgatttgtca gtttcaattt tagagtaggt    144660
tttgccgatt cccggctgtc aggttgtttc tacctttgct gaattcttca tagtcgttga    144720
ttatcttcag caggctcttg ttgatttggg cacagactct tttcaggatg tccaactttc    144780
cttctcccag gatgaccctc ttctccatct ctatgaaaat atccagcagg ttctaagagg    144840
aggagaaata aagttgggaa tctggattga gccctactgg tttttagatt agattttttt    144900
ttttaatttc caatttctcc aaccaaggac ctgcccttgc ttcccaagtt tctgacagtt    144960
tctgctggtc tctcacagcc agcaggctac tagggaagcg attccatgtt ttctggccca    145020
gaaagacaga agtgagagga taaggagaa gccatgtcag atgtcaccca gtccccaggc    145080
cctgtgctca aatctcctgc gaatgcatta cttggggact gtgaaacaac ctgagacagc    145140
agcccggtca tcatggtgac accctgggga acagcctcac ccccagcatt gcctctccag    145200
acctgagtac atacagacac acagacacac acacacagac accacatgca catacacaca    145260
cagatacaac acacacagag tatactcagt gatacacaca cagggcata aatacaatac    145320 acactacaca acacacagac acacatacca cacagagaac acacacacag agatacacag    145380
acacacacac cacttataca gagacacaca gagatacaca tatcacacac aaatacagac    145440
acacactata cacagagaaa ggcacacaca gacacggaaa tacacacaca acacacagac    145500
acaatataca cacagagttt caggtcccag gttgtttcgg ggactgcaga agtggaggaa    145560
atatctcaga cccaccgcag tctttcccag ctctgccggg tctgggctgc atctgcacag    145620
cctccttctc ccggcctctg actctgcctt gctcccaata attaacatga gcagcacttc    145680
ggtctaaagg aatcacatct gtaacactcg tgctgacaac tttcttcttc tagttaaaaa    145740
gtgagaatcc aggttgcttt taccaaaata cccctctctt tggtctcaga aatgcccct    145800 ggctaaccaa gtctcaggac taaatctcag taagatacca ggtcttacca tgtcatcatc    145860
cagtttgcat ttggagattt cctcttgcaa aagaaactta aaagacctca attctgatct    145920
gctcacttct tctgaaatct gatagagcat gaccctgtgg tgggaaatgg agacacttta    145980
gaaatctttt cccaaataat ttcccatttg atatatggag tcacagtggg cttgattcca    146040
aaggcctccc ttcaacataa agccagttaa tggcatggtt tatgagttga gcccttggaa    146100
agaggctggt gtggtgacac agaagtctac tggctcctcc ccgactttcc caccccttaac    146160 aatttaaagt tctatcaact tttctttcag tttatttcag ttgagtaaat cttgttttcc    146220
tttttttttt tctgtaaaat ggagattttg ttgcaatagc aaaatgcttt gccttttgga    146280
aattatgctt ttcaaaatgc acattggctc atgacttccc taatcaaaac tggtcagtat    146340
tctcccagtc attatcttca gtaagacggc caagcattcg gttctggaat acaaagtctc    146400
cgaatacatc cctatcacag accagaccgc aaacacgaaa ggacctgaag ccaaacacac    146460
ccagctgccc tgccctcacc cctttctgtg gtgccgctac accccatccc cttgtctatc    146520
tgcagaggcc catccatgaa caatcagctc aagcattgcc tgagcatcct caaagctgca    146580
ttcactccac tatgacttag taaccccaaa acgataacac acataattgt ctgttggcct    146640
```

```
ggtgcagtgg ttcatgcctc taattccagc gcattaggag gccaaggcag aaggaggatc    146700
acttgagccc aggggtttga gaccagcctg ggcaacatag caagacccca tctctaccaa    146760
aaacatttaa aaattagccg ggtgtggtgg catgcacctg tggtcccagc tactccagaa    146820
gctgaggtga gaggatcact tgagcccaga aggttgaggc tgcagtgagc tgtgatcatg    146880
ccaccacact aaaaataaaa acagaaaata attgtctgtt tagaaactgt tcaagtcccc    146940
tagtggccag gtccgtaccc ttttattttt cataaaccca gagggttgtg aggtgcaatg    147000
attgagctca gcggacccag gctattggtg ttggagcctt ggttccacta tctttgagca    147060
gtgttaactt tagacatgtt acacatttt tcctcgtcca tagactgaag ataattatcc    147120
gtaaccacat cataggaagg tttcgagggt tacacaaata agtttatgtg aagtacttaa    147180
atcagtcttt ggcaacacac taagtgctca atgagtgata ggtgttacta tttcctaatc    147240
tatgcctatc acatttatgt gattggcaca tttaggctct tggaatatgc ttgtcgaata    147300
ggtgaacaaa ggaatgtttt agaagtcagc aaacctttca atactatggt gtaaaggaaa    147360 ataatttta tacaaaaaca cgttgacttt aaaatttaat tagaaaagta aaattctgaa    147420
aataaaaatg gcgtagaaac agaaattact cagtattacc atctgcctta tccccttct    147480 catggactct ctaccctaga agtgtttatc taaagctttc agtttggcca aaattggatc    147540
taatccaaag ctactctgac tctttcacct ttattacaag gtatttaccc ttttgctttc    147600
ctcattattg aagcctatag gctttcttgt accatcacca tttagtaatg aacctgaata    147660
gtttataaga tctttatttt ataggtagca attataactg gaaaataaaa tgtctagtgt    147720
tttcttataa tggtaagtgg tcaccctagc atatttatta gcttctggct agtattcaat    147780
gataatgaac aagcagtaag tcaggattgc ccggacccct ttatctctaa gccaatacat    147840
taaagatttt aagagagatc ctgccttatt aatagatgat cgaccctccg ccagaaaggt    147900
acagactgtg tctggcactg gctgtttgct tcagcccagc tcatgcggca gaagtggaac    147960
cttcaaagga ccaagatggt gggcacaaga tgagaccccc ctcggctttc cttgttctgg    148020
ggctgtgggt ttttaggact aactggcgcc ttaatgaata agtgccttat aaagacttca    148080
caatgctagt aaaccaaagc tatctagtgt actggttgaa tagtgttctc ccctcttccc    148140
caaaattcat gtctatctgg aatatgagaa tgcgacctta tgtggaccca ggacgtttgc    148200
agataaaatc tcattaagat gaggtcatgc tggccaggcg cagtggctca tgcccgtaat    148260
cccagaactt gggaggctga ggtgggcaga ttgcatgagc ccaggagttc aagactagcc    148320
tgggcaacat tttgaaactc catctctaca aaaaaataca aaaattagcc agacatggtg    148380
gcgggtgcct gtagtcccag ctacttggga ggctgaggtg ggaggattgc ttgaacccag    148440
gaggtggagg ttgcactgag ccgagatcat gccactgcac tccagcttgg gcgatgtagt    148500
gagacactgt ctcacacaca cacacacaca cacacacaca cacacacaca cacacacaca    148560
aagatgaggc catactggat taggtgggcc ctaattccta atccagtgac tgtctcataa    148620
gagggagatt tagacacaga aagggaaca taggcagaga ctgctgtgcc tcatctacaa    148680
gacaaggagc actgaggatt cctccaccca cccgaagcag ggaaaggcat gaaaaagatt    148740
attcctcgga gcctcttaaa agggaaccaa cactgttggc atcttgactt ctgactcagg    148800
cctccagaac tgtgaaaaca cattttaaaa actgttttaa acctgctagt ttgtgttact    148860
ttgttacagc agccctagga aacttatata cccagaatat ctctttcttt ttttttttga    148920
gacagagttt cactcttgtt gcccaggctg gagtgcaatg gcataatctc agcttactgc    148980
aacctccacc tcctgggttc aagcaattct cctgcctcag cctcccaagt agctgggatt    149040
```

```
acaggcgtga gccgccacac ccagctaatt tttgtatttt tagtagagat gaggtttcac 149100
catgttggcc aggctagtct tgaactcctg acctcaggtg atcagctctc ctcagcatcc 149160
caaagtgctg ggattacagg cgtgagccac ctcacccggc ccagaatatc tcttttttca 149220
cttaaaatca aaatggtcaa gccttggctg gcatggtgg ctcacaccta taatcccagc 149280
actttgagag gtcaaggctg gtggataact taaggtcagg agttcgagac cagcctggcc 149340
aacatggtgg aactccgtcc tactaaaaat acaaaattag ctgggcatgg tggcacacac 149400
ctgtaatccc agctactcag gaggctgagg cagaagaatc acttgaaccc tggaggtaga 149460
tgttgcagtg agccgagatc atgccactgc actctagcct gggtgatgaa gcagactcc 149520
gtctcaaaaa caaaacaaaa caaaacaaaa aatagtcaag cctcaaaaca aaaatagtc 149580
tctgagaata gaaagaccag agcattcatg ggctgagcca tcagaggaca gcagctgtca 149640
gccctggttg tgaaccctt ccatctcaca tgccatagtt atcaacaagc aaacagagac 149700
aatgaaatgg gcccagaacg aagacttcag tagaagtttc ctgaaagcaa agctaaaatt 149760
gctttaagta gtgtccgata ataggagatg ttgaaagaga gaaagtgaca atgtgtttct 149820
gttttttaaag tcttgtcaca gcatcatgaa gttgtaactg aatggggttt ctctctcaca 149880
cctttggtta cccactctcc ctagggtggg gagaagctga gttttacagc ctttggcagg 149940
atgacccaac gtgccactgt cttcctatag aagcttagaa ctgtcataca gccgggctca 150000
caggaactgg gcagcctcgg tggagactgc ctagctgtat gtgccaggcc agcggcttac 150060
agctccgtaa agaacttagt cattcgagtc tttaagtgtg gcagaaaacc cttaaatctc 150120
attgaaaatt ttcatagcca tccgcaagca ggtgggaggg ggatttcagg gtgggaagcc 150180
atgatgcttt actcaatgga tgggcaaagt aagcacacaa tctggatatc gagaggcatc 150240
aagataagag aggaaaaaaa tgagaacact tagaaaaact ctattataac ttcagcatac 150300
ctctaagtaa tgtttcactt tgaaaaataa attttatt tatggtctta gcatttctat 150360
agaattatat ataaggcccc taaatttctt aatctggctc cggtgggaca tcttcccaaa 150420
gcctcccaag tgatactgaa tgtggttct ctctcacgcc tttgtttacc cactctctct 150480
agggtgggga gaagctaagt tttacagcct ttagcaggac cacccaaggc actactgtct 150540
ttctgtagaa gcttagaatt gtggcactgc tgggttccca ggcactaggc agggtaccac 150600
aaaaaaagc cccaatcagc tcagaggctg tccattcaac ccacacctcc cagtcccaca 150660
atgggagttt ccacccacct gtaggcagaa atttgagccc tgcctggtgt ctgaagttcc 150720
cttccatct cctcctttct agtgtttagg taggtaatca gcaaatccag tctattaatt 150780
cggaagagca gctccttcag gaaggacaga ttgctttcct ccaacattct cttttcctgg 150840
agtctctgga ataacatcaa ggcatccttg atgggttctt gcttcctttg cggaatgtag 150900
tccaggctca ggaacttgag ggaggccaga tcttcactgt ccagttgttc cccaatatca 150960
taaagatttc tgctgaagtc catcttttta aaaggcagga gaatataatc taagtcaaaa 151020
taaatggtat gttcagataa ggaagaaaag taccatttgc tggcttgttc atcaaaggct 151080
actgcaacta ctaggtactg gtcattgtgc tgtcagcaca ggagagaaaa aaagaacacc 151140
agacaagttc cctcttactg tttaggaagg tagacataca aacaagccaa tgggctgggc 151200
gcggtggctc acgcctctaa tcccaacact ttgggaggcc aaggcaggcg gatcacgagg 151260
tcaggagttt gagaccagcc tgactaacat ggtgaaaccc cgtctctact aaaagtgcaa 151320
aaattagcca ggtgtggagg cacgtgcctg taatcccagc tactcaggag ctggggcag 151380
gagaatcgct tgaacccagg aggtggaggt tgcagtgagc ggagattgca ccactgcact 151440
```

```
ccagcctggg tgacagggca agactccgtc tcacaaaaaa aaaaaaaaca caaaaaacaa    151500
aaaaaacaag ccaatggtta gagggttgtg accagagtgt ggtagggatg tagaggaaga    151560
aaccttaact tagcctggga aagggcttc  ctatggggaa gggattttgg ggagaatgcg    151620
agaaagcaca attcttacag gaaacaatta atgtaaaaga tggaggtaag aactttcaag    151680
tccattcagg caggcacaag gagctcaata aagtaactac aaagtgtctg ggatggagag    151740
tgatgggaca aagggatgaa gctctagcca ggtaccatgt cacaaagggg ccgcattacc    151800
atggggcgag gggtttaggc tttgtcctgg aggtgatgag gagctaagaa aggactgtaa    151860
aaatgagaat gacattatcc aacttggaat taacattcaa agtgcaaagg acagactgga    151920
agacttagaa gtaggggacg tactaggacc tattaggacc aacctcccat tcaaccccac    151980
catcaatccc caaagtccat tatatccctc tgtatgtctt tgcatcctca tagcttagct    152040
cccactttta agtgagaaca tacggtattt agttttcgtt ttttttttt  cttttgagac    152100 ccagtcttgc tctgtcaccc aagctggagt gcagtgtcgc gatctcggct cactgcaacc    152160
tccgcctccc aggttcaagc aatcctcctg cctcggcctc ctagtagttg ggattacagg    152220
gacacaccac cacacccagc taattaccta gaataatggc ctccagctcc aagattaaat    152280 attttttaaag tgacctaaag attttgagtt tttaagtgac ccaaaacttt tagttttcaa    152340
agtcttactt tcaaaaatat cctttccttc cattccctga aagaaaattt ttaaaaatct    152400
tttccccctc ctgattacag cagcagtggt tttttttgtgt ggaaatggaa accacagagg   152460
ctctggggac tcatccccta ctcccacccc actgcgatca tgtttgttcc ctgcagggag    152520
ctggccccca gccctaccgg cgtcaccctc ctgatgacaa actaccctct cactagaatg    152580
gaagctctgt gagggcagaa acttttgctg gtttattttt tattcttatt tttattttg    152640 agacagggtc tcactctgtc acccaggctg gagtgcaggg cgcaatcttg gctcattgca    152700
acctccacct cccaggctag agccatcctc ccacctcagc ctgctgagta gctgagacta    152760
caggagcaaa ctaccacacc aggctattac tggctactgt tcaggctgc  tggcatgata    152820 attgtctggg cttttcctgaa tgaatagtaa tagctatctt agacatgttc agtgtagaaa    152880
taatcaggtc tattgcaagt tggccagaat ttccaataga tactgctagc acgtgtcaat    152940
cgttgctcta ggccctggga atgcagtaaa ataaccaac gtggcccagg agttcaggtc     153000 tacccctgggc aagaccccag gtggcaagac cccaggtagc aagaccccaa ctcttaaaaa    153060
aaaaaagcaa aaccaaaacc aaaacaaaac aaaaaaacag gtgggtaatt tagccatctc    153120
tgtcaaaata taaaattcac ataaactggc ccacaattta acttccaaga gttttttccta   153180 cattcactta aacaagtata ctcaaaacca tatataaggc tattcatggt agcattcctt    153240
gaaataacga aagagcagaa acaactgttt atcagcatta gaagatttag gcaagctatt    153300
aatcatattc cagggaactc tatttggcta ctagaaagaa taggaagatc aatgtggttg    153360
agcctgcgtg atctacataa tgtattgatc agtacatatt ttgtgtattc acagaagagc    153420
tctgacaaaa aatgcacagg aagttccttc agtaatgtta aagaaaagca gaattacaca    153480
cagatgtggg cgtgcagtgt gagaaggctg atgggtggag gtgacagtga gagctgcttt    153540
atttcccata ccttgctgca cagtttgtac tgtttgaatt tttaccatgt acatgtatga    153600
cttattctaa aacatatacc tagttaaaat ctttatttaa agatccattc ttattcacat    153660
gctggaaaag atctaaacta gatctaaccc tgtttagtgc cattaggtca actgtctta    153720 caattttaaa tgcattctaa cctctgttaa agtctcatct tacagaataa aaccaaccaa    153780
agaatcaaat gaaagcagga cttcctttcc cccatccctc aattatttt  ttctgaggat    153840
```

```
aacaatgctt agtgtattca ttttagacaa tacagaaaag ataaaaagga aaattaaaat    153900
tatgtataat tccaccatcc aaatataaat gcccagtaat attttactct ttcctaccaa    153960
atattttatg catacacatt tttccttata tttgaacaca tcatatttct gtagtataag    154020
tggatttttc cactggtaag tacatcttgt attgtaagta cttttcctgtc tttagttttt    154080
cttctacagc atgggtttta atatctgtaa ggcacttaat cttagagatg gctataatt     154140
tacatagcca gttcctgatt acatttagga tgactttaaa acgcaaatct ttaagaatac    154200
ctctaattat tttcttagaa taatttccta aaagtagtat tatggtgtca aaatgaataa    154260
accttttga ggctcttgtt acacattcaa tagcattttc tgacagtata taataaaaat     154320
caatacaatc caaggctgag atgacatgaa tttggatata ataagattgg cgcatagctc    154380
cgtcctccat agccatctca tctcactcat ttcattacct tttcaacaac gtgacaatgc    154440
tttttaagtg gtttccccat caaatcataa ctgacattta gaagggaaaa tgctaacgtg    154500
gcttcttctc tggcctaggt gttccaggat acactgtcag atgatagtca gccttttctg    154560
tttttttgttt tttgcttaag ttacacatcc ctctagtcat agtacctaga aaacagtcac    154620
ttgcaaagga tttatgacac cattaacaac gggccatcca gcactgtaag gggagagaca    154680
tcgtgtggca gttcttgttt tatgggacct agattttctg cactagctta tgggctagaa    154740
actttgttaa gctagtattt tttaaacaat gtacttgtat ttttggttcc taaaaacagt    154800
aaaagtaaca cttgtttcat agagaaagta cagagaagta taaaagaaa ataaaaatta     154860
cttaaaaact tgccatttgg aagtaattct ttggtcacat tttgtggcct tttcccaatt    154920
tttttccac atgtatatat aacatatgta aatttgaata tgttgccatg taatacatat     154980
attttatata atctctgcta aatagtaaat gtatataagt ctatttgtat tacataagta    155040
tatttattat tttatatatt tatgccccaa agtatttaaa tataaatatg tgtttataat    155100
aatcatataa ataaatgata tataaatgtt tgtaatctat atatccatat aaacataaaa    155160
atatttttta acctcatttc actaaaagcc tctgaagaaa ctactattac tgtccccatt    155220
tttctgttgt gaaaaatcac ggcttggaaa taagctagta agagagagag ccacagccag    155280
atttaagtgt ctcactcaag ggcttcagtg acagatcaca aagatttaga cgtcattcta    155340
cttgcagctg gaaggcagtg aaagaatctc atgaagaaaa acataaaatc ataacttttt    155400
tagagaacaa catttcaaaa aattttataa taacaaagcc acaaaaacag aagttcttaa    155460
caaatccact ataggagagg gggttagagc ctcacaaagg aagtgctaga atctaggccc    155520
cagcatctca ttccagagtc ccattctacc actgtattac atgtcacaat taaactgtaa    155580
atacattcca tctcatcaca atcattccag taatattcta gcagcatcct agctcttgca    155640
gtgataacta aaaagcaaaa catgcatttg ccatcggaag cagaaacctg catctcatcc    155700
gaagcttgag agaacctgaa agccactcgc tctcaggccc aaaccctaa ccggcaggta     155760
gtattgccac tccctccaat ccaggctggc tgcctcagac tgcgggctgc cccggaacct    155820
gacagacatc cattctgcac gcacatgatg tccataacag ggcgctgcag ccacggcatt    155880
caaacaaccc agcaaggtg tccaaacctc agcaaaacat ataatcccat catttttcaaa    155940
cagaatgaaa cttgcaactt cacctgtaaa ttcttaaccc cacaagtgca ggtctctgat    156000
tgtgtctatc tagtcttccc attatattgt tttttgaact gttctgtatc tttttaattt    156060
ttttttttt tttttttga cacggagttt cgctcttgtt gcccaggctg gagtgcagtg     156120
gcacgatctc ggctcaccac aacttccacc tcccaggttc aagcgattct cctgcctcag    156180
cctcccgagt agctgggatt acaggcatgc gccatcatgc ccggctaatt ttgtattttt    156240
```

```
agtagagacg gggtttcttc atgttggtca agctggtctc aaactcccga cctcaggtga   156300
accaccgcct cgacctccca aagtgctggg atgacaggcg agagccacca cgcccagtct   156360 ttttaattt  ctttaaaaaa taaataattg aattagtagg accacatggg tgtgtttgtg    156420
tgtatgtgtg tgtgcgttta tgttggcaag tgtgtatgtt ggtgggtatg tgtgttggtg   156480
ggaggatagc tgtagcagca aagtcagtag agatttaaat tttggcttct attatttcac   156540
aagtttgact gggatcagga tgaggccttt atacaagtag ttaaacttgc agcatttcag   156600
aagctcctag gacttcatca gtctaagcta gaatggcctt cagatctgga aactgcacgg   156660
ccctcggcaa ggctctcaga gggactgcta cctcttacac taacttcatg gtttcccat    156720 ccacactcac atacgaggat cacctccatg gccccagggc cacccgatct cactctcagc   156780
agcctagaaa actccagaat caaaggcctt cctcccaaaa ggcccctctg accttaacaa   156840
agaggcaaat ccttacctta ctctcacgat ggtagcacct tcgtcacagg cctatccact   156900
accatctgag catctaagac aagagcaaac gtcaatgaa  ggacggaagg gcacagccag   156960
ccagctctac ttcctgtttc gaaactcctg agtcacaaac actagagggg aaagagcgct   157020
taccacttgc ccctgagtga gcagagtgcc ttctaaagct tctaaagctg caggaaaaag   157080
gcctggtggt ccaggagacc gcacgcaggg cacctggcca cctgagcact ggcccctggc   157140
tgtgactttg gatgggccat tttacctttg gggcctcatt tccacattcc aaaacaagga   157200
cgttggactg gattgtaact aagaacactt tcatttcata tttaggattt aaagattttt   157260
ctgggttcat cattaagact ttaattttt  cattcaatga atcttgatgg agcacctcag    157320
agaggtcttg agattggaca ctgcagagcc ctctcatctt ggttctcagg gtggctgtga   157380
actttcagag ctaaagcccc tggtttagcc aaggagcatc tctgtggccc caaggtcacc   157440
agattccacc ctcagcagcc taaaatactc taaaattaaa aaaaaaaaa  aactctaaaa    157500 agaaaaaact ctaaaatgaa aaacctctaa aagaaaaaa  ctctgaaata aaaaaattct    157560
aaaatgaaaa aaatctaaaa agaaaaaact ctaaaatgca aaaactcttt ggtaagatgg   157620
taagtccatc ttaccaaagg tgatccttgt atatgagtgt agctgaggaa accatgaagt   157680
tagctgaaag ctgggtttac catcttatca aagaagcaaa tcctggggcc ctcaccatgt   157740
tgggctctag ggatatacca gtaaacaaaa tattgccttc atactgagag ttagatgaaa   157800
tgttttctga tattaaaagt aggaaaagaa aatcaaacac ctctcttctt tgaaactgcc   157860
ttttgtcttt ccccaaatag aatataagct ttcagagggt agggactcat agctgagaag   157920
actgaacgaa gtatctgaaa aggactcttc accagagagg gctaggtcaa gatggcctca   157980
taatatcaat gcctggatgg ccaccgtggc tcatgcatgt aatcctagca ctttgagagg   158040
ccaaggtggg aggatccctt gagcatagga gtttgagacc agcctgggca acaaaatgag   158100
acaccatctc tatgaagaaa attttttaa  ttagccaggt gtggtagcac gcgcctgtgg    158160
tcccagctaa tctgaaggct gagatgggaa aattgcttga tcccaggatg ttgaggctgc   158220
agtgagccgt gattgcacca ctgcactgca gcctgggtga cagagcaaga ctttgtctca   158280
aaaaataaat aaataaaaaa gaaatagaaa cagaatgagc aaaataaaat accaatagta   158340
ttaatatgca ataataattg ctaactcgtg tagtaagtga tgtatgcgta ttatctcctt   158400
caagcctcac agtcacctct ggaggcatta ttaatcattt aatgatgaga taacagaggc   158460
acagaggaat tacttgcctg agatcgcata gttaaaaaac agtgtacaca tacaaaagaa   158520
aaatacattt tgcaaagata cagataaatt cacgaatcca catcaaaaca ttagagaact   158580
gtctttgggg aacaagagag agggcaggag ggcaagggtg ggggtggaga gataaaagga   158640
```

```
aacccttcag acacggaaga gggggaaggg gctgtgcacc tcagggcatc gtgattcgac   158700
agaatgacag aataaagtac ttaaccgtcg gccccagggc caaatgaaaa agaaaaaaaa   158760
gtggattgat aaagtcttct ggactctcca aacgggtcca caggagggag accgtgtatc   158820
tgcattcgag gcggcaggga agcttggagg acaaaaaggt agcagaggaa ctggagactg   158880
ctcagagtga aaaagtagca aagtcagagg caacggctca gagagaaacc acacaggaga   158940
cctgggccag gcagcaccca gaggtgtcct cagaagggca gatccaagtt gcttccccac   159000
ccccacagcc ctgtttctag agcaagtcaa gaaacaaaaa tattgtggtt tcctgttgaa   159060
gaggccacct tggcaacagg cactcacccg ctccacccct tcctggcacc atcgcagtct   159120
ccgagtcccc taacctgcct aactccacgt gctcagcagg aagggggtg ggaaaggctc     159180 ccaggaagaa gtttctttta ctttcaataa ccaccctggc tcttctgcct ccctccatgg   159240
cctcacttcc tgttgagttg actagcaaat tcagcagggc ttgaaaaaaa acacaaaaga   159300
taaaaggagg agaacctgtg aaaacacttc cctccagcag aaaggcagaa tctggtctcc   159360
gagagaaaga gaaaacttca ccacagaagg aactgcaggg taaactttac tcctaaagca   159420
gaacagagat gactcactcg aacaagaaat gtttcctgtt taaaggaaca gatgcccaat   159480
ttccaaccat tcagaagagg gatgtggcag acaattcatg gacgtgcaaa ctaaagcccg   159540
agcgctggac atgctttatt ggaaagcatt tatactgact ccatttagta ataataaccc   159600
ctgtcggtgg caagtaatat gccattcttt cttgcaaagg gtctgggaat aggaagtttc   159660
cctttgcctt gatcaaacct cagcactgaa gtcacagacc agccctctcc tccctcccgc   159720
cggactgggt aaagccagcc ctgtagctga aatgtaggta gattgttcag aaaaaaggag   159780
gaagtgttct ggctcagccc tacttggctt agccctgctc ggctcagccc tgctcaggct   159840
gagttcccat ccttggccat gttctccagt ttagttgtaa cccgtgtctt tgtagcattg   159900
atcctggagt gttggtgcta ctgaggtctg ttctccaaag ctctgagccc tagaccctcc   159960
cctgttctct cattttttt ttttttttga gacggagtct cggtgcgttg cccaggcaac   160020
agtacagtgg tgcgatcttg actcactgca acctccacct cctgagttca ggtgattctc   160080
ctgcctcagc ctcccgagta gctgggacta caggcaccca ccaccaccc cggctaattt     160140 ttgtatttt aatagagatg gggattcacc atgttggtca gactggtctt gaactcctga     160200
cctcaagaaa tccacccgcc ttggcctccc aaagtgctgg gattacaggc atgagccacg   160260
gtgcccagcc cctcccctgt tctctgccat ctgcctctct ttcccatttg aatttttgt     160320 tcggggacg gagtttcgct cttgttgccc aggctggagt gcaatggtgc catctcggct     160380
cacagcaacc tccgcctccc gggttcaagc gattctcctg cctcagcctc ctgggtagct   160440
gggattacag gcatgcgcca ccatgcccgg ctaattttgt attttagta gagacagggt    160500 ttctccatgt tggtcaggct ggtctcaaac tcacgacctc aggtgatcca cccgcctcgg   160560
cctggcagag tgctgggatt acaggcatga ggcagcgcgc ccagccatga attttaaaa     160620 agggttttct gcccttttgc tttcacatct tgtacatttt ataaccagaa caccagcaat   160680
aacacattac ctatatgttg caccttgaca tgaactatct ctaattctgg cagcagaatt   160740
ctctaattca gggtattgtt ctcccatgtt atggatgagg aaactaagac tcagacagtt   160800
acatggagtc aaactcagtc ctgctgagcc aaaaacagag atttttctat gacatactaa   160860
ctccctttct ccaacacttc aaatttggaa tgaatcatgt ggatggaaga gcaacaaatt   160920
taaactaata gtgactggtg cataaagggc agaaggtcct tggtttctca gtcacctaac   160980
aaaaaggagt tggcctaata aaggcacaag ctaatactta tcaaaccatt ggcgtatgcc   161040
```

```
agacacagcc acctaaacta gctcatttcc acttctgaac agttctcaga agtggatgct  161100
acgattggtc ccattttatg gatgaggaca ctgaggctta gagaggctga aagacttggc  161160
cacgctcagt cagtgagtga cagaataagg tctgtttgtc tctaaaaccc tgagtggtta  161220
gtcaccacct aaacattaat gcatagccat gaatctcaat ctgacccacc tcagaattaa  161280
ctgtaacatt tctaaaaata tgagtcttcc agctccagct ttggaactcc tatctgagca  161340
aaactgtggg agataaaaca gctggagcac ttagaatagt gcctgggcct tccacatttc  161400
tcaataaata ggctgtgggt gcagtggctc acaccagtaa tcccagcact ttggaagacc  161460
aaggcaggat gatcgcttga gcccaagaga tcgaggccag cctgggcaac atagggagac  161520
actgtctctg cagaaaattt taaaaaatta gtcagttatg gtggcatgca tctgttgtct  161580
caagctactc aggaggctga ggtgagagga taactggagt gtgggaggtc aaggctgcag  161640
tgagctatga tcacaccact gcactccagc ctaggtgaca gagcgaggcc ctgtctaaat  161700
aaataaataa acaaataaat aaatattcac tactatgtta tttaagctca caacatctct  161760
aagatggcta taaattatta ggcttacata cagatgatgc aattaaatgc aacatcaatt  161820
agctgacaaa tggcagggcc agtgcatgaa ctcaggagtg tctcactcaa aagtttctgc  161880
tcttagcccc tgtacacatc tccctgcatg tacccaggcc cagcctagca gaaatggatg  161940
atctgctgga ggcatctgag gagcagtact gagaatgggg ggagcagggt aggagtggga  162000
gtctcagggc ttcaacttgt gccatttgta aggcactgac cctagattct cccagtgtgt  162060
gtgtatatat atatgactga taatgaatt atggccaggc acagtggctt acccctgtaa  162120
tcccagcgct tgaagagatt gaggtaggcg gatcacttga agccaggagt ttgagaccag  162180
cctagccaac atggcaaaac cccatctcta ctaaaaatac aaaaaaatta gttgggcatg  162240
gtggcatgtg cctgtagtct cagccactca aggcacgaga ctcacttgag cccaggaggc  162300
ggaggttgca gtgagccgag atgacaccat tgcactccag cgtgagtgac agagggacac  162360
tccgtctcaa caaaaataaa aagtgttaat aagtgaatta taaacctcag gttggttgaa  162420
ttcctattgt gaagcacaaa gatcattatt acttcatttg ctgtaaccaa cttctcaccc  162480
tcatcttgag acatgtgcct gtgtgactgt ttatatcaga attaataatg tgcatggtcc  162540
ttagtcccag ggaagctgaa agatccggag gtgttgctgg agctgcaggg acatggagag  162600
ctggctcctg cccagcacag aatgaggaca ggtctgcttt gactcaatct ccaagtggtt  162660
tccaccctct agaatctcag ctcccacctg gaggcctggt cctgagacta ctgtgtctcc  162720
taccatgtcc accagccggc tgaaagcaga tttggacctg taagtgtccc taaaaaagcc  162780
aagaaagacc aaacctcagc tcaactgcaa cacacccttc ccattcatct tgatgtgaca  162840
ccccttcaaag ataaacactc acagtgaaag caaaatcccc tgaatgtgca tgcccttttgt  162900
ttgttgccaa tgtgggagtt tgtatataac ccatgggcca ggatggtgtg gtttgtggat  162960
tcaacggggc cgctcccctt tccttgactg gcagctggcc ttggctactg ccctagactc  163020
ctcctccaga gcgtggcaag ggaagggaaa acagattcca ttcacatcta tctcattcct  163080
ttctgggcct tgtagggaga ggctcaaaga gttgtctaag acaaagattt tagcaactgg  163140
gattttaagt tttctttttg gtattaaaat gatcagacag tcatggggca tttacagtta  163200
ctgacctcaa tctgcatact ctgcagcttg ttgattgcca atacctaccc cttctgcttt  163260
ctcagaaaaa ctactgcaga catgaatccg taccacggat ttagaaagga agaaattgag  163320
tttgttagac tctgattcca atattcatgt cactgaccta gctttccag aattttttttt  163380
tttttttga gatggagttt tgctcttgtt gcccaggctg gagtgcaatg gtgcaatctc  163440
```

```
ggctcaccgc aacctccgcc tcctgggttc aagcgattct cctgcctcag cctcccgagt   163500
agctgggatt acaggtgtgt gccaccacac ccagctaatt ttgtattttt agtagagacg   163560
ggttttctcc atgttggtca ggctggtctc gaactcccga ccttaggtga tcgacccacc   163620
tcggcttccc aaagtggtgg attacagctg tgagccgctg cgcctggccc agaattttct   163680
taaaggtttg gcatagaag aggtgaggat ccccaatatt cttgaggcac tatatgccca   163740
tacccaagaa atggggcacc tcagacgcta agaataattg tcaagaacca tcttttaaaa   163800
tgtattaatt gtggtaaaat atatatacca taaaatttac cattgtaacc agttttaagt   163860
gacatcaagt acattcacgt cgttatgcaa ccattcccac cacccaggag tcacttttaa   163920
tgatataata acagtgcatt tgttaagcac tgtgcagttt taaagcattt tccctatttt   163980
atatcattag atcctcactg gtaacatttt ttggtctcag gggtagaaga gcatgtgtct   164040
tacagacagg aagacgttga agaaacgaaa gctcagaaaa gtgaagtgac tctgaagggc   164100
ctacatagct actgtaacct acatacagca ctagtgactg tttcttaaaa aaaaaaaaaa   164160
aaaaaaaaaa aaaaagatc aggctaggtg cagtggctca catttataat cctagcactt   164220
tgagaggctg aagtgggagg atcacttgag ctcaggagtt taagatcagc ctgggcaaca   164280
tactgtcttt accaaaaatc aaaaaaatta gtcgggtgtg tggtgcagt ggtggtgcac   164340
acctgtggtc ccagctactc aggaggctga ggcaggagga ttgcttaaac ccaggagttc   164400
aaggctgcag tgagctatga ttgcatcact gcactccagc ctgggggacg gagcgagccc   164460
ctgtctaaaa caaaaaaaaa tcagatgttg ggagggttat tccctgaaac agatattttc   164520
tccattaggt ttcactcctc actttctgta aagaaaattc ctttttttc ccctccata   164580
ataagtggat tttaagagta tctgtggtag taacaaaaca cattcactac aaaatgaatt   164640
aggcaattat ttcttcctc aaaactgtta gtgataacac cacgtattct cagtagatct   164700
agaaggtggg ttataaaatt aacttttcgt ggtttacaac atatgacaca aaatcctagt   164760
ttctgagaaa atgagtcatc tctccacctga catgacatgt tgttgtgggg gaccagatgt   164820
tctttgagat ccccttcaa aagatacagt taagagtgaa gagacaaacc acagattggg   164880
agaaaatgtt tgcaaaacaa aagaccgtta cccaaaagcg tacaagaac tcttaaaact   164940
caaccatact ggtggatcac gaggtcaagt gatccagacc atcctggcca acatggtgaa   165000
agcccgtctc tactaaaaat acaaaaatta gctgggcatg gtggcacaca cctgtagtcc   165060
cagctactcg ggaggctgag gcaggagaat tgcttgaact tgggaggtag aggttgcagt   165120
gagccaagtt catgccactg tactacagcc tggtgacaga gcgagactct gtctcaaaaa   165180
aaaacaaaaa caaaaacaaa accatgctg ttatccaaaa atatacaaag aactcttgac   165240
actcaacaat aacaaaacaa acaacccaat tgaaaagtgg gcaagagatc tgaacagata   165300
cctcaccaaa aacatataca gatggcaaat aagcatatga aaagatgttc aacatcatat   165360
gtcattaggg aattgcaaat taaaacaaca gtgagatacc actacatatt tgccaaaatt   165420
gctaaaatcc gaaacactga caccaccaaa cattggcaag gatgtgaagt aacaggaact   165480
ctcattcatt actcgtggga atgaaaactc atacggacac tttggaagaa agtctggaag   165540
tttgtcatga agcttttttt tttttttagac ggagtctcac tctgtctccc aggctggagt   165600
gcaacggcaa gtgtgatctt ggctcactac agcctctgcc tctgggttca agcgattctc   165660
ctgcctcagc ctcccaagtt gctgggatta ccggcatgac caccacgccc agctaatttt   165720
tgtatttta gtagagacag ggtttcacca tgttggtcgg gctggtgtta aactcctgac   165780
ttcaaataat acacctgcct ccgcctccca aagtgctgag attacaggtg tgagccactg   165840
```

```
cgcctggcca ttttttttc ttttttttt ttttgacac agagtctcac tctattgccc   165900
aggctggagt gcagtggcgc catcttggct caatgcaacc tccacctccc aggttcaagc 165960
gattctcctg cctcagcttc ctgagtagct gggattacag gcacacgcca ccacgcccag 166020
ctaattttg tatttttttt agtagagatg aggtttcact gtgttagcca gactggtctt  166080
aaactgctga tctcaggtga tcccacctca gcctcccaaa gtgctgggat cacagtcatg 166140
agccaccgcg cctggccaaa gcatatgctt accgcaagat ccagcaatca cgtttctaga 166200
tatttaccca aattgaacat ttatgtccat gcaaaaacct gcacatgaat gtttatacca 166260
gctttattca taattcataa ctgccaaaag ttggaagcaa ccaagatgtc cctcaataaa 166320
tgaatggata aactgtggca catccatacc atagattatt attcagcaat aaaagaaat   166380
gagctatcaa accacgcaaa ggcatggaag agccttaatt gaatgttact atgtgaaaga 166440
aggcaatctg gagaggctac atactgtatg attccaacta tgtgacattc tgattaaaac 166500
tatagagaca gtggttgcca gggactcagg ggaggaagtg tgaataggtt cagcacaggg 166560
gattttagg ggagtgaaat tattctgtac aatattgtaa cggttctaca tggcattatt   166620
catttggcaa aaccggtagg atgtacacca aaagtgaacc ctaatggaaa ctatggaact 166680
ttagttcaga ataatttatt gatgggattc aggacgtgct accacaaaat atggcaccac 166740
gactgacatg gtttggattt tgtgtcctcac ccaaactcat gtccagttgt aattcctaat 166800
gttggaggcg gagcctggtg ggaggtgatt ggatcttggg ggtggtttct aatagtttag  166860
caccatcccc acagtgctgt ttgcatgata gaattctcat gatattctgg ttgtttaaaa 166920
atatgtggca cctccccgct ctcttgcttc ccctgctcta gccacatgag atgtctcgct  166980
cccccttgt cttccaccat aattgtaagt ttcctgaggc ctccccagaa gccaagcaga   167040
tgccagcatc atgcttccta tacagtctgt ggaaccatga gccaattaaa actcttttct 167100
ttatagattg cccaacctca ggtatctctt tagagcaatg caagaacaga ctaacacaat  167160
gacatattga atatttaag gtgaaggaat ttgcaaaagc agcatgtgca ggaagggttt   167220
tctgaccttc tcctgaagcc aggtcataag accctcaggt gagagatgcc ctccctatac 167280
ctggtggtat ctgtgaagac aaagggacac agagaggaat ctaactaaac aaacgggcct  167340
tgataagctt ctgccagcgg actacactta cttcaaactc tttgctctat catatcctcc   167400
acaactgtcc accctttatc aaacctacat caaactgtaa ctgcttcttg gagtcttcat 167460
ttccttataa aggcttccat gtcacataaa acttaaatat gtttatgcac ttttctctta   167520
ttaatctgtc ttctgttata gggttctcag ccatgaactt agaagggtag aaggaaaaca 167580
gatttgccct cccctacaat atcaatattg gttcatcact tgtaacaaat gtaccacact  167640
aatgcaagat gttaataacg ggaaagtgtg ggagggggag aagtgtagga ggcagagggt 167700
atatgggaac tctctacttt ctgctcttc ttttttttc tttctgagac agggtctctc    167760
tctgtcacct aggctagagt gcagtggtgt gatctcaact cactgcaacc tccgcctccc 167820
gcgctcaagc gatcctctcg ccttagcctc ccgaagccaa tctgattaag ctaatctgtt  167880
aagactcaac aataagaaaa caacccgatt gaaaagtggg caagaggtct gaacagacac 167940
ctcacaaaaa gatacgcaga tggcaaataa gcatatgaat aagctgggac tacaggtgca 168000
taccaccatg cccagctaat ctgctctgtt ttttctctaa acctgaaact gttcttaaaa  168060
aataatccat taatttttta aagtctcaca ctctattctc acttgataca tgggtaaagg 168120
tgacaatgag gtgaagtgaa aaaggatcg tctttatagt aaataacgac agatcaacaa   168180
gatagccata taaaaataaa atgagccttg atttcctacc cacacaaaat tcaaatccag 168240
```

```
atggatagtc aatctaaata taaaaaggaa gcaattgacc agggcgtggt ggctcacacc    168300
tataatccca gcactttggg aggccaaggc aggtggatca cctgaggtca ggagttgaag    168360
actagcctga ccaacatggc aagaccccca cctctactaa aaatacaaaa attggctggg    168420
catggtgggg ggcacctgta gtcccagcta ctcaggaggc tgagtcatga gaattgcttg    168480
aacccaggag gcagaggttg tagtgagcca agatcgcagc actgcactcc agcctgggca    168540
acagagtaag actctctcaa aaagaagga agcagtaaaa ctttatgaga aatcctaaga    168600
gaatgtcttt atgatattgg agtagacaaa aactcaaaaa ggacacaaaa agtgctgacc    168660
ataagggaa aaaaccacca acaggaccat tttagaatta agagcttctt ttcagaaaaa    168720
tgataccatt aagagagtga agaggcaggc tagagaatag gagaggaaat gctatgatag    168780
agagcaatct ccaacatgtg ttggtaagtg aaaaagggt gtggcagaac agcatggata    168840
gaacagtgaa cagataacgg acaaaaagag cggccactag aaattacaca atggtgtctc    168900
ctctgcatct cagcccttta atagatcaat agtaccaaag tgaaaacact ttcaacaaat    168960
ttctgaagga aaatttgcat cttgttttca gttgagtatt aactgaaagt ctcactcagg    169020
ctgaaaacct aaattgatga tgttgctact tgggatagtc cattacagtc gcctccattg    169080
tcagctgcat ccgcacctca tctggacgga cattcactcg gtacacaagg tggatgctca    169140
tcaaagcccc cttctgctgg ggccttcctg caaccagcta cactcaagga cccctgcact    169200
cgatccaccc acaggtcgtg gttcctcagg attttcttgc cctactccct attatattgt    169260
tctggatatt tttctttacc tgcttaatta ccgaaatagt agaaaagcg agagatttaa    169320
ttactatact aaagaagtgg aaagttttag cctcaaaagt caaggctgtc attcactaat    169380
aggtggtgct gtccaggcac agtgactcac acctgtaatc ctaccaattt gggaggctga    169440
ggcaggtgga tcacttgagg ccaggagtcc aagaccagcc tgacaaacat agtgagaccc    169500
ccatctctac taaaaataca aaagttggcc gggcgcagtg gctcacgcct gtaatcccag    169560
cactttggga ggccaaggcg gcggatcac gaggtcagga gatcgagact atcctggcta    169620
aaacagtgaa acgctgtctc cactaaaaat acaaaaaatt agccaggtgt ggtggcgggc    169680
acctgtagtc ccagctactc gggaggctga ggcaggagaa tcccttgaac ccggaggtg    169740
gaggttgcag tgagccgaga tcgcaccact gcactccagc ctgggcaaca gagcgagact    169800
ccatctcaaa aaaaaataca agaattagcc aggaatggtg gcacacgctt gtagtcccag    169860
ctacttggga ggctgaggca tgagaatcac ttgaacctgg gaggcagagg ttgcagtgag    169920
ccgagatcac accactgcat tgggcaacag agtgaggctc tgtttcagga aaaaaaaaa    169980
aaaaaatagg ttgtgctaat gaggattctg agaaatcctg cagcccctgg ggaaatgtgg    170040
agctgagggt caaggtcaca gacagaagga aggcgccttc agcatggatg ctatggggac    170100
ccagtgagct ctcagtaggc tccagaagca acctaattca catacatgca gttaaaagaa    170160
aagtctcacc ctgatgtccc agtggccacc agacacacat cctcaacagc ctagataatt    170220
ctagaatcag atagatttct tcctaaaatt cttctttttt tttttttttt ttttttttg    170280
agacagacag tctcactctg ccgcccagcc tggagtgcag tggtgtgatc ttggttcact    170340
gcaacctcca ccccgccagc tcaagcaatt ctcctgcctc agctccctag cagaatacag    170400
gcgcctgcca ctgcacccag ctagtttttg tattttagt agagacaggg tttcaccatc    170460
ttggccaggc tggtcttgaa ctcctgatct cgtgatccac ccacctcggc ctcccaaagt    170520
gctgggatta caggagtaag ccactgtgcc cagacaactt cttcctaaaa ttctaagcaa    170580
atcttaccca agggcaattg cagctccttt cttgctcctc cctggccccc caaaattcca    170640
```

```
aaaaacaatg aaagtcaaat gaagaacatt ttgcgttcca gttgacacaa cttttgggat   170700
ttttgcagac agaacagact cttagcaaag tggtgtggga gggttgggat ctgagcagga   170760
catgcagttc acatttttc aaagcctcag gacagatcct ggtgtggaat ggtgagaata   170820
caggctgggg agtcagtcag ctgaactggg ggtgagggtg gtcgattcag gtcttagtcc   170880
aacttccaga tttccaaatg tgagaaatta gactagaggt tgtctaagaa cactttctgt   170940
ccaaacattt gatgattgca taataatatg ttttttcac tcaagttctc atcttatttt    171000
tcttctgcaa ttctagtgtg tgtggggatg ggggtggact tccagttccg agacacgatg   171060
gcatagattc acttttccct gcttctcccc tctaaggaca cctaaatacc ctgggaataa   171120
atcaacagac aatcacacaa ccctgagagg tggaaagtag aggcagactg gcggggggacc  171180 cagaggcagg aacaacaccc tgttttgtgc cctgggctgt cttttattc ccacacatgc    171240 cagactgaaa acgaaagagg cctgcaatcc agaaccacca acaggcctaa attagaaaga   171300
acaaatggct gggcccagtg gctcacgcct gtaatcccag cactttggga ggccaaggca   171360
ggcagatcac ctgaggttgg gagttcgaga ccagcctcaa catggagaaa ccccgtctct   171420
actaaaaata caaaattagc cgggcatggt ggcacatgcc tgtaatccca gctacttggg   171480
aggctgaggc aggagaattg cttgaacctg ggaggtagag gttgcggtga ccgagattg    171540 caccattgca ctccagtctg ggcaacaaga gcgaaactcc gtctcaaaaa aaaaaaaaa    171600 aaaagaaca aacaaggaaa agcaacagaa agaaaagcct gctctctctg gccaagggc     171660 caggaagggg cagcaaagcg gaagcccagc agggagatac atgcccatga ttcacacctg   171720
ggcaaggaca gctgacctgg cctgcagcag cagggtcaac aggagctgcc tggaacctac   171780
gcctcactcc aaacctggag ccgtggcagg ctacactggt ggtcccctgg gtctatgata   171840
aggaagtgga agcagcagat gatgaggttg caaccagact cagatttcta gctttgttca   171900
tgatactccg gatggttatc aagtccagtg gctggggaca gtggctcacg cctgtaatcc   171960
caacactttg ggaggccgag gtgggcggat cacttgaagt taggagttcg agaccaggct   172020
agccaacatg gtgaaaccct gtctgtacta aaaatacaaa aattagccag gcatggtggt   172080
gcgtgtctgt aattccagct actcgggagg ctgaggcata gaatcactt gaacctggga    172140 gatggaagta gcagtgagat tgagccactg cactccaacc tgggtgacag agtgagactc   172200
tgtctcaaaa aaaaaacaa aaacaaataa aaaacctcct tgtgaggtca ggtcaatcaa    172260
tcggtgacac aatttcagat cttagatggt tgattcccag gcatagaatg catctgataa   172320
tggccccaga tttgtggccc aagccacaca tcaatgggcc caagcatggg gcatatatga   172380
tggacgccct atgctctcta tcgcctccaa gcagcaggga tgattgagtg ttttagtaga   172440
caattgaagg acaggttaa gtgactgaca ggagggaata aaagaacctc ggcctggact    172500
atgcatctca ggggaacagt ctgggtccc agtgtggcat tcctcaaagg ggcagtcatc    172560
atttgcgctg catatttgat cagactgtct acctgcttcc ttttattgca cagcctcagt   172620
ctctctgggg aaccctacaa gggcccccca ccccttcaa ttcctttcta aagactcaga    172680
taggtgagag attagattag ctattaaaaa acaaagcatg agagacagta accctcttca   172740
tcagttatcc ctttggtgct gagcatggat ttttttgcct gcaaaaaata atcactatca   172800
acttgaggct tctaattcaa tgttttccat aaagtggctt tgttgctttg cctggttatt   172860
ttcaagggat ggatatcaat gtacagaaga gaaactttt tttttagtca tcagaggatc    172920
caggccagat tacagcccac ctccctggag gatagtcgga agatgctacc cttacccatg   172980
tcacagtggt tggggaaaat tcccccaacg tgagcgccta tgaacccatg agccagggta   173040
```

```
cagaggaggg agaagtggga atctaacctt ccttctctct ctcctacaga atagactgtg   173100
tgacttccaa gtcactaaat tcattgatat gcctgtccca ggcagttccc cagtgaattt   173160
gacaaaatgc tggatgtatc cccacaaata aatattttgt tcctgtgcca ctgaatgctg   173220
caaacaaaca tttctgtaaa catggatttt tctggtacct aagctacccc aggcatatta   173280
atctgtacac gatgctggaa gtgatcttga tcctgaccat ggtctattta ttgtaactgc   173340
agactaataa cctggctcct aacagagacc ctcaaaatcc aacccattca ggtccatgat   173400
ggggtagcct atgtttctcg cttgggctct gaaaaatcaa aggatggagt ttaggaatta   173460
tttgggctcc aggccaaaat cctatgtgta atctgtcagg cccagccatt agcaattaca   173520
aaggctttac ctggcaggcc aaacagggga ttgctgcccc ccgacccttc actccctcaa   173580
cagacttgaa cagactttgt gtataatcca tgcgtggcag gtccttgggg agctgcagt   173640
caggactcag cccatcgcct cctgtatgcc tcgggacagc catgctgtta tgcgtattaa   173700
actaacttat caaatcacct aacttgttaa attggccagg ccctccaaaa cagggtggaa   173760
caatacatta ataacgatat tacacgttcc tgagtttaat gagaagcact ccagaacttc   173820
ctaattcata tgattttttga tttgggcatc tggtaggtat ttttatcaag ttagggactt   173880
ttccttacct attagcttcc tagtatttga caaaaatcag aaagggggcat taaattatca   173940
aaaagaaatg tcaggatctt ttgagatgat tataggattt ttctgtctga gtttcttaaa   174000
agtaaattat ttacattatg cttgtggatt caaggctatg tgcaccttgc aaagtgagtt   174060
gggaaatctc ttctatatcc tatagctgcc tcaataacag aaattgtctt gtgtgtaaat   174120
tgactattca ttgcttttaa ttaaatggaa attaggtatt gacctttta tgtataggaa   174180
tcctatgtat aggaatcctt ttctattgct ttatcaatta tattttattg tagtaagaac   174240
atttaagtga gatctaccct cttagcaaat gtttaagtgt acaatacagt attgttgact   174300
ataggtacaa tgttgtacag cagatctcta gaacttactc atcttgctta actaaaactt   174360
tatgcttgtt gacaggcaac tcatttcccc cctccccagc ccctggcaac caccattcca   174420
ctctttgatt ctataaattt gactacttta gataccacat gtaagtagaa tcatacagta   174480
tttgtctttt ggtgactggc ttatttcact tagcataatg tcttcaagat tcatccatgt   174540
tgtcttatat tatagaattt ccctcccttta taaggcaaat aatattccat tttatgtgac   174600
taccacattt tctttcccca tcctagatat ttaggttgtt tgcacatctt ggctactgta   174660
aatagtgctg ctatgaccat gggagtataa tatatttaga aatcaggaag tatggtgctt   174720
ctagctttgt tcttcctcaa aactgattta gctatttgtg gtccttttta tacttcagag   174780
gttttttttct gtaaaaaaaa aatccattgg gatgttaata gagatcacac caaatttgta   174840
gattgcttta ggtagtatat gcaatagact gatgtttgtt tcccctaaaa ttcatatgtt   174900
gaaacctaat cccctatgtg ttggtatttg gagatgggac ctttgggagg tgattaggtc   174960
atgaaggtag agcacttatg aatgggacta gtgccttata aaagaaatcc cagagcgctc   175020
catcacccta attccatgag gacacatgga gaagatggcc atttatgaac caagaagcag   175080
gccctcacta gatagcaaat ctgctagcta cttgatcttg aatttcctag cctccagaac   175140
tgtgaaaaat aaatttctgt gttttataag ccaccagtct atggtatttt gttttagcag   175200
gctgaatgga ctaaggcact gtatatgcat ggatttattt ctgagctctc tcttctcttc   175260
tgatggccta tgtgtttgtc tttatgctat tcccatgctg tttcaattac tatagctttg   175320
taatatattt gaaacatatt atgaatccca tatatgaaaa gctcacatct aatataatac   175380
tcaacagtga aaatttctct atatatggtc ttgatgatgt tgagactcta tttccagttt   175440
```

```
gttgaaaaat tgtttaatca cgaaagggta ttgaattttg tcaaatgctt tctctgcatc    175500
tattgagatg atcatgttat ctttatatct ttgccctgtt aataggccat ttcgcactga    175560 tttattttg tatgttgatc catacttgta tcctagggat aaatgccact cagtcaggat     175620
gtacgatcat ttaaatgtac tgttgaattt gatttgctag tattttgtta tgagttttta    175680
tatgtatatt catcagagat attgacctgc agttttcatt tcttgtggtg tctttgtttg    175740
gctttggtat cgggataatg ttggccacat aaaataaatt tggaagtgtg ccctcttctt    175800
caatttttaa aaatagttta agaagaactg gcattaattc ttcttgagat gtttggaaga    175860
attcacctgt gaagccatct ggtcctggac ttcttcgttt ggggaacatt tttgattatt    175920
gactaaacct ccacattagt tataagtctg ttcagacttt gtatttcttc atgattcagt    175980
catcgtagat tggaaggttt tgtgaattta ttcatttctt ctagattatc cagtttgttg    176040
gaatagaatt gttcattata gcctcatgtt tttatttctg tggcatcagt tgtaatgtct    176100
cctcttttat ttctgatatt gtttatttga gtcttctctc tttcttactt agcctaacta    176160
gggatttgtt gattttgttt atcttttcaa aaaaccaatt cttttgttat tcttttcaaa    176220
aaatttgttg attttttttc tattgctttt ctattctgta ttttcttggt tcctactcta    176280
atctttgtta tttccttcac taattttagg cttagttcct cttcttcttc atcttcttct    176340
cctctccttg aggcacgaag ttagactatt tacttgagat cttcttcttc tttcactgca    176400
gatgtgtatt gcaataaagt acctcttagt acttctttgc ttagtactgc ttttatcctg    176460
taagtttggg tatgttgtgc ttttcttttc atttatctca agatatttcc taatttcttt    176520 tttattttt atggcctaat tgttgttcaa gagtgtgttg tttaatttcc acatatttgt    176580
gaacttctta ttttttcctt ctgccattgat tttagtttc attccatcat ggtcagaaaa    176640
gatacatggt atgatttcag tctcttaaat ttgcaaagac ttgttttgtg acccaacttg    176700
tgatctacct tggagaaagt tccatgtgca tttgaggata atgtgtgttc tactgctgta    176760
gggtggaacg ttctgtgtat ttctgttcgg tccatttggt ctataatgtt gtttaagtcc    176820
cctgtttcct tattaatctt ctgtctgaat gttctatcca ttatttaaag tacagtgttg    176880
aagtctccta ctattttttgt atggctggct atttctccct tcagttctgt cattgtttgt    176940
ttcatatatt taggtgctct gatattgagt gcatatattt ataattgtta tatcttcatg    177000
gtggattgat gctttttttca ttatataata tacttttaatg tctcttgtga cagttttga    177060 cttaaagtcg atttttgtctg atataaatag agccactctt gctctctttg ggttgtcatc    177120
tgcatggaat gcctcgttcc atccctgaca ggaggcatca tagttctgct cttctaaagg    177180
gcaatgattc taatgtttct ctgtgggtag ggggaaaagg aaaagacaga aaataacag     177240 aaaatgtgag atagtgaatg gccttaagaa ttcttttctg tccttgtaga caatgggccc    177300
tgaaggagaa gagtgttcct gggccaaatc tgcatgcata cacacagttt gatctgcctg    177360
gcttatgagg gattcacatc taggccttac ctcccacatg ctaaaaatgg gcctatttga    177420
gtaacatggg tgcttcaaaa atctctatga actaatttga ggggaaaagg ggcacagatg    177480
cagaggtaac tagaagggat cataagtccc caaaatgctc tgaaactagg gccttgctgg    177540
tattggatag aagggcaaaa gagagccaga tctcaggaac ttggtttcac ttatcaacag    177600
acaaatgctg tcccagcttg catcagaagc catcaggaca aatatcaaaa gtttcataat    177660
tacggtgcag tgtgagcttc cagagagcaa gctgtgggag gatccgggta aggattgccc    177720
gccacccgtg acgcctcaac agggaggagc tccttgcttg aaaagggaaa aaattgccaa    177780
actgaagagg aaggaaactg aaagtagcca ctaagaaaaa gcaagatgaa cccaaagcac    177840
```

```
aatcaatcca aggtaactga gaattcagga gaaaacaaat tagaaaagta aactgataag  177900
agtctatgta actccttaaa aggtttgtta ttaaccaaaa agtaaaaatc aaataagcca  177960
acaacaacca aaaaaaacac tagaaattag atgaagatat ccaatagttg aagacaaacg  178020
tatttttaaa aagtaaggaa gccgccccgt ccgggaggga ggtgggggt cagcccccg    178080 cccggccagc cgccccgtct gggagatgag gggcgcctct gcccggccgc ccctactggg  178140
aggtgaggag cccctctgcc cggccaccac cccgtctggg aggtgtaccc agcagctcat  178200
tgagaacggg ccatgatgac aatggcggtt ttgtggaaca gaaggggg aaaggtgggg     178260 aaaagattga gaaattggat ggttgccgtg tctgtgtaga gagaggtaga catgggagac  178320
ttttcatttt gttctatact aagaaaaatt cttctgcctt gggatcctgt agatctgtga  178380
ccttaccccc aaccctgtgc tctctgaaac atgtgctgta ccactcagg gttgaatgga    178440 ttaagggcgg tgcaagatgt gctttgttaa acagatgctt gaaggcagca tgctccttaa  178500
gagtcatcac cactccctaa tctcaagtac ccagggacac aaacactgcg gaaggccgca   178560
gggtcctctg cctaggaaaa ccagagacct ttgttcactt gtttatctgc tgaccttccc  178620
tccactattg tcctgtgacc ctgccaaatc tcctctgtg agaaacaccc aagaatgatc    178680
aattaaaaaa taaataaata aataaataaa ataaaagta aggaaaagac tgggtgcagt    178740
ggctcacacc tgtaatccta gcacttttga agcccaaagc gggcagatta cttgaggcca  178800
ggagttcaag accagtctgg ccaacatgat gaaacccgt ctctactaaa aatacaaaaa    178860
attagccagg catagcggca catgcctatt gtcccagcta ctcggaggc tgaggcagga   178920 gaattgcttg aacccaggag gcggaggttg cagtgagcca agattacgcc actgcactcc  178980
agcctgagtg acagagtaag actccatctc aagaaaaaaa aagaaagaa aaagaaaag     179040 caaggaaaat aaataaataa atgtttcagg gtttcattgt ttcctacgct gaggtgggag  179100
cgaatattct ctgaaattat cttgtagata acctttagaa aatttaaatg atatcccata  179160
tattccaggc atattctctc aaacagagca agttccccac ttgctccaca agatgccaca  179220
agccttctca aggcttctct gggtcacctg gatttcagct cagccttagt ttcctgacaa  179280
catcctgttg ttccctcata cttttctttt ttgcctccct tgttatttgt tacccccact  179340
tggaatactc ttcctctttg atatctccaa agtgtgaatc cacacaacac tgtccacttc  179400
ctccaggaag tctaccctga ctgctcccac ctagtatatc tctttcattc acgttcttct  179460
tgcacattca gtcagaaacc tacagctgct ctccatttgc caagaggttg ttctctaagt  179520
ttatatcaag attgtttgat gagatcgcaa aatgccactt cccattttc ccctagctgg    179580 ctttttaacc cgtgtcatgc ctgacatcta acatactgc ttgatcacta cacaaggctg    179640
gcccacagac tgctttggca caaggccaa agactactag gctcaacgtt aattcctgtc   179700
tttctgggcc aagataaagc cagaagacac agagccatcc actgatgcac cagtaaatta  179760
atgactttac aaaccagcat gcattcttgc ggggagtgtg tgcaagtggg aaaaaaactg  179820
tctggatatc aaaatcagtc accaagctgt atatttacaa cttgtgaatt cttcagtatt  179880
tatgtaaggt ttcgatacaa attttacacc agaaaatcaa catgactcac tccagtcttc  179940
taattttcta tttttcctcc gagaccttgc tggatgtttt cttttctttt tctttttct    180000 tttcttttt ccttttttt tttttttttt tactctgaag atctactgga gagatgtttt    180060
cataaagata gagaaaaggg tctggacaag gtggctcacg cctgtaatcc cagcactttg  180120
ggaagccgag gcgggcagat cacttgaggt caaaagtttg agaccagcct ggctaacatg  180180
ttgaaacccc atctctacta aaaatacaaa aattatctgg gcaaggtggc aggcatctgt  180240
```

```
aatcccagct actcaggagg ctgaggtggg agaatctttt gaacctggga ggcggaggtt   180300
gcagtgagcc aagaacgtgc cactgcactc cagcctgggc gacacagcaa gactctgtct   180360
caaaaaaaaa aaaaaaaaa aaaatagaaa ggggtcatac tggggaaaag gaacaaacac   180420
agacgcactg aaaagaatcc aaatggttaa gaatatgaca aagagaatca gagactacga   180480
agatttaatt caggagggtg gggatagaaa taatttgaca ctgctcttca gctaaattta   180540
ttctttactt gaaaacttct gtctggccag gcacagtggc ccacgcctgt catctcggca   180600
ctttgggcag ccgaggcaga tggatagctt gagcccagga gttcaagaca agcctgggaa   180660
acatgatgaa actccatctc tacaaaaaat gcaaaaatta actaggtgcg gtggtgcgca   180720
cctatattcc agctactcgc agatggggag ctgaagtggg agaatcactt gagcctggga   180780
ggttgagtct gcggtggggc cagggttcgg taagccgagg tcacaccact gcactccagc   180840
ctgggcggca gagccaaact cttgtctcta aaaaagact ttttaataga attttcatgt   180900
tggcttgctg ccctctggtg gaattattag ggtttatcac aaacactgtg gaattcactc   180960
tggcaatgac cactaacaca aaataccgat ggttcttggg cataactctc cccctgggga   181020
gttagatctt tgacttcatg gcgtcaggaa tttgttattg gcctggacaa cagaaacatg   181080
tctggaaaat ccccaaatat ttggaaatga aataacacaa ctctaaataa tccatgggtc   181140
aaaaaagaaa                                                          181150

<210> SEQ ID NO 48
<211> LENGTH: 6065
<212> TYPE: DNA
<213> ORGANISM: Homo sapiens

<400> SEQUENCE: 48
gagaggagcc aagatggccg aatagcaaca gctccggtct acagctccca gcgtgagcga     60
cgcagaagac gggtgatttc tgcatttcca tctgaggtac tgggttcatc tcactaggga    120
gtgccagaca gtgggcgcag gtcagtgggt gcgcgcaccg tgcacgagcc gaagcagggc    180
gaggcattgt ctcacttggg aagcgcaagg ggtcagggag ttccctttcc gagtcaaaga    240
aaggggtgac ggacgcacct ggaaaatcgg gtctctccca cccgaatatt gcgctttcgg    300
accggcttaa aaaacggcgc accgcgagat tatatcttgc acctggctag gagggtccta    360
cgcccacgga gtctcgctga ttgctagcac agcagtctga gatcaaactg caaggccgca    420
gcaaggctgg gggaggggcg cccgccattg cccaggcttg cttgggtaaa caaagcagcc    480
tggcagctcg aactgggtgg agcccaccac agctcaagga ggcctgcctg cctttgtagg    540
ctccacctct gggggcaggg cacagacaaa taaaaagaca gcagtaacct ctgcagactt    600
aaatgtccct gtctgacagc tttgaagaga gcagtggttc tcccagcatg cagctggaga    660
tctgagaacg ggcagactgc ctcctcaagt gggtccctga cccctgaccc ccgagcagcc    720
taactgggag gcacccccca gcaggggcac actgacacct cacacggcag ggtattccaa    780
cagacctgca gctgagggtc ctgtctgtta aaggaaaac taacaaacag aaaggacatc    840
cacaccaaaa acccatctgt acatcaccat catcaaagat caaagtaga taaaaccacg    900
aagatgggga aaaacagaa cagaaaaact ggaaactgta aaatgcatag tgcctctcct    960
cctccaaagg aacacagttc ctcaccagca acgaacaaa gctggatgga gaatgacttt   1020
gacgagctga gagaagaagg cttcagatga tcaaattact ctgagctatg ggaggacatt   1080
caaaccaaag gcaagaagt tgaacctttt gaaaaaatt tagaagaatg tataactaga   1140
ataaccaata cagagaagtg cttaaaggag ctgatggagc tgaaaaccaa ggctcgagaa   1200
```

```
ctacgtgaag aatgcagaag cctcaggagc cgatgcgatc aactggaaga aagggtatca   1260
gcaatggaag atgaaatgaa tgaaatgaag caagaaggga agtttagaga caaaagaata   1320
aaaagaaatg agcaaagcct ccaagaaata tgggactatg tgaaaagacc aaatctatgt   1380
ctgatcggtg tacctgaaag tgatggggac aatggaacca agttggaaaa cacgctgcag   1440
gatattatcc aggagaactt ccccaatcta gcaaggaagg ccaacgttca gattcaggaa   1500
atacagagaa cgccacaaag atactcctcg agaagagcaa ctccaagaca cataattgtc   1560
agattcacca aagttgaaat gaaggaaaaa atgttaaggg cagccagaga gaaaggtcgg   1620
gttaccctca aagggaaacc catcagacta acagcggatc tctcagcaga aaccctacaa   1680
gccagaagag agtgggggcc aatattcaac attcttaaag aaaagaatt tcaacccaga   1740 atttcatatc cagccaaact aagcttcata agtgaaggaa aaataaaatc ctttacagac   1800
aagaaatgct gagagatttt gtcaccacca ggcctaccct aaaagagctc ctgaaggaag   1860
cgccaaacat ggaaaggaac aaccggtacc agccgctgca aaatcatgcc aaaatgtaaa   1920
gaccatcgag actaggaaga aactgcatca actaacgagc aaaatcacca gctaacatca   1980
taatgacagg atcaaattca cacataacaa tattaacttt aaatgtaaat ggattaaatg   2040
ctccaattaa aagacacaga ctggcaaatt ggataaagag tcaagaccca tcagtgtgct   2100
gtattcagga aacccatctc atgtgcagag acacacatag gctcaaaata aaaggatgga   2160
ggaagatcta ccaagcaaat gtaaaacaaa aaaaggcagg ggttgcaatc ctagtctctg   2220
ataaaacaga cttaaaccca acaaagatca aagagacaa agaaggccat tacataatgg   2280
taaagggatc aattcaacaa gaagagctaa ctatcctaaa tatatatgca cccaatacag   2340
gagcacccag attcataaag aaagtcatga gtgacctaca aagagactta gactcccaca   2400
cattaataat gggagacttt aacacccac tgtcaacatt agacagatca acgagacaga   2460
aagtcaacaa ggatacccag gaattgaacc tctgcaccaa gcagacctaa tagacatcta   2520
cagaactctc caccccaaat caacagaatc tacatttttt tcagcaccac accacaccta   2580
ttccaaaatt gaccacatac ttggaagtaa agctctcctc agcaaatgta aaagaacaga   2640
aattataaca aactatctct cagaccacag tgcaatcaaa ctagaactca ggattaagaa   2700
tctcattcaa aaccgctcaa ctacatggaa actgaacaac ctgctcctga atgactactg   2760
ggtacataac gaaatgaagg cagaaataaa gatgttcttt gaaaccaacg agaacaaaga   2820
cacaacatac cagaatctct gggacgcatt caaagcagtg tgtagaggga aatttatagc   2880
actaaatggc tacaagagaa agcaggaaag atccaaaatt gacacccgaa catcacaatt   2940
aaaagaacta gaaaagcaag agcaaacaca ttcaaaagct agcagaaggc aagaaataac   3000
taaaatcaga gcagaactga aggaaataga gacacaaaaa acccttcaaa aaattaatga   3060
atccaggagc ttgttttttg aaaggatcaa caaaattgat agaccgctag caagactaat   3120
aaagaaaaaa agagagaaga atctaataga cacaataaaa aatgataaag gggatatcac   3180
caccgatccc acagaaatac aaactaccat cagagaatac tacaaacacc tctactcaaa   3240
taaactagaa aatctagaag aaatggataa attcctcgac acatacactc tcccaagact   3300
aaaccaggaa gaagttgaat ctctgaatag accaaaaaca ggatctgaaa ttgtggcaat   3360
aatcaatagt ttaccaacca aaaagagtcc aggaccagat ggattcacag ccgaattcta   3420
ccagaggtac aaggaggaac tggtaccatt ccttctgaaa ctattccaat caatagaaaa   3480
agagggaatc ctccctaact catttttatga ggccagcatc attctgatac caaagccggg   3540
cagagacaca accaaaaaag agaattttag accaatatcc ttgatgaaca ttgatgcaaa   3600
```

```
aatcctcaat aaaatactgg caaaatgaat ccagcagcac atcaaaaagt ttatccaccg   3660
tgattaagtg ggcttcatcc ctgggatgca agactggttc aatatgcaca atcaataaa    3720 tgtaatccag catataaaca gaaccaaaga caaaaaccac atgattgtct caatagatgc   3780
agaaaaagcc tttgacaaaa ttcaacaacc cttcatgcta aaaactctca ataaattagg   3840
tattgatggg acgtatttca aaataataag agctatctat gacaaaccca cagccaatat   3900
catactgaat ggtcaaaaac tggaagcatt ccctttgaaa actggcacaa gacagggatg   3960
ccctctctca ccactcctat tcaacatagt gttggaagtt ctggccaggg caattaggca   4020
ggagaaggaa ataaagggta ttcaattagg aaaagaggaa gtcaaattgt ccctgtttgc   4080
agacgacatg attgtatatc tagaaacccc cattgtctca gcccaaaatc tccttaagcc   4140
gataagcaac ttcagcaaag tctcaggata caaaatcaat gtacaaaaat cacaagcatt   4200
cttatacacc aacaacagac aaacagagag ccaaatcatg aatgaactac cattcacaat   4260
tgcttcaaag agaataaaat acttaggaat ccaaattaca agggatgtga aggacctctt   4320
caaggagaac tacaaaccac tgctcaagga aataaaagag gatacaaaca aatggaagaa   4380
cattccatgc tcatgggtag gaagaatcaa tatcatgaaa atggccatac tgcccaaggt   4440
aatttacaga ttcaatacca tccccataaa gctaccaatg actttcttca cagaattgga   4500
aaaaactact ttaaagttca tatggaacca aaaaagggcc cgcattgcca aggcaatccg   4560
aagccaaaag aacaaatctg gaggcatcac actacctgac ttcaaactat actacaaggc   4620
tacagtaacc aaaacagcat ggtactggta ccaaaacaga gatatagatc aatggaacag   4680
aacagagccc tcagaaataa cgccgcatat ctacaactat ctgatctttg acaaacctga   4740 gaaaatgag caatggggaa aggattccct atttaataaa tggtgctggg aaaactggct   4800
agccatatgt agaaagctga aactggatcc tttccttaca ccttatacaa aaatcaattc   4860
aagatggatt aaagacttaa tcgttagacc taaaaccata aaaaacccag aagaaaaacct   4920 aggcattacc attcaggaca taggcatggg caaggacttc atgtctaaaa caccaaaagc   4980
aatggcaaca aaagccaaaa ttgacaaatg ggatctaatt aaactaaaga gcttctgcac   5040
agcaaaagaa actaccatca gagtgaacag gcaacctaca aatgggaga aactttcgc    5100 aacctactca tctgacaaag ggctaatatc cagaatctac aatgaactca acaaattta    5160 caagaaaaaa acaaacaacc ccatcaaaaa gtgggcgaag gacatgaaca gacacttctc   5220
aaaagaagac atttatgcag ccaaaaaaca catgaaaaaa tgctcaccat cactggccat   5280
cagagaaatg caaatcaaaa ccacaatgag ataccatctc acaccagtta gaatggcaat   5340
cattaaaaag tcaggaaaca acaggtgctg gagaggatgt ggagaaatag gaacactttt   5400
acactgttgg tgggactgta aactagttca accgttgtgg aagtcagtgt ggcgattcct   5460
cagggatcta gaaccagaaa taccatttga cccagccatc ccattactgg gtatatatccc   5520 aaaggactct aaatcatgct gctataaaga cacatgcaca cgtatgttta ttgcggcatt   5580
attcacaata gcaaagactt ggaaccaacc caaatgtcca acaatgatag actggattaa   5640
gaaaatgtgg cacatataca ccatggaata ctatgcagcc ataaaaaatg atgagttcgt   5700
gtcctttgta gggacatgga tgaaattgga aatcatcatt cttagtaaac tatcgcaaga   5760
acaaaaaacc aaacactgca tattctcact cataggtggg aattgaacaa tgagatcaca   5820
tggacacagg aaggggaata tcacactctg gggactgtgg tggggtgggg ggagagggga   5880
gggatagcat tggagatat acctaatgct agatgacgag ttagtgggtg cagtgcacca   5940
gcatggcaca tttatacata tgtaactaac ctgcacaatg tgcacatgta ccctaaaact   6000
```

```
taaagtataa taaaaaaaaa taaaaaaaat aaaaataaaa aagaaaatat gggaaaggta    6060
aaaaa                                                                6065

<210> SEQ ID NO 49
<211> LENGTH: 507
<212> TYPE: DNA
<213> ORGANISM: Homo sapiens

<400> SEQUENCE: 49
aatctgcaag tggagatttg gacctctttg aggcctgtcg tagtaaagga aagaacttca      60
tctaaaaaca agacagaagc attctcagaa aattctttgc gatcattgag tttaactcac     120
agagcagagc aggtcttttg atggagcatt ttcaaaacac acgttttgta gtatatgcaa     180
gtggatattg ggacttctct gagaatttcg ttggaaacgg gataaacctc acgtaactga     240
agaggaacat tctcagaact tctttgtgat gttgaacttc aactgacaga ggtgaacctt     300
cccttgtgag ttcaggttga aacgctcctt tcgtggcatc tgcaagtgaa gatttggaac     360
gctatgaggc ctacggtagt aaaggaaaca gcttcatgta aaaactgaac agaagcattc     420
tcagaaaata ctttgggatg attgagttca actcacagag ctgaacattc ctttgggtga     480
agcagttttg aaacacactt tttgtag                                        507

<210> SEQ ID NO 50
<211> LENGTH: 1352
<212> TYPE: DNA
<213> ORGANISM: Homo sapiens

<400> SEQUENCE: 50
gatcatcatc gaatggaccc gaatggaatc aatcatccaa cggaagctaa tggaatcaac      60
atcgaatgaa tcgaatggaa acaccatcga attgaaacga atggaattct catgaaattg     120
aaatggatgg actcgtcatc gaatggattc gaatggaatc atcgaataaa attgattgaa     180
atcatcatca gtggaatcg aatggtatca ttgaatggaa tcgaatggaa tcatcagatg     240
gaaatgaatt gaatcgtcat agaatggaat cgaatggatt cattgaatgg aatcagatgg     300
aatcatcgaa tggactggaa tggaatcatt gaatggactc gaaggaatc atcatcaaat     360 ggaaccgaat gaatcctcat tgaatggaaa tgaaggggt catcatctaa tggaatcgca     420
tggaatcatc atcaaatgga atcgaatgga atcatcatca aatggcaatc taatggaatc     480
attgaacaga attgaatgga atcgtcatcg aatgaattga atgcaatcat cgaatggtct     540
cgaatggaat catcttctaa tggaaaggaa tggaatcatc gcatagaatc gaatggaatt     600
atcatcgaat ggaatcgaat ggtatcaaac ggaaaaaaac ggaattatcg aatggaatcg     660
aagagaatct tcgaacggac ccgaatgaa tcatctaatg gaatgaatg gaataatcca     720 ctggactcga atgcaatcat catcgaatgg aatggaatgg aatcatcgaa tggactcgaa     780
tggatggaac attgaatcga atggaatcat caatcggatg gaaacgaatg gaatcatcat     840
cgaatggaaa tgaaggagt catcatctaa tggaattgca tggaatcatc ataaaatgga     900
atcgaatgga atcaacatca atggaatca atggaatca ttgaacggaa ttgaatggaa     960
tcgtcatcga atgaattgac tgcaatcatc caatggtcgc gaatggaatc atcttcaaat    1020
ggaatggaat ggaatcatcg catagaatcg atggaatta tcatcgaatg gaatcgaatg    1080
gaatcaacat ccaacggaaa aaacggaat tatcgaatgg aatcgaagag aatcatcgaa    1140
tggacccgaa tggaatcatc taatggaatg gaatggaata tccatggac tcgaatgcaa    1200 tcatcatcga atggaatcga atggaatcat cgaatggact cgaatggaat aatcattgaa    1260
```

```
cggcatcgaa tggaatcatc atcggatgga aatgaatgga atcatcatcg aatggaatcg    1320
aatagaatta tggaatgaaa tccagtgtga tc                                  1352

<210> SEQ ID NO 51
<211> LENGTH: 11
<212> TYPE: DNA
<213> ORGANISM: artificial sequence
<220> FEATURE:
<223> OTHER INFORMATION: SEQ ID NO:51 for scheme of figure 2

<400> SEQUENCE: 51
ttcgaggacc a                                                           11

<210> SEQ ID NO 52
<211> LENGTH: 11
<212> TYPE: DNA
<213> ORGANISM: artificial sequence
<220> FEATURE:
<223> OTHER INFORMATION: SEQ ID NO:52 for scheme of figure 2
<220> FEATURE:
<221> NAME/KEY: modified_base
<222> LOCATION: (3)..(3)
<223> OTHER INFORMATION: 5-methylcytosine at this position

<400> SEQUENCE: 52
ttcgaggacc a                                                           11

<210> SEQ ID NO 53
<211> LENGTH: 11
<212> TYPE: DNA
<213> ORGANISM: artificial sequence
<220> FEATURE:
<223> OTHER INFORMATION: SEQ ID NO:53 for scheme of figure 2
<220> FEATURE:
<221> NAME/KEY: modified_base
<222> LOCATION: (3)..(3)
<223> OTHER INFORMATION: evolutionary deamination event at this position
      (5-methylcytosine to thymidine)

<400> SEQUENCE: 53
tttgaggacc a                                                           11

<210> SEQ ID NO 54
<211> LENGTH: 11
<212> TYPE: DNA
<213> ORGANISM: artificial sequence
<220> FEATURE:
<223> OTHER INFORMATION: SEQ ID NO:54 for scheme of figure 2

<400> SEQUENCE: 54
ttcgaggacc a                                                           11

<210> SEQ ID NO 55
<211> LENGTH: 11
<212> TYPE: DNA
<213> ORGANISM: artificial sequence
<220> FEATURE:
<223> OTHER INFORMATION: SEQ ID NO:55 for scheme of figure 2

<400> SEQUENCE: 55
ttcgaggatt a                                                           11

<210> SEQ ID NO 56
<211> LENGTH: 11
<212> TYPE: DNA
<213> ORGANISM: artificial sequence
<220> FEATURE:
<223> OTHER INFORMATION: SEQ ID NO:56 for scheme of figure 2
```

```
<400> SEQUENCE: 56
tttgaggatt a                                                             11

<210> SEQ ID NO 57
<211> LENGTH: 11
<212> TYPE: DNA
<213> ORGANISM: artificial sequence
<220> FEATURE:
<223> OTHER INFORMATION: SEQ ID NO:57 for scheme of figure 2
<220> FEATURE:
<221> NAME/KEY: modified_base
<222> LOCATION: (3)..(3)
<223> OTHER INFORMATION: 5-methylcytosine converted to cytosine during
      amplificaton in scheme of figure 2

<400> SEQUENCE: 57
ttcgaaaacc a                                                             11

<210> SEQ ID NO 58
<211> LENGTH: 11
<212> TYPE: DNA
<213> ORGANISM: artificial sequence
<220> FEATURE:
<223> OTHER INFORMATION: SEQ ID NO:58 for scheme of figure 2

<400> SEQUENCE: 58
tttaaaaacc a                                                             11

<210> SEQ ID NO 59
<211> LENGTH: 11
<212> TYPE: DNA
<213> ORGANISM: artificial sequence
<220> FEATURE:
<223> OTHER INFORMATION: SEQ ID NO:59 for scheme of figure 2

<400> SEQUENCE: 59
ttcaaaaacc a                                                             11
```